(12) United States Patent
Norman et al.

(10) Patent No.: US 8,476,297 B2
(45) Date of Patent: Jul. 2, 2013

(54) TRP-M8 RECEPTOR LIGANDS AND THEIR USE IN TREATMENTS

(75) Inventors: Mark H. Norman, Thousand Oaks, CA (US); Yunxin Y. Bo, Thousand Oaks, CA (US); Vijay K. Gore, Thousand Oaks, CA (US); Daniel Horne, Thousand Oaks, CA (US); Matthew Kaller, Ventura, CA (US); Vu Van Ma, Simi Valley, CA (US); Holger Monenschein, Camarillo, CA (US); Thomas Nguyen, Thousand Oaks, CA (US); Nobuko Nishimura, West Hills, CA (US); Nuria Tamayo, Newbury Park, CA (US)

(73) Assignee: Amgen Inc., Thousand Oaks, CA (US)

(*) Notice: Subject to any disclaimer, the term of this patent is extended or adjusted under 35 U.S.C. 154(b) by 174 days.

(21) Appl. No.: 12/746,292

(22) PCT Filed: Dec. 4, 2008

(86) PCT No.: PCT/US2008/013375
§ 371 (c)(1),
(2), (4) Date: Jun. 4, 2010

(87) PCT Pub. No.: WO2009/073203
PCT Pub. Date: Jun. 11, 2009

(65) Prior Publication Data
US 2010/0261728 A1    Oct. 14, 2010

Related U.S. Application Data

(60) Provisional application No. 61/008,892, filed on Dec. 21, 2007, provisional application No. 61/005,457, filed on Dec. 4, 2007.

(51) Int. Cl.
*C07D 217/04*    (2006.01)
*A61K 31/47*    (2006.01)

(52) U.S. Cl.
USPC .......................................... 514/307; 546/144

(58) Field of Classification Search
None
See application file for complete search history.

(56) References Cited

U.S. PATENT DOCUMENTS

| | | | |
|---|---|---|---|
| 4,001,244 A | 1/1977 | Yonan | |
| 6,177,443 B1 | 1/2001 | Madsen et al. | |
| 6,649,626 B1 | 11/2003 | Dodd et al. | |
| 2005/0054651 A1 | 3/2005 | Natarajan et al. | |
| 2005/0070570 A1 | 3/2005 | Garcia et al. | |
| 2009/0082358 A1 | 3/2009 | Nishimura et al. | |

FOREIGN PATENT DOCUMENTS

| | | |
|---|---|---|
| EP | 0 801 067 A1 | 10/1997 |
| JP | 48-034180 A | 5/1973 |
| JP | 48-048479 A | 7/1973 |
| WO | WO 01/29030 A1 | 4/2001 |
| WO | WO 2004/007468 A1 | 1/2004 |
| WO | WO 2005/070929 A1 | 8/2005 |
| WO | WO 2005/087743 A1 | 9/2005 |
| WO | WO 2006/035280 A1 | 4/2006 |
| WO | WO 2007/098608 A1 | 9/2007 |
| WO | WO2008/062282 A2 | 5/2008 |
| WO | WO 2009/038812 A1 | 3/2009 |
| WO | WO 2012/004722 A1 | 1/2012 |

OTHER PUBLICATIONS

International Search Report for parent PCT Application No. PCT/US2008/013375, mailed on Mar. 25, 2009.
Written Opinion for parent PCT Application No. US2008/013375, dated Mar. 25, 2009.
International Preliminary Report on Patentability for parent PCT Application No. PCT/US2008/013375, dated Jun. 8, 2010.
Bach et al., "α-Arylation of Cyclic Amines by Aryl Transfer in Lithiated Ureas", Synlett (2009), pp. 421-424, 3, USA.
Colandrea, et al., "Synthesis and Regioselective Alkylation of 1,6- and 1,7-naphthyridines," Tet. Lett., (2000), pp. 8053-8057, 41 (42), USA.
Database Chemcats, Chemical Abstracts Service, Columbus, OH, US Jun. 13, 2008 XP002519324 Order No. kam-021285 & "Aurora Screening Library", Jun. 13, 2008, Aurora Fine Chemicals LLC, San Diego, CA 92126, USA.
Gitto et al., "Solution-phase parallel synthesis and evaluation of anticonvulsant activity of N-substituted-3,4-dihydroisoquinoline-2(1H)-carboxamides", European J. Med. Chem., (2009), pp. 1349-1354, 44(3).

(Continued)

*Primary Examiner* — Zinna Northington Davis
(74) *Attorney, Agent, or Firm* — Bernard P. Friedrichsen

(57) ABSTRACT

Tetrahydroisoquinoline compounds of formula (I), and compositions containing them, for the treatment of acute, inflammatory and neurophatic pain, dental pain, general headache, migraine, cluster headache, mixed-vascular and non-vascular syndromes, tension headache, general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neurophatic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders.

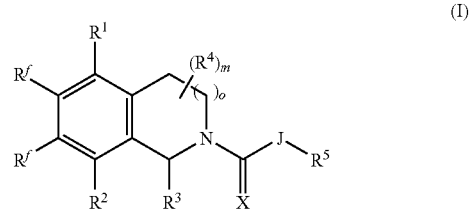

(I)

11 Claims, No Drawings

OTHER PUBLICATIONS

Ivanov et al., "Synthesis and contractile activity of substituted 1,2,3,4-tetrahydroisoquinolines", Molecules (2011), pp. 7019-7042, 16.

Naito, R. et al., "Synthesis and Antimuscarinic Properties of Quinuclidin-3-yl 1, 2, 3, 4-Tetrahydroisoquinoline-2-carboxylate Derivatives as Novel Muscarinic Receptor Antagonists," J. Med. Chem. (2005), pp. 6597-6606, 48(21), USA.

Tamayo et al., "Fused Piperidines as a Novel Class of Potent and Orally Available Transient Receptor Potential Melastatin Type 8 (TRPM8) Antagonists", J. Med. Chem., (2012), pp. 1593-1611, 55(4).

Venkov, A. P. et al., "New Modification of the Intramolecular α-Amidoalkylation for the Synthesis of 2-Acyl-1,2,3,4-tetrahydroisoquinolines," Synthesis, (1989), pp. 59-61, 1, DE.

Venkov, A. P. et al., "Synthesis of 1-Phenyl-2-acyl-tetrahydroisoquinolines by Intermolecular α-Amidoalkylation reaction," Synthetic Comm. (1992), pp. 125-134, 22(1), Great Britain.

Zara-Kaczian et al., "Synthesis of 1-aryl-2-carbamoyl-1,4-dihydro-3(2H)-isoquinolinones from 2-tritylcarbamoyl derivatives", Acta Chimica Hungarica (1984), pp. 89-94, 116(1).

Zara-Kaczian et al., "Selective reduction of 2-carbamoyl-1-phenyl-1,4-dihydroisoquinolin-3(2H)-ones", J. Chem. Research, Synopses (1984), pp. 282,(9).

Zhang et al., "Unprecedented $FeCl_3 \cdot 6 H_2O$-Promoted Skeleton Rearrangement of 1-Aryl-2,3,4,5-tetrahydro-1H-3-benzazepines: A New Strategy for the Synthesis of C1 Quaternary Tetrahydroisoquinolines", Chem. A Euro. J., (2009), pp. 11119-11122, S11119/1-S11119/71, 15(42).

English Language Abstract for Zhou, Z. et al, "Syntheses of 1,2-Disubstituted Tetrahydroisoquinoline Derivatives and their Antiarrhythmic Effects" XP 002519323 retrieved from STN Database CA [Online] Chemical Abstracts Service, Columbus, OH, Database Accession No. 1988;94357. Shanghai Yike Daxue Xuebao (1987) 14(1), pp. 15-20, Coden: Sydxee; ISSN: 0257-8131, China.

TRP-M8 RECEPTOR LIGANDS AND THEIR USE IN TREATMENTS

CONTINUING DATA

This application is a 371 of PCT/US/08/13375 filed Dec. 4, 2008 which claims the benefit of two U.S. Provisional Application Nos. 61/005,457, filed Dec. 4, 2007 and 61/008,892 filed Dec. 21, 2007, which are hereby incorporated by reference.

BACKGROUND

Cold sensation is derived from activation of the somatosensory system by a cold stimulus. Calcium imaging and patch clamp experiments in dissociated trigeminal and dorsal root ganglia neurons have revealed that cold stimuli induced calcium influx, suggesting the direct opening of a calcium-permeable ion channels by cold (Thut et al., 2003; Reid, 2005). A recently cloned non-selective cation channel, TRPM8 (transient receptor potential melastatin 8) or trp-p8 (identified as a prostate-specific gene, up-regulated in prostate cancer and other malignancies, (Tsavaler et al., 2001)) is activated by cold stimulus of 10 to 24° C. temperature (McKemy et al., 2002; Peier et al., 2002). In addition, TRPM8 is also activated by compounds that elicit cool sensation such as menthol, icilin (AG-3-5) (McKemy et al., 2002), and the endogenous lipid $PIP_2$ (Rohacs et al., 2005). Correlating with the cold sensitivity of both A delta and C-fibers, TRPM8 is highly expressed in sensory neurons of the trigeminal and dorsal root ganglia (McKemy et al., 2002; Peier et al., 2002; Thut et al., 2003). TRPM8 is also expressed in nerve fibers innervating urinary bladder in guinea pigs (Tsukimi et al., 2005) and humans (Mukerji et al., 2006) and believed to contribute to the bladder hypersensitivity.

Activation mechanism of TRPM8 by menthol and icilin appears to differ. Icilin requires calcium for robust activation of TRPM8, whereas menthol and cold do not (Chuang et al., 2004). Typically, activation by all these agonists follows a period of calcium-dependent desensitization. The domain swap analysis of chicken and rat TRPM8 and further mutational studies revealed that determinants of icilin sensitivity map to a region of TRPM8 that corresponds to the capsaicin binding site in TRPV1 transmembrane domain 3 to 4 region (Chuang et al., 2004).

Cold allodynia and mechanical hyperalgesia are associated with neuropathic pain in humans and in rodent models of neuropathic and chemotherapy-induced pain. TRPM8 is shown to mediate the analgesia by agonists such as menthol and icilin (by desensitization of the receptor) during experimental neuropathic pain in rodents (Proudfoot et al., 2006). Further, attenuation of cold sensation and cold allodynia after chronic constriction injury model of neuropathic pain in TRPM8 knockout mice (Colburn et al., 2007; Dhaka et al., 2007) suggests that antagonists of TRPM8 may be considered as pain therapeutics for chemotherapy-induced pain, neuropathic pain and bladder disorders.

Mint oil that contains menthol, an agonist of TRPM8 has been reported to alleviate pain in post-herpetic neuralgia (Davies et al., 2002), a neuropathic pain condition. Furthermore, oral or intracerebroventricular injection of menthol decreased nociceptive responses to hot-plate test and acetic acid-induced writhing in mice (Galeotti et al., 2002). These responses are believed to be mediated by the activation and desensitization of the TRPM8. These observations and the knockout mice studies indicate that TRPM8 modulation by antagonists might be beneficial for patients experiencing neuropathic pain.

SUMMARY

The present invention comprises a new class of compounds useful in the treatment of diseases, such as TRPM8-mediated diseases and other maladies, such as inflammatory or neuropathic pain and diseases involving sensory nerve function such as asthma, rheumatoid arthritis, osteoarthritis, inflammatory bowel disorders, urinary incontinence, migraine and psoriasis. In particular, the compounds of the invention are useful for the treatment of acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, anxiety, depression, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders. Accordingly, the invention also comprises pharmaceutical compositions comprising the compounds, methods for the treatment of TRP-M8-receptor-mediated diseases, such as inflammatory or neuropathic pain, asthma, rheumatoid arthritis, osteoarthritis, inflammatory bowel disorders, urinary incontinence, migraine and psoriasis diseases, using the compounds and compositions of the invention, and intermediates and processes useful for the preparation of the compounds of the invention.

The compounds of the invention are represented by the following general structure:

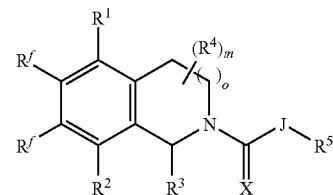

or a pharmaceutically acceptable salt thereof, wherein $R^1$, $R^2$, $R^3$, $R^4$, $R^5$, $R^f$, J and X are defined below.

The foregoing merely summarizes certain aspects of the invention and is not intended, nor should it be construed, as limiting the invention in any way. All patents, patent applications and other publications recited herein are hereby incorporated by reference in their entirety.

DETAILED DESCRIPTION

One aspect of the current invention relates to compounds having the general structure:

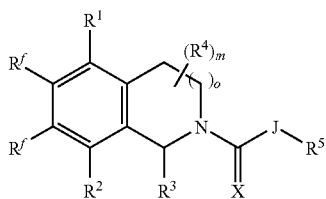

or any pharmaceutically-acceptable salt thereof, wherein:

J is —N(R$^a$)(CR$^c$R$^c$)$_n$—, —O(CR$^c$R$^c$)$_n$—, —S(CR$^c$R$^c$)$_n$— or —(CR$^c$R$^c$)$_n$—;

m is 0, 1 or 2;

n is independently in each instance 0, 1, 2 or 3;

o is 0 or 1

X is O, NR$^a$ or S;

R$^1$ is selected from H, halo, cyano, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$ and —NR$^a$C$_{2-6}$alkOR$^a$; or R$^1$ is C$_{1-6}$alk or a saturated, partially saturated or unsaturated 5-, 6- or 7-membered ring containing 0, 1, 2, 3 or 4 atoms selected from N, O and S, wherein the C$_{1-6}$alk and ring are substituted by 0, 1, 2 or 3 substituents selected from C$_{1-8}$alk, C$_{1-4}$haloalk, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$ and —NR$^a$C$_{2-6}$alkOR$^a$;

R$^2$ is selected from H, halo, cyano, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, R$^2$ is C$_{1-6}$alk or a saturated, partially saturated or unsaturated 5-, 6- or 7-membered ring containing 0, 1, 2, 3 or 4 atoms selected from N, O and S, wherein the C$_{1-6}$alk and ring are substituted by 0, 1, 2 or 3 substituents selected from C$_{1-8}$alk, C$_{1-4}$haloalk, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$ and —NR$^a$C$_{2-6}$alkOR$^a$;

R$^3$ is

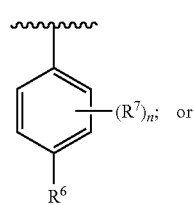

R$^3$ is a saturated, partially-saturated or unsaturated 5-, 6- or 7-membered monocyclic or 8-, 9-, 10- or 11-membered bicyclic ring containing 1, 2, 3 or 4 atoms selected from N, O and S, substituted with 0, 1, 2 or 3 groups selected from C$_{1-6}$alk, C$_{1-3}$haloalk, —OC$_{1-6}$alk, —N(C$_{1-6}$alk)C$_{1-6}$alk, —NHC$_{1-6}$alk, —NC(=O)C$_{1-6}$alk, —N(C$_{1-6}$alk)C$_{1-6}$alk, F, Cl, Br, CN, OH and NH$_2$; or R$^3$ is benzyl substituted with 1, 2 or 3 groups selected from C$_{1-6}$alk, C$_{1-3}$haloalk, —OC$_{1-6}$alk, —N(C$_{1-6}$alk)C$_{1-6}$alk, —NHC$_{1-6}$alk, —NC(=O)C$_{1-6}$alk, —N(C$_{1-6}$alk)C$_{1-6}$alk, F, Cl, Br, CN, OH and NH$_2$; or R$^3$ is napthyl substituted with 1, 2 or 3 groups selected from C$_{1-6}$alk, C$_{1-3}$haloalk, —OC$_{1-6}$alk, —N(C$_{1-6}$alk)C$_{1-6}$alk, —NHC$_{1-6}$alk, —NC(=O)C$_{1-6}$alk, —N(C$_{1-6}$alk)C$_{1-6}$alk, F, Cl, Br, CN and NH$_2$; or R$^3$ is benzyl substituted with 1, 2 or 3 groups selected from C$_{1-6}$alk, C$_{1-3}$haloalk, —OC$_{1-6}$alk, —N(C$_{1-6}$alk)C$_{1-6}$alk, —NHC$_{1-6}$alk, —NC(=O)C$_{1-6}$alk, —N(C$_{1-6}$alk)C$_{1-6}$alk, F, Cl, Br, CN, OH and NH$_2$;

R$^4$ is selected from H, C$_{1-6}$alk, C$_{1-3}$haloalk, —OC$_{1-6}$alk, —N(C$_{1-6}$alk)C$_{1-6}$alk, —NHC$_{1-6}$alk, —NC(=O)C$_{1-6}$alk, —N(C$_{1-6}$alk)C$_{1-6}$alk, F, Cl, Br, CN, OH and NH$_2$;

R$^5$ is C$_{1-11}$alkyl, C$_{6-11}$cycloalkyl or a saturated, partially saturated or unsaturated 5-, 6- or 7-membered monocyclic or 8-, 9-, 10- or 11-membered bicyclic ring containing 0, 1, 2, 3 or 4 atoms selected from N, O and S, wherein the C$_{1-6}$alkyl and ring are substituted by 0, 1 or 2 oxo groups and the C$_{1-11}$alkyl, C$_{6-11}$ cycloalkyl and ring are additionally substituted by 0, 1, 2 or 3 substituents selected from C$_{1-8}$alk, C$_{1-4}$haloalk, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$ alkNR$^a$R$^a$ and —NR$^a$C$_{2-6}$alkOR$^a$; or if J is —N(R$^a$)(CR$^c$R$^c$)$_n$—, —O(CR$^c$R$^c$)$_n$— or —S(CR$^c$R$^c$)$_n$—, then R$^5$ may also be C$_{3-5}$cycloalkyl substituted by 0, 1, 2 or 3 substituents selected from C$_{1-8}$alk, C$_{1-4}$haloalk, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$ and —NR$^a$C$_{2-6}$alkOR$^a$; or if J is —N(R$^a$)(CR$^c$R$^c$)$_n$—, then R$^5$ may also be H;

R$^6$ is independently in each instance, selected from F, Cl, Br, I, C$_{2-6}$alk, cyano, —OR$^a$, —C(=O)R$^b$, —C(=O)OR$^b$, —C(=O)NR$^a$R$^a$, —C(=NR$^a$)NR$^a$R$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$ and —NR$^a$C$_{2-6}$alkOR$^a$; or R$^6$ is C$_{1-6}$alk substituted by 1, 2 or 3 substituents selected from C$_{1-4}$haloalk, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$ and —NR$^a$C$_{2-6}$alkOR$^a$; or R$^6$ is a saturated, partially saturated or unsaturated 5-, 6- or 7-membered ring containing 0, 1, 2, 3 or 4 atoms selected from N, O and S, wherein the ring is substituted by 0, 1, 2 or 3 substituents selected from C$_{1-8}$alk, C$_{1-4}$haloalk, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$ and —NR$^a$C$_{2-6}$alkOR$^a$;

R$^7$ is selected from C$_{1-6}$alk, cyano, —C(=O)R$^b$, —C(=O)OR$^b$, —C(=O)NR$^a$R$^a$, —C(=NR$^a$)NR$^a$R$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$ and —NR$^a$C$_{2-6}$alkOR$^a$; or R$^7$ is C$_{1-6}$alk substituted by 1, 2 or 3 substituents selected from C$_{1-4}$haloalk, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$ and —NR$^a$C$_{2-6}$alkOR$^a$; or R$^7$ is a saturated, partially saturated or unsaturated 5-, 6- or 7-membered ring containing 0, 1, 2, 3 or 4 atoms selected from N, O and S, wherein the ring is substituted by 0, 1, 2 or 3 substituents selected from C$_{1-8}$alk, C$_{1-4}$haloalk, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$ and —NR$^a$C$_{2-6}$alkOR$^a$;

R$^a$ is independently, at each instance, H or R$^b$;

R$^b$ is independently, at each instance, phenyl, benzyl or C$_{1-6}$alk, the phenyl, benzyl and C$_{1-6}$alk being substituted by 0, 1, 2 or 3 substituents selected from halo, C$_{1-4}$alk, C$_{1-3}$haloalk, —OC$_{1-4}$alk, —NH$_2$, —NHC$_{1-4}$alk, and —N(C$_{1-4}$alk)C$_{1-4}$alk;

R$^c$ is independently, at each instance, H, halo, C$_{1-4}$alk, C$_{1-4}$haloalk, —OC$_{1-4}$alk, —OC$_{1-4}$haloalk, —NH$_2$, —NHC$_{1-4}$alk or —N(C$_{1-4}$alk)C$_{1-4}$alk; and R$^f$ is independently in each instance H or F.

Another aspect of the current invention relates to compounds having the general structure:

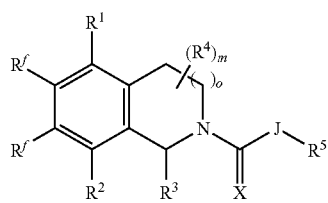

or any pharmaceutically-acceptable salt thereof, wherein:

J is —N(R$^a$)(CR$^c$R$^c$)$_n$—, —O(CR$^c$R$^c$)$_n$—, —S(CR$^c$R$^c$)$_n$— or —(CR$^c$R$^c$)$_n$—;

m is 0, 1 or 2;

n is independently in each instance 0, 1, 2 or 3;

o is 0 or 1

X is O, NR$^a$ or S;

R$^1$ is selected from H, halo, cyano, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$ and —NR$^a$C$_{2-6}$alkOR$^a$; or R$^1$ is C$_{1-6}$alk or a saturated, partially saturated or unsaturated 5-, 6- or 7-membered ring containing 0, 1, 2, 3 or 4 atoms selected from N, O and S, wherein the C$_{1-6}$alk and ring are substituted by 0, 1, 2 or 3 substituents selected from C$_{1-8}$alk, C$_{1-4}$haloalk, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$ and —NR$^a$C$_{2-6}$alkOR$^a$;

R$^2$ is selected from H, halo, cyano, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$ and —NR$^a$C$_{2-6}$alkOR$^a$; or R$^2$ is C$_{1-6}$alk or a saturated, partially saturated or unsaturated 5-, 6- or 7-membered ring containing 0, 1, 2, 3 or 4 atoms selected from N, O and S, wherein the C$_{1-6}$alk and ring are substituted by 0, 1, 2 or 3 substituents selected from C$_{1-6}$alk, C$_{1-4}$haloalk, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$ and —NR$^a$C$_{2-6}$alkOR$^a$;

R$^3$ is

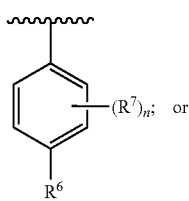

R$^3$ is a saturated, partially-saturated or unsaturated 5-, 6- or 7-membered monocyclic or 8-, 9-, 10- or 11-membered bicyclic ring containing 1, 2, 3 or 4 atoms selected from N, O and S, substituted with 0, 1, 2 or 3 groups selected from C$_{1-6}$alk, C$_{1-3}$haloalk, —OC$_{1-6}$alk, —N(C$_{1-6}$alk)C$_{1-6}$alk, —NHC$_{1-6}$alk, —NC(=O)C$_{1-6}$alk, —N(C$_{1-6}$alk)C$_{1-6}$alk, F, Cl, Br, CN, OH and NH$_2$; or R$^3$ is benzyl substituted with 1, 2 or 3 groups selected from C$_{1-6}$alk, C$_{1-3}$haloalk, —OC$_{1-6}$alk, —NHC$_{1-6}$alk, —NC(=O)C$_{1-6}$alk, —N(C$_{1-6}$alk)C$_{1-6}$alk, F, Cl, Br, CN, OH and NH$_2$; or R$^3$ is napthyl substituted with 1, 2 or 3 groups selected from C$_{1-6}$alk, C$_{1-3}$haloalk, —OC$_{1-6}$alk, —N(C$_{1-6}$alk)C$_{1-6}$alk, —NHC$_{1-6}$alk, —NC(=O)C$_{1-6}$alk, —N(C$_{1-6}$alk)C$_{1-6}$alk, F, Cl, Br, CN and NH$_2$; or R$^3$ is benzyl substituted with 1, 2 or 3 groups selected from C$_{1-6}$alk, C$_{1-3}$haloalk, —OC$_{1-6}$alk, —N(C$_{1-6}$alk)C$_{1-6}$alk, —NHC$_{1-6}$alk, —NC(=O)C$_{1-6}$alk, —N(C$_{1-6}$alk)C$_{1-6}$alk, F, Cl, Br, CN, OH and NH$_2$;

R⁴ is selected from H, C₁₋₆alk, C₁₋₃haloalk, —OC₁₋₆alk, —N(C₁₋₆alk)C₁₋₆alk, —NHC₁₋₆alk, —NC(═O)C₁₋₆alk, —N(C₁₋₆alk)C₁₋₆alk, F, Cl, Br, CN, OH and NH₂;

R⁵ is C₁₋₁₁alkyl, C₆₋₁₁cycloalkyl or a saturated, partially saturated or unsaturated 5-, 6- or 7-membered monocyclic or 8-, 9-, 10- or 11-membered bicyclic ring containing 0, 1, 2, 3 or 4 atoms selected from N, O and S, wherein the C₁₋₆alkyl and ring are substituted by 0, 1 or 2 oxo groups and the C₁₋₁₁alkyl, C₆₋₁₁cycloalkyl and ring are additionally substituted by 0, 1, 2 or 3 substituents selected from C₁₋₈alk, C₁₋₄haloalk, halo, cyano, nitro, —C(═O)Rᵇ, —C(═O)ORᵇ, —C(═O)NRᵃRᵃ, —C(═NRᵃ)NRᵃRᵃ, —ORᵃ, —OC(═O)Rᵇ, —OC(═O)NRᵃRᵃ, —OC₂₋₆alkNRᵃRᵃ, —OC₂₋₆alkORᵃ, —SRᵃ, —S(═O)Rᵇ, —S(═O)₂Rᵇ, —S(═O)₂NRᵃRᵃ, —NRᵃRᵃ, —N(Rᵃ)C(═O)Rᵇ, —N(Rᵃ)C(═O)ORᵇ, —N(Rᵃ)C(═O)NRᵃRᵃ, —N(Rᵃ)C(═NRᵃ)NRᵃRᵃ, —N(Rᵃ)S(═O)₂Rᵇ, —N(Rᵃ)S(═O)₂NRᵃRᵃ, —NRᵃC₂₋₆alkNRᵃRᵃ and —NRᵃC₂₋₆alkORᵃ; or if J is —N(Rᵃ)(CRᶜRᶜ)ₙ—, then R⁵ may also be H;

R⁶ is independently in each instance, selected from F, Cl, Br, I, C₂₋₆alk, cyano, —ORᵃ, —C(═O)Rᵇ, —C(═O)ORᵇ, —C(═O)NRᵃRᵃ, —C(═NRᵃ)NRᵃRᵃ, —S(═O)Rᵇ, —S(═O)₂Rᵇ, —S(═O)₂NRᵃRᵃ, —NRᵃRᵃ, —N(Rᵃ)C(═O)Rᵇ, —N(Rᵃ)C(═O)ORᵇ, —N(Rᵃ)C(═O)NRᵃRᵃ, —N(Rᵃ)C(═NRᵃ)NRᵃRᵃ, —N(Rᵃ)S(═O)₂Rᵇ, —N(Rᵃ)S(═O)₂NRᵃRᵃ, —NRᵃC₂₋₆alkNRᵃRᵃ and —NRᵃC₂₋₆alkORᵃ; or R⁶ is C₁₋₆alk substituted by 1, 2 or 3 substituents selected from C₁₋₄haloalk, halo, cyano, nitro, —C(═O)Rᵇ, —C(═O)ORᵇ, —C(═O)NRᵃRᵃ, —C(═NRᵃ)NRᵃRᵃ, —ORᵃ, —OC(═O)Rᵇ, —OC(═O)NRᵃRᵃ, —OC₂₋₆alkNRᵃRᵃ, —OC₂₋₆alkORᵃ, —SRᵃ, —S(═O)Rᵇ, —S(═O)₂Rᵇ, —S(═O)₂NRᵃRᵃ, —NRᵃRᵃ, —N(Rᵃ)C(═O)Rᵇ, —N(Rᵃ)C(═O)ORᵇ, —N(Rᵃ)C(═O)NRᵃRᵃ, —N(Rᵃ)C(═NRᵃ)NRᵃRᵃ, —N(Rᵃ)S(═O)₂Rᵇ, —N(Rᵃ)S(═O)₂NRᵃRᵃ, —NRᵃC₂₋₆alkNRᵃRᵃ and —NRᵃC₂₋₆alkORᵃ; or R⁶ is a saturated, partially saturated or unsaturated 5-, 6- or 7-membered ring containing 0, 1, 2, 3 or 4 atoms selected from N, O and S, wherein the ring is substituted by 0, 1 or 2 substituents selected from C₁₋₈alk, C₁₋₄haloalk, halo, cyano, nitro, —C(═O)Rᵇ, —C(═O)ORᵇ, —C(═O)NRᵃRᵃ, —C(═NRᵃ)NRᵃRᵃ, —ORᵃ, —OC(═O)Rᵇ, —OC(═O)NRᵃRᵃ, —OC₂₋₆alkNRᵃRᵃ, —OC₂₋₆alkORᵃ, —SRᵃ, —S(═O)Rᵇ, —S(═O)₂Rᵇ, —S(═O)₂NRᵃRᵃ, —NRᵃRᵃ, —N(Rᵃ)C(═O)Rᵇ, —N(Rᵃ)C(═O)ORᵇ, —N(Rᵃ)C(═O)NRᵃRᵃ, —N(Rᵃ)C(═NRᵃ)NRᵃRᵃ, —N(Rᵃ)S(═O)₂Rᵇ, —N(Rᵃ)S(═O)₂NRᵃRᵃ, —NRᵃC₂₋₆alkNRᵃRᵃ and —NRᵃC₂₋₆alkORᵃ;

R⁷ is selected from C₁₋₆alk, cyano, —C(═O)Rᵇ, —C(═O)ORᵇ, —C(═O)NRᵃRᵃ, —C(═NRᵃ)NRᵃRᵃ, —S(═O)Rᵇ, —S(═O)₂Rᵇ, —S(═O)₂NRᵃRᵃ, —NRᵃRᵃ, —N(Rᵃ)C(═O)Rᵇ, —N(Rᵃ)C(═O)ORᵇ, —N(Rᵃ)C(═O)NRᵃRᵃ, —N(Rᵃ)C(═NRᵃ)NRᵃRᵃ, —N(Rᵃ)S(═O)₂Rᵇ, —N(Rᵃ)S(═O)₂NRᵃRᵃ, —NRᵃC₂₋₆alkNRᵃRᵃ and —NRᵃC₂₋₆alkORᵃ; or R⁷ is C₁₋₆alk substituted by 1, 2 or 3 substituents selected from C₁₋₄haloalk, halo, cyano, nitro, —C(═O)Rᵇ, —C(═O)ORᵇ, —C(═O)NRᵃRᵃ, —C(═NRᵃ)NRᵃRᵃ, —OC(═O)Rᵇ, —OC(═O)NRᵃRᵃ, —OC₂₋₆alkNRᵃRᵃ, —OC₂₋₆alkORᵃ, —SRᵃ, —S(═O)Rᵇ, —S(═O)₂Rᵇ, —S(═O)₂NRᵃRᵃ, —NRᵃRᵃ, —N(Rᵃ)C(═O)Rᵇ, —N(Rᵃ)C(═O)ORᵇ, —N(Rᵃ)C(═O)NRᵃRᵃ, —N(Rᵃ)C(═NRᵃ)NRᵃRᵃ, —N(Rᵃ)S(═O)₂Rᵇ, —N(Rᵃ)S(═O)₂NRᵃRᵃ, —NRᵃC₂₋₆alkNRᵃRᵃ and —NRᵃC₂₋₆alkORᵃ; or R⁷ is a saturated, partially saturated or unsaturated 5-, 6- or 7-membered ring containing 0, 1, 2, 3 or 4 atoms selected from N, O and S, wherein the ring is substituted by 0, 1, 2 or 3 substituents selected from C₁₋₈alk, C₁₋₄haloalk, halo, cyano, nitro, —C(═O)Rᵇ, —C(═O)ORᵇ, —C(═O)NRᵃRᵃ, —C(═NRᵃ)NRᵃRᵃ, —ORᵃ, —OC(═O)Rᵇ, —OC(═O)NRᵃRᵃ, —OC₂₋₆alkNRᵃRᵃ, —OC₂₋₆alkORᵃ, —SRᵃ, —S(═O)Rᵇ, —S(═O)₂Rᵇ, —S(═O)₂NRᵃRᵃ, —NRᵃRᵃ, —N(Rᵃ)C(═O)Rᵇ, —N(Rᵃ)C(═O)ORᵇ, —N(Rᵃ)C(═O)NRᵃRᵃ, —N(Rᵃ)C(═NRᵃ)NRᵃRᵃ, —N(Rᵃ)S(═O)₂Rᵇ, —N(Rᵃ)S(═O)₂NRᵃRᵃ, —NRᵃC₂₋₆alkNRᵃRᵃ and —NRᵃC₂₋₆alkORᵃ;

Rᵃ is independently, at each instance, H or Rᵇ;

Rᵇ is independently, at each instance, phenyl, benzyl or C₁₋₆alk, the phenyl, benzyl and C₁₋₆alk being substituted by 0, 1, 2 or 3 substituents selected from halo, C₁₋₄alk, C₁₋₃haloalk, —OC₁₋₄alk, —NH₂, —NHC₁₋₄alk, and —N(C₁₋₄alk)C₁₋₄alk;

Rᶜ is independently, at each instance, H, halo, C₁₋₄alk, C₁₋₄haloalk, —OC₁₋₄alk, —OC₁₋₄haloalk, —NH₂, —NHC₁₋₄alk or —N(C₁₋₄alk)C₁₋₄alk; and Rᶠ is independently in each instance H or F.

Another aspect of the current invention relates to compounds having the general structure:

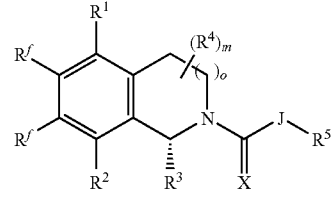

or any pharmaceutically-acceptable salt thereof, wherein:

J is —N(Rᵃ)(CRᶜRᶜ)ₙ—, —O(CRᶜRᶜ)ₙ—, —S(CRᶜRᶜ)ₙ— or —(CRᶜRᶜ)—;

m is 0, 1 or 2;

n is independently in each instance 0, 1, 2 or 3;

o is 0 or 1

X is O, NRᵃ or S;

R¹ is selected from H, halo, cyano, —C(═O)Rᵇ, —C(═O)ORᵇ, —C(═O)NRᵃRᵃ, —C(═NRᵃ)NRᵃRᵃ, —ORᵃ, —OC(═O)Rᵇ, —OC(═O)NRᵃRᵃ, —OC₂₋₆alkNRᵃRᵃ, —OC₂₋₆alkORᵃ, —SRᵃ, —S(═O)Rᵇ, —S(═O)₂Rᵇ, —S(═O)₂NRᵃRᵃ, —NRᵃRᵃ, —N(Rᵃ)C(═O)Rᵇ, —N(Rᵃ)C(═O)ORᵇ, —N(Rᵃ)C(═O)NRᵃRᵃ, —N(Rᵃ)C(═NRᵃ)NRᵃRᵃ, —N(Rᵃ)S(═O)₂Rᵇ, —N(Rᵃ)S(═O)₂NRᵃRᵃ, —NRᵃC₂₋₆alkNRᵃRᵃ and —NRᵃC₂₋₆alkORᵃ; or R¹ is C₁₋₆alk or a saturated, partially saturated or unsaturated 5-, 6- or 7-membered ring containing 0, 1, 2, 3 or 4 atoms selected from N, O and S, wherein the C₁₋₆alk and ring are substituted by 0, 1, 2 or 3 substituents selected from C₁₋₈alk, C₁₋₄haloalk, halo, cyano, nitro, —C(═O)Rᵇ, —C(═O)ORᵇ, —C(═O)NRᵃRᵃ, —C(═NRᵃ)NRᵃRᵃ, —ORᵃ, —OC(═O)Rᵇ, —OC(═O)NRᵃRᵃ, —OC₂₋₆alkNRᵃRᵃ, —OC₂₋₆alkORᵃ, —SRᵃ, —S(═O)Rᵇ, —S(═O)₂Rᵇ, —S(═O)₂NRᵃRᵃ, —NRᵃRᵃ, —N(Rᵃ)C(═O)Rᵇ, —N(Rᵃ)C(═O)ORᵇ, —N(Rᵃ)C(═O)NRᵃRᵃ, —N(Rᵃ)C(═NRᵃ)NRᵃRᵃ, —N(Rᵃ)S(═O)₂Rᵇ, —N(Rᵃ)S(═O)₂NRᵃRᵃ, —NRᵃC₂₋₆alkNRᵃRᵃ and —NRᵃC₂₋₆alkORᵃ;

R² is selected from H, halo, cyano, —C(═O)Rᵇ, —C(═O)ORᵇ, —C(═O)NRᵃRᵃ, —C(═NRᵃ)NRᵃRᵃ, —ORᵃ, —OC(═O)Rᵇ, —OC(═O)NRᵃRᵃ, —OC₂₋₆alkNRᵃRᵃ, —OC₂₋₆alkORᵃ, —SRᵃ, —S(═O)Rᵇ, —S(═O)₂Rᵇ, —S(═O)₂NRᵃRᵃ, —NRᵃRᵃ, —N(Rᵃ)C(═O)Rᵇ, —N(Rᵃ)C(═O)ORᵇ, —N(Rᵃ)C(═NRᵃ)NRᵃRᵃ, —N(Rᵃ)S(═O)₂Rᵇ, —N(Rᵃ)S(═O)₂NRᵃRᵃ, —NRᵃC₂₋₆alkNRᵃRᵃ and —NRᵃC₂₋₆alkORᵃ; or R² is C₁₋₆alk or a saturated, partially saturated or unsaturated 5-, 6- or 7-membered ring containing 0, 1, 2, 3 or 4 atoms selected from N, O and S, wherein the $C_{1-6}$alk and ring are substituted by 0, 1, 2 or 3 substituents selected from $C_{1-8}$alk, $C_{1-4}$haloalk, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —O$C_{2-6}$alkN$R^aR^a$, —O$C_{2-6}$alkO$R^a$, —S$R^a$, —S(=O)$R^b$, —S(=O)$_2R^b$, —S(=O)$_2$N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkN$R^aR^a$ and —N$R^aC_{2-6}$alkO$R^a$;

$R^3$ is

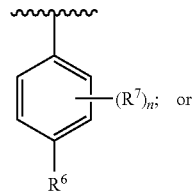

$R^3$ is a saturated, partially-saturated or unsaturated 5-, 6- or 7-membered monocyclic or 8-, 9-, 10- or 11-membered bicyclic ring containing 1, 2, 3 or 4 atoms selected from N, O and S, substituted with 0, 1, 2 or 3 groups selected from $C_{1-6}$alk, $C_{1-3}$haloalk, —O$C_{1-6}$alk, —N($C_{1-6}$alk)$C_{1-6}$alk, —NH$C_{1-6}$alk, —NC(=O)$C_{1-6}$alk, —N($C_{1-6}$alk)$C_{1-6}$alk, F, Cl, Br, CN, OH and NH$_2$; or $R^3$ is benzyl substituted with 1, 2 or 3 groups selected from $C_{1-6}$alk, $C_{1-3}$haloalk, —O$C_{1-6}$alk, —N($C_{1-6}$alk)$C_{1-6}$alk, —NH$C_{1-6}$alk, —NC(=O)$C_{1-6}$alk, —N($C_{1-6}$alk)$C_{1-6}$alk, F, Cl, Br, CN, OH and NH$_2$; or $R^3$ is napthyl substituted with 1, 2 or 3 groups selected from $C_{1-6}$alk, $C_{1-3}$haloalk, —O$C_{1-6}$alk, —N($C_{1-6}$alk)$C_{1-6}$alk, —NH$C_{1-6}$alk, —NC(=O)$C_{1-6}$alk, —N($C_{1-6}$alk)$C_{1-6}$alk, F, Cl, Br, CN and NH$_2$; or $R^3$ is benzyl substituted with 1, 2 or 3 groups selected from $C_{1-6}$alk, $C_{1-3}$haloalk, —O$C_{1-6}$alk, —N($C_{1-6}$alk)$C_{1-6}$alk, —NH$C_{1-6}$alk, —NC(=O)$C_{1-6}$alk, —N($C_{1-6}$alk)$C_{1-6}$alk, F, Cl, Br, CN, OH and NH$_2$;

$R^4$ is selected from H, $C_{1-6}$alk, $C_{1-3}$haloalk, —O$C_{1-6}$alk, —N($C_{1-6}$alk)$C_{1-6}$alk, —NH$C_{1-6}$alk, —NC(=O)$C_{1-6}$alk, —N($C_{1-6}$alk)$C_{1-6}$alk, F, Cl, Br, CN, OH and NH$_2$;

$R^5$ is $C_{1-11}$alkyl, $C_{6-11}$cycloalkyl or a saturated, partially saturated or unsaturated 5-, 6- or 7-membered monocyclic or 8-, 9-, 10- or 11-membered bicyclic ring containing 0, 1, 2, 3 or 4 atoms selected from N, O and S, wherein the $C_{1-6}$alkyl and ring are substituted by 0, 1 or 2 oxo groups and the $C_{1-11}$alkyl, $C_{6-11}$cycloalkyl and ring are additionally substituted by 0, 1, 2 or 3 substituents selected from $C_{1-8}$alk, $C_{1-4}$haloalk, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N$R^aR^a$, —O$C_{2-6}$alkN$R^aR^a$, —O$C_{2-6}$alkO$R^a$, —S$R^a$, —S(=O)$R^b$, —S(=O)$_2R^b$, —S(=O)$_2$N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkN$R^aR^a$ and —N$R^aC_{2-6}$alkO$R^a$; or if J is —N($R^a$)(C$R^cR^c$)$_n$—, then $R^5$ may also be H;

$R^6$ is independently in each instance, selected from F, Cl, Br, I, $C_{2-6}$alk, cyano, —O$R^a$, —C(=O)$R^b$, —C(=O)O$R^b$, —C(=O)N$R^aR^a$, —C(=N$R^a$)N$R^aR^a$, —S(=O)$R^b$, —S(=O)$_2R^b$, —S(=O)$_2$N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkN$R^aR^a$ and —N$R^aC_{2-6}$alkO$R^a$; or $R^6$ is $C_{1-6}$alk substituted by 1, 2 or 3 substituents selected from $C_{1-4}$haloalk, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —O$C_{2-6}$alkN$R^aR^a$, —O$C_{2-6}$alkO$R^a$, —S$R^a$, —S(=O)$R^b$, —S(=O)$_2R^b$, —S(=O)$_2$N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkN$R^aR^a$ and —N$R^aC_{2-6}$alkO$R^a$; or $R^6$ is a saturated, partially saturated or unsaturated 5-, 6- or 7-membered ring containing 0, 1, 2, 3 or 4 atoms selected from N, O and S, wherein the ring is substituted by 0, 1 or 2 substituents selected from $C_{1-8}$alk, $C_{1-4}$haloalk, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —O$C_{2-6}$alkN$R^aR^a$, —O$C_{2-6}$alkO$R^a$, —S$R^a$, —S(=O)$R^b$, —S(=O)$_2R^b$, —S(=O)$_2$N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkN$R^aR^a$ and —N$R^aC_{2-6}$alkO$R^a$;

$R^7$ is selected from $C_{1-6}$alk, cyano, —C(=O)$R^b$, —C(=O)O$R^b$, —C(=O)N$R^aR^a$, —C(=N$R^a$)N$R^aR^a$, —S(=O)$R^b$, —S(=O)$_2R^b$, —S(=O)$_2$N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkN$R^aR^a$ and —N$R^aC_{2-6}$alkO$R^a$; or $R^7$ is $C_{1-6}$alk substituted by 1, 2 or 3 substituents selected from $C_{1-4}$haloalk, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —O$C_{2-6}$alkN$R^aR^a$, —O$C_{2-6}$alkO$R^a$, —S$R^a$, —S(=O)$R^b$, —S(=O)$_2R^b$, —S(=O)$_2$N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkN$R^aR^a$ and —N$R^aC_{2-6}$alkO$R^a$; or $R^7$ is a saturated, partially saturated or unsaturated 5-, 6- or 7-membered ring containing 0, 1, 2, 3 or 4 atoms selected from N, O and S, wherein the ring is substituted by 0, 1 or 2 substituents selected from $C_{1-8}$alk, $C_{1-4}$haloalk, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —O$C_{2-6}$alkN$R^aR^a$, —O$C_{2-6}$alkO$R^a$, —S$R^a$, —S(=O)$R^b$, —S(=O)$_2R^b$, —S(=O)$_2$N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkN$R^aR^a$ and —N$R^aC_{2-6}$alkO$R^a$;

$R^a$ is independently, at each instance, H or $R^b$;

$R^b$ is independently, at each instance, phenyl, benzyl or $C_{1-6}$alk, the phenyl, benzyl and $C_{1-6}$alk being substituted by 0, 1, 2 or 3 substituents selected from halo, $C_{1-4}$alk, $C_{1-3}$haloalk, —O$C_{1-4}$alk, —NH$_2$, —NH$C_{1-4}$alk, and —N($C_{1-4}$alk)$C_{1-4}$alk;

$R^c$ is independently, at each instance, H, halo, $C_{1-4}$alk, $C_{1-4}$haloalk, —O$C_{1-4}$alk, —O$C_{1-4}$haloalk, —NH$_2$, —NH$C_{1-4}$alk or —N($C_{1-4}$alk)$C_{1-4}$alk; and $R^f$ is independently in each instance H or F.

Another aspect of the current invention relates to compounds having the general structure:

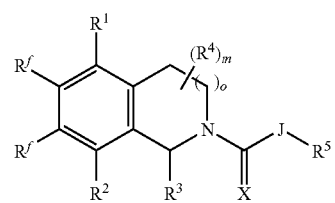

or any pharmaceutically-acceptable salt thereof, wherein:

J is —N($R^a$)(C$R^c R^c$)$_n$—, —O(C$R^c R^c$)$_n$—, —S(C$R^c R^c$)$_n$— or —(C$R^c R^c$)$_n$—;

m is 0, 1 or 2;

n is independently in each instance 0, 1, 2 or 3;

o is 0 or 1

X is O, N$R^a$ or S;

$R^1$ is selected from H, halo, cyano, —C(=O)$R^b$, —C(=O)O$R^b$, —C(=O)N$R^a R^a$, —C(=N$R^a$)N$R^a R^a$, —O$R^a$, —OC(=O)$R^b$, —OC(=O)N$R^a R^a$, —OC$_{2-6}$alkN$R^a R^a$, —OC$_{2-6}$alkO$R^a$, —S$R^a$, —S(=O)$R^b$, —S(=O)$_2 R^b$, —S(=O)$_2$N$R^a R^a$, —N$R^a R^a$, —N($R^a$)C(=O)$R^b$, —N($R^a$)C(=O)O$R^b$, —N($R^a$)C(=O)N$R^a R^a$, —N($R^a$)C(=N$R^a$)N$R^a R^a$, —N($R^a$)S(=O)$_2 R^b$, —N($R^a$)S(=O)$_2$N$R^a R^a$, —N$R^a$C$_{2-6}$alkN$R^a R^a$ and —N$R^a$C$_{2-6}$alkO$R^a$; or $R^1$ is C$_{1-6}$alk or a saturated, partially saturated or unsaturated 5-, 6- or 7-membered ring containing 0, 1, 2, 3 or 4 atoms selected from N, O and S, wherein the C$_{1-6}$alk and ring are substituted by 0, 1, 2 or 3 substituents selected from C$_{1-8}$alk, C$_{1-4}$haloalk, halo, cyano, nitro, —C(=O)$R^b$, —C(=O)O$R^b$, —C(=O)N$R^a R^a$, —C(=N$R^a$)N$R^a R^a$, —O$R^a$, —OC(=O)$R^b$, —OC(=O)N$R^a R^a$, —OC$_{2-6}$alkN$R^a R^a$, —OC$_{2-6}$alkO$R^a$, —S$R^a$, —S(=O)$R^b$, —S(=O)$_2 R^b$, —S(=O)$_2$N$R^a R^a$, —N$R^a R^a$, —N($R^a$)C(=O)$R^b$, —N($R^a$)C(=O)O$R^b$, —N($R^a$)C(=O)N$R^a R^a$, —N($R^a$)C(=N$R^a$)N$R^a R^a$, —N($R^a$)S(=O)$_2 R^b$, —N($R^a$)S(=O)$_2$N$R^a R^a$, —N$R^a$C$_{2-6}$alkN$R^a R^a$ and —N$R^a$C$_{2-6}$alkO$R^a$;

$R^2$ is selected from H, halo, cyano, —C(=O)$R^b$, —C(=O)O$R^b$, —C(=O)N$R^a R^a$, —C(=N$R^a$)N$R^a R^a$, —O$R^a$, —OC(=O)$R^b$, —OC(=O)N$R^a R^a$, —OC$_{2-6}$alkN$R^a R^a$, —OC$_{2-6}$alkO$R^a$, —S$R^a$, —S(=O)$R^b$, —S(=O)$_2 R^b$, —S(=O)$_2$N$R^a R^a$, —N$R^a R^a$, —N($R^a$)C(=O)$R^b$, —N($R^a$)C(=O)O$R^b$, —N($R^a$)C(=O)N$R^a R^a$, —N($R^a$)C(=N$R^a$)N$R^a R^a$, —N($R^a$)S(=O)$_2 R^b$, —N($R^a$)S(=O)$_2$N$R^a R^a$, —N$R^a$C$_{2-6}$alkN$R^a R^a$ and —N$R^a$C$_{2-6}$alkO$R^a$; or $R^2$ is C$_{1-6}$alk or a saturated, partially saturated or unsaturated 5-, 6- or 7-membered ring containing 0, 1, 2, 3 or 4 atoms selected from N, O and S, wherein the C$_{1-6}$alk and ring are substituted by 0, 1, 2 or 3 substituents selected from C$_{1-8}$alk, C$_{1-4}$haloalk, halo, cyano, nitro, —C(=O)$R^b$, —C(=O)O$R^b$, —C(=O)N$R^a R^a$, —C(=N$R^a$)N$R^a R^a$, —O$R^a$, —OC(=O)$R^b$, —OC(=O)N$R^a R^a$, —OC$_{2-6}$alkN$R^a R^a$, —OC$_{2-6}$alkO$R^a$, —S$R^a$, —S(=O)$R^b$, —S(=O)$_2 R^b$, —S(=O)$_2$N$R^a R^a$, —N$R^a R^a$, —N($R^a$)C(=O)$R^b$, —N($R^a$)C(=O)O$R^b$, —N($R^a$)C(=O)N$R^a R^a$, —N($R^a$)C(=N$R^a$)N$R^a R^a$, —N($R^a$)S(=O)$_2 R^b$, —N($R^a$)S(=O)$_2$N$R^a R^a$, —N$R^a$C$_{2-6}$alkN$R^a R^a$ and —N$R^a$C$_{2-6}$alkO$R^a$;

$R^3$ is

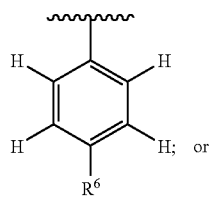

$R^3$ is selected from 4-pyrimidinyl, 2-pyridinyl, both of which are substituted with 0, 1, 2 or 3 groups selected from C$_{1-6}$alk, C$_{1-3}$haloalk, —OC$_{1-6}$alk, —NHC$_{1-6}$alk, —NC(=O)C$_{1-6}$alk, —N(C$_{1-6}$alk)C$_{1-6}$alk, F, Cl, Br, CN, OH and NH$_2$; or $R^3$ is benzyl substituted with 1, 2 or 3 groups selected from C$_{1-6}$alk, C$_{1-3}$haloalk, —OC$_{1-6}$alk, —N(C$_{1-6}$alk)C$_{1-6}$alk, —NHC$_{1-6}$alk, —NC(=O)C$_{1-6}$alk, —N(C$_{1-6}$alk)C$_{1-6}$alk, F, Cl, Br, CN, OH and NH$_2$;

$R^4$ is selected from H, C$_{1-6}$alk, C$_{1-3}$haloalk, —OC$_{1-6}$alk, —N(C$_{1-6}$alk)C$_{1-6}$alk, —NHC$_{1-6}$alk, —NC(=O)C$_{1-6}$alk, —N(C$_{1-6}$alk)C$_{1-6}$alk, F, Cl, Br, CN, OH and NH$_2$;

$R^5$ is C$_{1-11}$alkyl, C$_{6-11}$cycloalkyl or a saturated, partially saturated or unsaturated 5-, 6- or 7-membered monocyclic or 8-, 9-, 10- or 11-membered bicyclic ring containing 0, 1, 2, 3 or 4 atoms selected from N, O and S, wherein the C$_{1-6}$alkyl and ring are substituted by 0, 1 or 2 oxo groups and the C$_{1-11}$alkyl, C$_{6-11}$cycloalkyl and ring are additionally substituted by 0, 1, 2 or 3 substituents selected from C$_{1-8}$alk, C$_{1-4}$haloalk, halo, cyano, nitro, —C(=O)$R^b$, —C(=O)O$R^b$, —C(=O)N$R^a R^a$, —C(=N$R^a$)N$R^a R^a$, —O$R^a$, —OC(=O)$R^b$, —OC(=O)N$R^a R^a$, —OC$_{2-6}$alkN$R^a R^a$, —OC$_{2-6}$alkO$R^a$, —S$R^a$, —S(=O)$R^b$, —S(=O)$_2 R^b$, —S(=O)$_2$N$R^a R^a$, —N$R^a R^a$, —N($R^a$)C(=O)$R^b$, —N($R^a$)C(=O)O$R^b$, —N($R^a$)C(=O)N$R^a R^a$, —N($R^a$)C(=N$R^a$)N$R^a R^a$, —N($R^a$)S(=O)$_2 R^b$, —N($R^a$)S(=O)$_2$N$R^a R^a$, —N$R^a$C$_{2-6}$alkN$R^a R^a$ and —N$R^a$C$_{2-6}$alkO$R^a$; or if J is —N($R^a$)(C$R^c R^c$)$_n$—, then $R^5$ may also be H;

$R^6$ is selected from C$_{2-6}$alk, cyano, —C(=O)$R^b$, —C(=O)O$R^b$, —C(=O)N$R^a R^a$, —C(=N$R^a$)N$R^a R^a$, —S(=O)$R^b$, —S(=O)$_2 R^b$, —S(=O)$_2$N$R^a R^a$, —N$R^a R^a$, —N($R^a$)C(=O)$R^b$, —N($R^a$)C(=O)O$R^b$, —N($R^a$)C(=O)N$R^a R^a$, —N($R^a$)C(=N$R^a$)N$R^a R^a$, —N($R^a$)S(=O)$_2 R^b$, —N($R^a$)S(=O)$_2$N$R^a R^a$, —N$R^a$C$_{2-6}$alkN$R^a R^a$ and —N$R^a$C$_{2-6}$alkO$R^a$; or $R^6$ is C$_{1-6}$alk substituted by 1, 2 or 3 substituents selected from C$_{1-4}$haloalk, halo, cyano, nitro, —C(=O)$R^b$, —C(=O)O$R^b$, —C(=O)N$R^a R^a$, —C(=N$R^a$)N$R^a R^a$, —O$R^a$, —OC(=O)$R^b$, —OC(=O)N$R^a R^a$, —OC$_{2-6}$alkN$R^a R^a$, —OC$_{2-6}$alkO$R^a$, —S$R^a$, —S(=O)$R^b$, —S(=O)$_2 R^b$, —S(=O)$_2$N$R^a R^a$, —N$R^a R^a$, —N($R^a$)C(=O)$R^b$, —N($R^a$)C(=O)O$R^b$, —N($R^a$)C(=O)N$R^a R^a$, —N($R^a$)C(=N$R^a$)N$R^a R^a$, —N($R^a$)S(=O)$_2 R^b$, —N($R^a$)S(=O)$_2$N$R^a R^a$, —N$R^a$C$_{2-6}$alkN$R^a R^a$ and —N$R^a$C$_{2-6}$alkO$R^a$; or $R^6$ is a saturated, partially saturated or unsaturated 5-, 6- or 7-membered ring containing 0, 1, 2, 3 or 4 atoms selected from N, O and S, wherein the C$_{1-6}$alk is and C$_{1-6}$alk and ring are substituted by 0, 1, 2 or 3 substituents selected from C$_{1-8}$alk, C$_{1-4}$haloalk, halo, cyano, nitro, —C(=O)$R^b$, —C(=O)O$R^b$, —C(=O)N$R^a R^a$, —C(=N$R^a$)N$R^a R^a$, —O$R^a$, —OC(=O)$R^b$, —OC(=O)N$R^a R^a$, —OC$_{2-6}$alkN$R^a R^a$, —OC$_{2-6}$alkO$R^a$, —S$R^a$, —S(=O)$R^b$, —S(=O)$_2 R^b$, —S(=O)$_2$N$R^a R^a$, —N$R^a R^a$, —N($R^a$)C(=O)$R^b$, —N($R^a$)C(=O)O$R^b$, —N($R^a$)C(=O)N$R^a R^a$, —N($R^a$)C(=N$R^a$)N$R^a R^a$, —N($R^a$)S(=O)$_2 R^b$, —N($R^a$)S(=O)$_2$N$R^a R^a$, —N$R^a$C$_{2-6}$alkN$R^a R^a$ and —N$R^a$C$_{2-6}$alkO$R^a$;

$R^a$ is independently, at each instance, H or $R^b$;

$R^b$ is independently, at each instance, phenyl, benzyl or C$_{1-6}$alk, the phenyl, benzyl and C$_{1-6}$alk being substituted by 0, 1, 2 or 3 substituents selected from halo, C$_{1-4}$alk, C$_{1-3}$haloalk, —OC$_{1-4}$alk, —NH$_2$, —NHC$_{1-4}$alk, and —N(C$_{1-4}$alk)C$_{1-4}$alk;

$R^c$ is independently, at each instance, H, halo, C$_{1-4}$alk, C$_{1-4}$haloalk, —OC$_{1-4}$alk, —OC$_{1-4}$haloalk, —NH$_2$, —NHC$_{1-4}$ alk or —N(C$_{1-4}$alk)C$_{1-4}$alk; and $R^f$ is independently in each instance H or F.

In one embodiment, in conjunction with any above or below embodiments, J is —N($R^a$)—, —O—, —S— or —CH$_2$—.

In another embodiment, in conjunction with any above or below embodiments, o is 1.

In another embodiment, in conjunction with any above or below embodiments, $R^3$ is

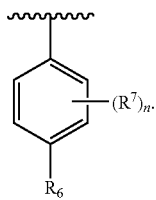

In another embodiment, in conjunction with any above or below embodiments, $R^3$ is a saturated, partially-saturated or unsaturated 5-, 6- or 7-membered monocyclic or 8-, 9-, 10- or 11-membered bicyclic ring containing 1, 2, 3 or 4 atoms selected from N, O and S, substituted with 0, 1, 2 or 3 groups selected from $C_{1-6}$alk, $C_{1-3}$haloalk, —$OC_{1-6}$alk, —$N(C_{1-6}$alk$)C_{1-6}$alk, —$NHC_{1-6}$alk, —$NC(=O)C_{1-6}$alk, —$N(C_{1-6}$alk$)C_{1-6}$alk, F, Cl, Br, CN, OH and $NH_2$; or $R^3$ is benzyl substituted with 1, 2 or 3 groups selected from $C_{1-6}$alk, $C_{1-3}$haloalk, —$OC_{1-6}$alk, —$N(C_{1-6}$alk$)C_{1-6}$alk, —$NHC_{1-6}$alk, —$NC(=O)C_{1-6}$alk, —$N(C_{1-6}$alk$)C_{1-6}$alk, F, Cl, Br, CN, OH and $NH_2$.

In another embodiment, in conjunction with any above or below embodiments, $R^3$ is napthyl substituted with 1, 2 or 3 groups selected from $C_{1-6}$alk, $C_{1-3}$haloalk, —$OC_{1-6}$alk, —$N(C_{1-6}$alk$)C_{1-6}$alk, —$NHC_{1-6}$alk, —$NC(=O)C_{1-6}$alk, —$N(C_{1-6}$alk$)C_{1-6}$alk, F, Cl, Br, CN and $NH_2$.

In another embodiment, in conjunction with any above or below embodiments, $R^3$ is

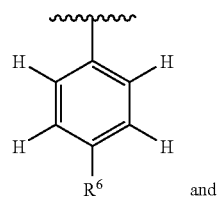

and $R^6$ is $C_{1-6}$alk substituted by 1, 2 or 3 substituents selected from $C_{1-4}$haloalk, halo, cyano, nitro, —$C(=O)R^b$, —$C(=O)OR^b$, —$C(=O)NR^aR^a$, —$C(=NR^a)NR^aR^a$, —$OR^a$, —$OC(=O)R^b$, —$OC(=O)NR^aR^a$, —$OC_{2-6}$alkNR$^aR^a$, —$OC_{2-6}$alkOR$^a$, —$SR^a$, —$S(=O)R^b$, —$S(=O)_2R^b$, —$S(=O)_2NR^aR^a$, —$NR^aR^a$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}$alkNR$^aR^a$ and —$NR^aC_{2-6}$alkOR$^a$; or $R^6$ is a saturated, partially saturated or unsaturated 5-, 6- or 7-membered ring containing 0, 1, 2, 3 or 4 atoms selected from N, O and S, wherein the $C_{1-6}$alk is and $C_{1-6}$alk and ring are substituted by 0, 1, 2 or 3 substituents selected from $C_{1-8}$alk, $C_{1-4}$haloalk, halo, cyano, nitro, —$C(=O)R^b$, —$C(=O)OR^b$, —$C(=O)NR^aR^a$, —$C(=NR^a)NR^aR^a$, —$OR^a$, —$OC(=O)R^b$, —$OC(=O)NR^aR^a$, —$OC_{2-6}$alkNR$^aR^a$, —$OC_{2-6}$alkOR$^a$, —$SR^a$, —$S(=O)R^b$, —$S(=O)_2R^b$, —$S(=O)_2NR^aR^a$, —$NR^aR^a$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}$alkNR$^aR^a$ and —$NR^aC_{2-6}$alkOR$^a$.

In another embodiment, in conjunction with any above or below embodiments, $R^3$ is

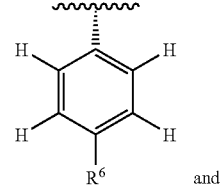

and $R^6$ is $C_{1-6}$alk substituted by 1, 2 or 3 substituents selected from $C_{1-4}$haloalk, halo, cyano, nitro, —$C(=O)R^b$, —$C(=O)OR^b$, —$C(=O)NR^aR^a$, —$C(=NR^a)NR^aR^a$, —$OR^a$, —$OC(=O)R^b$, —$OC(=O)NR^aR^a$, —$OC_{2-6}$alkNR$^aR^a$, —$OC_{2-6}$alkOR$^a$, —$SR^a$, —$S(=O)R^b$, —$S(=O)_2R^b$, —$S(=O)_2NR^aR^a$, —$NR^aR^a$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}$alkNR$^aR^a$ and —$NR^aC_{2-6}$alkOR$^a$; or $R^6$ is a saturated, partially saturated or unsaturated 5-, 6- or 7-membered ring containing 0, 1, 2, 3 or 4 atoms selected from N, O and S, wherein the $C_{1-6}$alk is and $C_{1-6}$alk and ring are substituted by 0, 1, 2 or 3 substituents selected from $C_{1-8}$alk, $C_{1-4}$haloalk, halo, cyano, nitro, —$C(=O)R^b$, —$C(=O)OR^b$, —$C(=O)NR^aR^a$, —$C(=NR^a)NR^aR^a$, —$OR^a$, —$OC(=O)R^b$, —$OC(=O)NR^aR^a$, —$OC_{2-6}$alkNR$^aR^a$, —$OC_{2-6}$alkOR$^a$, —$SR^a$, —$S(=O)R^b$, —$S(=O)_2R^b$, —$S(=O)_2NR^aR^a$, —$NR^aR^a$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}$alkNR$^aR^a$ and —$NR^aC_{2-6}$alkOR$^a$.

In another embodiment, in conjunction with any above or below embodiments, m is 0.

In another embodiment, in conjunction with any above or below embodiments, m is 1 or 2; and $R^4$ is independently in each instance selected from $CH_3$, $CF_3$, F, Cl or —$CH_2CH_2$— (forming a Spiro cyclopropyl).

In another embodiment, in conjunction with any above or below embodiments, $R^5$ is $C_{1-11}$alkyl or $C_{5-11}$cycloalkyl substituted by 0, 1, 2 or 3 substituents selected from $C_{1-4}$haloalk, halo, cyano, nitro, —$C(=O)R^b$, —$C(=O)OR^b$, —$C(=O)NR^aR^a$, —$C(=NR^a)NR^aR^a$, —$OR^a$, —$OC(=O)R^b$, —$OC(=O)NR^aR^a$, —$OC_{2-6}$alkNR$^aR^a$, —$OC_{2-6}$alkOR$^a$, —$SR^a$, —$S(=O)R^b$, —$S(=O)_2R^b$, —$S(=O)_2NR^aR^a$, —$NR^aR^a$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}$alkNR$^aR^a$ and —$NR^aC_{2-6}$alkOR$^a$.

In another embodiment, in conjunction with any above or below embodiments, $R^5$ is $C_{1-11}$alkyl or $C_{5-11}$cycloalkyl substituted by 0, 1, 2 or 3 substituents selected from $C_{1-4}$haloalk, halo, cyano, nitro, —$C(=O)R^b$, —$C(=O)OR^b$, —$C(=O)NR^aR^a$, —$C(=NR^a)NR^aR^a$, —$OR^a$, —$OC(=O)R^b$, —$OC(=O)NR^aR^a$, —$OC_{2-6}$alkNR$^aR^a$, —$OC_{2-6}$alkOR$^a$, —$SR^a$, —$S(=O)R^b$, —$S(=O)_2R^b$, —$S(=O)_2NR^aR^a$, —$NR^aR^a$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}$alkNR$^aR^a$ and —$NR^aC_{2-6}$alkOR$^a$.

In another embodiment, in conjunction with any above or below embodiments, J is —$N(R^a)(CR^cR^c)$, —, —$O(CR^cR^c)_n$— or —$S(CR^cR^c)_n$—; and $R^5$ is $C_{3-5}$cycloalkyl substituted by 0, 1, 2 or 3 substituents selected from $C_{1-8}$alk, $C_{1-4}$haloalk, halo, cyano, nitro, —$C(=O)R^b$, —$C(=O)OR^b$, —$C(=O)NR^aR^a$, —$C(=NR^a)NR^aR^a$, —$OR^a$, —$OC(=O)R^b$, —$OC(=O)NR^aR^a$, —$OC_{2-6}$alkNR$^aR^a$, —$OC_{2-6}$alkOR$^a$, —$SR^a$, —$S(=O)R^b$, —$S(=O)_2R^b$, —$S(=O)_2$ $NR^aR^a$, —$NR^aR^a$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}$ alk$NR^aR^a$ and —$NR^aC_{2-6}$alk$OR^a$.

In another embodiment, in conjunction with any above or below embodiments, J is —$N(R^a)(CR^cR^c)_n$—; and $R^5$ is $C_{3-5}$cycloalkyl substituted by 0, 1, 2 or 3 substituents selected from $C_{1-8}$alk, $C_{1-4}$haloalk, halo, cyano, nitro, —$C(=O)R^b$, —$C(=O)OR^b$, —$C(=O)NR^aR^a$, —$C(=NR^a)NR^aR^a$, —$OR^a$, —$OC(=O)R^b$, —$OC(=O)NR^aR^a$, —$OC_{2-6}$alk$NR^aR^a$, —$OC_{2-6}$alk$OR^a$, —$SR^a$, —$S(=O)R^b$, —$S(=O)_2R^b$, —$S(=O)_2NR^aR^a$, —$NR^aR^a$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}$alk$NR^aR^a$ and —$NR^aC_{2-6}$alk$OR^a$.

In another embodiment, in conjunction with any above or below embodiments, $R^5$ is cyclopropyl substituted by 1, 2 or 3 substituents selected from $C_{1-4}$haloalk, halo, cyano, nitro, —$C(=O)R^b$, —$C(=O)OR^b$, —$C(=O)NR^aR^a$, —$C(=NR^a)NR^aR^a$, —$OR^a$, —$OC(=O)R^b$, —$OC(=O)NR^aR^a$, —$OC_{2-6}$alk$NR^aR^a$, —$OC_{2-6}$alk$OR^a$, —$SR^a$, —$S(=O)R^b$, —$S(=O)_2R^b$, —$S(=O)_2NR^aR^a$, —$NR^aR^a$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}$alk$NR^aR^a$ and —$NR^aC_{2-6}$alk$OR^a$.

In another embodiment, in conjunction with any above or below embodiments, $R^5$ is $C_{3-6}$alkyl.

In another embodiment, in conjunction with any above or below embodiments, $R^5$ is $C_{3-6}$alkyl substituted by 0, 1, 2 or 3 substituents selected from $C_{1-8}$alk, $C_{1-4}$haloalk, halo, cyano, nitro, —$C(=O)R^b$, —$C(=O)OR^b$, —$C(=O)NR^aR^a$, —$C(=NR^a)NR^aR^a$, —$OR^a$, —$OC(=O)R^b$, —$OC(=O)NR^aR^a$, —$OC_{2-6}$alk$NR^aR^a$, —$OC_{2-6}$alk$OR^a$, —$SR^a$, —$S(=O)R^b$, —$S(=O)_2R^b$, —$S(=O)_2NR^aR^a$, —$NR^aR^a$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}$alk$NR^aR^a$ and —$NR^aC_{2-6}$alk$OR^a$.

In another embodiment, in conjunction with any above or below embodiments, $R^5$ is $C_{5-11}$cycloalkyl substituted by 0, 1, 2 or 3 substituents selected from $C_{1-4}$haloalk, halo, cyano, nitro, —$C(=O)R^b$, —$C(=O)OR^b$, —$C(=O)NR^aR^a$, —$C(=NR^a)NR^aR^a$, —$OR^a$, —$OC(=O)R^b$, —$OC(=O)NR^aR^a$, —$OC_{2-6}$alk$NR^aR^a$, —$OC_{2-6}$alk$OR^a$, —$SR^a$, —$S(=O)R^b$, —$S(=O)_2R^b$, —$S(=O)_2NR^aR^a$, —$NR^aR^a$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}$alk$NR^aR^a$ and —$NR^aC_{2-6}$alk$OR^a$.

In another embodiment, in conjunction with any above or below embodiments, $R^5$ is a saturated, partially saturated or unsaturated 5-, 6- or 7-membered monocyclic or 8-, 9-, 10- or 11-membered bicyclic ring containing 0, 1, 2, 3 or 4 atoms selected from N, O and S, wherein the ring is substituted by 0, 1 or 2 oxo groups and the ring is additionally substituted by 0, 1, 2 or 3 substituents selected from $C_{1-8}$alk, $C_{1-4}$haloalk, halo, cyano, nitro, —$C(=O)R^b$, —$C(=O)OR^b$, —$C(=O)NR^aR^a$, —$C(=NR^a)NR^aR^a$, —$OR^a$, —$OC(=O)R^b$, —$OC(=O)NR^aR^a$, —$OC_{2-6}$alk$NR^aR^a$, —$OC_{2-6}$alk$OR^a$, —$SR^a$, —$S(=O)R^b$, —$S(=O)_2R^b$, —$S(=O)_2NR^aR^a$, —$NR^aR^a$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}$alk$NR^aR^a$ and —$NR^aC_{2-6}$alk$OR^a$.

In another embodiment, in conjunction with any above or below embodiments, $R^5$ is an unsaturated 6-membered monocyclic ring containing 1 or 2 N atoms and the ring is substituted by 0, 1, 2 or 3 substituents selected from $C_{1-8}$alk, $C_{1-4}$haloalk, halo, cyano, nitro, —$C(=O)R^b$, —$C(=O)OR^b$, —$C(=O)NR^aR^a$, —$C(=NR^a)NR^aR^a$, —$OR^a$, —$OC(=O)R^b$, —$OC(=O)NR^aR^a$, —$OC_{2-6}$alk$NR^aR^a$, —$OC_{2-6}$alk$OR^a$, —$SR^a$, —$S(=O)R^b$, —$S(=O)_2R^b$, —$S(=O)_2NR^aR^a$, —$NR^aR^a$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}$ alk$NR^aR^a$ and —$NR^aC_{2-6}$alk$OR^a$.

In another embodiment, in conjunction with any above or below embodiments, $R^5$ is phenyl substituted by 0, 1, 2 or 3 substituents selected from $C_{1-8}$alk, $C_{1-4}$haloalk, halo, cyano, nitro, —$C(=O)R^b$, —$C(=O)OR^b$, —$C(=O)NR^aR^a$, —$C(=NR^a)NR^aR^a$, —$OR^a$, —$OC(=O)R^b$, —$OC(=O)NR^aR^a$, —$OC_{2-6}$alk$NR^aR^a$, —$OC_{2-6}$alk$OR^a$, —$SR^a$, —$S(=O)R^b$, —$S(=O)_2R^b$, —$S(=O)_2NR^aR^a$, —$NR^aR^a$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}$alk$NR^aR^a$ and —$NR^aC_{2-6}$alk$OR^a$.

In another embodiment, in conjunction with any above or below embodiments, J is —$N(R^a)(CR^cR^c)_n$—.

In another embodiment, in conjunction with any above or below embodiments, J is —$O(CR^cR^c)_n$—.

In another embodiment, in conjunction with any above or below embodiments, J is —$NR^a$—.

In another embodiment, in conjunction with any above or below embodiments, J is —O—.

In another embodiment, in conjunction with any above or below embodiments, J is —$CH_2$—.

In another embodiment, in conjunction with any above or below embodiments, $R^1$ is selected from halo, cyano, —$C(=O)R^b$, —$C(=O)OR^b$, —$C(=O)NR^aR^a$, —$C(=NR^a)NR^aR^a$, —$OR^a$, —$OC(=O)R^b$, —$OC(=O)NR^aR^a$, —$OC_{2-6}$alk$NR^aR^a$, —$OC_{2-6}$alk$OR^a$, —$SR^a$, —$S(=O)R^b$, —$S(=O)_2R^b$, —$S(=O)_2NR^aR^a$, —$NR^aR^a$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}$alk$NR^aR^a$ and —$NR^aC_{2-6}$alk$OR^a$; or $R^1$ is $C_{1-6}$alk or a saturated, partially saturated or unsaturated 5-, 6- or 7-membered ring containing 0, 1, 2, 3 or 4 atoms selected from N, O and S, wherein the $C_{1-6}$alk and ring are substituted by 0, 1, 2 or 3 substituents selected from $C_{1-8}$alk, $C_{1-4}$haloalk, halo, cyano, nitro, —$C(=O)R^b$, —$C(=O)OR^b$, —$C(=O)NR^aR^a$, —$C(=NR^a)NR^aR^a$, —$OR^a$, —$OC(=O)R^b$, —$OC(=O)NR^aR^a$, —$OC_{2-6}$alk$NR^aR^a$, —$OC_{2-6}$alk$OR^a$, —$SR^a$, —$S(=O)R^b$, —$S(=O)_2R^b$, —$S(=O)_2NR^aR^a$, —$NR^aR^a$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}$alk$NR^aR^a$ and —$NR^aC_{2-6}$alk$OR^a$.

In another embodiment, in conjunction with any above or below embodiments, $R^1$ is H or F.

In another embodiment, in conjunction with any above or below embodiments, $R^1$ is H.

In another embodiment, in conjunction with any above or below embodiments, $R^2$ is selected from halo, cyano, —$C(=O)R^b$, —$C(=O)OR^b$, —$C(=O)NR^aR^a$, —$C(=NR^a)NR^aR^a$, —$OR^a$, —$OC(=O)R^b$, —$OC(=O)NR^aR^a$, —$OC_{2-6}$alk$NR^aR^a$, —$OC_{2-6}$alk$OR^a$, —$SR^a$, —$S(=O)R^b$, —$S(=O)_2R^b$, —$S(=O)_2NR^aR^a$, —$NR^aR^a$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}$alk$NR^aR^a$ and —$NR^aC_{2-6}$alk$OR^a$; or $R^2$ is $C_{1-6}$alk or a saturated, partially saturated or unsaturated 5-, 6- or 7-membered ring containing 0, 1, 2, 3 or 4 atoms selected from N, O and S, wherein the $C_{1-6}$alk and ring are substituted by 0, 1, 2 or 3 substituents selected from $C_{1-8}$alk, $C_{1-4}$haloalk, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —O$C_{2-6}$alkN$R^aR^a$, —O$C_{2-6}$alkO$R^a$, —S$R^a$, —S(=O)$R^b$, —S(=O)$_2R^b$, —S(=O)$_2$N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$(=N$R^a$)N$R^aR^a$, —N($R^a$)S(=O)$_2R^b$, —N($R^a$)S(=O)$_2$N$R^aR^a$, —N$R^aC_{2-6}$alkN$R^aR^a$ and —N$R^aC_{2-6}$alkO$R^a$.

In another embodiment, in conjunction with any above or below embodiments, $R^2$ is H or F.

In another embodiment, in conjunction with any above or below embodiments, $R^2$ is H.

In another embodiment, in conjunction with any above or below embodiments, $R^f$ is H.

In another embodiment, in conjunction with any above or below embodiments, $R^3$ is selected from 4-pyrimidinyl, 2-pyridinyl, both of which are substituted with 0, 1, 2 or 3 groups selected from $C_{1-6}$alk, $C_{1-3}$haloalk, —O$C_{1-6}$alk, —N($C_{1-6}$alk)$C_{1-6}$alk, —NH$C_{1-6}$alk, —NC(=O)$C_{1-6}$alk, —N($C_{1-6}$alk)$C_{1-6}$alk, F, Cl, Br, CN, OH and NH$_2$.

In another embodiment, in conjunction with any above or below embodiments, $R^3$ is benzyl substituted with 1, 2 or 3 groups selected from $C_{1-6}$alk, $C_{1-3}$haloalk, —O$C_{1-6}$alk, —N($C_{1-6}$alk)$C_{1-6}$alk, —NH$C_{1-6}$alk, —NC(=O)$C_{1-6}$alk, —N($C_{1-6}$alk)$C_{1-6}$alk, F, Cl, Br, CN, OH and NH$_2$.

In another embodiment, in conjunction with any above or below embodiments, m is 1; and $R^4$ is selected from $C_{1-6}$alk, $C_{1-3}$haloalk, —O$C_{1-6}$alk, —N($C_{1-6}$alk)$C_{1-6}$alk, —NH$C_{1-6}$alk, —NC(=O)$C_{1-6}$alk, —N($C_{1-6}$alk)$C_{1-6}$alk, F, Cl, Br, CN, OH and NH$_2$;

In another embodiment, in conjunction with any above or below embodiments, $R^6$ is selected from $C_{3-6}$alk, —C(=O)$R^b$, —C(=O)O$R^b$, —C(=O)N$R^aR^a$, —C(=N$R^a$)N$R^aR^a$, —S(=O)$R^b$, —S(=O)$_2R^b$, —S(=O)$_2$N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkN$R^aR^a$ and —N$R^aC_{2-6}$alkO$R^a$.

In another embodiment, in conjunction with any above or below embodiments, $R^6$ is $C_{1-6}$alk substituted by 1, 2 or 3 substituents selected from $C_{1-4}$haloalk, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —O$C_{2-6}$alkN$R^aR^a$, —O$C_{2-6}$alkO$R^a$, —S$R^a$, —S(=O)$R^b$, —S(=O)$_2R^b$, —S(=O)$_2$N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkN$R^aR^a$ and —N$R^aC_{2-6}$alkO$R^a$.

In another embodiment, in conjunction with any above or below embodiments, $R^6$ is a saturated, partially saturated or unsaturated 5-, 6- or 7-membered ring containing 0, 1, 2 or 3 or 4 atoms selected from N, O and S, wherein the ring is substituted by 0, 1, 2 or 3 substituents selected from $C_{1-8}$alk, $C_{1-4}$haloalk, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —O$C_{2-6}$alkN$R^aR^a$, —O$C_{2-6}$alkO$R^a$, —S$R^a$, —S(=O)$R^b$, —S(=O)$_2R^b$, —S(=O)$_2$N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkN$R^aR^a$ and —N$R^aC_{2-6}$alkO$R^a$;

Another aspect of the invention relates to a method of treating acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, depression, anxiety, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders, comprising the step of administering a compound according to claim 1.

Another aspect of the invention relates to a pharmaceutical composition comprising a compound according to claim 1 and a pharmaceutically-acceptable diluent or carrier.

Another aspect of the invention relates to the use of a compound according to any of the above embodiments as a medicament.

Another aspect of the invention relates to the use of a compound according to any of the above embodiments in the manufacture of a medicament for the treatment of acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, anxiety, depression, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders.

The compounds of this invention may have in general several asymmetric centers and are typically depicted in the form of racemic mixtures. This invention is intended to encompass racemic mixtures, partially racemic mixtures and separate enantiomers and diastereomers.

Unless otherwise specified, the following definitions apply to terms found in the specification and claims:

"$C_{\alpha-\beta}$alk" means an alkyl group comprising a minimum of α and a maximum of β carbon atoms in a branched, cyclical or linear relationship or any combination of the three, wherein α and β represent integers. The alkyl groups described in this section may also contain one or two double or triple bonds. A designation of $C_0$alk indicates a direct bond. Examples of $C_{1-6}$alkyl include, but are not limited to the following:

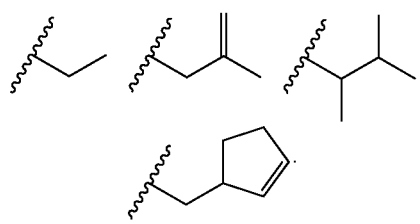

Where the term "$C_{\alpha\text{-}\beta}$alkyl" and "$C_{\alpha\text{-}\beta}$cycloalkyl" are used, they relate to acyclic saturated alkyls and cyclic saturated alkyls, respectively.

"Benzo group", alone or in combination, means the divalent radical $C_4H_4$=, one representation of which is —CH=CH—CH=CH—, that when vicinally attached to another ring forms a benzene-like ring—for example tetrahydronaphthylene, indole and the like.

The terms "oxo" and "thioxo" represent the groups =O (as in carbonyl) and =S (as in thiocarbonyl), respectively.

"Halo" or "halogen" means a halogen atoms selected from F, Cl, Br and I.

"$C_{v\text{-}w}$haloalk" means an alk group, as described above, wherein any number—at least one—of the hydrogen atoms attached to the alk chain are replaced by F, Cl, Br or I.

The group $N(R^a)R^a$ and the like include substituents where the two $R^a$ groups together form a ring, optionally including a N, O or S atom, and include groups such as:

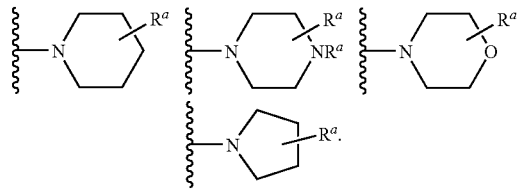

The group $N(C_{\alpha\text{-}\beta}\text{alk})C_{\alpha\text{-}\beta}\text{alk}$, wherein $\alpha$ and $\beta$ are as defined above, include substituents where the two $C_{\alpha\text{-}\beta}$alk groups together form a ring, optionally including a N, O or S atom, and include groups such as:

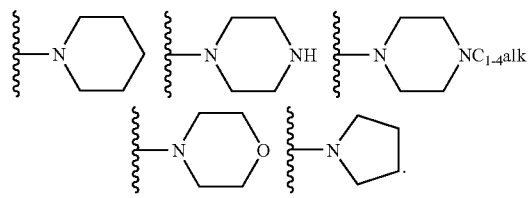

"Heterocycle" means a ring comprising at least one carbon atom and at least one other atom selected from N, O and S. Examples of heterocycles that may be found in the claims include, but are not limited to, the following:

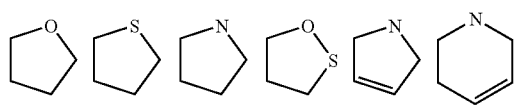

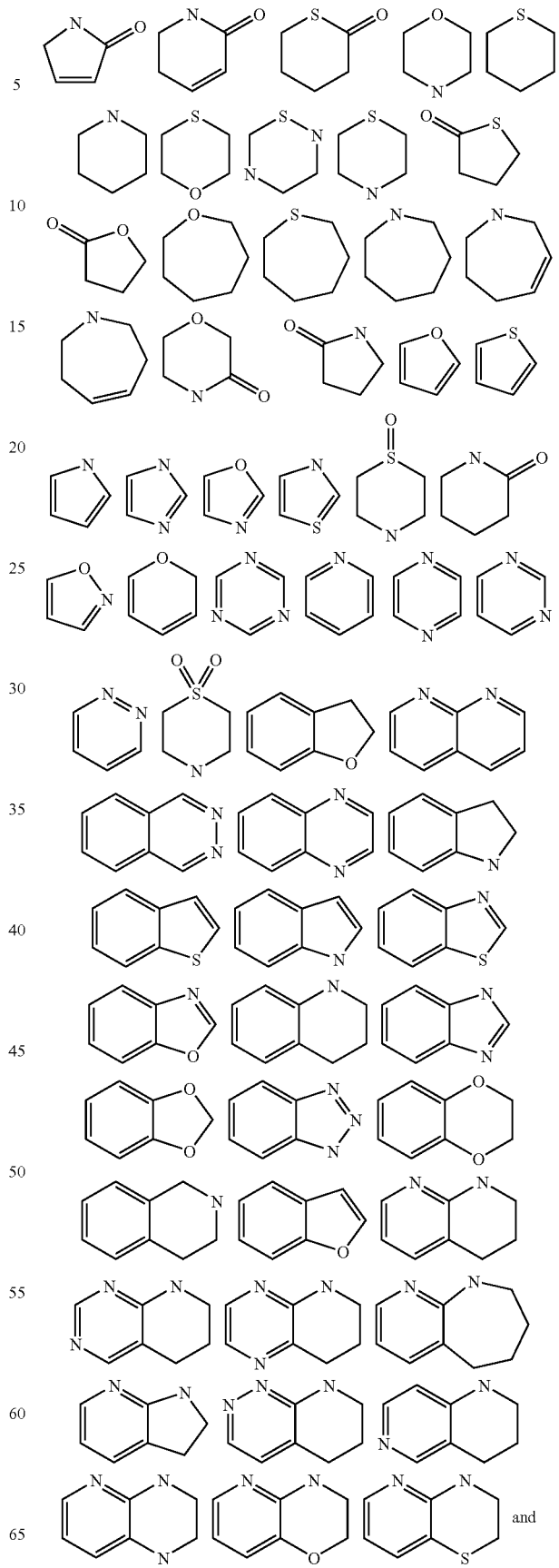

"Pharmaceutically-acceptable salt" means a salt prepared by conventional means, and are well known by those skilled in the art. The "pharmacologically acceptable salts" include basic salts of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. When compounds of the invention include an acidic function such as a carboxy group, then suitable pharmaceutically acceptable cation pairs for the carboxy group are well known to those skilled in the art and include alkaline, alkaline earth, ammonium, quaternary ammonium cations and the like. For additional examples of "pharmacologically acceptable salts," see infra and Berge et al., J. Pharm. Sci. 66:1 (1977).

"Saturated, partially-saturated or unsaturated" includes substituents saturated with hydrogens, substituents completely unsaturated with hydrogens and substituents partially saturated with hydrogens.

"Leaving group" generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

"Protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkylenylalkyl radicals, preferably have 6-10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, trifluoroacetyl, trichloro acetyl, phthaloyl and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups are also suitable for protecting carboxy, hydroxy and mercapto groups. For example, aralkyl groups. Alkyl groups are also suitable groups for protecting hydroxy and mercapto groups, such as tert-butyl.

Silyl protecting groups are silicon atoms optionally substituted by one or more alkyl, aryl and aralkyl groups. Suitable silyl protecting groups include, but are not limited to, trimethylsilyl, triethylsilyl, triisopropylsilyl, tert-butyldimethylsilyl, dimethylphenylsilyl, 1,2-bis(dimethylsilyl)benzene, 1,2-bis(dimethylsilyl)ethane and diphenylmethylsilyl. Silylation of an amino groups provide mono- or di-silylamino groups. Silylation of aminoalcohol compounds can lead to a N,N,O-trisilyl derivative. Removal of the silyl function from a silyl ether function is readily accomplished by treatment with, for example, a metal hydroxide or ammonium fluoride reagent, either as a discrete reaction step or in situ during a reaction with the alcohol group. Suitable silylating agents are, for example, trimethylsilyl chloride, tert-butyl-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydrolysis and hydrogenolysis conditions well known to those skilled in the art.

It should be noted that compounds of the invention may contain groups that may exist in tautomeric forms, such as cyclic and acyclic amidine and guanidine groups, heteroatom substituted heteroaryl groups (Y'=O, S, NR), and the like, which are illustrated in the following examples:

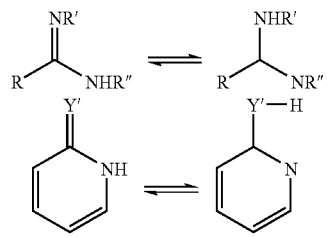

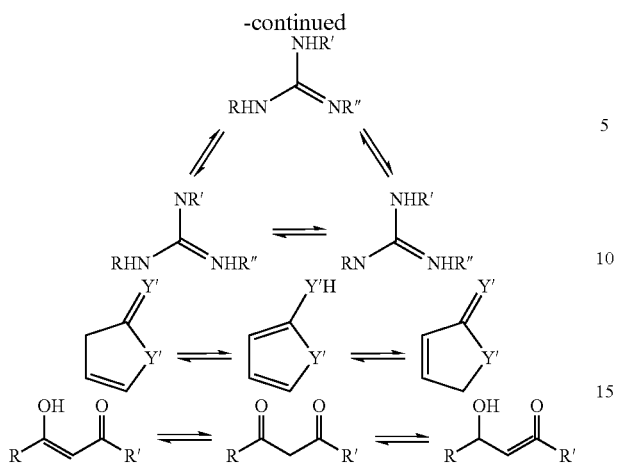

and though one form is named, described, displayed and/or claimed herein, all the tautomeric forms are intended to be inherently included in such name, description, display and/or claim.

Prodrugs of the compounds of this invention are also contemplated by this invention. A prodrug is an active or inactive compound that is modified chemically through in vivo physiological action, such as hydrolysis, metabolism and the like, into a compound of this invention following administration of the prodrug to a patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use.

The specification and claims contain listing of species using the language like "selected from . . . and . . . " and "is . . . or . . . " (sometimes referred to as Markush groups). When this language is used in this application, unless otherwise stated it is meant to include the group as a whole, or any single members thereof, or any subgroups thereof. The use of this language is merely for shorthand purposes and is not meant in any way to limit the removal of individual elements or subgroups as needed.

EXPERIMENTAL

Unless otherwise noted, all materials were obtained from commercial suppliers and used without further purification. All parts are by weight and temperatures are in degrees centigrade unless otherwise indicated. All microwave assisted reactions were conducted with a Smith Synthesizer from Biotage. Mass spectral data was determined by electrospray ionization technique. All examples were purified to >90% purity as determined by high-performance liquid chromatography. Unless otherwise stated, reactions were run at RT. The following abbreviations are used:

| | |
|---|---|
| DCE | dichloroetane |
| DCM | dichloromethane |
| DIAE | diisopropyl ethylamine |
| DMSO - | dimethyl sulfoxide |
| DMF - | N,N-dimethylformamide |
| THF - | tetrahydrofuran |
| Et$_2$O - | diethyl ether |
| EtOAc - | ethyl acetate |
| MeOH - | methyl alcohol |
| EtOH - | ethyl alcohol |
| MeCN - | acetonitrile |
| MeI - | iodomethane |
| NMP - | 1-methyl-2-pyrrolidinone |
| TFA - | trifluoroacetic acid |
| SFC - | supercritical fluid chromatography |
| h - | h |
| min - | min |
| mL | milliliters |
| μL | microliters |
| g | grams |
| μg | micrograms |
| mg | milligrams |
| μmoL | micromolars |

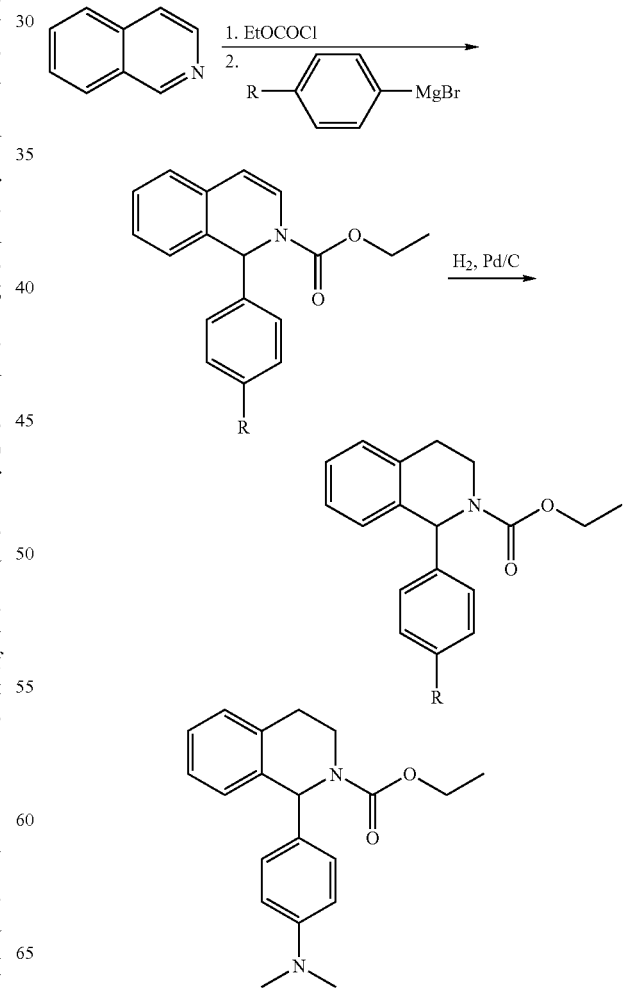

Scheme 1

Example 1

Ethyl 1-(4-(dimethylamino)phenyl)-3,4-dihydroisoquinoline-2(1H)-carboxylate

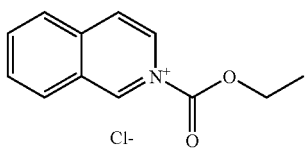

Step 1. Ethyl 1-isoquinoline-carboxylate chloride

Isoquinoline (5.50 g, 42.5 mmol) was dissolved into 50 mL of anhydrous THF and ethyl chloroformate (4.47 mL, 46.8 mmol) was added slowly. The resulting pale yellow mixture was stirred at RT for 30 min. Then, the resulting precipitate was collected via filtration through a cintered glass funnel and dried under vacuum for 2 days to yield the title compound as a pale yellow solid.

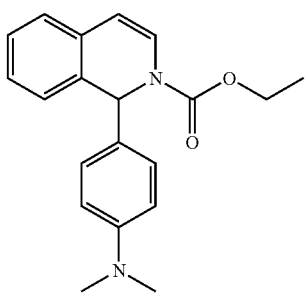 [SMILES: CCOC(=O)N1C=Cc2ccccc2C1c1ccc(N(C)C)cc1]

Step 2. Ethyl 1-(4-(dimethylamino)phenyl)isoquinoline-2(1H)-carboxylate

To a 25-mL round-bottomed flask containing the above ethyl 1-isoquinoline-carboxylate chloride (0.584 g, 2.46 mmol) in anhydrous THF (10 mL) was added with 4-N,N-dimethylaminophenylmagnesium bromide (0.5 M solution in THF, 7.50 mL, 3.75 mmol) under a stream of $N_2$ and the mixture was stirred at RT for 1.5 h. This mixture was quenched with saturated $NH_4Cl$ and extracted with EtOAc. The organic layer was washed with water and brine, dried over $Na_2SO_4$, filtered, and concentrated in vacuo. The crude product was purified by silica gel chromatography (0-50% EtOAc in hexanes) to give the title compound as pale yellow oil. MS (ESI pos. ion) m/z: 323 (M+1).

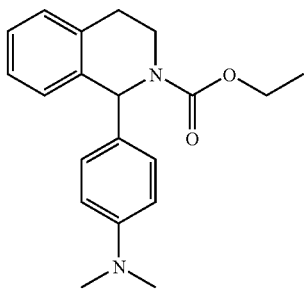 [SMILES: CCOC(=O)N1CCc2ccccc2C1c1ccc(N(C)C)cc1]

Step 3. Ethyl 1-(4-(dimethylamino)phenyl)-3,4-dihydroisoquinoline-2(1H)-carboxylate A solution of ethyl 1-(4-(dimethylamino)phenyl)isoquinoline-2(1H)-carboxylate (79 mg, 0.24 mmol) in EtOH (4 mL) was stirred with 10% Pd/C (0.062 g, 0.58 mmol) under hydrogen atmosphere at RT for 14 h. The reaction mixture was filtered through a celite pad and the filtrate was concentrated in vacuo. The crude product was purified by silica gel chromatography (0-30% EtOAc in hexanes) to provide the title compound as a clear oil. MS (ESI pos. ion) m/z: 325 (M+1).

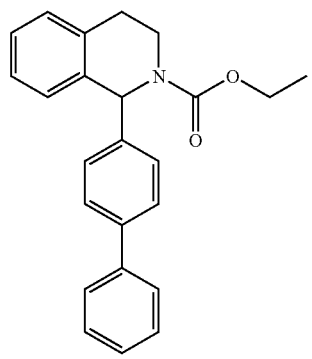 [SMILES: CCOC(=O)N1CCc2ccccc2C1c1ccc(-c2ccccc2)cc1]

Example 2

Ethyl 1-(4-biphenyl)-3,4-dihydroisoquinoline-2(1H)-carboxylate

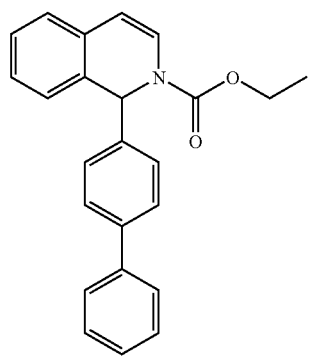 [SMILES: CCOC(=O)N1C=Cc2ccccc2C1c1ccc(-c2ccccc2)cc1]

Step 1. Ethyl 1-(4-biphenyl)isoquinoline-2(1H)-carboxylate

A round-bottomed flask containing isoquinoline (0.545 g, 4.22 mmol) in anhydrous THF (10 mL) was charged with ethyl chloroformate (0.450 mL, 4.71 mmol) under a stream of $N_2$ and the mixture was stirred at RT for 15 min. 4-Biphenylmagnesium bromide (0.5 M solution in THF, 16.0 mL, 8.0 mmol) was added dropwise and the mixture was stirred at RT for 1.5 h, this mixture was quenched with saturated $NH_4Cl$ and extracted with EtOAc. The organic layer was washed with water and brine, dried over $Na_2SO_4$, filtered, and concentrated in vacuo. The crude product was purified by silica gel chromatography (0-20% EtOAc in hexanes) to give ethyl 1-(4-biphenyl)isoquinoline-2(1H)-carboxylate as a white solid. MS (ESI pos. ion) m/z: 356 (M+1).

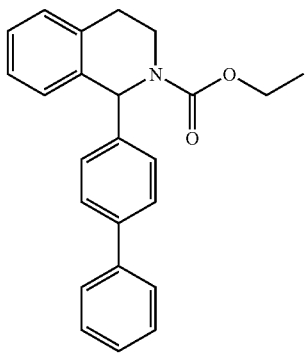 [SMILES: CCOC(=O)N1CCc2ccccc2C1c1ccc(-c2ccccc2)cc1]

Step 2. Ethyl 1-(4-biphenyl)-3,4-dihydroisoquinoline-2(1H)-carboxylate

A solution of ethyl 1-(4-biphenyl)isoquinoline-2(11)-carboxylate (1.05 g, 2.94 mmol) in EtOH (10 mL) and EtOAc (7 mL) was stirred with 10% Pd/C (0.272 g, 2.56 mmol) under hydrogen atmosphere at RT for 14 h. Then the mixture was transferred to a pressure tube and hydrogenated at 46 psi of hydrogen for 4 h. The reaction mixture was filtered through a celite pad and the filtrate was concentrated in vacuo. The crude product was purified by silica gel chromatography (0-20% EtOAc in hexanes) to provide the title compound as a clear oil. MS (ESI pos. ion) m/z: 358 (M+1).

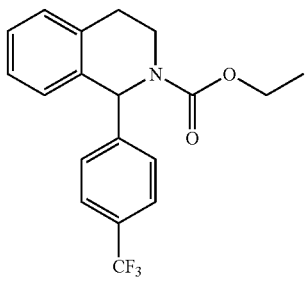 [SMILES: CCOC(=O)N1CCc2ccccc2C1c1ccc(C(F)(F)F)cc1]

Example 3

Ethyl 1-(4-(trifluoromethyl)phenyl)-3,4-dihydroisoquinoline-2(1H)-carboxylate

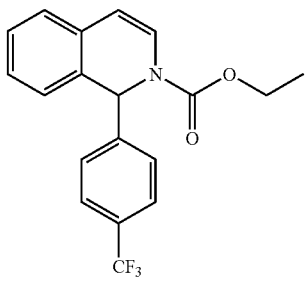 [SMILES: CCOC(=O)N1C=Cc2ccccc2C1c1ccc(C(F)(F)F)cc1]

Step 1. Ethyl 1-(4-(trifluoromethyl)phenyl)isoquinoline-2(1H)-carboxylate

The 4-trifluoromethylphenyl Grignard reagent was prepared by adding 1-bromo-4-(trifluoromethyl)benzene (1.3 mL, 9.2 mmol) to a suspension of magnesium turnings (240 mg, 10.0 mmol), a catalytic amount of iodine in THF (10 mL) and stirred at RT for 1.5 h. A separate round-bottomed flask containing isoquinoline (1.1 g, 8.3 mmol) in anhydrous THF (10 mL) was charged with ethyl chloroformate (0.88 mL, 9.2 mmol) under a stream of $N_2$ and the mixture was stirred at RT for 15 min, and then cooled to 0° C. The previously made Grignard reagent was then cannulated into this solution dropwise and the reaction mixture was stirred for 1 h at 0° C. followed by 1 h at RT. The reaction mixture was quenched with saturated $NH_4Cl$ and extracted with EtOAc. The organic layer was washed with brine, dried over $Na_2SO_4$, filtered, and concentrated in vacuo. The crude product was purified by silica gel chromatography (10% EtOAc in hexanes) to give ethyl 1-(4-(trifluoromethyl)phenyl)isoquinoline-2(1H)-carboxylate as a white solid. MS (ESI pos. ion) m/z: 348 (M+1).

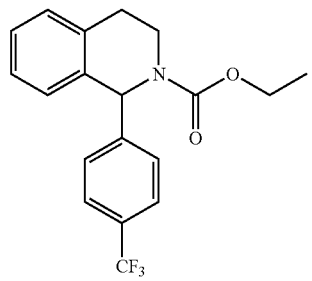 [SMILES: CCOC(=O)N1CCc2ccccc2C1c1ccc(C(F)(F)F)cc1]

Step 2. Ethyl 1-(4-(trifluoromethyl)phenyl)-3,4-dihydroisoquinoline-2(1H)-carboxylate A solution of ethyl 1-(4-(trifluoromethyl)phenyl)isoquinoline-2(1H)-carboxylate (2.0 g, 5.7 mmol) in EtOH (20 mL) was stirred with 10% Pd/C (0.6 g, 5.7 mmol) under a hydrogen atmosphere at RT for 2 h. The reaction mixture was filtered through a celite pad and the filtrate was concentrated in vacuo to provide the title compound as colorless oil. MS (ESI pos. ion) m/z: 350 (M+1).

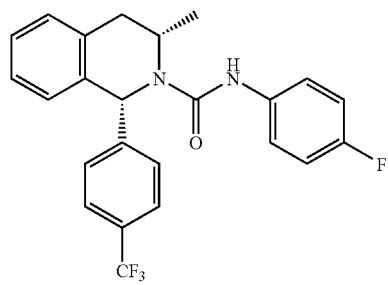

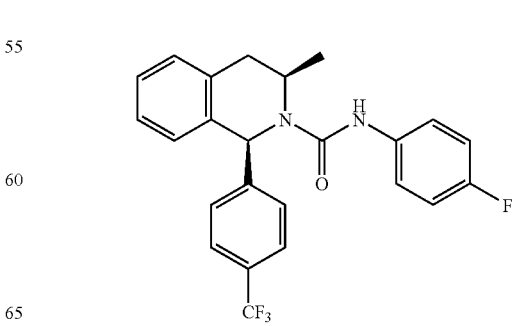

Example 4

(1S,3R)—N-(4-Fluorophenyl)-3-methyl-1-(4-(trifluoromethyl)phenyl)-3,4-dihydroisoquinoline-2(1H)-carboxamide and (1R,3S)—N-(4-fluorophenyl)-3-methyl-1-(4-(trifluoromethyl)phenyl)-3,4-dihydroisoquinoline-2(1H)-carboxamide [stereochemistry is arbitrarily assigned]

Step 1: (4-(Trifluoromethyl)phenyl)magnesium bromide

To a solution of magnesium turnings (238 mg, 9.8 mmol) and iodine (10 mg) in THF (20 mL) under N₂ was added 4-bromobenzotrifluoride (1.24 mL, 8.9 mmol). After the addition was completed, the mixture was stirred at RT for 2 h to give the title compound, which was used in the next step without further purification.

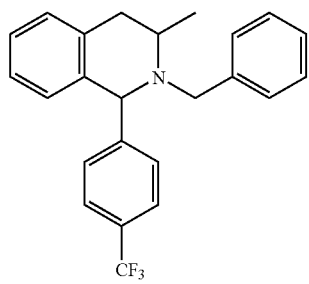 [SMILES: CC1Cc2ccccc2C(c2ccc(C(F)(F)F)cc2)N1Cc1ccccc1]

Step 2: 2-Benzyl-3-methyl-1-(4-(trifluoromethyl)phenyl)-1,2,3,4-tetrahydro-isoquinoline To a solution of 3-methylisoquinoline (1.0 g, 6.98 mmol) in THF (6 mL) was added benzyl bromide (0.78 mL, 6.63 mmol). After the addition was completed, the mixture was heated at 70° C. under N₂ for 16 h. The mixture was cooled down to RT and THF (10 mL). Then, the mixture was cooled to 0° C. and (4-(trifluoromethyl)phenyl)magnesium bromide was added, and then stirred at RT for 16 h. After quenching with saturated ammonium chloride solution, the mixture was extracted several times with EtOAc. The combined organic extracts were dried over MgSO₄ and concentrated. The residue was mixed with silica gel and the solid mixture was purified by silica gel flash column chromatography (30%-100% EtOAc/hexane, then 20% MeOH in DCM) to give a mixture of 2-benzyl-3-methyl-1-(4-(trifluoromethyl)phenyl)-1,2-dihydroisoquinoline & 2-benzyl-3-methyl-1-(4-(trifluoromethyl)phenyl)-isoquinolinium, which was used without further purification.

This mixture was dissolved in THF (45 mL) and sodium borohydride (2.6 g, 68.9 mmol) was added. The resulting mixture was stirred at RT 15 min, and then glacial acetic acid (1 mL) was added. The mixture was stirred at RT for 2 h, and then at 55° C. for an additional 2 h. After cooling down to RT, it was basified with NaOH (10 N) (to pH>12). The organic layer was collected and the aqueous layer was extracted several times with EtOAc. The combined organic extracts were then dried over MgSO₄ and concentrated. The residue was dissolved MeOH (5 mL) and the solution mixture was purified by preparative HPLC (0% MeCN 0.1% TFA/H₂O 0.1% TFA). All fractions of the product were combined and MeCN was removed in vacuo. The aqueous phase was basified with NaHCO₃ and extracted with EtOAc. The combined organic extracts were dried over MgSO₄, concentrated, and dried to give the title compound as a yellow oil.

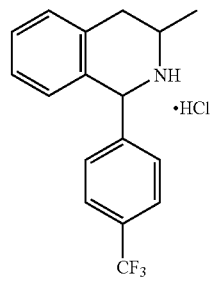 [SMILES: CC1Cc2ccccc2C(c2ccc(C(F)(F)F)cc2)N1 ; Cl]

Step 3: 3-Methyl-1-(4-(trifluoromethyl)phenyl)-1,2,3,4-tetrahydroisoquinoline hydrogen chloride To a solution of 2-benzyl-3-methyl-1-(4-(trifluoromethyl)phenyl)-1,2,3,4-tetrahydroisoquinoline (485 mg, 1.27 mmol) in MeOH (5 mL) was added palladium, 10 wt. % on activated carbon (41 mg, 0.38 mmol). The resulting mixture was then stirred under H₂ for 16 h. Then, 5 N HCl (0.2 mL) was added followed by palladium, 10 wt. % on activated carbon (41 mg, 0.38 mmol). The resulting mixture was stirred at RT under H₂ (45 psi) for 30 min. The mixture was filtered through celite and the celite was washed with MeOH (2×5 mL). The combined filtrates were concentrated to give the title compound as a light yellow solid (HCl salt), which was used in the next step without further purification.

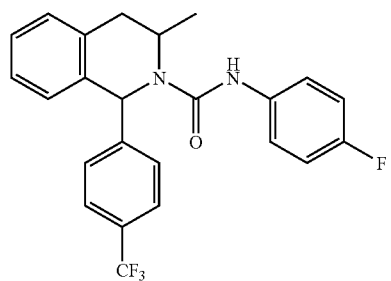 [SMILES: CC1Cc2ccccc2C(c2ccc(C(F)(F)F)cc2)N1C(=O)Nc1ccc(F)cc1]

Step 4: N-(4-Fluorophenyl)-3-methyl-1-(4-(trifluoromethyl)phenyl)-3,4-dihydroisoquinoline-2(1H)-carboxamide To a solution of 3-methyl-1-(4-(trifluoromethyl)phenyl)-1,2,3,4-tetrahydroisoquinoline hydrogen chloride (370 mg, 1.27 mmol) and DIEA (1.1 mL, 6.35 mmol) in DCM (5 mL) was added 4-fluorophenyl isocyanate (143 μL, 1.27 mmol). The mixture was then stirred at RT for 0.5 h. Water (10 mL) was added and the mixture was extracted with DCM (2×15 mL). The combined organic extracts were dried over MgSO₄ and concentrated to give the title compound as a light yellow solid. MS (ESI, positive ion) m/z: 429 (M+H).

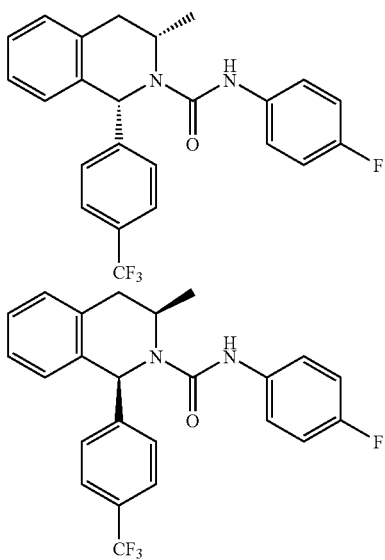

Step 5: (1S,3R)—N-(4-Fluorophenyl)-3-methyl-1-(4-(trifluoromethyl)phenyl)-3,4-dihydroisoquinoline-2(1H)-carboxamide and (1R,3S)—N-(4-fluorophenyl)-3-methyl-1-(4-(trifluoromethyl)phenyl)-3,4-dihydroisoquinoline-2(1H)-carboxamide [stereochemistry is arbitrarily assigned]

Isomers of N-(4-fluorophenyl)-3-methyl-1-(4-(trifluoromethyl)phenyl)-3,4-dihydroisoquinoline-2(1H)-carboxamide were separated by preparative HPLC (0%-100% MeCN 0.1% TFA/H₂O 0.1% TFA) to give the title compounds as a light yellow solid. MS (ESI, positive ion) m/z: 429 (M+H).

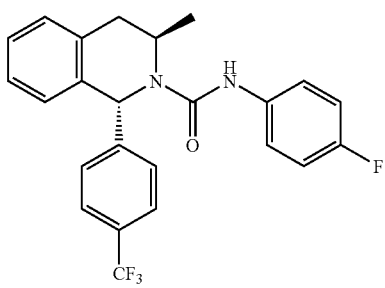

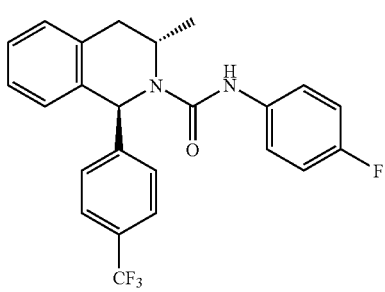

Example 5

(1R,3R)—N-(4-Fluorophenyl)-3-methyl-1-(4-(trifluoromethyl)phenyl)-3,4-dihydroisoquinoline-2(1H)-carboxamide(1S,3S)—N-(4-Fluorophenyl)-3-methyl-1-(4-(trifluoromethyl)phenyl)-3,4-dihydroisoquinoline-2(1H)-carboxamide [stereochemistry is arbitrarily assigned]

Isomers of N-(4-fluorophenyl)-3-methyl-1-(4-(trifluoromethyl)phenyl)-3,4-dihydroisoquinoline-2(1H)-carboxamide (example 4) were separated by preparative HPLC (0%-400% MeCN 0.1% TFA/H₂O 0.1% TFA) to give the title compounds as a white solid. MS (ESI, positive ion) m/z: 429 (M+H).

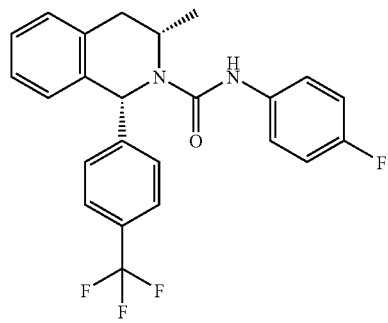 [SMILES: C[C@H]1Cc2ccccc2[C@@H](c2ccc(C(F)(F)F)cc2)N1C(=O)Nc1ccc(F)cc1]

Example 6

(1R,3S)—N-(4-Fluorophenyl)-3-methyl-1-(4-(trifluoromethyl)phenyl)-3,4-dihydroisoquinoline-2(1H)-carboxamide [stereochemistry is arbitrarily assigned]

Enantiomers, (1S,3R)—N-(4-fluorophenyl)-3-methyl-1-(4-(trifluoromethyl)phenyl)-3,4-dihydroisoquinoline-2(1H)-carboxamide & (1R,3S)—N-(4-fluorophenyl)-3-methyl-1-(4-(trifluoromethyl)phenyl)-3,4-dihydroisoquinoline-2(1H)-carboxamide (example 4) were separated using chiral SFC (Chiralcel AD-H (250×21 Mm), 45% methanol/CO₂ (100 bar), 65 mL/min, 220 nm) to give the title compound as a colorless solid. MS (ESI, positive ion) m/z: 429 (M+H).

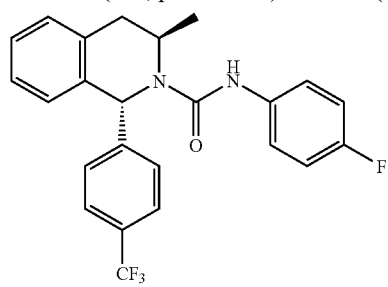

Example 7

(1R,3R)—N-(4-Fluorophenyl)-3-methyl-1-(4-(trifluoromethyl)phenyl)-3,4-dihydroisoquinoline-2(1H)-carboxamide [stereochemistry is arbitrarily assigned]

Enantiomers (1R,3R)—N-(4-fluorophenyl)-3-methyl-1-(4-(trifluoromethyl)phenyl)-3,4-dihydroisoquinoline-2(1H)-carboxamide & (1S,3S)—N-(4-fluorophenyl)-3-methyl-1-(4-(trifluoromethyl)phenyl)-3,4-dihydroisoquinoline-2(1H)-carboxamide (example 5) were separated using chiral SFC (Chiralcel AD-H (250×21 Mm), 45% methanol/CO2 (100 bar), 65 mL/min, 220 nm) to give the title compound as a colorless solid. MS (ESI, positive ion) m/z: 429 (M+H).

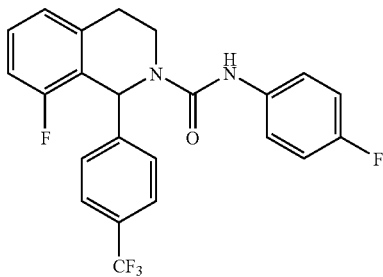 [SMILES: O=C(Nc1ccc(F)cc1)N1CCc2cccc(F)c2C1c1ccc(C(F)(F)F)cc1]

Example 8

8-Fluoro-N-(4-fluorophenyl)-1-(4-(trifluoromethyl)phenyl)-3,4-dihydroisoquinoline-2(1H)-carboxamide

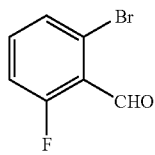

Step 1: 2-Bromo-6-fluorobenzaldehyde

A solution of diisopropylamine (7.9 mL, 55 mmol) in anhydrous tetrahydrofuran (70 mL) cooled to 0° C. was treated dropwise with butyllithium (1.6 M in hexanes, 34.9 mL, 56 mmol). The mixture was stirred at 0° C. for 15 min, then it was cooled to −78° C., and 1-bromo-3-fluoro-benzene (6.1 mL, 56 mmol) was added over 10 min. The mixture was stirred at −78° C. for 1 h, then anhydrous N,N-dimethylformamide (4.9 mL, 64 mmol) was added dropwise over 5 min. The mixture was stirred for another 20 min, then acetic acid (8 mL) and water (180 mL) were added, warmed up to RT, and extracted with ethyl acetate (2×175 mL). The combined organic layers were washed with water (2×75 mL), brine (100 mL), dried over anhydrous sodium sulfate, and concentrated to yield the crude product which was purified by silica gel chromatography (20-30% EtOAc in hexanes) to give 2-bromo-6-fluorobenzaldehyde as a pale yellow solid. MS (ESI, pos. ion) m/z: 204 (M+1).

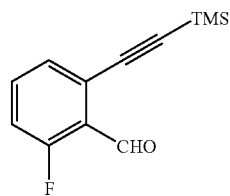 [SMILES: C[Si](C)(C)C#Cc1cccc(F)c1C=O]

Step 2: 2-Fluoro-6-(2-(trimethylsilyl)ethynyl)benzaldehyde

A solution of 2-bromo-6-fluorobenzaldehyde (3.3 g, 16 mmol) and (trimethylsilyl)acetylene (4.5 mL, 32 mmol) in anhydrous N,N-dimethylformamide (60 mL) was treated with triethylamine (3.5 mL, 25 mmol), copper(I) iodide (0.3 g, 1.6 mmol), and Pd(PPh$_3$)$_2$Cl$_2$ (0.6 g, 0.80 mmol) under argon atmosphere. The mixture was stirred at RT for 2.5 h. The mixture was poured into water (150 mL) and extracted with ethyl acetate (2×150 mL). The combined organic layers were washed with water (2×75 mL), brine (100 mL) then dried over anhydrous sodium sulfate and evaporated to yield the crude product which was purified by silica gel chromatography (20-30% EtOAc in hexanes) to give 2-fluoro-6-(2-(trimethylsilyl)ethynyl)benzaldehyde 2-bromo-6-fluorobenzaldehyde as a brown oil. MS (ESI, pos. ion) m/z: 221 (M+1).

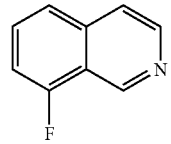 [SMILES: Fc1cccc2ccncc12]

Step 3: 8-Fluoroisoquinoline

2-Fluoro-6-(2-(trimethylsilyl)ethynyl)benzaldehyde (2.3 g, 10.5 mmol) was dissolved in ammonia (2M in methanol, 15 mL, 30 mmol) and the resulting mixture was heated at 80° C. in a sealed tube for 2.5 h. The solvent was removed under high vacuum and the resulting crude product purified by silica gel chromatography (20-30% EtOAc in hexanes) to give 8-fluoroisoquinoline as a pale yellow solid. MS (ESI, pos. ion) m/z: 148 (M+1).

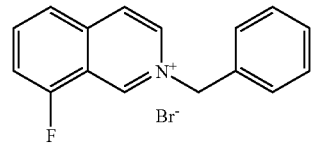 [SMILES: Fc1cccc2cc[n+](Cc3ccccc3)cc12 ; [Br-]]

Step 4: 2-Benzyl-8-fluoro-1-(4-(trifluoromethyl)phenyl)-isoquinolium bromide A solution of 8-fluoroisoquinoline (0.4 g, 2.7 mmol) in acetonitrile (5 mL) was treated with benzyl bromide (0.37 mL, 3.0 mmol) and the solution was refluxed for 3 h. The reaction mixture was cooled down to RT and concentrated to give 2-benzyl-8-fluoro-1-(4-(trifluoromethyl)phenyl)-isoquinolium bromide as a pale yellow solid. MS (ESI, pos. ion) m/z: 238 (M$^+$).

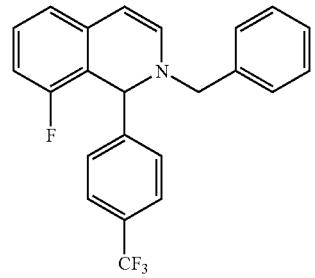

Step 5: 2-Benzyl-8-fluoro-1-(4-(trifluoromethyl)phenyl)-1,2-dihydroisoquinoline The 4-trifluoromethylphenyl Grignard reagent was prepared by adding 1-bromo-4-(trifluoromethyl)benzene (1.2 mL, 8.3 mmol) to a suspension of magnesium turnings (0.3 g, 11 mmol) and catalytic amount of iodine in THF (10 mL) at RT. A different round-bottomed flask containing 2-benzyl-8-fluoro-1-(4-(trifluoromethyl)phenyl)-isoquinolium bromide (0.87 g, 2.7 mmol) in anhydrous tetrahydrofuran (15 mL) was cooled to 0° C., and to this flask was added the Grignard reagent, (4-(trifluoromethyl)phenyl)magnesium bromide over a period of 5 min. The reaction mixture was allowed to stir at 0° C. for 1 h after which the cooling bath was removed and allowed to stir the reaction at RT for 16 h. The reaction was quenched with saturated ammonium chloride (35 mL), followed by ethyl acetate (125 mL), stirred the resulting mixture for 10 min, then transferred to a separatory funnel, added ethyl acetate (100 mL), water (50 mL), brine (50 mL). The ethyl acetate layer was separated, dried over anhydrous sodium sulfate and concentrated to yield 2-benzyl-8-fluoro-1-(4-(trifluoromethyl)phenyl)-1,2-dihydroisoquinoline as a brown oil. MS (ESI, pos. ion) m/z: 384 (M+1).

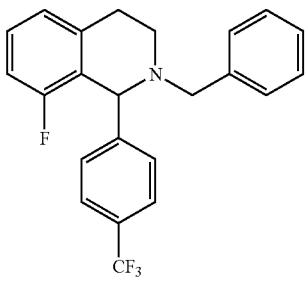 [SMILES: Fc1cccc2c1C(c1ccc(C(F)(F)F)cc1)N(Cc1ccccc1)CC2]

Step 6: 2-Benzyl-8-fluoro-1-(4-(trifluoromethyl)phenyl)-1,2,3,4-tetrahydroisoquinoline A 250-mL round-bottomed flask containing a solution of 2-benzyl-8-fluoro-1-(4-(trifluoromethyl)phenyl)-1,2-dihydroisoquinoline (1.0 g, 2.6 mmol) in anhydrous tetrahydrofuran (20 mL) was treated with sodium borohydride (0.3 g, 8.4 mmol) at RT. After 20 min, acetic acid (3.3 mL) was added and the reaction was stirred at RT for 2.5 h. The reaction mixture was concentrated and the resulting residue was taken up in ethyl acetate (150 mL), water (25 mL), 1N sodium hydroxide, and brine (35 mL). The ethyl acetate layer was separated, dried over anhydrous sodium sulfate, and concentrated to yield the crude product. The crude product was purified by silica gel chromatography (20-30% EtOAc in hexanes) to give 2-benzyl-8-fluoro-1-(4-(trifluoromethyl)phenyl)-1,2,3,4-tetrahydroisoquinoline as a colorless oil. MS (ESI, pos. ion) m/z: 386 (M+1).

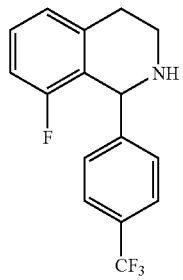 [SMILES: Fc1cccc2c1C(c1ccc(C(F)(F)F)cc1)NCC2]

Step 7: 8-Fluoro-1-(4-(trifluoromethyl)phenyl)-1,2,3,4-tetrahydroisoquinoline

A solution of 2-benzyl-8-fluoro-1-(4-(trifluoromethyl)phenyl)-1,2,3,4-tetrahydro-isoquinoline (0.7 g, 2.1 mmol) in EtOH (20 mL) was stirred with 20% Pd(OH)$_2$/C (0.20 g) under hydrogen atmosphere at 50 psi and at RT for 3 h. The reaction mixture was filtered through a celite pad and the filtrate was concentrated in vacuo. The residue was purified by preparative HPLC [gradient 10-90% MeCN (0.1% TFA)/H$_2$O (0.1% TFA)] to give the pure product which was dissolved in methanol (10 mL) and neutralized by passing the solution through a Polymer Lab-HCO$_3$ Macroporous resin cartridge, and the filtrate was concentrated to give 8-fluoro-1-(4-(trifluoromethyl)phenyl)-1,2,3,4-tetrahydroisoquinoline as an off-white solid. MS (ESI pos. ion) m/z: 296 (M+1).

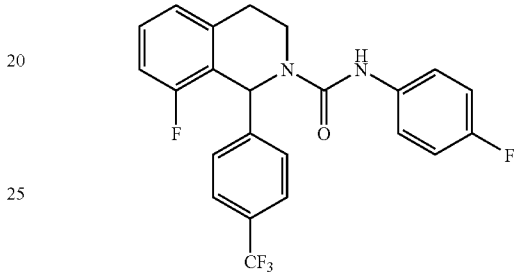

Step 8: 8-Fluoro-N-(4-fluorophenyl)-1-(4-(trifluoromethyl)phenyl)-3,4-dihydroisoquinoline-2(1H)-carboxamide A solution of 8-fluoro-1-(4-(trifluoromethyl)phenyl)-1,2,3,4-tetrahydroisoquinoline (0.4 g, 1.4 mmol) and diisopropylethylamine (0.5 mL, 2.9 mmol) in anhydrous 1,2-dichloroethane (10 mL) was treated with 4-fluorophenyl isocyanate (0.14 mL, 1.2 mmol) and stirred at RT for 16 h. The solvent was removed under vacuum and the residue was purified by preparative HPLC [gradient 10-90% MeCN (0.1% TFA)/H$_2$O (0.1% TFA)] to give the pure product which was dissolved in methanol (10 mL) and neutralized by passing the solution through a Polymer Lab-HCO$_3$ Macroporous resin cartridge, and the filtrate was concentrated to give 8-fluoro-N-(4-fluorophenyl)-1-(4-(trifluoromethyl)phenyl)-3,4-dihydroisoquinoline-2(1H)-carboxamide as a white solid. MS (ESI pos. ion) m/z: 433 (M+1).

Scheme 2

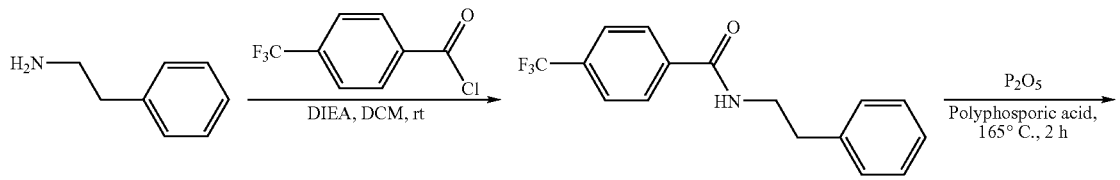

-continued

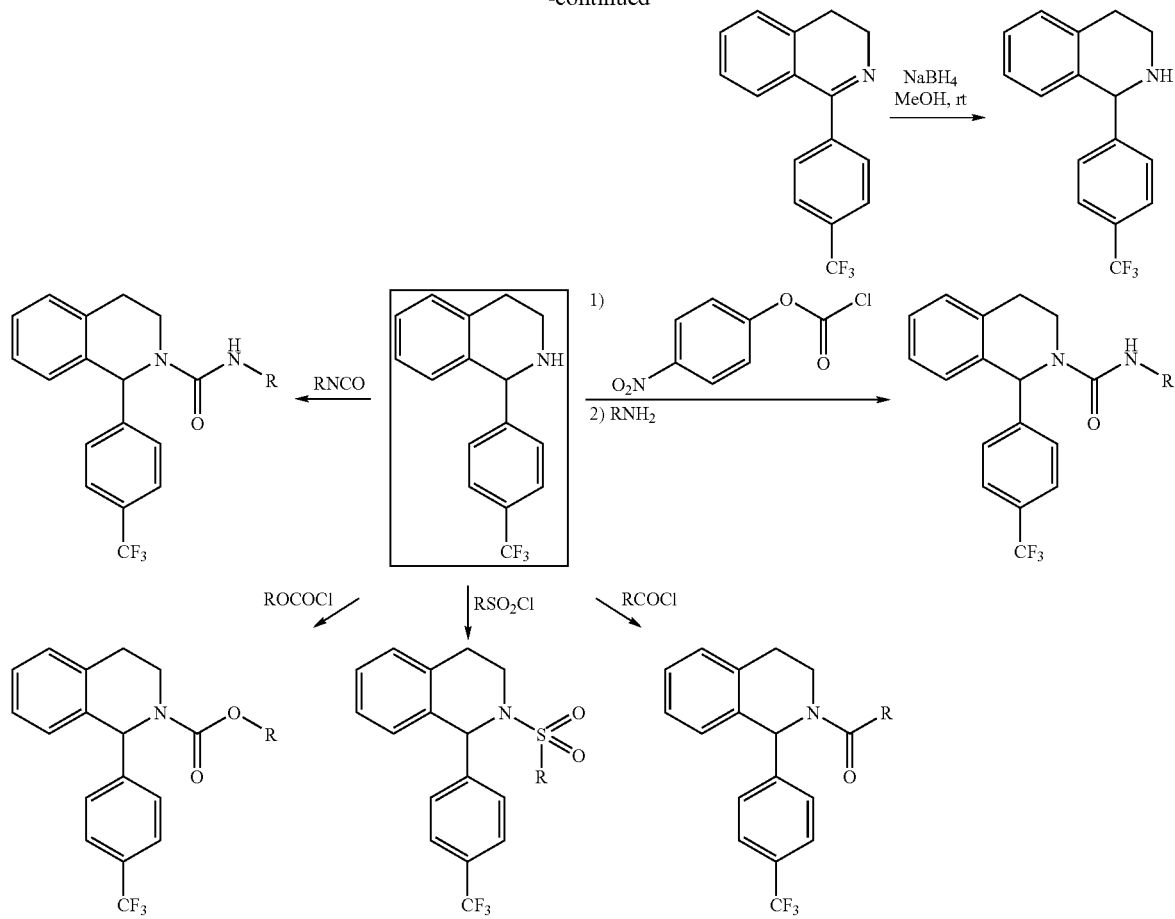

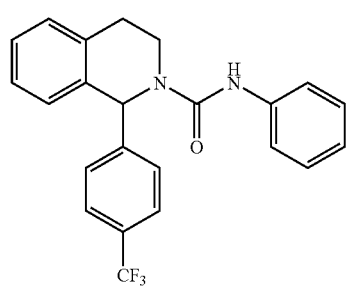

Example 9

N-Phenyl-1-(4-(trifluoromethyl)phenyl)-3,4-dihydroisoquinoline-2(1H)-carboxamide

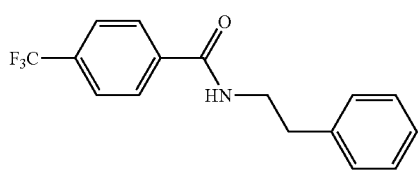 [SMILES: O=C(NCCc1ccccc1)c1ccc(C(F)(F)F)cc1]

Step 1. N-Phenethyl-4-(trifluoromethyl)benzamide

To a solution of phenylethylamine (14.0 g, 14.6 mL, 0.11 mol) and DIEA (20.1 mL, 0.11 mol in DCM (500 mL) at 0° C.

was added 4-(trifluoromethyl)benzoyl chloride (17.2 mL, 0.11 mol) dropwise. After the addition was completed, the reaction mixture was stirred at 0° C. and warmed up itself to RT for 16 h. An off-white solid precipitated was observed. The off-white solid was collected by filtration. The solid was then washed with DCM (2×50 mL), and dried under vacuum to give the title compound as a white solid. MS (ESI, positive ion) m/z: 294 (M+H).

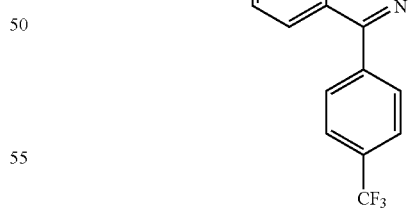

Step 2: 1-(4-(Trifluoromethyl)phenyl)-3,4-dihydroisoquinoline

To a 100-mL round-bottomed flask was added N-phenethyl-4-(trifluoromethyl)benzamide (5.0 g, 17 mmol), phosphoric pentoxide (0.526 mL, 8.52 mmol), and polyphosphoric acid (60.0 g). The reaction mixture was heated to 165° C. for 2 h. Then, the hot solution was carefully poured into ice/water and a solution of KOH (20%, 40 mL) was added to break up the oil. The mixture was stirred at RT for 5 min and an additional amount of KOH solution was added until pH 7. Ethyl ether (250 mL) was added and the mixture was stirred at RT for 15 min. The organic layer was collected and the aqueous layer was extracted with EtOAc (2×200 mL). The combined organic extracts were dried over MgSO$_4$ and concentrated in vacuo to give the title compound as orange oil, which was used in the next step without further purification. MS (ESI, positive ion) m/z: 276 (M+H).

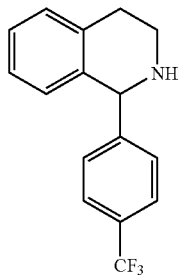

Step 3: 1-(4-(Trifluoromethyl)phenyl)-1,2,3,4-tetrahydroisoquinoline

To a solution of 1-(4-(trifluoromethyl)phenyl)-3,4-dihydroisoquinoline (4.69 g, 17 mmol) in MeOH (24 mL) was added sodium borohydride (1.94 g, 51.1 mmol) slowly at 0° C. Then, the mixture was stirred at 0° C. for 15 min and at RT for 2 h. The solvent was then removed and H$_2$O (20 mL) was added to the residue. A saturated NaHCO$_3$ solution (150 mL) was added slowly and the mixture was extracted with EtOAc (2×200 mL). The combined organic extracts were dried over MgSO$_4$ and concentrated. The residue was mixed with silica gel (4:1; residue:silica gel) and purified by silica gel chromatography (20%-100% EtOAc/hexane) to give the title compound as a white solid. MS (ESI, positive ion) m/z: 278 (M+H).

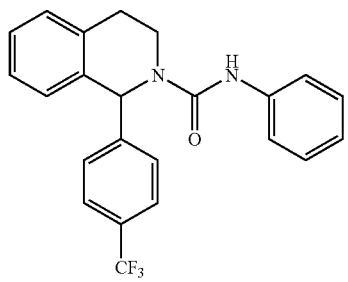

Step 4. N-Phenyl-1-(4-(trifluoromethyl)phenyl)-3,4-dihydroisoquinoline-2(1H)-carboxamide To a solution of 1-(4-(trifluoromethyl)phenyl)-1,2,3,4-tetrahydroisoquinoline (500 mg, 1.80 mmol) and DIEA (0.314 mL, 1.80 mmol) in DCM (9 mL) was added phenyl isocyanate (0.196 mL, 1.80 mmol). The resulting mixture was stirred at RT for 3 h. Then, MeOH (50 mL) was added and the mixture was concentrated. The residue was purified by silica gel flash column chromatography (0%-50% EtOAc/hexane) to give the title compound as a light yellow solid. The solid was then washed with MeOH (3×20 mL) to give 440 mg of the title compound as a white solid. MS (ESI, positive ion) m/z: 397 (M+H).

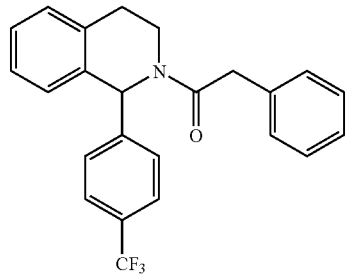 [SMILES: O=C(Cc1ccccc1)N1CCc2ccccc2C1c1ccc(C(F)(F)F)cc1]

Example 10

2-Phenyl-1-(1-(4-(trifluoromethyl)phenyl)-3,4-dihydroisoquinolin-2(1H)-yl)ethanone To a solution of 1-(4-(trifluoromethyl)phenyl)-1,2,3,4-tetrahydroisoquinoline (100 mg, 0.36 mmol, example 9 (step 3) and DIEA (62.8 µL, 0.36 mmol) in DCM (2 mL) was added phenylacetyl chloride (47.7 µL, 0.36 mmol). The resulting mixture was stirred at RT for 16 h. Then, H$_2$O (3 mL) was added and the mixture was extracted with DCM (2×5 mL). The combined organic extracts were concentrated and the residue was dissolved in MeOH (1 mL). The solution mixture was purified by preparative HPLC (10-100% of MeCN (0.1% TFA)/H$_2$O (0.1% TFA) to give the title compound as an off-white thick oil. MS (ESI, positive ion) m/z: 396 (M+H).

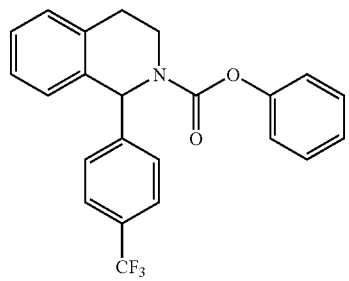 [SMILES: O=C(Oc1ccccc1)N1CCc2ccccc2C1c1ccc(C(F)(F)F)cc1]

Example 11

Phenyl 1-(4-(trifluoromethyl)phenyl)-3,4-dihydroisoquinoline-2(1H)-carboxylate

To a solution of 1-(4-(trifluoromethyl)phenyl)-1,2,3,4-tetrahydroisoquinoline (100 mg, 0.36 mmol, example 9 (step 3) and DIEA (62.8 µL, 0.36 mmol) in DCM (2 mL) was added phenyl chloroformate (45.2 µL, 0.36 mmol). The resulting mixture was reacted under the same conditions as described for example 10 to give 112 mg (78% yield) of the title compound as an off-white oil. MS (ESI, positive ion) m/z: 398 (M+H).

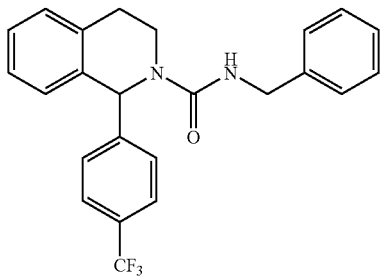 [SMILES: O=C(NCc1ccccc1)N1CCc2ccccc2C1c1ccc(C(F)(F)F)cc1]

Example 12

N-Benzyl-1-(4-(trifluoromethyl)phenyl)-3,4-dihydroisoquinoline-2(1H)-carboxamide

To a solution of 1-(4-(trifluoromethyl)phenyl)-1,2,3,4-tetrahydroisoquinoline (100 mg, 0.36 mmol, example 9 (step 3) and DIEA (62.8 µL, 0.36 mmol) in DCM (2 mL) was added benzyl isocyanate (44.2 µL, 0.36 mmol). The resulting mixture was reacted under the same conditions as described for example 10 to give the title compound as a white solid. MS (ESI, positive ion) m/z: 411 (M+H).

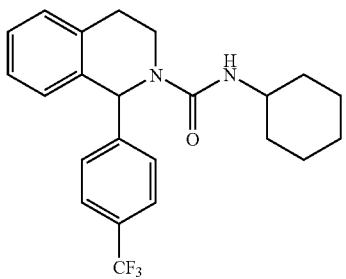

Example 13

N-Cyclohexyl-1-(4-(trifluoromethyl)phenyl)-3,4-dihydroisoquinoline-2(1H)-carboxamide

To a solution of 1-(4-(trifluoromethyl)phenyl)-1,2,3,4-tetrahydroisoquinoline (100 mg, 0.36 mmol, example 9 (step 3) and DIEA (63 pt, 0.36 mmol) in DCM (2 mL) was added isocyanatocyclohexane (46 µL, 0.36 mmol). The resulting mixture was reacted under the same conditions as described for example 10 give the title compound as a white solid. MS (ESI, positive ion) m/z: 403 (M+H).

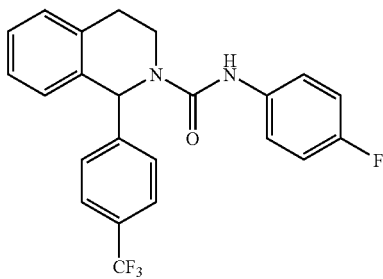

Example 14

N-(4-Fluorophenyl)-1-(4-(trifluoromethyl)phenyl)-3,4-dihydroisoquinoline-2(1H)-carboxamide

To a solution of 1-(4-(trifluoromethyl)phenyl)-1,2,3,4-tetrahydroisoquinoline (100 mg, 0.36 mmol, example 9 (step 3) and DIEA (62.8 µL, 0.36 mmol) in DCM (2 mL) was added 4-fluorophenyl isocyanate (40.5 µL, 0.36 mmol). The resulting mixture was reacted under the same conditions as described for example 10 to give the title compound as a white solid. MS (ESI, positive ion) m/z: 415 (M+H).

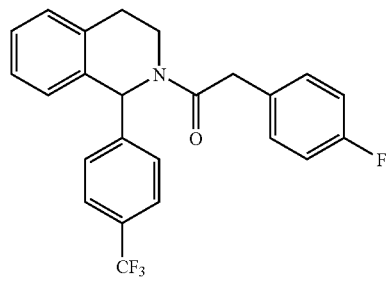 [SMILES: O=C(Cc1ccc(F)cc1)N1CCc2ccccc2C1c1ccc(C(F)(F)F)cc1]

Example 15

2-(4-Fluorophenyl)-1-(1-(4-(trifluoromethyl)phenyl)-3,4-dihydro-isoquinolin-2(1H)-yl)ethanone

To a solution of 1-(4-(trifluoromethyl)phenyl)-1,2,3,4-tetrahydroisoquinoline (100 mg, 0.36 mmol, example 9 (step 3) and DIEA (63 µL, 0.36 mmol) in DCM (2 mL) was added 4-fluorophenylacetyl chloride (62 µL, 0.36 mmol). The resulting mixture was reacted under the same conditions as described for example 10 give the title compound as a white oil. MS (ESI, positive ion) m/z: 414 (M+H).

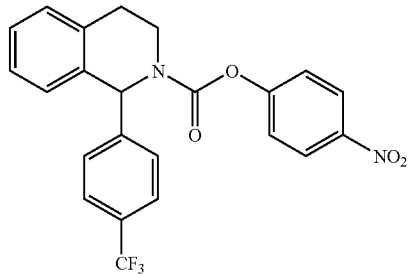 [SMILES: O=C(Oc1ccc([N+](=O)[O-])cc1)N1CCc2ccccc2C1c1ccc(C(F)(F)F)cc1]

Example 16

4-Nitrophenyl 1-(4-(trifluoromethyl)phenyl)-3,4-dihydroisoquinoline-2(1H)-carboxylate

To a solution of 1-(4-(trifluoromethyl)phenyl)-1,2,3,4-tetrahydroisoquinoline (200 mg, 0.721 mmol, example 9 (step 3) and DIEA (126 µL, 0.721 mmol) in DCM (4 mL) was added 4-nitrophenyl chloroformate (145 mg, 0.721 mmol). The resulting mixture was stirred at RT for 16 h. Then, $H_2O$ (10 mL) was added and the mixture was extracted with DCM (2×5 mL). The combined organic extracts were dried over $MgSO_4$ and concentrated. The residue was purified by silica gel flash column chromatography (0%-50% EtOAc/hexane) to give the title compound as a white oil. MS (ESI, positive ion) m/z: 443 (M+H).

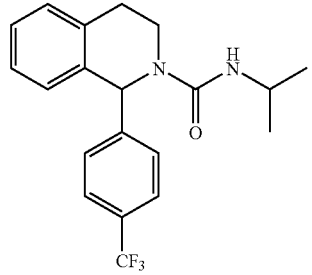 [SMILES: CC(C)NC(=O)N1CCc2ccccc2C1c1ccc(C(F)(F)F)cc1]

Example 17

N-Isopropyl-1-(4-(trifluoromethyl)phenyl)-3,4-dihydroisoquinoline-2(1H)-carboxamide To a solution of 1-(4-(trifluoromethyl)phenyl)-1,2,3,4-tetrahydroisoquinoline (70 mg, 0.252 mmol, example 9 (step 3) and DIEA (44 µL, 0.252 mmol) in DCM (1.6 mL) was added 2-isocyanatopropane (25 µL, 0.252 mmol). The resulting mixture was reacted under the same conditions as described for example 10 to give the title compound as a white solid. MS (ESI, positive ion) m/z: 363 (M+H).

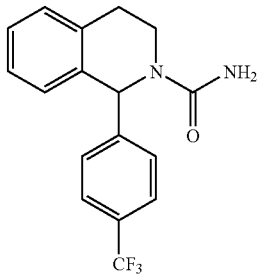 [SMILES: NC(=O)N1CCc2ccccc2C1c1ccc(C(F)(F)F)cc1]

Example 18

1-(4-(Trifluoromethyl)phenyl)-3,4-dihydroisoquinoline-2(1H)-carboxamide

A solution of 1-(4-(trifluoromethyl)phenyl)-1,2,3,4-tetrahydroisoquinoline (0.5 g, 2 mmol) (Example 9, step 3) in dichloromethane (10 mL) was treated with pyridine (1.4 mL, 17 mmol), triethylamine (0.5 mL, 4 mmol), potassium cyanate (0.3 g, 3 mmol), glacial acetic acid (1.00 mL, 17 mmol) and the resulting suspension was stirred at RT for 12 h. The reaction mixture was concentrated to a gummy residue which was taken up in dichloromethane (75 mL), washed with brine (35 mL), dried over anhydrous sodium sulfate, removed dichloromethane, and dried under high vacuum to yield (4-(trifluoromethyl)phenyl)-3,4-dihydroisoquinoline-2(1H)-carboxamide as a white solid. MS (ESI pos. ion) m/z: 321 (M+1).

Example 19

1-(4-(Trifluoromethyl)phenyl)-3,4-dihydroisoquinoline-2(1H)-carbothioamide

A solution of 1-(4-(trifluoromethyl)phenyl)-1,2,3,4-tetrahydroisoquinoline (0.5 g, 2 mmol) (Example 9, step 3) in dry tetrahydrofuran (10 mL) was treated with 1,1'-thiocarbonyldiimidazole (0.5 g, 3 mmol) and stirred at RT for 4 h. The solvent was removed and the resulting residue was dissolved in ammonia (2.0 M solution in methanol, 15 mL, 30 mmol) and stirred the resulting solution in a pressure tube at RT for 1 h followed by heating at 55° C. for 5 h. The solvent was removed under vacuum and the residue was purified by preparative HPLC [gradient 10-90% MeCN (0.1% TFA)/H₂O (0.1% TFA)] to give 1-(4-(trifluoromethyl)phenyl)-3,4-dihydroisoquinoline-2(1H)-carbothioamide as a white solid. MS (ESI, pos. ion) m/z: 337 (M+1).

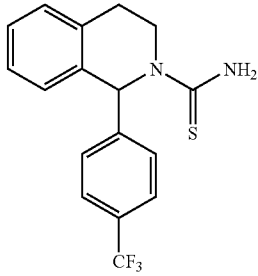

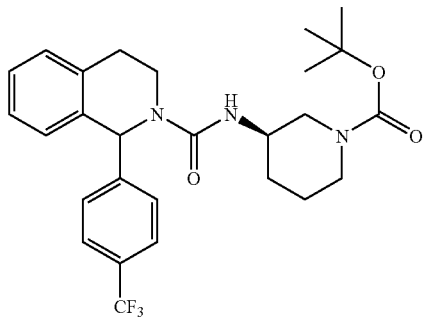 [SMILES: CC(C)(C)OC(=O)N1CCC[C@@H](NC(=O)N2CCc3ccccc3C2c2ccc(C(F)(F)F)cc2)C1]

Example 20

(3R)-tert-Butyl 3-(1-(4-(trifluoromethyl)phenyl)-1,2,3,4-tetrahydroisoquinoline-2-carboxamido)piperidine-1-carboxylate A mixture of 4-nitrophenyl 1-(4-(trifluoromethyl)phenyl)-3,4-dihydroisoquinoline-2(1H)-carboxylate (350 mg, 0.79 mmol, example 15) and (R)-1-Boc-3-amino-piperidine (1.6 mL, 7.91 mmol) was subjected to a microwave irradiation at 120° C. for 45 min. Then, MeOH (2 mL) was added to the mixture and the mixture was filtered. The solution mixture was purified by preparative HPLC (10%-100% of MeCN (0.1% TFA)/H₂O (0.1% TFA). All fractions of the product were combined, saturated NaHCO₃ (1 mL) was added and the solvents were removed. Then, an additional amount of saturated NaHCO₃ (10 mL) was added and the aqueous mixture was extracted with EtOAc (2×10 mL). The combined organic extracts were dried over MgSO₄ and concentrated to give the title compound as a white solid. MS (ESI, positive ion) m/z: 504 (M+H).

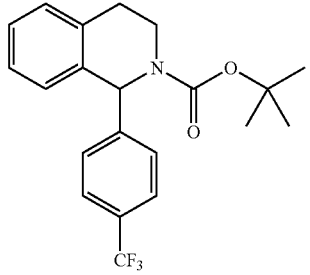 [SMILES: CC(C)(C)OC(=O)N1CCc2ccccc2C1c1ccc(C(F)(F)F)cc1]

Example 21 tert-Butyl 1-(4-(trifluoromethyl)phenyl)-3,4-dihydroisoquinoline-2(1H)-carboxylate To a mixture of 1-(4-(trifluoromethyl)phenyl)-1,2,3,4-tetrahydroisoquinoline (100 mg, 0.361 mmol, example 9 (step 3) and DIEA (62.8 µL, 0.361 mmol), and DCM (1 mL) was added di-tert-butyldicarbonate (82.9 µL, 0.361 mmol). The resulting mixture was stirred at RT for 16 h. Then, H₂O (1 mL) was added and the mixture was extracted with DCM (2×2 mL). The combined organic extracts were dried over MgSO₄ and concentrated. The residue was purified by silica gel chromatography (0%-100% EtOAc/hexane) to give the title compound as an off-white oil. MS (ESI, positive ion) m/z: 322 (M-tert-butyl).

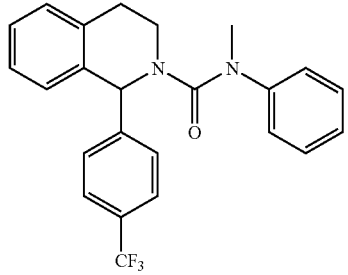 [SMILES: CN(C(=O)N1CCc2ccccc2C1c1ccc(C(F)(F)F)cc1)c1ccccc1]

Example 22

N-Methyl-N-phenyl-1-(4-(trifluoromethyl)phenyl)-3,4-dihydroisoquinoline-2(1H)-carboxamide To a solution of N-phenyl-1-(4-(trifluoromethyl)phenyl)-3,4-dihydroisoquinoline-2(1H)-carboxamide (100 mg, 0.252 mmol, example 9 (step 3) in THF (1 mL) was added sodium hydride (12 mg, 0.505 mmol) slowly. The resulting mixture was stirred at RT for 15 min and iodomethane (16 µL, 0.252 mmol) was added. The mixture was stirred at RT for 16 h. Then, H₂O (2 mL) was added and the mixture was extracted with EtOAc (2×2 mL). The combined organic extracted were dried over MgSO₄ and concentrated. The residue was then dissolved in DMSO (1 mL) and the solution mixture was purified by preparative HPLC (10%-400% of MeCN (0.1% TFA)/H₂O (0.1% TFA) to give the title compound as an off-white solid. MS (ESI, positive ion) m/z: 411 (M+H).

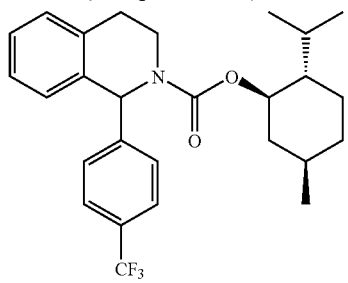

Example 23

(1R,2S,5R)-2-Isopropyl-5-methylcyclohexyl 1-(4-(trifluoromethyl)phenyl)-3,4-dihydroisoquinoline-2(1H)-carboxylate A solution of 1-(4-(trifluoromethyl)phenyl)-1,2,3,4-tetrahydroisoquinoline (100 mg, 0.361 mmol, example 9 (step 3) and (1R,2S,5R)-2-isopropyl-5-methylcyclohexyl carbonochloridate (76.5 µL, 0.361 mmol) in DCM (1 mL) was stirred at RT for 16 h. Then, H₂O (2 mL) was added and the mixture was extracted with EtOAc (2×5 mL). The combined organic extracts were dried over MgSO₄ and concentrated. The residue was purified by silica gel flash column chromatography (0%-100% EtOAc/hexane) to give the title compound as an off-white oil. MS (ESI, positive ion) m/z: 460 (M+H).

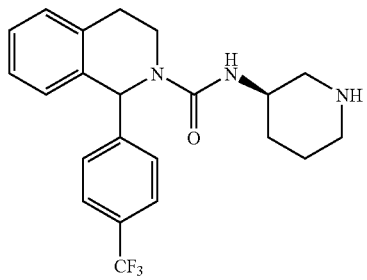 [SMILES: O=C(N[C@@H]1CCCNC1)N1CCc2ccccc2C1c1ccc(C(F)(F)F)cc1]

Example 24

N—((R)-Piperidin-3-yl)-1-(4-(trifluoromethyl)phenyl)-3,4-dihydroisoquinoline-2(1H)-carboxamide A solution of (3R)-tert-butyl 3-(1-(4-(trifluoromethyl)phenyl)-1,2,3,4-tetrahydro-isoquinoline-2-carboxamido)piperidine-1-carboxylate (44 mg, 87 µmol, example 20) in TFA (30% in DCM, 2 mL) was stirred at RT for 30 min. The solvents were removed and EtOAc (5 mL) and saturated NaHCO₃ (3 mL) were added to the residue. The solution mixture was then stirred at RT for 10 min. The organic layer was collected and the aqueous layer was extracted with EtOAc (2×2 mL). The combined organic extracts were dried over MgSO₄, concentrated, and dried under vacuum to give the title compound as an off-white solid. MS (ESI, positive ion) m/z: 404 (M+H).

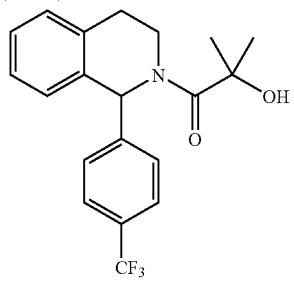

Example 25

2-Hydroxy-2-methyl-1-(1-(4-(trifluoromethyl)phenyl)-3,4-dihydroisoquinolin-2(1H)-yl)propan-1-one To a solution of (4-(trifluoromethyl)phenyl)-1,2,3,4-tetrahydroisoquinoline (240 mg, 0.87 mmol, example 9 (step 3) and DIEA (151 µL, 0.87 mmol) in DCM (3 mL) was added 1-chlorocarbonyl-1-methylethyl acetate (125 µL, 0.87 mmol) slowly. After addition, the mixture was stirred at RT for 16 h. Then, an additional amount of 1-chlorocarbonyl-1-methylethyl acetate (60 µL) was added and the mixture was stirred at RT for 16 h. Then, H₂O (2 mL) was added and the mixture was stirred at RT for 10 min. The organic layer was collected and the aqueous layer was extracted with EtOAc (2×3 mL). The combined organic extracts were then dried over MgSO₄ and concentrated to give a crude intermediate. Then, the crude intermediate was dissolved in MeOH (10 mL), and then potassium carbonate (239 mg, 1.7 mmol) was added. The resulting mixture was then stirred at RT for 16 h. Then, the mixture was filtered and the solid was washed with DCM (2×5 mL). The combined filtrates were concentrated and the residue was purified by silica gel flash column chromatogra phy (0%-400% EtOAc/hexane) to give the title compound as a white solid. MS (ESI, positive ion) m/z: 364 (M+H).

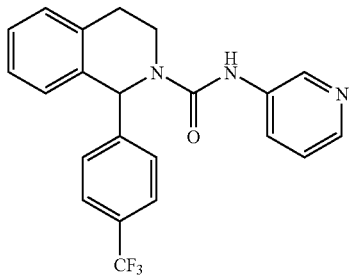

Example 26

N-(Pyridin-3-yl)-1-(4-(trifluoromethyl)phenyl)-3,4-dihydroisoquinoline-2(1H)-carboxamide A solution of 1-(4-(trifluoromethyl)phenyl)-1,2,3,4-tetrahydroisoquinoline (97 mg, 0.350 mmol, example 9 (step 3), DIEA (61 μL, 0.35 mmol), and 3-iso-cyanatopyridine (42 mg, 0.35 mmol) in DCM (1 mL) was stirred at RT for 16 h. A white precipitate was observed. The reaction mixture was then filtered and the solid was dried in vacuo to give the title compound as a white solid. MS (ESI, positive ion) m/z: 398 (M+H).

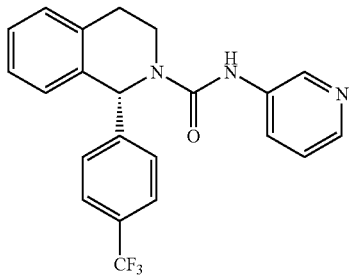 [SMILES: O=C(Nc1cccnc1)N1CCc2ccccc2C1c1ccc(C(F)(F)F)cc1]

Example 27

(R)—N-(Pyridin-3-yl)-1-(4-(trifluoromethyl)phenyl)-3,4-dihydro-isoquinoline-2(1H)-carboxamide Enantiomers of N-(pyridin-3-yl)-1-(4-(trifluoromethyl)phenyl)-3,4-dihydroisoquinoline-2(1H)-carboxamide (1.3 g, racemic mixture) were separated using chiral SFC (Chiralcel AD-H (250×21 Mm), 45% methanol/CO₂ (100 bar), 65 mL/min, 220 nm) to give the title compound as a light yellow solid. MS (ESI, positive ion) m/z: 398 (M+H).

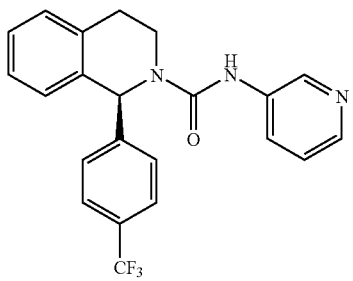

Example 28

(S)—N-(Pyridin-3-yl)-1-(4-(trifluoromethyl)phenyl)-3,4-dihydroisoquinoline-2(1H)-carboxamide Enantiomers of N-(pyridin-3-yl)-1-(4-(trifluoromethyl)phenyl)-3,4-dihydroisoquinoline-2(1H)-carboxamide (1.3 g, racemic mixture) were separated by using chiral SFC (Chiralcel AD-H (250×21 Mm), 45% methanol/CO₂ (100 bar), 65 mL/min, 220 nm) to give the title compound as a light yellow solid. MS (ESI, positive ion) m/z: 398 (M+H).

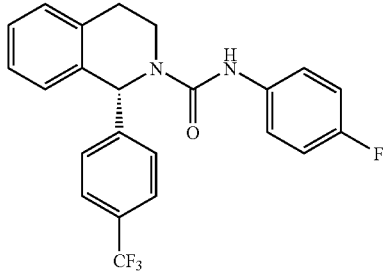 [SMILES: O=C(Nc1ccc(F)cc1)N1CCc2ccccc2[C@H]1c1ccc(C(F)(F)F)cc1]

Example 29

(R)—N-(4-Fluorophenyl)-1-(4-(trifluoromethyl)phenyl)-3,4-dihydroisoquinoline-2(1H)-carboxamide Enantiomers of N-(4-fluorophenyl)-1-(4-(trifluoromethyl)phenyl)-3,4-dihydroisoquinoline-2(1H)-carboxamide (100 mg, racemic mixture) were separated using chiral SFC (Chiralcel AD-H (250×21 Mm), 45% methanol/CO₂ (100 bar), 65 mL/min, 220 nm) to give the title compound as a white solid. MS (ESI, positive ion) m/z: 415 (M+H).

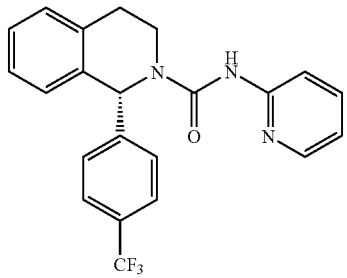 [SMILES: O=C(Nc1ccccn1)N1CCc2ccccc2[C@H]1c1ccc(C(F)(F)F)cc1]

Example 30

(R)—N-(Pyridin-2-yl)-1-(4-(trifluoromethyl)phenyl)-3,4-dihydroisoquinoline-2(1H)-carboxamide

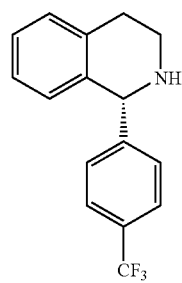 [SMILES: FC(F)(F)c1ccc([C@H]2NCCc3ccccc32)cc1]

Step 1: (R)-1-(4-(trifluoromethyl)phenyl)-1,2,3,4-tetrahydroisoquinoline

Enantiomers of 1-(4-(trifluoromethyl)phenyl)-1,2,3,4-tetrahydroisoquinoline (2.120 g, 7.46 mmol, racemic mixture) were separated using chiral SFC (Chiralcel AD-H (250×21 Mm), 45% methanol/CO₂ (100 bar), 65 mL/min, 220 nm) to give the title compound as a light yellow solid. MS (ESI, positive ion) m/z: 278 (M+H).

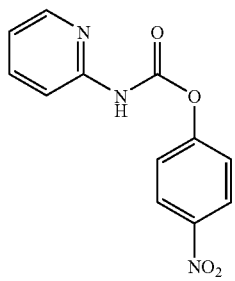 [SMILES: O=C(Nc1ccccn1)Oc1ccc([N+](=O)[O-])cc1]

Step 2: 4-Nitrophenyl pyridin-2-ylcarbamate

To a solution of 2-aminopyridine (2.0 mL, 21.25 mmol) in DCM (35 mL) at 0° C. was added a solution of 4-nitrophenyl chloroformate (4.28 g, 21.25 mmol) in DCM (35 mL) and pyridine (1.73 mL, 21.25 mmol, anhydrous). After the addition was completed, the reaction mixture was stirred at RT for 16 h under an atmosphere of nitrogen. A white precipitated was observed and it was collected by filtration. The filtrate was washed with DCM (3×50 mL) to give the title compound as a white solid. MS (ESI, positive ion) m/z: 260 (M+H).

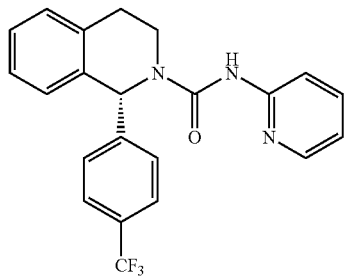 [SMILES: O=C(Nc1ccccn1)N1CCc2ccccc2[C@H]1c1ccc(C(F)(F)F)cc1]

Step 3: (R)—N-(Pyridin-2-yl)-1-(4-(trifluoromethyl) phenyl)-3,4-dihydroisoquinoline-2(1H)-carboxamide To a solution of (R)-1-(4-(trifluoromethyl)phenyl)-1,2,3,4-tetrahydroisoquinoline (100 mg, 0.361 mmol) in MeCN (2 mL) was added 4-nitrophenyl pyridin-2-ylcarbamate (467 mg, 1.80 mmol). The resulting mixture was then heated at 70° C. for 16 h, cooled to RT and filtered. The white solid obtained was washed with DCM (2×2 mL). The combined filtrates were then concentrated and the residue purified by silica gel flash column chromatography (0%-100% EtOAc/hexane) to give the title compound as a colorless solid. MS (ESI, positive ion) m/z: 398 (M+H).

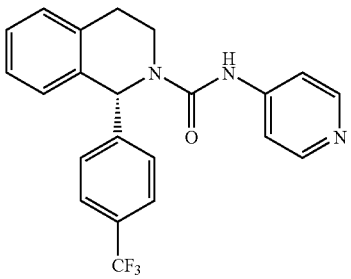

Example 31

(R)—N-(Pyridin-4-yl)-1-(4-(trifluoromethyl)phenyl)-3,4-dihydroisoquinoline-2(1H)-carboxamide

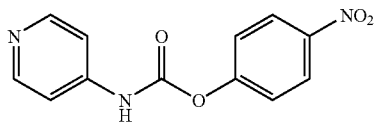 [SMILES: O=C(Nc1ccncc1)Oc1ccc([N+](=O)[O-])cc1]

Step 1: 4-Nitrophenyl pyridin-4-ylcarbamate

To a solution of 4-aminopyridine (1.97 g, 20.9 mmol) in DCM (75 mL) at 0° C. was added 4-nitrophenyl chloroformate (4.21 g, 20.9 mmol) and pyridine (1.7 mL, 20.9 mmol). Then, the mixture was stirred at RT overnight. The white precipitated was filtered off and washed with DCM (2×50 mL), and then dried in vacuo to give the title compound as a white solid, which was used in the next step without further purification. MS (ESI, positive ion) m/z: 260 (M+H).

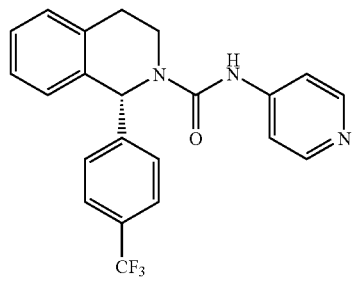 [SMILES: O=C(Nc1ccncc1)N1CCc2ccccc2[C@H]1c1ccc(C(F)(F)F)cc1]

Step 2: (R)—N-(Pyridin-4-yl)-1-(4-(trifluoromethyl) phenyl)-3,4-dihydroisoquinoline-2(1H)-carboxamide To a solution of (R)-1-(4-(trifluoromethyl)phenyl)-1,2,3,4-tetrahydroisoquinoline (200 mg, 0.721 mmol) in MeCN (3 mL) was added 4-nitrophenyl pyridin-4-ylcarbamate (561 mg, 2.164 mmol). The resulting mixture was heated to 55° C. overnight. After cooling down to RT the white precipitated obtained was filtered off and washed with DCM (2×1 mL). The combined filtrates were then concentrated and the residue purified by silica gel flash column chromatography (0%-100% EtOAc/hexane) to give the title compound as a white solid. MS (ESI, positive ion) m/z: 398 (M+H).

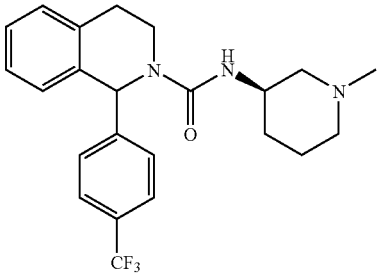 [SMILES: CN1CCC[C@@H](NC(=O)N2CCc3ccccc3C2c2ccc(C(F)(F)F)cc2)C1]

Example 32

N—((R)-1-Methylpiperidin-3-yl)-1-(4-(trifluoromethyl)phenyl)-3,4-dihydroisoquinoline-2(1H)-carboxamide To a solution of N—((R)-piperidin-3-yl)-1-(4-(trifluoromethyl)phenyl)-3,4-dihydro-isoquinoline-2(1H)-carboxamide (30 mg, 74 µmol, example 24) in DCE (0.5 mL) was added formaldehyde (28 µL, 372 mol). The resulting mixture was stirred at RT for 1 h and then sodium triacetoxyborohydride (16 mg, 74 µmol) was added. The mixture was then stirred at RT for 4 h. Then, saturated NaHCO₃ (0.4 mL) was added and the mixture was extracted with EtOAc (2×3 mL). The combined organic extracts were dried over MgSO₄ and concentrated. The residue was purified by silica gel flash column chromatography (0%-10% MeOH (2M NH₃)/EtOAc) to give the title compound as an off-white solid. MS (ESI, positive ion) m/z: 418 (M+H).

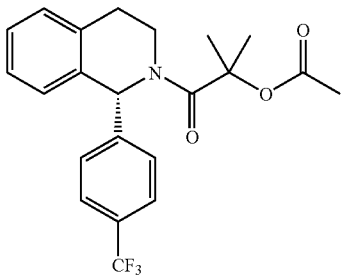 [SMILES: CC(=O)OC(C)(C)C(=O)N1CCc2ccccc2[C@H]1c1ccc(C(F)(F)F)cc1]

Example 33

(R)-2-Methyl-1-oxo-1-(1-(4-(trifluoromethyl)phenyl)-3,4-dihydroisoquinolin-2(1H)-yl)propan-2-yl acetate To a solution of (R)-1-(4-(trifluoromethyl)phenyl)-1,2,3,4-tetrahydroisoquinoline (207 mg, 747 µmol, example 30 (step 1) and DIEA (130 µL, 747 µmol) in DCM (2.5 mL) was added 1-chlorocarbonyl-1-methylethyl acetate (119 µL, 821 µmol). The mixture was stirred at RT for 3 h. Then, 1-chlorocarbonyl-1-methylethyl acetate (50 µL) was added and the mixture was stirred at RT for 16 h. MeOH (1 mL) was added and the mixture was filtered. The filtrate was purified by preparative HPLC (0%-100% MeCN 0.1% TFA/water 0.1% TFA) to give the title compound in a solution of H₂O 0.1% TFA and MeCN 0.1% TFA. The solvent was removed and saturated NaHCO₃ (5 mL) was added. The mixture was extracted with EtOAc (2×30 mL). The combined organic extracts were dried over MgSO₄, concentrated, and dried in vacuo to give the title compound as a white solid. MS (ESI, positive ion) m/z: 406 (M+H).

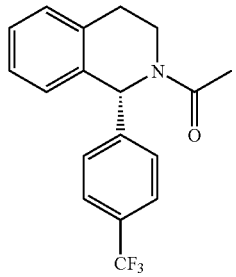 [SMILES: CC(=O)N1CCc2ccccc2[C@H]1c1ccc(C(F)(F)F)cc1]

Example 34

(R)-1-(1-(4-(Trifluoromethyl)phenyl)-3,4-dihydroisoquinolin-2(1H)-yl)ethanone

To a solution of (R)-1-(4-(trifluoromethyl)phenyl)-1,2,3,4-tetrahydroisoquinoline (100 mg, 361 µmol, example 30 (step 1) in DCM (2 mL) was added DIEA (62.8 µL, 361 µmol) and acetic acid anhydride (34.0 µL, 361 mop. The resulting mixture was then stirred at RT for 16 h. Then, H₂O (1 mL) was added and the mixture was extracted with DCM (2×5 mL). The combined organic extracts were dried over MgSO₄ and concentrated. The residue was purified by silica gel flash column chromatography (0%-100% EtOAc/hexane) to give the title compound as a white solid. MS (ESI, positive ion) m/z: 320 (M+H).

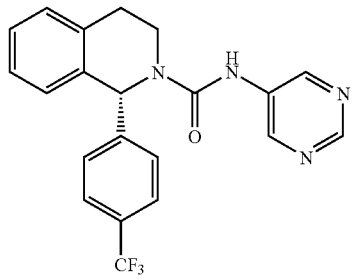

Example 35

(R)—N-(Pyrimidin-5-yl)-1-(4-(trifluoromethyl)phenyl)-3,4-dihydroisoquinoline-2(1H)-carboxamide

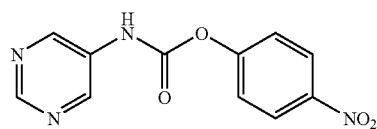 [SMILES: O=C(Nc1cncnc1)Oc1ccc([N+](=O)[O-])cc1]

Step 1: 4-Nitrophenyl pyrimidin-5-ylcarbamate

To a solution of pyrimidin-5-amine (190 mg, 2.0 mmol) in pyrimidine (3 mL) was added 4-nitrophenyl chloroformate (403 mg, 2.0 mmol). The resulting mixture was stirred at RT overnight, and then heated to 60° C. overnight. After cooling to RT, the solvent was removed under vacuum to give the title compound as a brown solid, which was used in the next step without further purification. MS (ESI, positive ion) m/z: 261 (M+H).

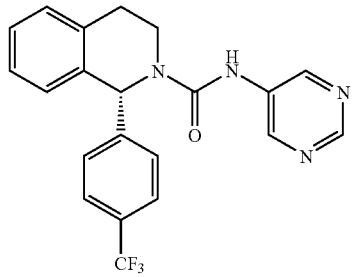 [SMILES: O=C(Nc1cncnc1)N1CCc2ccccc2[C@H]1c1ccc(C(F)(F)F)cc1]

Step 2: (R)—N-(Pyrimidin-5-yl)-1-(4-(trifluoromethyl)phenyl)-3,4-dihydroisoquinoline-2(1H)-carboxamide A solution of (R)-1-(4-(trifluoromethyl)phenyl)-1,2,3,4-tetrahydroisoquinoline (100 mg, 0.30 mmol, example 30 (step 1)) and 4-nitrophenyl pyrimidin-5-ylcarbamate (93.8 mg, 0.36 mmol) in MeCN (3 mL) was heated to 70° C. overnight, and then was subjected to microwave irradiation at 120° C. for 15 min. The mixture was filtered and the filtrate was purified by preparative HPLC (0%-100% MeCN 0.1% TFA/ H₂O 0.1% TFA) to give the title compound in solution of H₂O (0.1% TFA) and MeCN (0.1% TFA). The solvent was partially removed and saturated NaHCO₃ (10 mL) was added. The mixture was extracted with EtOAc (2×5 mL). The combined organic extracts were dried over MgSO₄, concentrated, and dried in vacuo to give the title compound as a light yellow solid. MS (ESI, positive ion) m/z: 399 (M+H).

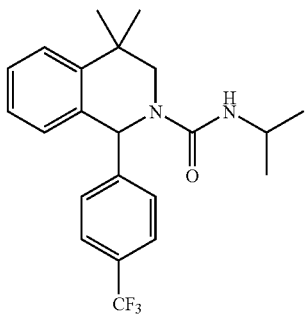 [SMILES: CC(C)NC(=O)N1CC(C)(C)c2ccccc2C1c1ccc(C(F)(F)F)cc1]

Example 36

N-Isopropyl-4,4-dimethyl-1-(4-(trifluoromethyl) phenyl)-3,4-dihydroisoquinoline-2(1H)-carboxamide

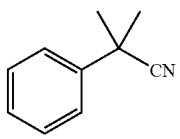

Step 1. 2-Methyl-2-phenylpropanenitrile

A solution of phenylacetonitrile (5.0 mL, 43 mmol) and sodium hydroxide (7 g, 0.17 mol) in dimethylsulfoxide (40 mL):water (7 mL) was cooled to 0° C. and then treated with methyl iodide (11 mL, 0.17 mol). After stirring at RT for 1 h, the reaction mixture was quenched with water (15 mL) and extracted with EtOAc. The organic layer was washed with water, brine, dried over MgSO₄, filtered, and concentrated in vacuo to provide 2-methyl-2-phenylpropanenitrile as a yellow oil.

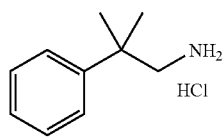

Step 2. 2-Methyl-2-phenylpropan-1-amine hydrochloride

To a stirred suspension of lithium aluminum hydride (2.44 g, 64.2 mmol) in dry ether (100 mL) at RT was added under a nitrogen atmosphere 2-methyl-2-phenylpropanenitrile (5.83 g, 40.2 mmol) in dry ether (50 mL) over 30 min. Then, it was heated under reflux for 3 h and allowed to cool to RT. The reaction mixture was then treated sequentially with water (2.3 mL), NaOH (5 N, 2.3 mL) and water (6.9 mL), stirred at RT for 1.5 h and the solids were filtered off. The filtrate was dried over Na₂SO₄ and the solids were removed by filtration. Then the solution was treated with 1N HCl in ether (40 mL) and the white precipitated was separated by filtration. 2-Methyl-2-phenylpropan-1-amine hydrochloride was obtained as a white solid.

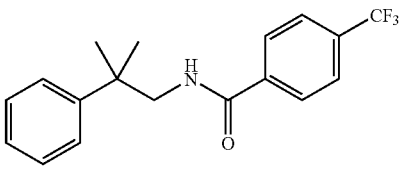 [SMILES: CC(C)(CNC(=O)c1ccc(C(F)(F)F)cc1)c1ccccc1]

Step 3: N-(2-Methyl-2-phenylpropyl)-4-(trifluoromethyl)benzamide

To a suspension of 2-methyl-2-phenylpropan-1-amine hydrochloride (5.32 g, 28.6 mmol) in dry DCM (60 mL) at 0° C. was added triethylamine (8.3 mL, 60.1 mmol) and then slowly 4-(trifluoromethyl)benzoyl chloride (4.48 mL, 30.1 mmol). Then, the mixture was stirred at RT for 45 min, diluted with EtOAc, washed with 10% HCl, sat NaHCO₃ and water. After drying over Na₂SO₄ the solvent was removed under vacuum and the title compound was obtained as a white solid. MS (ESI, positive ion) m/z: 322 (M+H).

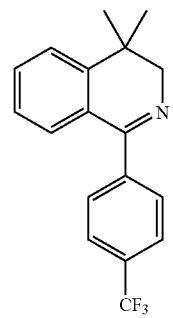 [SMILES: CC1(C)CN=C(c2ccc(C(F)(F)F)cc2)c2ccccc21]

Step 4: 4,4-Dimethyl-1-(4-(trifluoromethyl)phenyl)-3,4-dihydroisoquinoline

A 100-mL round-bottomed flask was charged with N-(2-methyl-2-phenylpropyl)-4-(trifluoromethyl)benzamide (2.69 g, 8.39 mmol), phosphorus pentaoxide (1.88 g, 16.8 mmol), toluene (40 mL) and phosphorous oxychloride (6.3 mL, 67.1 mmol). The reaction mixture was heated at 110° C. for 16 h and allowed to cool down to RT. Then it was poured over ice-water and neutralized with NaOH (10%). The organic phase was taken and the aqueous phase was extracted several times with EtOAc. The combined organic layers were washed with sat NaHCO₃, water, brine and dried over Na₂SO₄. The solvent was removed under vacuum and the product used without further purification.

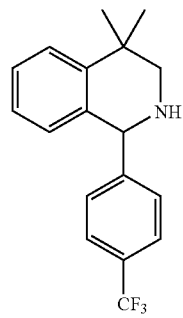 [SMILES: CC1(C)CNC(c2ccc(C(F)(F)F)cc2)c2ccccc21]

Step 5: 4,4-Dimethyl-1-(4-(trifluoromethyl)phenyl)-1,2,3,4-tetrahydroisoquinoline A 50-mL round-bottomed flask was charged with 4,4-dimethyl-1-(4-(trifluoromethyl)phenyl)-3,4-dihydroisoquinoline (2.52 g, 8.3 mmol) and dry MeOH (10 mL). After cooling down to 0° C. sodium borohydride (943 mg, 24.9 mmol) was added and the mixture was stirred at RT for 45 min. Then, the solvent was removed and the residue redissolved in EtOAc, washed with sat NaHCO$_3$, water and dried over Na$_2$SO$_4$. The residue was purified by silica gel chromatography (25-35% EtOAc in hexanes) to give the title compound as a white solid. MS (ESI, positive ion) m/z: 306 (M+H).

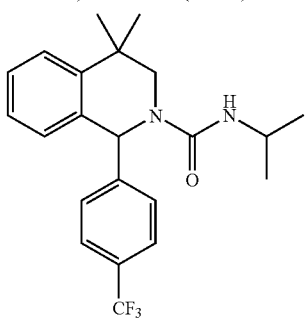

Step 6: N-Isopropyl-4,4-dimethyl-1-(4-(trifluoromethyl)phenyl)-3,4-dihydro-isoquinoline-2(1H)-carboxamide A 25-mL round-bottomed flask was charged with 4,4-dimethyl-1-(4-(trifluoromethyl)phenyl)-1,2,3,4-tetrahydroisoquinoline (366 mg, 1.2 mmol), iso-propyl isocyanate (141 μL, 1.4 mmol), DCE (5 mL) and stirred at RT for 1 h. Then the solvent was removed under vacuum and the product was purified by recrystallization from a mixture of ether/hexane. MS (ESI, positive ion) m/z: 391 (M+H).

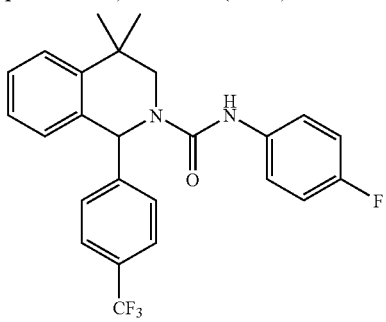

Example 37

N-(4-Fluorophenyl)-4,4-dimethyl-1-(4-(trifluoromethyl)phenyl)-3,4-dihydro-isoquinoline-2(1H)-carboxamide A 25-mL round-bottomed flask was charged with 4,4-dimethyl-1-(4-(trifluoromethyl)phenyl)-1,2,3,4-tetrahydroisoquinoline (118 mg, 0.39 mmol), 4-fluorophenyl isocyanate (43.4 μL, 0.39 mmol) and DCE (5 mL). The reaction mixture was heated at 80° C. for 2 h and the solvent was then removed under vacuum. Purification by silica gel chromatography (20-30% EtOAc in hexanes) provided the title compound as a white solid. MS (ESI, positive ion) m/z: 443 (M+H).

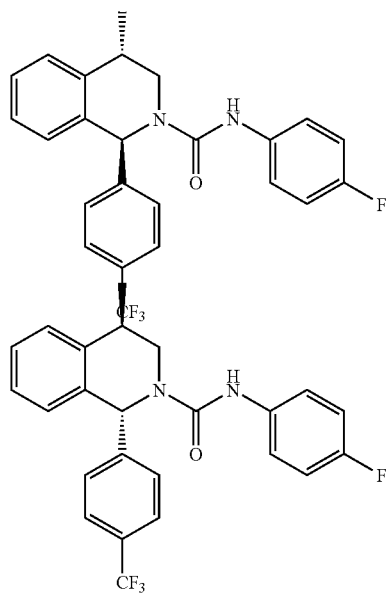

Example 38

(1S,4S)—N-(4-Fluorophenyl)-4-methyl-1-(4-(trifluoromethyl)phenyl)-3,4-dihydroisoquinoline-2(1H)-carboxamide and (1R,4R)—N-(4-fluorophenyl)-4-methyl-1-(4-(trifluoromethyl)phenyl)-3,4-dihydroisoquinoline-2(1H)-carboxamide

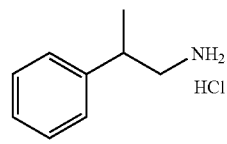

Step 1: 2-Phenylpropan-1-amine hydrochloride

To a stirred suspension of lithium aluminum hydride (2.94 g, 77.4 mmol) in dry ether (100 mL) at RT was added, under nitrogen, alpha-methylbenzyl cyanide (6.4 mL, 48.4 mmol) in dry ether (50 mL) over a 30 min period. Then it was heated under reflux for 3 h, cooled to 0° C. and treated sequentially with water (2.3 mL), NaOH (5N, 2.3 mL) and water (6.9 mL). The mixture was then stirred at RT for 1.5 h, filtered and the filtrate dried over Na$_2$SO$_4$ the solids were removed by filtration. The solution was treated with 1N HCl in ether (40 mL) and the white precipitated was separated by filtration to provide the title compound as a white solid.

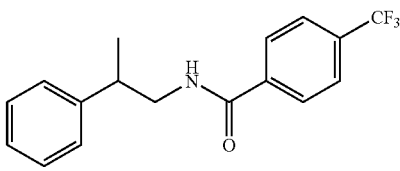 [SMILES: CC(CNC(=O)c1ccc(C(F)(F)F)cc1)c1ccccc1]

Step 2: N-(2-Phenylpropyl)-4-(trifluoromethyl)benzamide

A 250-mL round-bottomed flask was charged with 2-phenylpropan-1-amine hydrochloride (7.75 g, 45.1 mmol), DCM (75 mL) and cooled down to 0° C. Triethylamine (13.8 mL, 99.3 mmol) was added followed by slow addition of 4-(trifluoromethyl)benzoyl chloride (7.4 mL, 49.7 mmol). After the addition was completed the mixture was stirred at RT for 1 h, diluted with EtOAc, washed with 10% HCl, sat NaHCO₃, sat NaCl and dried over Na₂SO₄. The white residue was recrystallized from ether:hexanes and the title compound was obtained as a white solid. MS (ESI, positive ion) m/z: 308 (M+H).

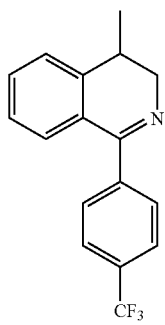 [SMILES: CC1CN=C(c2ccc(C(F)(F)F)cc2)c2ccccc21]

Step 3: 4-Methyl-1-(4-(trifluoromethyl)phenyl)-3,4-dihydroisoquinoline

A 250-mL round-bottomed flask was charged with N-(2-phenylpropyl)-4-(trifluoromethyl)benzamide (5.19 g, 16.9 mmol), phosphorous pentoxide (4.8 g, 33.8 mmol) and toluene (75 mL). The reaction mixture was heated at 110° C. overnight and allowed to cool down to RT. Then it was poured over ice-water and neutralized with NaOH (10%). The organic phase was separated and the aqueous phase was extracted several times with EtOAc. The combined organics were washed with satd. NaHCO₃, water, brine and dried over Na₂SO₄. The solvent was removed under vacuum and the product used without further purification.

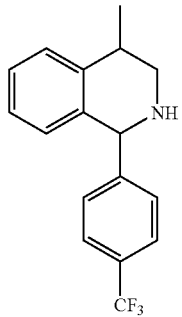 [SMILES: CC1CNC(c2ccc(C(F)(F)F)cc2)c2ccccc21]

Step 4: 4-Methyl-1-(4-(trifluoromethyl)phenyl)-1,2,3,4-tetrahydroisoquinoline A 100-mL round-bottomed flask was charged with 4-methyl-1-(4-(trifluoromethyl)phenyl)-3,4-dihydroisoquinoline (4.89 g, 16.9 mmol) and MeOH (30 mL). After cooling down to 0° C., sodium borohydride (1.93 g, 50.7 mmol) was added and the mixture was stirred at RT for 45 min. Then, the solvent was removed and the residue redissolved in EtOAc, washed with sat NaHCO₃, water and dried over Na₂SO₄. The mixture was used crude in the next step.

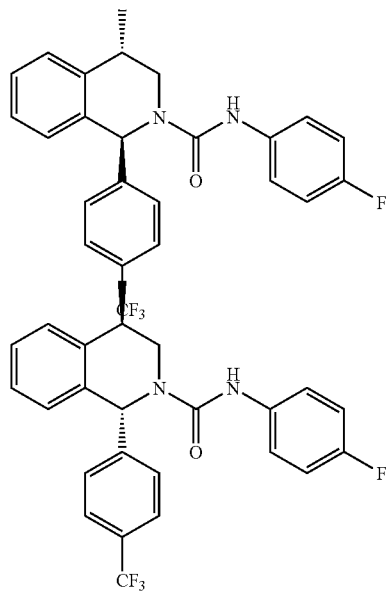

Step 5

(1S,4S)—N-(4-Fluorophenyl)-4-methyl-1-(4-(trifluoromethyl)phenyl)-3,4-dihydroisoquinoline-2(1H)-carboxamide and (1R,4R)—N-(4-fluorophenyl)-4-methyl-1-(4-(trifluoromethyl)phenyl)-3,4-dihydroisoquinoline-2(1H)-carboxamide A 25-mL round-bottomed flask was charged with 4-methyl-1-(4-(trifluoromethyl)phenyl)-1,2,3,4-tetrahydroisoquinoline (1.24 g, 4.3 mmol), DCE (10 mL) and 4-fluorophenyl isocyanate (528 µL, 4.7 mmol) and stirred at RT for 30 min. The solvent was then removed under vacuum and the residue purified by flash chromatography (10-20% EtOAc in hexanes). The title compounds were further purified by preparative HPLC (10%-100% of MeCN (0.1% TFA)/H₂O (0.1% TFA) (white solid). MS (ESI, positive ion) m/z: 429 (M+H).

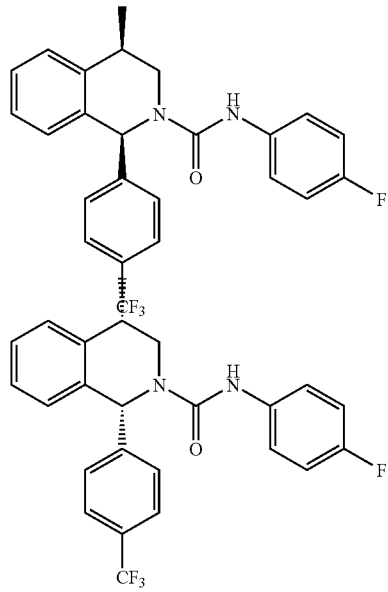

Example 39

(1S,4R)—N-(4-Fluorophenyl)-4-methyl-1-(4-(trifluoromethyl)phenyl)-3,4-dihydroisoquinoline-2(1H)-carboxamide and (1R,4S)—N-(4-Fluorophenyl)-4-methyl-1-(4-(trifluoromethyl)phenyl)-3,4-dihydroisoquinoline-2(1H)-carboxamide The title compounds were obtained as the second fraction after column chromatography from example 38 (step 5) (white solid). MS (ESI, positive ion) m/z: 429 (M+H).

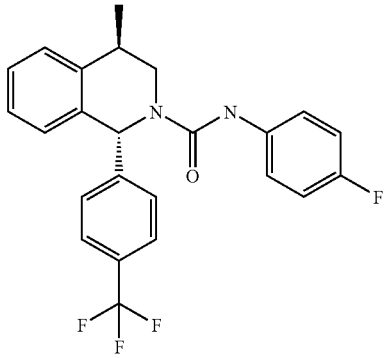 [SMILES: C[C@H]1CN(C(=O)Nc2ccc(F)cc2)[C@H](c2ccc(C(F)(F)F)cc2)c2ccccc21]

Example 40

(1R,4R)—N-(4-Fluorophenyl)-4-methyl-1-(4-(trifluoromethyl)phenyl)-3,4-dihydroisoquinoline-2(1H)-carboxamide Enantiomers of example 38 were separated using chiral SFC (Chiralcel AD-H (250×21 Mm), 45% methanol/CO$_2$ (100 bar), 65 mL/min, 220 nm) to give the title compound as a white solid. MS (ESI, positive ion) m/z: 429 (M+H).

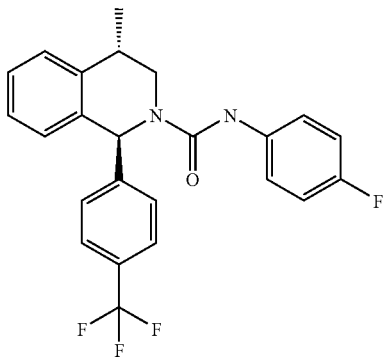 [SMILES: C[C@@H]1CN(C(=O)Nc2ccc(F)cc2)[C@@H](c2ccc(C(F)(F)F)cc2)c2ccccc21]

Example 41

(1S,4S)—N-(4-Fluorophenyl)-4-methyl-1-(4-(trifluoromethyl)phenyl)-3,4-dihydroisoquinoline-2(1H)-carboxamide Enantiomers of example 38 were separated using chiral SFC (Chiralcel AD-H (250×21 Mm), 45% methanol/CO$_2$ (100 bar), 65 mL/min, 220 nm) to give the title compound as a white solid. MS (ESI, positive ion) m/z: 429 (M+H).

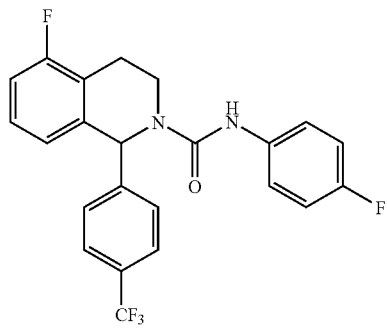 [SMILES: O=C(Nc1ccc(F)cc1)N1CCc2c(F)cccc2C1c1ccc(C(F)(F)F)cc1]

Example 42

5-Fluoro-N-(4-fluorophenyl)-1-(4-(trifluoromethyl)phenyl)-3,4-dihydroisoquinoline-2(1H)-carboxamide

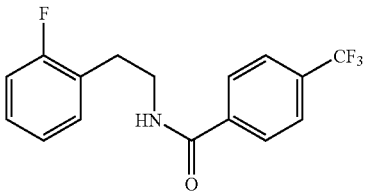 [SMILES: O=C(NCCc1ccccc1F)c1ccc(C(F)(F)F)cc1]

Step 1: N-(2-Fluorophenethyl)-4-(trifluoromethyl)benzamide

A 250-mL, round-bottomed flask containing a solution of 2-fluorophenethylamine (4.7 mL, 35.9 mmol) and diisopropylethylamine (6.3 mL, 35.9 mmol) in dichloromethane (35 mL) was cooled to 0° C. and treated dropwise with 4-(trifluoromethyl)benzoyl chloride (5.4 mL, 35.9 mmol) over 5 min. The ice-bath was removed after 2 h and the reaction mixture was stirred overnight. The precipitate formed was collected by filtration. The filtrate was diluted with dichloromethane (100 mL) and transferred to a separatory funnel, extracted with water (35 mL), brine (25 mL), and 1N HCl (25 mL). The dichloromethane layer was separated and formation of more precipitate was observed which was collected by filtration. The solids collected were combined and dried under vacuum to yield N-(2-fluorophenethyl)-4-(trifluoromethyl)benzamide as an off-white solid. MS (ESI pos. ion) m/z: 312 (M+H).

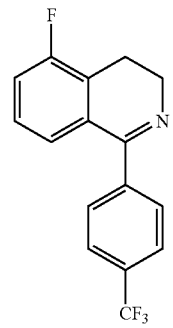 [SMILES: Fc1cccc2c1CCN=C2c1ccc(C(F)(F)F)cc1]

Step 2: 5-Fluoro-1-(4-(trifluoromethyl)phenyl)-3,4-dihydroisoquinoline

A suspension of N-(2-fluorophenethyl)-4-(trifluoromethyl)benzamide (2.0 g, 6.5 mmol) and phosphoric pentoxide (2.7 g, 19.1 mmol) in anhydrous toluene (40 mL) was heated at 125° C. for 4 h. At this stage more phosphoric pentoxide (2.7 g, 19.1 mmol) was added and continued stirring the reaction at 125° C. for additional 16 h. The reaction was cooled to RT, added ethyl acetate (100 mL), and the resulting slurry was slowly poured into ice-water (100 mL). Then more ethyl acetate (75 mL) was added and the resulting suspension was treated with KOH (3.0 N) until pH~11.0 was achieved. The ethyl acetate layer was separated, dried over anhydrous sodium sulfate, and concentrated under vacuum to provide 5-fluoro-1-(4-(trifluoromethyl)phenyl)-3,4-dihydroiso-quinoline as a yellow oil. MS (ESI pos. ion) m/z: 294 (M+H).

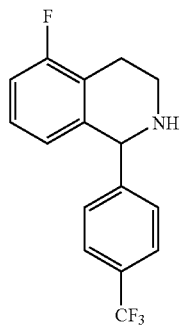

Step 3: 5-Fluoro-1-(4-(trifluoromethyl)phenyl)-1,2,3,4-tetrahydroisoquinoline

A solution of 5-fluoro-1-(4-(trifluoromethyl)phenyl)-3,4-dihydroisoquinoline (1.9 g, 6.6 mmol) in methanol (40 mL) from step 2 was cooled to 0° C. and sodium borohydride (0.6 g, 17 mmol) was added in small portions over 5 min and the reaction mixture was stirred at RT for 16 h. The reaction was quenched with ethyl acetate (20 mL) and concentrated to yield a reddish-yellow residue which was taken up in ethyl acetate (100 mL), water (30 mL), and saturated sodium bicarbonate (30 mL). After stirring for 15 min, it was transferred to a separatory funnel, the organic layer was separated, dried over anhydrous sodium sulfate, and concentrated to yield the crude product. The crude product was purified by silica gel chromatography (20-30% EtOAc in hexanes) to give 5-fluoro-1-(4-(trifluoromethyl)phenyl)-1,2,3,4-tetrahydroisoquinoline as a pale-yellow solid. MS (ESI pos. ion) m/z: 296 (M+H).

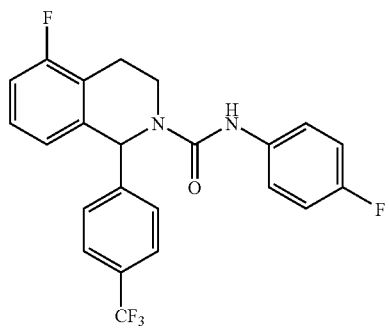 [SMILES: O=C(Nc1ccc(F)cc1)N1CCc2c(F)cccc2C1c1ccc(C(F)(F)F)cc1]

Step 4: 5-Fluoro-N-(4-fluorophenyl)-1-(4-(trifluoromethyl)phenyl)-3,4-dihydroisoquinoline-2(1H)-carboxamide A solution of 5-fluoro-1-(4-(trifluoromethyl)phenyl)-1,2,3,4-tetrahydroisoquinoline (0.27 g, 0.897 mmol) and diisopropylethylamine (0.2 mL, 0.919 mmol) in anhydrous dichloromethane (6 mL) was treated with 4-fluorophenyl isocyanate (0.105 mL, 0.934 mmol) and stirred at RT for 16 h. The solvent was removed in vacuo and the residue was purified by preparative HPLC [gradient 10-90% MeCN (0.1% TFA)/H$_2$O (0.1% TFA)] to give the pure product which was dissolved in methanol (10 mL) and neutralized by passing the solution through a Polymer Lab-HCO$_3$ Macroporous resin cartridge, and the filtrate was concentrated to give 5-fluoro-N-(4-fluorophenyl)-1-(4-(trifluoromethyl)phenyl)-3,4-dihydroisoquinoline-2(1H)-carboxamide as a colorless oil. MS (ESI pos. ion) m/z: 433 (M+H).

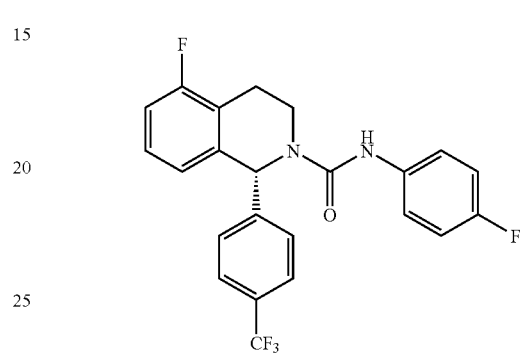

Example 43

(R)-5-Fluoro-N-(4-fluorophenyl)-1-(4-(trifluoromethyl)phenyl)-3,4-dihydro-isoquinoline-2(1H)-carboxamide Purification of racemic 5-fluoro-N-(4-fluorophenyl)-1-(4-(trifluoromethyl)-phenyl)-3,4-dihydroisoquinoline-2(1H)-carboxamide on chiral SFC using the following conditions (Chiralcel AD-H (250×21 Mm), 45% methanol/CO$_2$ (100 bar), 65 mL/min, 220 nm) provided (R)-5-fluoro-N-(4-fluorophenyl)-1-(4-(trifluoromethyl)phenyl)-3,4-dihydroisoquinoline-2(1H)-carboxamide as a white solid. MS (ESI pos. ion) m/z: 433 (M+H).

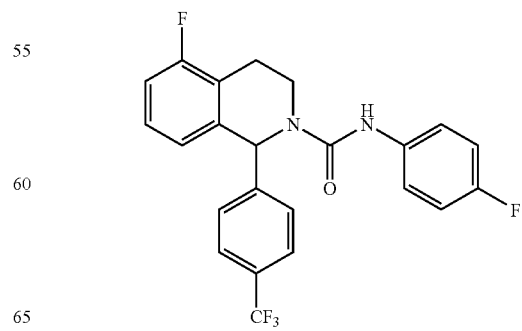

Example 44

6-Fluoro-N-(4-fluorophenyl)-1-(4-(trifluoromethyl)phenyl)-3,4-dihydroisoquinoline-2(1H)-carboxamide

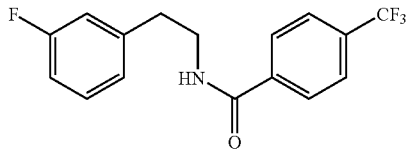 [SMILES: O=C(NCCc1cccc(F)c1)c1ccc(C(F)(F)F)cc1]

Step 1: N-(3-fluorophenethyl)-4-(trifluoromethyl)benzamide

A 250-mL, round-bottomed flask containing a solution of 2-(3-fluorophenyl)ethanamine (1.3 mL, 9.6 mmol) and diisopropylethylamine (1.7 mL, 9.6 mmol) in dichloromethane (32 mL) was cooled to 0° C. and treated dropwise with 4-(trifluoromethyl)benzoyl chloride (2.0 mL, 9.6 mmol) over 5 min. The ice-bath was removed after 2 h and the reaction mixture was stirred overnight. The precipitate formed was collected by filtration. The filtrate was diluted with dichloromethane (100 mL) and transferred to a separatory funnel and extracted with water (35 mL). The dichloromethane layer was separated and formation of precipitate was observed which was collected by filtration. The filtrate was concentrated to yield more solid and the combined solids were dried under vacuum to yield N-(3-fluorophenethyl)-4-(trifluoromethyl)benzamide as a white solid. MS (ESI pos. ion) m/z: 312 (M+H).

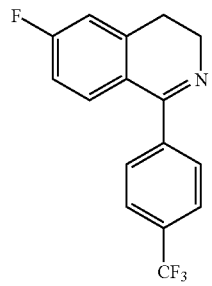 [SMILES: Fc1ccc2c(c1)CCN=C2c1ccc(C(F)(F)F)cc1]

Step 2: 6-fluoro-1-(4-(trifluoromethyl)phenyl)-3,4-dihydroisoquinoline

A suspension of N-(3-fluorophenethyl)-4-(trifluoromethyl)benzamide (2.8 g, 8.9 mmol) and phosphoric pentoxide (0.6 g, 0.45 mmol) in polyphosphoric acid (62.0 g, 8.9 mmol) was heated at 170° C. for 75 min. The hot reaction mixture was poured into ice and KOH (20% W/V, 50 mL) was added followed by diethyl ether (100 mL) and stirred for 5 mins. Additional KOH was added until pH~11.0 was achieved. Then, EtOAc (200 mL) was added and the mixture continued stirring at RT for an additional 5 min. and the ethyl acetate layer was separated. The aqueous layer was back-extracted with ethyl acetate (3×200 mL). The combined ethyl acetate layers were dried over anhydrous sodium sulfate, and concentrated under vacuum to provide 6-fluoro-1-(4-(trifluoromethyl)phenyl)-3,4-dihydroisoquinoline as a yellow oil. MS (ESI pos. ion) m/z: 294 (M+H).

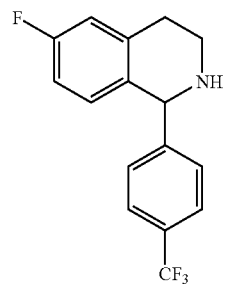 [SMILES: Fc1ccc2c(c1)CCNC2c1ccc(C(F)(F)F)cc1]

Step 3: 6-fluoro-1-(4-(trifluoromethyl)phenyl)-1,2,3,4-tetrahydroisoquinoline A solution of 6-fluoro-1-(4-(trifluoromethyl)phenyl)-3,4-dihydroisoquinoline (2.6 g, 8.9 mmol) in methanol (50 mL) from step 2 was cooled to 0° C. and sodium borohydride (1.0 g, 2.7 mmol) was added in small portions over 5 min and the reaction mixture was stirred at RT for 16 h. The reaction was quenched with ethyl acetate (20 mL) and concentrated to yield a reddish-yellow residue which was taken up in ethyl acetate (100 mL), water (30 mL), and saturated sodium bicarbonate (30 mL). After stirring for 15 min, it was transferred to a separatory funnel, the organic layer was separated, dried over anhydrous sodium sulfate, and concentrated to yield the crude product. The crude product was purified by silica gel chromatography (20-30% EtOAc in hexanes) to give 6-fluoro-1-(4-(trifluoromethyl)phenyl)-1,2,3,4-tetrahydroisoquinoline as a pale-yellow solid. MS (ESI pos. ion) m/z: 296 (M+H).

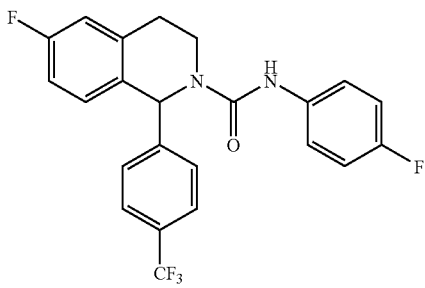 [SMILES: O=C(Nc1ccc(F)cc1)N1CCc2cc(F)ccc2C1c1ccc(C(F)(F)F)cc1]

Step 4: 6-fluoro-N-(4-fluorophenyl)-1-(4-(trifluoromethyl)phenyl)-3,4-dihydroisoquinoline-2(1H)-carboxamide A solution of 6-fluoro-1-(4-(trifluoromethyl)phenyl)-1,2,3,4-tetrahydroisoquinoline (0.3 g, 1.0 mmol) and diisopropylethylamine (0.2 mL, 0.919 mmol) in anhydrous dichloromethane (6 mL) was treated with 4-fluorophenyl isocyanate (0.14 g, 1.0 mmol) and stirred at RT for 16 h. Formation of a white precipitate was observed which was collected by filtration. The solid was dried under high vacuum to give 6-fluoro-N-(4-fluorophenyl)-1-(4-(trifluoromethyl)phenyl)-3,4-dihy droisoquinoline-2(1H)-carboxamide (0.35 g, 80%). MS (ESI pos. ion) m/z: 433 (M+H).

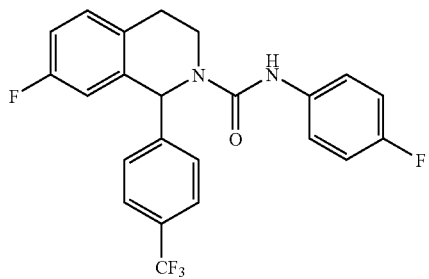 [SMILES: O=C(Nc1ccc(F)cc1)N1CCc2ccc(F)cc2C1c1ccc(C(F)(F)F)cc1]

Example 45

7-Fluoro-N-(4-fluorophenyl)-1-(4-(trifluoromethyl)phenyl)-3,4-dihydroisoquinoline-2(1H)-carboxamide

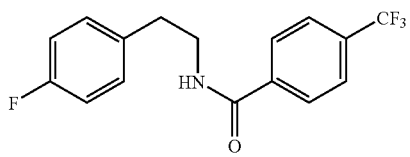 [SMILES: O=C(NCCc1ccc(F)cc1)c1ccc(C(F)(F)F)cc1]

Step 1: N-(4-fluorophenethyl)-4-(trifluoromethyl)benzamide

A 250-mL, round-bottomed flask containing a solution of 4-fluorophenethylamine (4.8 mL, 37 mmol) and diisopropylethylamine (6.4 mL, 37 mmol) in dichloromethane (40 mL) was cooled to 0° C. and treated dropwise with 4-(trifluoromethyl)benzoyl chloride (5.5 mL, 37 mmol) over 5 min. The ice-bath was removed after 2 h and the reaction mixture was stirred overnight. The precipitate formed was collected by filtration. The filtrate was diluted with dichloromethane (100 mL) and transferred to a separatory funnel, extracted with water (35 mL), brine (25 mL), and 1N HCl (25 mL). The dichloromethane layer was separated and formation of more precipitate was observed which was collected by filtration. The solids collected were combined and dried under vacuum to yield N-(4-fluorophenethyl)-4-(trifluoromethyl)benzamide as an off-white solid. MS (ESI pos. ion) m/z: 312 (M+H).

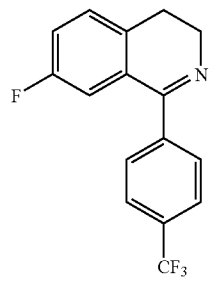 [SMILES: Fc1ccc2c(c1)C(c1ccc(C(F)(F)F)cc1)=NCC2]

Step 2: 7-Fluoro-1-(4-(trifluoromethyl)phenyl)-3,4-dihydroisoquinoline

A suspension of N-(4-fluorophenethyl)-4-(trifluoromethyl)benzamide (5.3 g, 17.1 mmol) and phosphoric pentoxide (1.2 g, 8.6 mmol) in polyphosphoric acid (40 g) was heated at 165° C. for 4 h and The reaction was cooled to RT and ice was added followed by ethyl acetate (100 mL), KOH (3N, 25 mL), and water (75 mL). The mixture was stirred for 15 min and the organic layer was separated. The aqueous layer was neutralized with KOH (3N) till pH~7.0 was achieved and extracted with ethyl acetate (250 mL). The ethyl acetate layer was separated, dried over anhydrous sodium sulfate, and concentrated under vacuum to provide 7-fluoro-1-(4-(trifluoromethyl)phenyl)-3,4-dihydroisoquinoline. MS (ESI pos. ion) m/z: 294 (M+H).

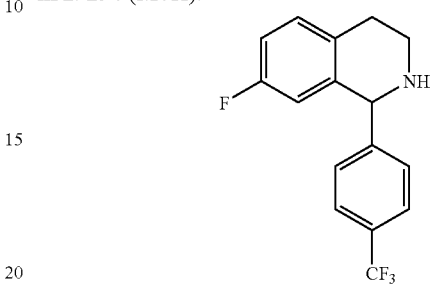

Step 3: 7-Fluoro-1-(4-(trifluoromethyl)phenyl)-1,2,3,4-tetrahydroisoquinoline A solution of 7-fluoro-1-(4-(trifluoromethyl)phenyl)-3,4-dihydroisoquinoline (0.6 g, 2.1 mmol) in methanol (10 mL) from step 2 was cooled to 0° C. and sodium borohydride (0.2 g, 6.2 mmol) was added in small portions over 5 min and the reaction mixture was stirred at RT for 16 h. The reaction was quenched with ethyl acetate (10 mL) and concentrated to yield a light-yellow residue which was dissolved in ethyl acetate (40 mL), water (10 mL), and saturated sodium bicarbonate (20 mL). After stirring for 15 min, it was transferred to a separatory funnel, the organic layer was separated, dried over anhydrous sodium sulfate, and concentrated to yield the crude product. The crude product was purified by silica gel chromatography (20-30% EtOAc in hexanes) to give 7-fluoro-1-(4-(trifluoromethyl)phenyl)-1,2,3,4-tetrahydroisoquinoline as a pale-yellow solid. MS (ESI pos. ion) m/z: 296 (M+H).

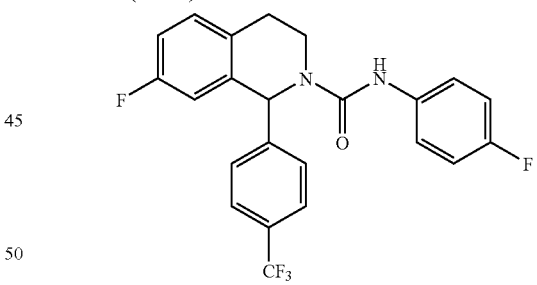

Step 4: 7-fluoro-N-(4-fluorophenyl)-1-(4-(trifluoromethyl)phenyl)-3,4-dihydroisoquinoline-2(1H)-carboxamide A solution of 7-fluoro-1-(4-(trifluoromethyl)phenyl)-1,2,3,4-tetrahydroisoquinoline (0.09 g, 0.3 mmol) and diisopropylethylamine (0.06 mL, 0.32 mmol) in anhydrous dichloromethane (3 mL) was treated with 4-fluorophenyl isocyanate (0.04 mL, 0.4 mmol) and stirred at RT for 16 h. The solvent was removed in vacuo and the residue was purified by preparative HPLC [gradient 10-90% MeCN (0.1% TFA)/H$_2$O (0.1% TFA)] to give the pure product which was dissolved in methanol (10 mL) and neutralized by passing the solution through a Polymer Lab-HCO$_3$ Macroporous resin cartridge, and the filtrate was concentrated to give 5-fluoro-N-(4-fluorophenyl)-1-(4-(trifluoromethyl)phenyl)-3,4-dihydroiso-quinoline-2(1H)-carboxamide as an off-white solid. MS (ESI pos. ion) m/z: 433 (M+H).

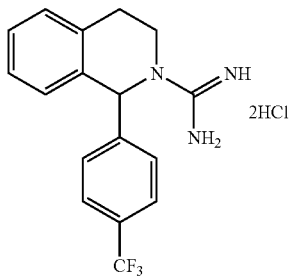 [SMILES: N=C(N)N1CCc2ccccc2C1c1ccc(C(F)(F)F)cc1 ; "2HCl"]

Example 46

1-(4-(trifluoromethyl)phenyl)-3,4-dihydroisoquino-line-2(1H)-carboxamidine dihydrochloride

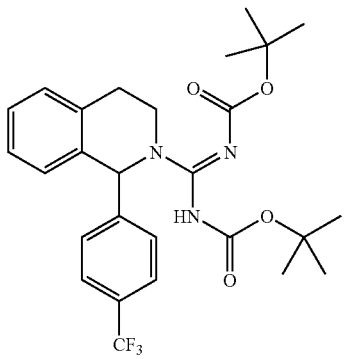 [SMILES: CC(C)(C)OC(=O)/N=C(/NC(=O)OC(C)(C)C)N1CCc2ccccc2C1c1ccc(C(F)(F)F)cc1]

Step 1: Bis-boc-guanidine derivative

A solution of 1-(4-(trifluoromethyl)phenyl)-1,2,3,4-tetrahy-droisoquinoline (0.6 g, 2.3 mmol) and 1,3-bis(tert-butoxycar-bonyl)-2-methyl-2-thiopseudourea (0.75 g, 2.6 mmol) in dichloromethane (12 mL) was treated with mercuric chloride (0.645 g, 2.4 mmol) followed by triethylamine (0.5 mL, 3.5 mmol) and stirred the reaction at RT for 16 h. Formation of a very fine grayish-white precipitate was seen. The precipitate was removed by filtration through a sintered funnel, washed with 25 mL dichloromethane. The combined filtrates were transferred to a separatory funnel, washed with water (50 mL), brine (50 mL), dried over anhydrous sodium sulfate and, concentrated on the rotary evaporator to yield the crude product. The crude product was purified by silica gel chromatography (20-30% EtOAc in hexanes) to give the desired product as an off-white solid. MS (ESI pos. ion) m/z: 296 (M+H).

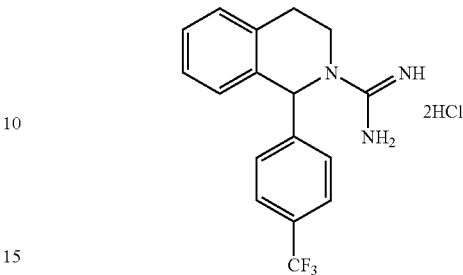

Step 2: 1-(4-(Trifluoromethyl)phenyl)-3,4-dihy-droisoquinoline-2(1H)-carboxamidine dihydrochloride A solution of the product from step 1 (0.9 g, 2 mmol) in 1,4-dioxane (10 mL) was treated with hydrogen chloride (4.0M solution in 1,4-dioxane, 20 mL, 80 mmol) was stirred at RT for 16 h. During work up the solvent was removed under high vacuum and the resulting gummy solid was re-dissolved in methanol (50 mL), and concentrated again on the rotary evaporator. The resulting solid was stirred with hexanes (75 mL) for 30 min, after which the solid was collected by filtration. The solid 1-(4-(trifluoromethyl)phenyl)-3,4-dihy-droisoquinoline-2(1H)-carboxamidine dihydrochloride (0.62 g, 87% yield) was collected as an off-white solid. MS (ESI pos. ion) m/z: 320 (M+H).

General Procedure for Examples (47-65)

To a solution of (R)-1-(4-(trifluoromethyl)phenyl)-1,2,3,4-tetrahydroisoquinoline (70 mg, 0.25 mmol, example 30, step 1) in DCM (0.8 mL) and pyridine (0.2 mL) was added the corresponding acid chloride (0.3 mmol). The reaction mixture was stirred at RT for 16 h. Then, $H_2O$ (0.1 mL) and MeOH (0.5 mL) were added. The solvents were removed under vacuum and the residue was dissolved in DMSO (1 mL). The solution mixture was purified by preparative HPLC to provide the target compound. The product was dissolved in MeOH (1 mL) and washed through $PL-HCO_3$ MP-resin, the resin was further washed with MeOH (2×0.4 mL). The combined filtrates were then concentrated and dried in vacuo to give the title compounds.

| Example | Structure | Name | MS (ESI, positive ion) M + H |
|---|---|---|---|
| 47 | 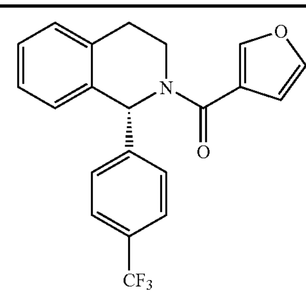 | (R)-Furan-3-yl(1-(4-(trifluoromethyl)phenyl)-3,4-dihydroisoquinolin-2(1H)-yl)methanone | 372 |

| Example | Structure | Name | MS (ESI, positive ion) M + H |
|---|---|---|---|
| 48 | 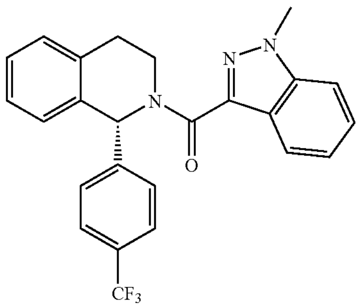 [SMILES: Cn1nc(C(=O)N2CCc3ccccc3[C@H]2c2ccc(C(F)(F)F)cc2)c2ccccc21] | (R)-(1-Methyl-1H-indazol-3-yl)(1-(4-(trifluoromethyl)phenyl)-3,4-dihydroisoquinolin-2(1H)-yl)methanone | 436 |
| 49 | 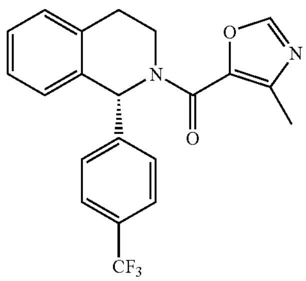 [SMILES: Cc1ncoc1C(=O)N1CCc2ccccc2[C@H]1c1ccc(C(F)(F)F)cc1] | (R)-(4-Methyloxazol-5-yl)(1-(4-(trifluoromethyl)phenyl)-3,4-dihydroisoquinolin-2(1H)-yl)methanone | 387 |
| 50 | 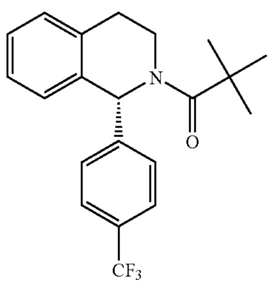 [SMILES: CC(C)(C)C(=O)N1CCc2ccccc2[C@H]1c1ccc(C(F)(F)F)cc1] | (R)-2,2-Dimethyl-1-(1-(4-(trifluoromethyl)phenyl)-3,4-dihydroisoquinolin-2(1H)-yl)propan-1-one | 362 |
| 51 | 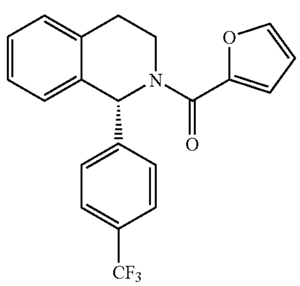 [SMILES: O=C(c1ccco1)N1CCc2ccccc2[C@H]1c1ccc(C(F)(F)F)cc1] | (R)-Furan-2-yl(1-(4-(trifluoromethyl)phenyl)-3,4-dihydroisoquinolin-2(1H)-yl)methanone | 372 |
| 52 | 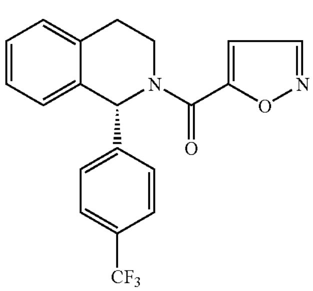 [SMILES: O=C(c1ccno1)N1CCc2ccccc2[C@H]1c1ccc(C(F)(F)F)cc1] | (R)-Isoxazol-5-yl(1-(4-(trifluoromethyl)phenyl)-3,4-dihydroisoquinolin-2(1H)-yl)methanone | 373 |

| Example | Structure | Name | MS (ESI, positive ion) M + H |
|---|---|---|---|
| 53 | 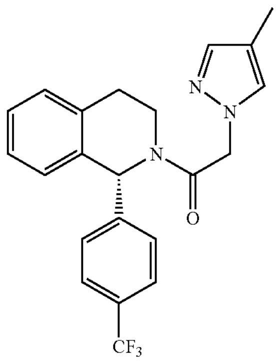 [SMILES: Cc1cnn(CC(=O)N2CCc3ccccc3[C@H]2c2ccc(C(F)(F)F)cc2)c1] | (R)-2-(4-Methyl-1H-pyrazol-1-yl)-1-(1-(4-(trifluoromethyl)phenyl)-3,4-dihydroisoquinolin-2(1H)-yl)ethanone | 400 |
| 54 | 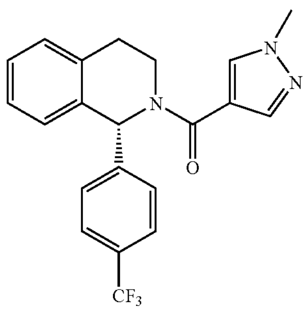 [SMILES: Cn1cc(C(=O)N2CCc3ccccc3[C@H]2c2ccc(C(F)(F)F)cc2)cn1] | (R)-(1-Methyl-1H-pyrazol-4-yl)(1-(4-(trifluoromethyl)phenyl)-3,4-dihydroisoquinolin-2(1H)-yl)methanone | 386 |
| 55 | 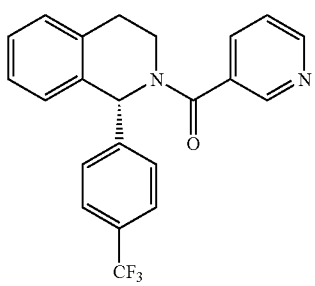 [SMILES: O=C(c1cccnc1)N1CCc2ccccc2[C@H]1c1ccc(C(F)(F)F)cc1] | (R)-Pyridin-3-yl(1-(4-(trifluoromethyl)phenyl)-3,4-dihydroisoquinolin-2(1H)-yl)methanone | 383 |
| 56 | 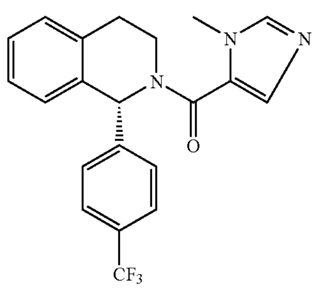 [SMILES: Cn1cncc1C(=O)N1CCc2ccccc2[C@H]1c1ccc(C(F)(F)F)cc1] | (R)-(1-Methyl-1H-imidazol-5-yl)(1-(4-(trifluoromethyl)phenyl)-3,4-dihydroisoquinolin-2(1H)-yl)methanone | 386 |
| 57 | 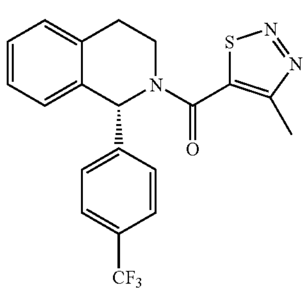 [SMILES: Cc1nnsc1C(=O)N1CCc2ccccc2[C@H]1c1ccc(C(F)(F)F)cc1] | (R)-(4-Methyl-1,2,3-thiadiazol-5-yl)(1-(4-(trifluoromethyl)phenyl)-3,4-dihydroisoquinolin-2(1H)-yl)methanone | 404 |

-continued

| Example | Structure | Name | MS (ESI, positive ion) M + H |
|---|---|---|---|
| 58 | 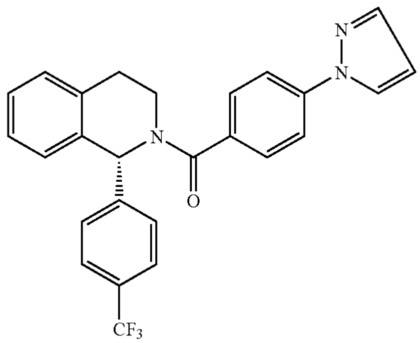 [SMILES: O=C(c1ccc(-n2cccn2)cc1)N1CCc2ccccc2[C@H]1c1ccc(C(F)(F)F)cc1] | (R)-(4-(1H-Pyrazol-1-yl)phenyl)(1-(4-(trifluoromethyl)phenyl)-3,4-dihydroisoquinolin-2(1H)-yl)methanone | 448 |
| 59 | 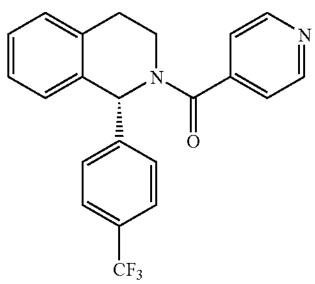 [SMILES: O=C(c1ccncc1)N1CCc2ccccc2[C@H]1c1ccc(C(F)(F)F)cc1] | (R)-Pyridin-4-yl(1-(4-(trifluoromethyl)phenyl)-3,4-dihydroisoquinolin-2(1H)-yl)methanone | 383 |
| 60 | 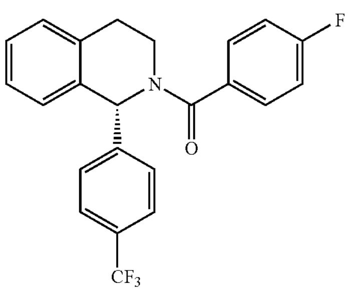 [SMILES: O=C(c1ccc(F)cc1)N1CCc2ccccc2[C@H]1c1ccc(C(F)(F)F)cc1] | (R)-(4-Fluorophenyl)(1-(4-(trifluoromethyl)phenyl)-3,4-dihydroisoquinolin-2(1H)-yl)methanone | 400 |
| 61 | 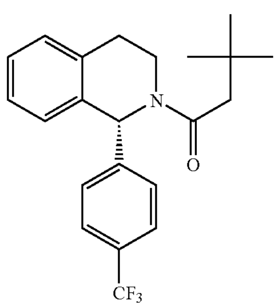 [SMILES: CC(C)(C)CC(=O)N1CCc2ccccc2[C@H]1c1ccc(C(F)(F)F)cc1] | (R)-3,3-Dimethyl-1-(1-(4-(trifluoromethyl)phenyl)-3,4-dihydroisoquinolin-2(1H)-yl)butan-1-one | 376 |
| 62 | 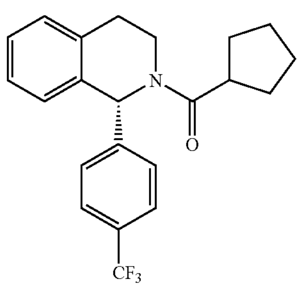 [SMILES: O=C(C1CCCC1)N1CCc2ccccc2[C@H]1c1ccc(C(F)(F)F)cc1] | (R)-Cyclopentyl(1-(4-(trifluoromethyl)phenyl)-3,4-dihydroisoquinolin-2(1H)-yl)methanone | 374 |

-continued

| Example | Structure | Name | MS (ESI, positive ion) M + H |
|---|---|---|---|
| 63 | 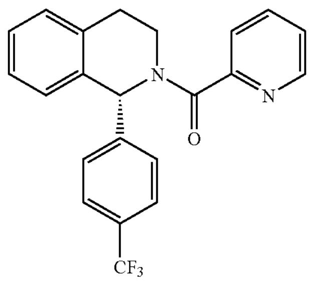 [SMILES: O=C(c1ccccn1)N1CCc2ccccc2[C@H]1c1ccc(C(F)(F)F)cc1] | (R)-Pyridin-2-yl(1-(4-(trifluoromethyl)phenyl)-3,4-dihydroisoquinolin-2(1H)-yl)methanone | 383 |
| 64 | 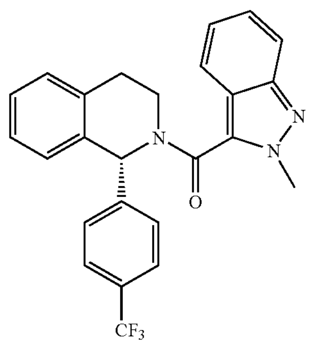 [SMILES: Cn1nc2ccccc2c1C(=O)N1CCc2ccccc2[C@H]1c1ccc(C(F)(F)F)cc1] | (R)-(2-Methyl-2H-indazol-3-yl)(1-(4-(trifluoromethyl)phenyl)-3,4-dihydroisoquinolin-2(1H)-yl)methanone | 436 |
| 65 | 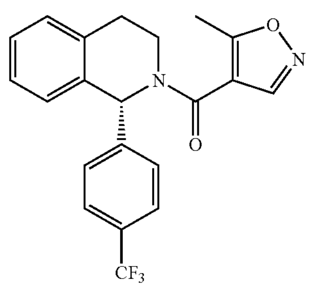 [SMILES: Cc1oncc1C(=O)N1CCc2ccccc2[C@H]1c1ccc(C(F)(F)F)cc1] | (R)-(5-Methylisoxazol-4-yl)(1-(4-(trifluoromethyl)phenyl)-3,4-dihydroisoquinolin-2(1H)-yl)methanone | 387 |

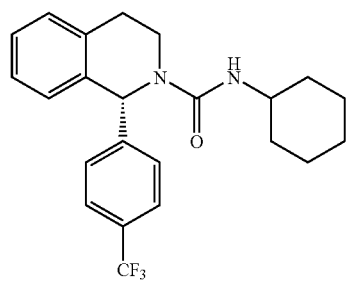 [SMILES: O=C(NC1CCCCC1)N1CCc2ccccc2[C@H]1c1ccc(C(F)(F)F)cc1]

Example 66

(R)—N-Cyclohexyl-1-(4-(trifluoromethyl)phenyl)-3,4-dihydroisoquinoline-2(1H)-carboxamide Enantiomers, N-cyclohexyl-1-(4-(trifluoromethyl)phenyl)-3,4-dihydroisoquinoline-2(1H)-carboxamide (example 13) were separated using chiral SFC (Chiralcel AD-H (250×21 Mm), 45% methanol/$CO_2$ (100 bar), 65 mL/min, 220 nm) to give the title compound as a white solid. MS (ESI, positive ion) m/z: 403 (M+H).

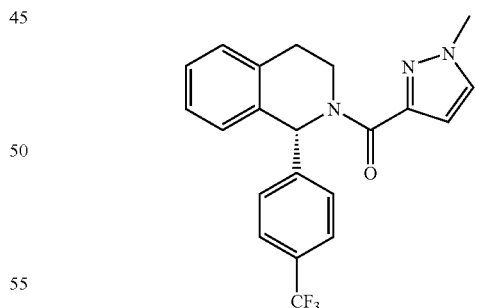

Example 67

(R)-(1-Methyl-4H-pyrazol-3-yl)(1-(4-(trifluoromethyl)phenyl)-3,4-dihydroisoquinolin-2(1H)-yl)methanone A solution of (R)-1-(4-(trifluoromethyl)phenyl)-1,2,3,4-tetrahydroisoquinoline (58 mg, 0.21 mmol, example 30, step 1) in DMF (1 mL) was added 1-methyl-1H-pyrazole-3-carboxylic acid (Fluorochem, 34 mg, 0.27 mmol), 1-hydroxybenzotriazole hydrate (42 mg, 0.27 mmol), and N-((isopropylimino)methylene)propan-2-amine (66 μL, 0.42 mmol). The resulting mixture was then stirred at RT for 16 h. Then, the mixture was filtered and the filtrate was purified by preparative HPLC to give the target compound. The product was dissolved in MeOH and passed through PL-HCO₃ MP resin and the resin was washed with MeOH (2×0.3 mL). The combined filtrates were concentrated and dried under vacuum to give the title compound as a light-yellow solid. MS (ESI, positive ion) m/z: 386 (M+H).

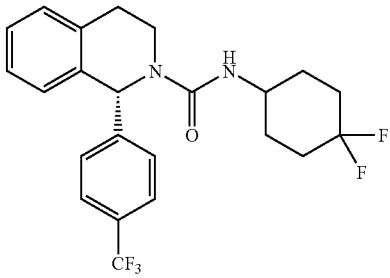 [SMILES: O=C(NC1CCC(F)(F)CC1)N1CCc2ccccc2[C@H]1c1ccc(C(F)(F)F)cc1]

Example 68

(R)—N-(4,4-Difluorocyclohexyl)-1-(4-(trifluoromethyl)phenyl)-3,4-dihydroisoquinoline-2(1H)-carboxamide Step 1: 4-Nitrophenyl 4,4-difluorocyclohexylcarbamate

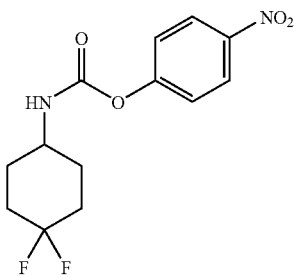 [SMILES: O=C(NC1CCC(F)(F)CC1)Oc1ccc([N+](=O)[O-])cc1]

To a solution of 4,4-difluorocyclohexanamine hydrochloride (Matrix scientific, 250 mg, 1.45 mmol) in DCM (5 mL) was added 4-nitrophenyl chloroformate (367 mg, 1.82 mmol) and DIEA (507 μl, 0.29 mmol). The resulting mixture was then stirred at RT for 16 h. Then, MeOH (2 mL) was added and the solvents were removed. The residue was purified by silica gel flash column chromatography (0%-100% EtOAc/hexane) to give the title compound as a yellow solid.

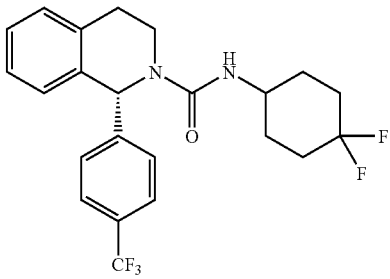

Step 2: (R)—N-(4,4-Difluorocyclohexyl)-1-(4-(trifluoromethyl)phenyl)-3,4-dihydroisoquinoline-2(1H)-carboxamide To a solution of (R)-1-(4-(trifluoromethyl)phenyl)-1,2,3,4-tetrahydroisoquinoline (80 mg, 0.29 mmol) in MeCN (2 mL) was added 4-nitrophenyl 4,4-difluoro-cyclohexylcarbamate (217 mg, 0.72 mmol). The resulting mixture was then subjected to microwave irradiation at 120° C. for 15 min. Then, MeOH (0.5 mL) was added and the mixture was filtered. The filtrate was purified by preparative HPLC (0%-100% MeCN 0.1% TFA/H₂O 0.1% TFA) to give the title compound, which was dissolved in MeOH (1 mL). The solution was then passed through PL-HCO₃ and the resin was washed with MeOH (2×0.3 mL). The combined filtrates were concentrated and dried in vacuo to give the title compound as a light-yellow solid. MS (ESI, positive ion) m/z: 439 (M+H).

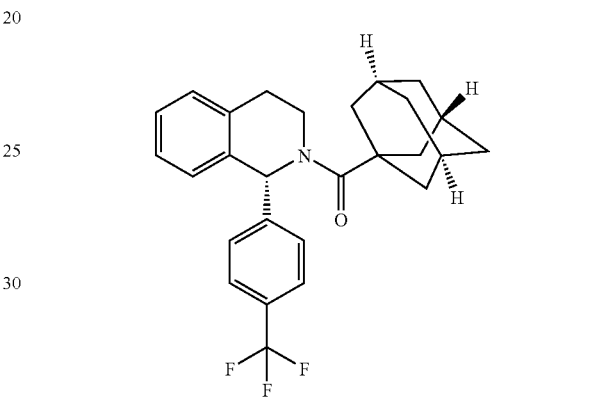

Example 69

(1R)-2-(tricyclo[3.3.1.1~3,7~]dec-1-ylcarbonyl)-1-(4-(trifluoromethyl)phenyl)-1,2,3,4-tetrahydroisoquinoline A solution of (R)-1-(4-(trifluoromethyl)phenyl)-1,2,3,4-tetrahydroisoquinoline (0.05 g, 0.2 mmol) in DMF (1 mL) was treated with N-((isopropylimino)methyl-ene)propan-2-amine (0.07 mL, 0.5 mmol), 1H-benzo[d][1,2,3]triazol-1-ol hydrate (0.04 g, 0.2 mmol), and 1-adamantanecarboxylic acid (TCI, 0.04 g, 0.2 mmol). The resulting mixture was heated at 65° C. for 12 h. The reaction was cooled to RT and the filtrate was purified by preparative HPLC [gradient 10-90% MeCN (0.1% TFA)/H₂O (0.1% TFA)] to give the pure product. It was dissolved in methanol (10 mL) and neutralized by passing the solution through a Polymer Lab-HCO₃ Macroporous resin cartridge, and the filtrate was concentrated to give (1R)-2-(tricyclo[3.3.1.1~3,7~]dec-1-ylcarbonyl)-1-(4-(trifluoromethyl)phenyl)-1,2,3,4-tetrahydroisoquinoline as a colorless solid. MS (ESI, positive ion) m/z: 440 (M+H).

Example 70

1-(3,4-Difluorophenyl)-N-(4-fluorophenyl)-3,4-dihydroisoquinoline-2(1H)-carboxamide

Step 1. 3,4-Difluoro-N-phenethylbenzamide

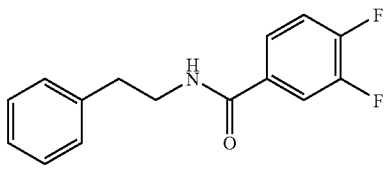 [SMILES: O=C(NCCc1ccccc1)c1ccc(F)c(F)c1]

To a stirred solution of phenethylamine (1.01 mL, 7.95 mmol) and DIEA (1.38 mL, 7.95 mmol) in 20 mL of DCM, 3,4-difluorobenzoyl chloride (1.00 mL, 7.95 mmol) was added dropwise. The clear solution was stirred for 1 h. The reaction mixture was concentrated and the crude product was purified by silica gel chromatography (0-30% EtOAc in hexanes) to give the title compound as a white solid. $^1$H NMR (300 MHz, CHLOROFORM-d) δ ppm 7.57 (ddd, J=10.63, 7.56, 2.12 Hz, 1H) 7.31-7.44 (m, 3H) 7.15-7.31 (m, 4H) 6.02 (br. s., 1H) 3.67-3.78 (m, 2H) 2.94 (t, J=6.87 Hz, 2H).

Step 2. 1-(3,4-Difluorophenyl)-3,4-dihydroisoquinoline

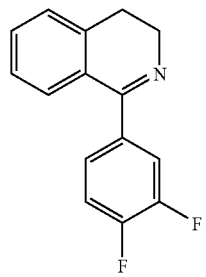 [SMILES: Fc1ccc(C2=NCCc3ccccc32)cc1F]

To a 250-mL round-bottomed flask, 3,4-difluoro-N-phenethylbenzamide (1.97 g, 7.54 mmol) and phosphorus pentoxide (3.25 g, 22.9 mmol) were suspended into 40 mL of toluene. Phosphorus oxychloride (3.51 mL, 37.7 mmol) was added and the mixture was refluxed for overnight. The mixture was cooled to RT. The supernatant contained only the starting material and was removed. Ice water (75 mL) was added to the residue in the flask and stirred to break up the solid into powder. EtOAc was added and the pH was adjusted to ~12 with 3N aqueous potassium hydroxide. The layers were separated and the aqueous phase was extracted with EtOAc. The combined organic phases were washed with water and saturated aqueous sodium chloride. The organic phase was dried over sodium sulfate, filtered and concentrated in vacuo to afford a yellow viscous oil. The crude product was purified by silica gel chromatography (20-70% EtOAc in hexanes) to afford the title compound as a clear oil. $^1$H NMR (300 MHz, CHLOROFORM-d) δ ppm 7.17-7.52 (m, 7H) 3.78-3.92 (m, 2H) 2.73-2.89 (m, 2H)

Step 3. 1-(3,4-Difluorophenyl)-1,2,3,4-tetrahydroisoquinoline

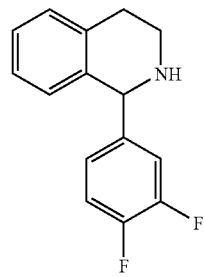 [SMILES: Fc1ccc(C2NCCc3ccccc32)cc1F]

To a stirred solution of 1-(3,4-difluorophenyl)-3,4-dihydroisoquinoline (1.34 g, 5.51 mmol) in 20 mL of MeOH, sodium borohydride (0.4366 g, 11.5 mmol) was added. The mixture was stirred for 1 h. MeOH was evaporated and the residue was partitioned between EtOAc and saturated aqueous sodium bicarbonate. The aqueous phase was extracted with EtOAc. The combined organic phases were washed with water and saturated aqueous sodium chloride. The organic phase was dried over sodium sulfate, filtered and concentrated in vacuo to afford a white solid. The crude product was purified by silica gel chromatography (0-5% iso-propanol (with 10% ammonium hydroxide) in CHCl$_3$) to afford the title compound as a white solid. $^1$H NMR (300 MHz, CHLOROFORM-d) δ ppm 6.99-7.22 (m, 6H) 6.74 (d, J=7.60 Hz, 1H) 5.08 (s, 1H) 3.18-3.32 (m, 1H) 2.96-3.18 (m, 2H) 2.76-2.90 (m, 1H).

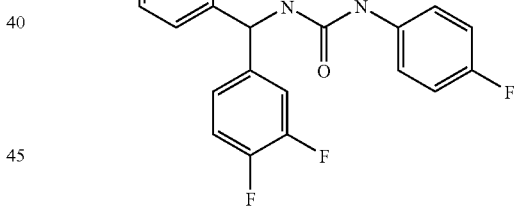

tep 4. 1-(3,4-Difluorophenyl)-N-(4-fluorophenyl)-3,4-dihydroisoquinoline-2(1H)-carboxamide To a stirred solution of 1-(3,4-difluorophenyl)-1,2,3,4-tetrahydroisoquinoline (0.1019 g, 0.415 mmol) in 3 mL of DCM, 4-fluorophenyl isocyanate (0.0550 mL, 0.484 mmol) was added. The clear solution was stirred for 1 h. The solvent was evaporated and residue was taken into small amount of DCM. The resulting precipitate was collected to yield the title compound as a white solid. The filtrate was concentrated and purified by silica gel chromatography (0-30% EtOAc in hexanes) to afford another batch of the title compound as a white solid. MS (ESI pos. ion) m/z: 383 (M+1). $^1$H NMR (300 MHz, CHLOROFORM-d) δ ppm 7.16-7.37 (m, 6H) 6.93-

7.13 (m, 5H) 6.54 (s, 1H) 6.40 (s, 1H) 3.66 (t, J=6.28 Hz, 2H) 2.77-3.08 (m, 2H).

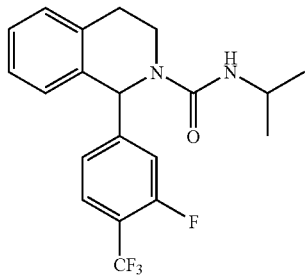 [SMILES: CC(C)NC(=O)N1CCc2ccccc2C1c1ccc(C(F)(F)F)c(F)c1]

Example 71

1-(3-Fluoro-4-(trifluoromethyl)phenyl)-N-isopropyl-3,4-dihydroisoquinoline-2(1H)-carboxamide

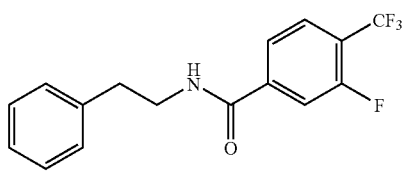 [SMILES: O=C(NCCc1ccccc1)c1ccc(C(F)(F)F)c(F)c1]

Step 1.
3-Fluoro-N-phenethyl-4-(trifluoromethyl)benzamide

To a 100-mL round-bottomed flask, 3-fluoro-4-(trifluoromethyl)benzoic acid (1.036 g, 4.98 mmol) and 2-phenylethanamine (0.700 mL, 5.53 mmol) were dissolved into 25 mL of DMF. Triethylamine (0.840 mL, 6.03 mmol) was added followed by 1-ethyl-3-(3-dimethylaminopropyl)carbodiimide hydrochloride (0.955 g, 4.98 mmol) and 1-hydroxybenzotriazole (0.915 g, 5.97 mmol). The mixture was stirred for 28 h. The reaction mixture was poured into 80 mL of saturated aqueous sodium bicarbonate. The aqueous phase was extracted with EtOAc. The combined organic phases were washed with saturated aqueous sodium bicarbonate, water and saturated aqueous sodium chloride. The organic phase was dried over sodium sulfate, filtered and concentrated in vacuo to afford a yellowish solid. DCM was added to the crude product and the resulting solid was collected via filtration to afford the title compound as a white solid. The filtrate was concentrated and purified by silica gel chromatography (100% EtOAc) to afford another batch of the title compound as a white solid. $^1$H NMR (300 MHz, CHLOROFORM-d) δ ppm 7.66 (t, J=7.45 Hz, 1H) 7.46-7.59 (m, 2H) 7.28-7.41 (m, 3H) 7.20-7.26 (m, 2H) 6.14 (br. s., 1H) 3.69-3.81 (m, 2H) 2.96 (t, J=6.87 Hz, 2H).

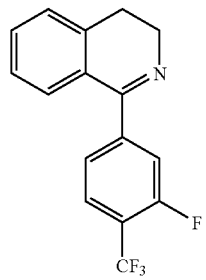 [SMILES: Fc1cc(C2=NCCc3ccccc32)ccc1C(F)(F)F]

Step 2. 1-(3-Fluoro-4-(trifluoromethyl)phenyl)-3,4-dihydroisoquinoline

To a stirred mixture of 3-fluoro-N-phenethyl-4-(trifluoromethyl)benzamide (1.27 g, 4.08 mmol) in 30 mL of toluene, phosphorus pentoxide (1.751 g, 12.3 mmol) and phosphorus oxychloride (1.90 mL, 20.4 mmol) were added. The mixture was refluxed for overnight. The reaction mixture was cooled to RT. Supernatant was removed and the ice-water was added to the flask containing the residue. The mixture was stirred to break the chunks into powder. EtOAc was added and the pH was adjusted to ~12 with 3N aqueous potassium hydroxide. The layers were separated and the aqueous phase was extracted with EtOAc. The combined organic phases were washed with water and saturated aqueous sodium chloride. The organic phase was dried over sodium sulfate, filtered and concentrated in vacuo to afford 0.887 g of yellow viscous oil. The crude product was purified by silica gel chromatography (0-30% EtOAc in hexanes) to afford the title compound as a clear oil. $^1$H NMR (300 MHz, CHLOROFORM-d) δ ppm 7.63-7.73 (m, 1H) 7.39-7.54 (m, 3H) 7.31 (d, J=7.60 Hz, 2H) 7.16-7.24 (m, 1H) 3.84-3.96 (m, 2H) 2.77-2.89 (m, 2H).

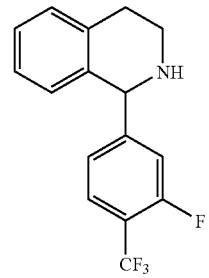 [SMILES: Fc1cc(C2NCCc3ccccc32)ccc1C(F)(F)F]

Step 3. 1-(3-Fluoro-4-(Frifluoromethyl)phenyl)-1,2,3,4-tetrahydroisoquinoline

To a stirred solution of 1-(3-fluoro-4-(trifluoromethyl)phenyl)-3,4-dihydroisoquinoline (0.750 g, 2.6 mmol) in 10 mL of MeOH, sodium borohydride (0.197 g, 5.2 mmol) was added. The mixture was stirred for 2.5 h. MeOH was evaporated and the residue was partitioned between EtOAc and saturated aqueous sodium bicarbonate. The aqueous phase was extracted with EtOAc. The combined organic phases were washed with water and saturated aqueous sodium chloride. The organic phase was dried over sodium sulfate, filtered and concentrated in vacuo to afford a white solid. The crude product was purified by silica gel chromatography (30-70% EtOAc in hexanes to afford the title compound as a white solid. $^1$H NMR (400 MHz, CHLOROFORM-d) δ ppm 7.56 (t, J=7.63 Hz, 1H) 7.05-7.24 (m, 5H) 6.73 (d, J=7.63 Hz, 1H) 5.16 (s, 1H) 3.19-3.29 (m, 1H) 2.97-3.16 (m, 2H) 2.79-2.89 (m, 11-1).

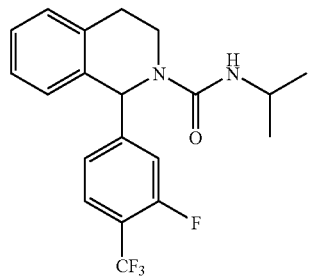 [SMILES: CC(C)NC(=O)N1CCc2ccccc2C1c1ccc(C(F)(F)F)c(F)c1]

Step 4. 1-(3-Fluoro-4-(trifluoromethyl)phenyl)-N-isopropyl-3,4-dihydroisoquinoline-2(1H)-carboxamide To a stirred solution of 1-(3-fluoro-4-(trifluoromethyl)phenyl)-1,2,3,4-tetrahydro-isoquinoline (0.1020 g, 0.345 mmol) in 3 mL of DCM, isopropyl isocyanate (0.0400 mL, 0.407 mmol) was added. The solution was stirred for 1 h. Solvent was evaporated and the residue was purified by silica gel chromatography (0-50% EtOAc in hexanes) then again with 10-40% EtOAc in hexanes to afford the title compound as a white solid. MS (ESI pos. ion) m/z: 381.1 (M+1). $^1$H NMR (300 MHz, CHLOROFORM-d) δ ppm 7.48 (t, J=7.75 Hz, 1H) 7.19-7.32 (m, 2H) 7.01-7.14 (m, 2H) 6.55 (s, 1H) 4.30 (s, 1H) 3.98-4.13 (m, 1H) 3.38-3.63 (m, 2H) 2.69-2.98 (m, 2H) 1.13-1.25 (m, 6H).

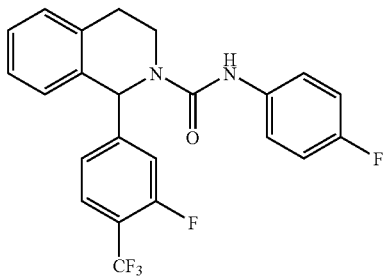 [SMILES: O=C(Nc1ccc(F)cc1)N1CCc2ccccc2C1c1ccc(C(F)(F)F)c(F)c1]

Example 72

1-(3-Fluoro-4-(trifluoromethyl)phenyl)-N-(4-fluorophenyl)-3,4-dihydroisoquinoline-2(1H)-carboxamide To a stirred solution of 1-(3-fluoro-4-(trifluoromethyl)phenyl)-1,2,3,4-tetrahydro-isoquinoline (0.0845 g, 0.286 mmol, Example 71 Step 3) in 3 mL of DCM, 4-fluorophenyl isocyanate (0.0358 mL, 0.315 mmol) was added. The solution was stirred for 1 h. Solvent was evaporated and the residue was purified by silica gel chromatography (0-50% EtOAc in hexanes) to yield the title compound as a white solid. MS (ESI pos. ion) m/z: 433.1 (M+1). $^1$H NMR (300 MHz, CHLOROFORM-d) δ ppm 7.51 (t, J=7.75 Hz, 1H) 7.22-7.39 (m, 6H) 7.06-7.19 (m, 2H) 6.96-7.05 (m, 2H) 6.63 (s, 1H) 6.45 (s, 1H) 3.59-3.81 (m, 2H) 2.76-3.08 (m, 2H).

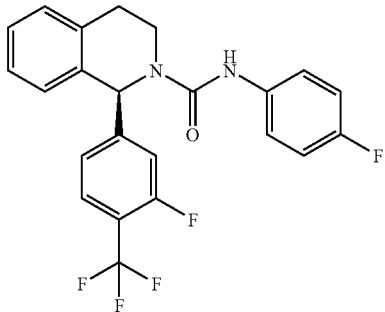 [SMILES: O=C(Nc1ccc(F)cc1)N1CCc2ccccc2[C@@H]1c1ccc(C(F)(F)F)c(F)c1]

Example 73

(S)-1-(3-Fluoro-4-(trifluoromethyl)phenyl)-N-(4-fluorophenyl)-3,4-dihydro-isoquinoline-2(1H)-carboxamide After chiral separation (SFC) of the enantiomers of the previous example 72, the title compound was obtained. MS (ESI pos. ion) m/z: 433.1 (M+1).

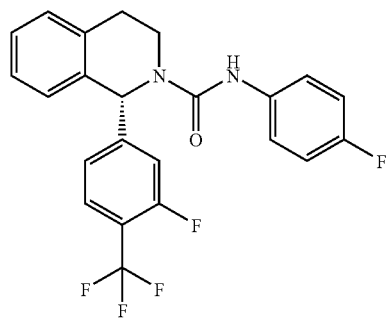 [SMILES: O=C(Nc1ccc(F)cc1)N1CCc2ccccc2[C@H]1c1ccc(C(F)(F)F)c(F)c1]

Example 74

(R)-1-(3-Fluoro-4-(trifluoromethyl)phenyl)-N-(4-fluorophenyl)-3,4-dihydroisoquinoline-2(1H)-carboxamide After chiral separation (SFC) of the enantiomers of the previous example 72, the title compound was obtained. MS (ESI pos. ion) m/z: 433.1 (M+1).

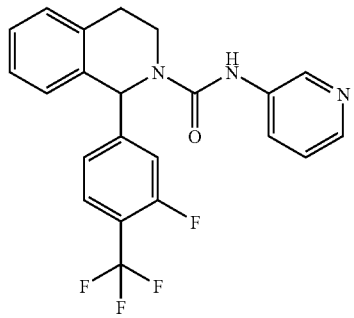 [SMILES: O=C(Nc1cccnc1)N1CCc2ccccc2C1c1ccc(C(F)(F)F)c(F)c1]

Example 75

1-(3-Fluoro-4-(trifluoromethyl)phenyl)-N-(pyridin-3-yl)-3,4-dihydroisoquinoline-2(1H)-carboxamide 1-(3-fluoro-4-(trifluoromethyl)phenyl)-1,2,3,4-tetrahydroisoquinoline (0.1500 g, 0.508 mmol, Example 71 Step 3) was dissolved in 3 mL CH$_2$Cl$_2$ and DIEA (0.0884 mL, 0.508 mmol) and 3-pyridyl isocyanate (0.0732 g, 0.610 mmol) were added at RT. The mixture was stirred over night and hydrolyzed with 2 mL water. The reaction was extracted 3 times with EtOAc (3×20 mL), dried over MgSO$_4$ and evaporated. The crude product was purified via glass column chromatography providing 1-(3-fluoro-4-(trifluoromethyl)phenyl)-N-(pyridin-3-yl)-3,4-dihydroisoquinoline-2(1H)-carboxamide as a white solid. MS (ESI, positive ion) m/z: 416.0 (M+H). The majority of the material was submitted for chiral purification (SFC):

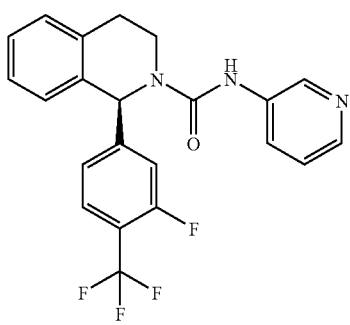 [SMILES: O=C(Nc1cccnc1)N1CCc2ccccc2[C@@H]1c1ccc(C(F)(F)F)c(F)c1]

Example 76

(S)-1-(3-Fluoro-4-(trifluoromethyl)phenyl)-N-(pyridin-3-yl)-3,4-dihydroisoquinoline-2(1H)-carboxamide After chiral separation (SFC) of the enantiomers of the previous example the title compound was obtained. MS (ESI, positive ion) m/z: 416.0 (M+H)

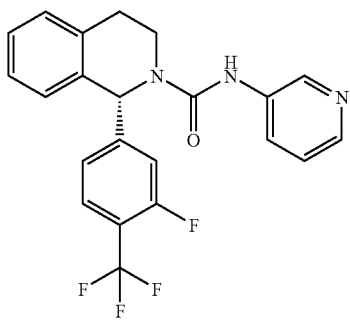 [SMILES: O=C(Nc1cccnc1)N1CCc2ccccc2[C@H]1c1ccc(C(F)(F)F)c(F)c1]

Example 77

(R)-1-(3-Fluoro-4-(trifluoromethyl)phenyl)-N-(pyridin-3-yl)-3,4-dihydroisoquinoline-2(1H)-carboxamide After chiral separation (SFC) of the enantiomers of the previous example the title compound was obtained. MS (ESI, positive ion) m/z: 416.0 (M+H)

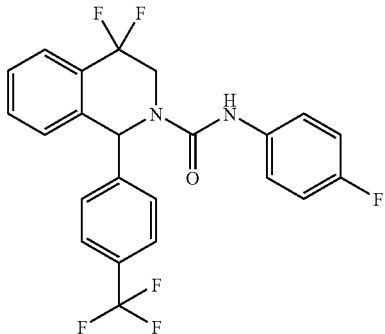 [SMILES: O=C(Nc1ccc(F)cc1)N1CC(F)(F)c2ccccc2C1c1ccc(C(F)(F)F)cc1]

Example 78

4,4-Difluoro-N-(4-fluorophenyl)-1-(4-(trifluoromethyl)phenyl)-3,4-dihydro-isoquinoline-2(1H)-carboxamide

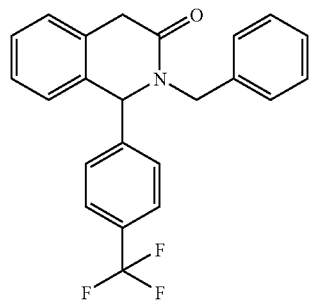 [SMILES: O=C1Cc2ccccc2C(c2ccc(C(F)(F)F)cc2)N1Cc1ccccc1]

Step 1. 2-Benzyl-1-(4-(trifluoromethyl)phenyl)-1,2-dihydroisoquinolin-3(4H)-one 4-(Trifluoromethyl)benzaldehyde (1.87 mL, 14.0 mmol) and benzylamine (1.53 mL, 14.0 mmol) were dissolved into 40 mL of DCM and 4 Å molecular sieve was added. The mixture was left under nitrogen for 3 days. Molecular sieve was removed via filtration. 25 mL of DCM was used to wash the filter cake. To the filtrate, phenylacetyl chloride (1.90 mL, 14.4 mmol) was added and the pale yellow solution was stirred for 2 h. Then trifluoromethanesulfonic acid (6.20 mL, 70.1 mmol) was added. The mixture was stirred for 1.5 h then poured into a mixture of ice (~100 mL) and 5N sodium hydroxide (~50 mL). The phases were separated and the aqueous phase was extracted with DCM. The combined organic phases were dried over sodium sulfate, filtered and concentrated in vacuo to afford a yellow oil. The crude product was purified by silica gel chromatography (0-30% EtOAc in hexanes) twice to afford the title compound as a light yellow semi-solid. $^1$H NMR (300 MHz, DMSO-$d_6$) δ ppm 7.56-7.74 (m, 4H) 7.41 (d, J=6.87 Hz, 1H) 7.13-7.33 (m, 8H) 5.80 (s, 1H) 5.30 (d, J=15.20 Hz, 1H) 3.81-4.01 (m, 2H) 3.66-3.78 (m, 1H).

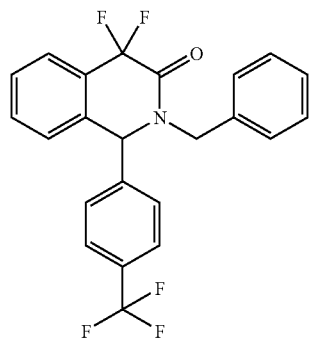 [SMILES: O=C1N(Cc2ccccc2)C(c2ccc(C(F)(F)F)cc2)c2ccccc2C1(F)F]

Step 2. 2-Benzyl-4,4-difluoro-1-(4-(trifluoromethyl)phenyl)-1,2-dihydroisoquinolin-3(4H)-one To a stirred solution of 2-benzyl-1-(4-(trifluoromethyl)phenyl)-1,2-dihydroisoquinolin-3(4H)-one (1.472 g, 3.86 mmol) in 20 mL of THF, lithium bis(trimethyl-silyl)amide (1.0M in THF/ethyl benzene, 8.49 mL, 8.49 mmol) was added slowly at −78° C. The solution was stirred at −78° C. for 30 min, then n-fluorobenzenesulfonimide (2.799 g, 8.875 mmol) in a total of 15 mL THF was added slowly. After the solution was stirred at −78° C. for 1 h, the cold bath was removed and the reaction mixture was allowed to warm up to RT. EtOAc was added followed by 100 mL saturated aqueous NH$_4$Cl. Layers were separated and the aqueous phase was extracted with EtOAc. The organic phase was washed with water and saturated aqueous sodium chloride. The aqueous washes were combined and back-extracted with EtOAc. The combined organic phases were dried over sodium sulfate, filtered and concentrated in vacuo to afford 2.90 g of slurry. DCM and methyl t-butyl ether were added to the crude product and the resulting white precipitate was removed via filtration. The filtrate was concentrated to give a light yellow residue. The crude product was purified by silica gel chromatography (0-30% EtOAc in hexanes) to afford the title compound as a pale yellow solid. $^1$H NMR (300 MHz, CHLOROFORM-d) δ ppm 7.83-7.91 (m, 1H) 7.65 (d, J=8.04 Hz, 2H) 7.30-7.52 (m, 7H) 7.19-7.26 (m, 2H) 7.07 (s, 1H) 5.65 (d, J=14.91 Hz, 1H) 5.53 (d, J=3.51 Hz, 1H) 3.64 (dd, J=14.91, 1.61 Hz, 1H).

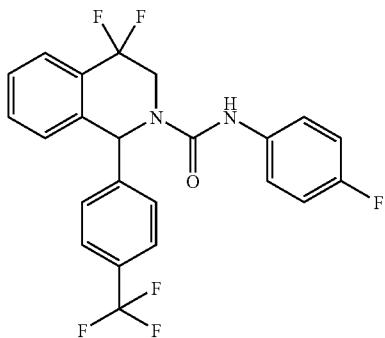 [SMILES: O=C(Nc1ccc(F)cc1)N1CC(F)(F)c2ccccc2C1c1ccc(C(F)(F)F)cc1]

Step 3. 2-Benzyl-4,4-difluoro-1-(4-(trifluoromethyl)phenyl)-1,2,3,4-tetrahydroisoquinoline To a stirred solution of borane tetrahydrofuran complex (1M in THF, 0.750 mL, 0.750 mmol) in 5 mL of THF, 2-benzyl-4,4-difluoro-1-(4-(trifluoromethyl)-phenyl)-1,2-dihydroisoquinolin-3(4H)-one (0.103 g, 0.246 mmol) in a total of 5 mL THF was added dropwise. The clear solution was refluxed for 5 h. After the reaction mixture was cooled to 0° C., 5 mL of 5 N hydrochloric acid was added. The solution was stirred at 0° C. to RT over 1 h. Then the most organic solvent was evaporated and the pH was adjusted to ~8 by solid sodium bicarbonate. The aqueous phase was extracted with EtOAc. The combined organic phases were washed with water and saturated aqueous sodium chloride. The organic phase was dried over sodium sulfate, filtered and concentrated in vacuo to afford the title compound as a white solid. 11-1 NMR (300 MHz, CHLOROFORM-d) δ ppm 7.76 (d, J=7.75 Hz, 1H) 7.62 (d, J=8.18 Hz, 2H) 7.46 (d, J=8.04 Hz, 2H) 7.28-7.42 (m, 7H) 6.77 (d, J=7.75 Hz, 1H) 4.80 (d, J=3.65 Hz, 1H) 3.82 (dd, J=13.59, 1.75 Hz, 1H) 3.37-3.54 (m, 2H) 2.87-3.06 (m, 1H).

Step 4. 4,4-Difluoro-N-(4-fluorophenyl)-1-(4-(trifluoromethyl)phenyl)-3,4-dihydroisoquinoline-2(1H)-carboxamide To a 50-mL round-bottomed flask, 2-benzyl-4,4-difluoro-1-(4-(trifluoromethyl)-phenyl)-1,2,3,4-tetrahydroisoquinoline (0.0418 g, 0.10 mmol) and Pd/C (0.0729 g, 0.69 mmol) were mixed into 5 mL of EtOH. The reaction mixture was evacuated under vacuum and refilled with hydrogen (4 times). The mixture was hydrogenated under balloon pressure of hydrogen for 4 h. The catalyst was removed via filtration through a pad of Celite. The filtrate was concentrated to give 0.0291 g of clear film. This product was dissolved in DCM (~2 mL) and 1-isocyanato-4-(trifluoromethyl)benzene (0.0200 mL, 0.13 mmol) was added and the mixture was stirred for 30 min. The reaction mixture was directly purified by silica gel chromatography (0-30% EtOAc in hexanes) twice to afford the title compound as a white solid. MS (ESI pos. ion) m/z: 451.1 (M+1) and 473.1 (M+23). $^1$H NMR (300 MHz, CHLOROFORM-d) δ ppm 7.79-7.88 (m, 1H) 7.60 (d, J=8.18 Hz, 2H) 7.47-7.56 (m, 2H) 7.41 (d, J=8.18 Hz, 2H) 7.28-7.36 (m, 2H) 7.14-7.22 (m, 1H) 6.96-7.07 (m, 2H) 6.84 (s, 1H) 6.54 (s, 1H) 4.07-4.23 (m, 1H) 3.53-3.76 (m, 1H).

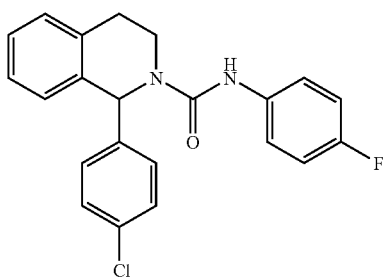 [SMILES: O=C(Nc1ccc(F)cc1)N1CCc2ccccc2C1c1ccc(Cl)cc1]

Example 79

1-(4-Chlorophenyl)-N-(4-fluorophenyl)-3,4-dihydroisoquinoline-2(1H)-carboxamide

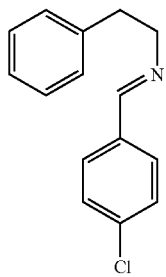 [SMILES: Clc1ccc(/C=N/CCc2ccccc2)cc1]

Step 1: N-(4-Chlorobenzylidene)-2-phenylethanamine

To a rb-flask containing MgSO₄ (3.06 g, 25.4 mmol) in benzene (10 mL) was added 4-chlorobenzaldehyde (2.02 g, 14.4 mmol) and 4-chlorobenzaldehyde (2.02 g, 14.4 mmol) and the suspension stirred at RT 2 h. The suspension was filtered and the solid washed with benzene (2×2 mL). The combined filtrates were concentrated to give the crude imine as a yellow/white solid.

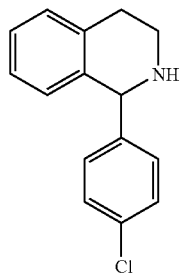

Step 2: 1-(4-Chlorophenyl)-1,2,3,4-tetrahydroisoquinoline

To a solution of trifluoromethanesulfonic acid (15.3 mL, 173 mmol) at 0° C. was added N-(4-chlorobenzylidene)-2-phenylethanamine (3.38 g) and the reaction was heated to 120° C. and stirred 17 h under N₂. The reaction was poured into ice water (100 mL) and basisified with 5N NaOH (45 mL). The aqueous layer was extracted with CH₂Cl₂ (3×100 mL). The combined organic layers were washed with saturated NaCl (100 mL), dried (MgSO₄) and concentrated to give a yellow/brown oil. The residue was purified by ISCO (120 g SiO₂, 0-50% EtOAc/hexane) to give 1-(4-chlorophenyl)-1,2,3,4-tetrahydroisoquinoline as a tan solid.

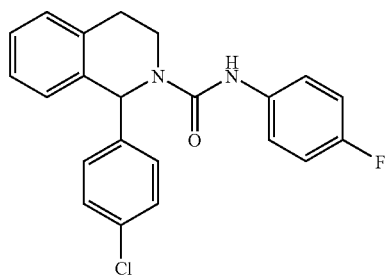 [SMILES: O=C(Nc1ccc(F)cc1)N1CCc2ccccc2C1c1ccc(Cl)cc1]

Step 3: 1-(4-Chlorophenyl)-N-(4-fluorophenyl)-3,4-dihydroisoquinoline-2(1H)-carboxamide To a solution of 1-(4-chlorophenyl)-1,2,3,4-tetrahydroisoquinoline (150 mg, 615 µmol) in CH₂Cl₂ (2.0 mL) at RT was added 1-fluoro-4-isocyanatobenzene (85.8 µL, 739 µmol). The reaction was stirred 3 h and then directly purified by reverse phase HPLC to give the title compound as a white solid. MS (ESI pos. ion) m/z: 381 (M+1).

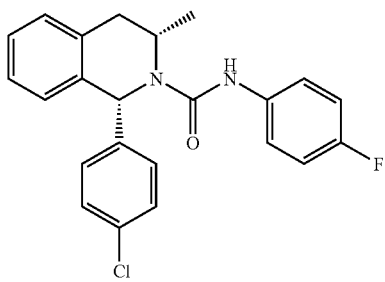 [SMILES: C[C@H]1Cc2ccccc2[C@@H](c2ccc(Cl)cc2)N1C(=O)Nc1ccc(F)cc1]

Example 80

(1R,3S)-1-(4-Chlorophenyl)-N-(4-fluorophenyl)-3-methyl-3,4-dihydroisoquinoline-2(1H)-carboxamide [stereochemistry is arbitrarily assigned]

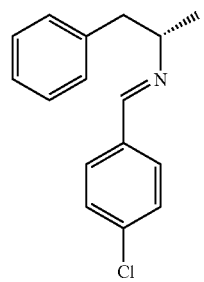 [SMILES: C[C@@H](Cc1ccccc1)/N=C/c1ccc(Cl)cc1]

Step 1: (S)—N-(4-Chlorobenzylidene)-1-phenylpropan-2-amine [stereochemistry is arbitrarily assigned]

To a solution of (S)-1-phenylpropan-2-amine (626 mg, 4630 µmol) in benzene (10 mL) was added 4-chlorobenzaldehyde (651 mg, 4630 µmol) and MgSO₄ (1000 mg, 8308 µmol) and the suspension stirred at RT 4 h. The suspension was filtered and the solid washed with benzene (2×2 mL). The combined filtrates were concentrated to give (S)—N-(4-chlorobenzylidene)-1-phenylpropan-2-amine, which was carried on into the next step without purification.

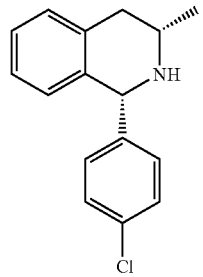

Step 2: (1R,3S)-1-(4-Chlorophenyl)-3-methyl-1,2,3,4-tetrahydroisoquinoline [stereochemistry is arbitrarily assigned]

To a flask with trifluoromethanesulfonic acid (3.00 mL, 34 mmol) at 0° C. was added dropwise (S)—N-(4-chlorobenzylidene)-1-phenylpropan-2-amine (1.20 g, 1.61 mmol) and the reaction was heated to 120° C. and stirred 19 h under N₂. The reaction was cooled, poured into ice water (20 mL), and basisified with 5 N NaOH (6 mL). The aqueous layer was extracted with CH₂Cl₂ (3×10 mL). The combined organic layers were washed with saturated NaCl (20 mL), dried (MgSO₄), and concentrated to give a yellow/brown oil. The residue was purified by ISCO (40 g SiO₂, 0-100% EtOAc/hexane) to give (1R,3S)-1-(4-chlorophenyl)-3-methyl-1,2,3,4-tetrahydroisoquinoline as a light yellow oil.

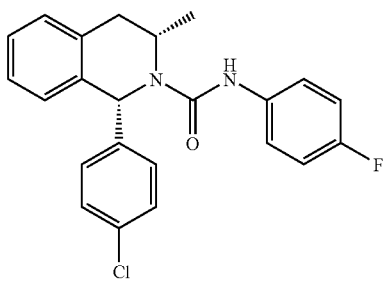 [SMILES: C[C@H]1Cc2ccccc2[C@@H](c2ccc(Cl)cc2)N1C(=O)Nc1ccc(F)cc1]

Step 3: (1R,3S)-1-(4-Chlorophenyl)-N-(4-fluorophenyl)-3-methyl-3,4-dihydro-isoquinoline-2(1H)-carboxamide [stereochemistry is arbitrarily assigned]

To a solution of (1R,3S)-1-(4-chlorophenyl)-3-methyl-1,2,3,4-tetrahydroisoquinoline (60 mg, 233 μmol) in CH₂Cl₂ (1.0 mL) at RT was added 1-fluoro-4-isocyanatobenzene (42 μL, 361 μmol). The reaction was stirred 4 h and directly purified by reverse phase HPLC to give (1R,3S)-1-(4-chlorophenyl)-N-(4-fluorophenyl)-3-methyl-3,4-dihydroisoquinoline-2(1H)-carboxamide as a light purple solid. MS (ESI pos. ion) m/z: 395 (M+1).

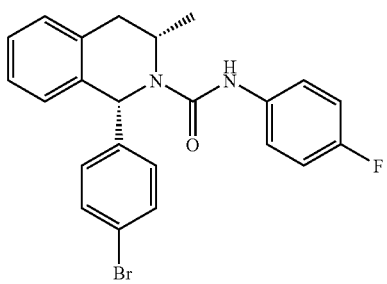 [SMILES: C[C@H]1Cc2ccccc2[C@@H](c2ccc(Br)cc2)N1C(=O)Nc1ccc(F)cc1]

Example 81

(1R,3S)-1-(4-Bromophenyl)-N-(4-fluorophenyl)-3-methyl-3,4-dihydroisoquinoline-2(1H)-carboxamide [stereochemistry is arbitrarily assigned]

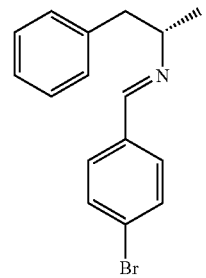

Step 1: (S)—N-(4-Bromobenzylidene)-1-phenylpropan-2-amine [stereochemistry is arbitrarily assigned]

To a solution of (S)-1-phenylpropan-2-amine (323 mg, 2389 μmol) in benzene (5 mL) was added 4-bromobenzaldehyde (442 mg, 2389 μmol and MgSO₄ (500 mg, 4154 μmol) and the suspension was stirred at RT 4 h. The suspension was filtered and the solid washed with benzene (2×2 mL). The combined filtrates were concentrated to give (S)—N-(4-bromobenzylidene)-1-phenylpropan-2-amine which was used without purification in the next step.

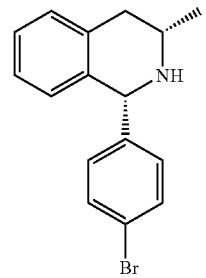 [SMILES: C[C@H]1Cc2ccccc2[C@@H](c2ccc(Br)cc2)N1]

Step 2: (1R,3S)-1-(4-bromophenyl)-3-methyl-1,2,3,4-tetrahydroisoquinoline [stereochemistry is arbitrarily assigned]

To a flask with trifluoromethanesulfonic acid (3.00 mL, 34 mmol) at 0° C. was added dropwise the (S)—N-(4-bromobenzylidene)-1-phenylpropan-2-amine and the reaction was heated to 120° C. and stirred 19 h under N₂. The reaction was poured into ice water (20 mL) and basisified with 5 N NaOH (6 mL). The aqueous layer was extracted with CH₂Cl₂ (3×10 mL). The combined organic layers were washed with saturated NaCl (20 mL), dried (MgSO₄), and concentrated to give a yellow/brown oil (410 mg). ¹H-NMR shows 92:8 diastereomeric ratio. The residue was purified by ISCO (40 g SiO₂, 0-100% EtOAc/hexane) to give the title compound as a light yellow oil.

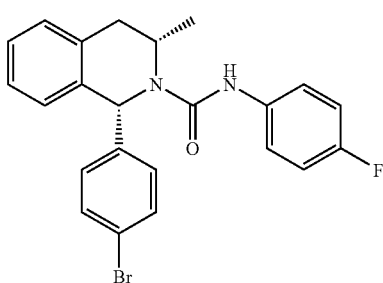

Step 3: (1R,3S)-1-(4-Bromophenyl)-N-(4-fluorophenyl)-3-methyl-3,4-dihydro-isoquinoline-2(1H)-carboxamide [stereochemistry is arbitrarily assigned]

To a solution of (1R,3S)-1-(4-bromophenyl)-3-methyl-1,2,3,4-tetrahydroisoquinoline (48.5 mg, 160 μmol) in CH$_2$Cl$_2$ (1.0 mL) at RT was added 1-fluoro-4-isocyanatobenzene (28.9 μL, 249 μmol). The reaction was stirred 4 h and directly purified by reverse phase HPLC to give (1R,3S)-1-(4-bromophenyl)-N-(4-fluorophenyl)-3-methyl-3,4-dihydroisoquinoline-2(1H)-carboxamide as a white solid. MS (ESI pos. ion) m/z: 439, 441 (M+1).

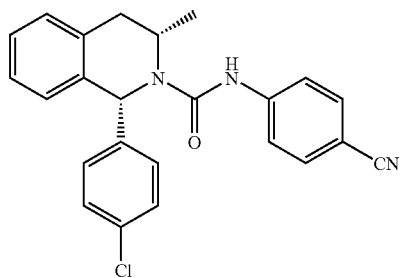 [SMILES: C[C@H]1Cc2ccccc2[C@@H](c2ccc(Cl)cc2)N1C(=O)Nc1ccc(C#N)cc1]

Example 82

((1R,3S)-1-(4-Chlorophenyl)-N-(4-cyanophenyl)-3-methyl-3,4-dihydroisoquinoline-2(1H)-carboxamide [stereochemistry is arbitrarily assigned]

To a solution of (1R,3S)-1-(4-chlorophenyl)-3-methyl-1,2,3,4-tetrahydroisoquinoline (50 mg, 194 μmol, example 80, step 2) in CH$_2$Cl$_2$ (1.0 mL) at RT was added 4-isocyanatobenzonitrile (42 mg, 291 μmol). The reaction was stirred 5 h and directly purified by reverse phase HPLC to give (1R,3S)-1-(4-chlorophenyl)-N-(4-cyanophenyl)-3-methyl-3,4-dihydroisoquinoline-2(1H)-carboxamide as a white solid. MS (ESI pos. ion) m/z: 402 (M+1).

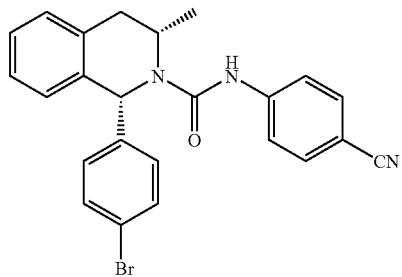 [SMILES: C[C@H]1Cc2ccccc2[C@@H](c2ccc(Br)cc2)N1C(=O)Nc1ccc(C#N)cc1]

Example 83

(1R,3S)-1-(4-Bromophenyl)-N-(4-cyanophenyl)-3-methyl-3,4-dihydroisoquinoline-2(1H)-carboxamide [stereochemistry is arbitrarily assigned]

To a solution of (1R,3S)-1-(4-bromophenyl)-3-methyl-1,2,3,4-tetrahydroisoquinoline (50 mg, 165 example 81, step 2) in CH$_2$Cl$_2$ (1.0 mL) at RT was added 4-isocyanatobenzonitrile (37 mg, 256 μmol). The reaction was stirred 5 h and directly purified by reverse phase HPLC to give (1R,3S)-1-(4-bromophenyl)-N-(4-cyanophenyl)-3-methyl-3,4-dihydroisoquinoline-2(1H)-carboxamide as a white solid. MS (ESI pos. ion) m/z: 446, 448 (M+1).

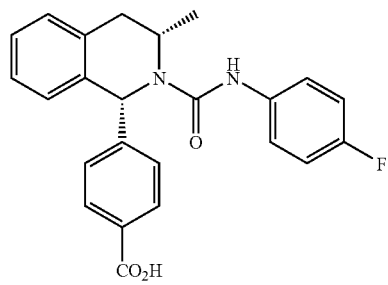 [SMILES: C[C@H]1Cc2ccccc2[C@@H](c2ccc(C(=O)O)cc2)N1C(=O)Nc1ccc(F)cc1]

Example 84

4-((1R,3S)-2-(4-Fluorophenylcarbamoyl)-3-methyl-1,2,3,4-tetrahydroisoquinolin-1-yl)benzoic acid [stereochemistry is arbitrarily assigned]

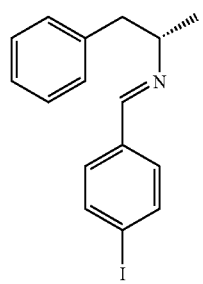

Step 1: (S)—N-(4-iodobenzylidene)-1-phenylpropan-2-amine

To a solution of (S)-1-phenylpropan-2-amine (0.500 g, 3698 μmol) in benzene (5 mL) was added 4-iodobenzaldehyde (858 mg, 3698 μmol) and MgSO$_4$ (1.000 g, 8308 μmol) and the suspension stirred at RT 4 h. The suspension was filtered and the solid washed with benzene (2×2 mL). The combined filtrates were concentrated to give (S)—N-(4-iodobenzylidene)-1-phenylpropan-2-amine as a yellow oil which was used without purification in the next step.

95

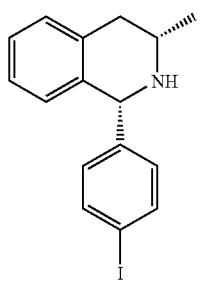 [SMILES: C[C@H]1Cc2ccccc2[C@@H](c2ccc(I)cc2)N1]

Step 2: (1R,3S)-1-(4-Iodophenyl)-3-methyl-1,2,3,4-tetrahydroisoquinoline [stereochemistry is arbitrarily assigned]

To a flask with the crude N-(4-iodobenzylidene)-1-phenyl-propan-2-amine (1.17 g) was added trifluoromethanesulfonic acid (6.00 mL, 67805 μmol) and the reaction was heated to 120° C. and stirred 5 h under N₂. The reaction was cooled to RT, poured into ice water (20 mL), and basisified with 5 N NaOH (15 mL). The aqueous layer was extracted with CH₂Cl₂ (3×10 mL). The combined organic layers were washed with saturated NaCl (20 mL), dried (MgSO₄), and concentrated to give a yellow/brown oil. The residue was purified by ISCO (40 g SiO₂, 0-100% EtOAc/hexane) to give (1R,3S)-1-(4-iodophenyl)-3-methyl-1,2,3,4-tetrahydroisoquinoline as a brown oil.

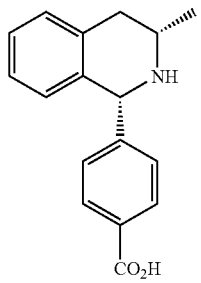 [SMILES: C[C@H]1Cc2ccccc2[C@@H](c2ccc(C(=O)O)cc2)N1]

Step 3: 4-((1R,3S)-3-Methyl-1,2,3,4-tetrahydroisoquinolin-1-yl)benzoic acid [stereochemistry is arbitrarily assigned]

To a vial with (1R,3S)-1-(4-iodophenyl)-3-methyl-1,2,3,4-tetrahydroisoquinoline (56.2 mg, 161 μmol) under N₂ was added THF (1.0 mL) and the reaction was cooled to −78° C. n-butyllithium (129 μL, 322 μmol) was added and the reaction stirred 5 min. CO₂ gas was bubbled through the solution and the reaction warmed to RT and stirred 20 min. The reaction mixture was quenched with MeOH (1 mL) and diluted with DMF (1 mL). The reaction mixture was directly purified by HPLC to give 4-((1R,3S)-3-methyl-1,2,3,4-tetrahydroisoquinolin-1-yl)benzoic acid as a white solid.

96

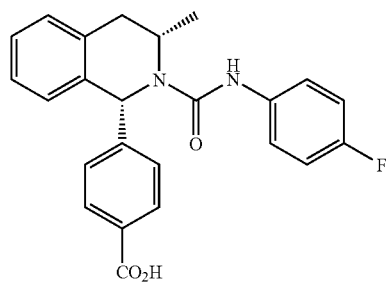 [SMILES: C[C@H]1Cc2ccccc2[C@@H](c2ccc(C(=O)O)cc2)N1C(=O)Nc1ccc(F)cc1]

Step 4: 4-((1R,3S)-2-(4-Fluorophenylcarbamoyl)-3-methyl-1,2,3,4-tetrahydro-isoquinolin-1-yl)benzoic acid [stereochemistry is arbitrarily assigned]

To a solution of 4-((1R,3S)-3-methyl-1,2,3,4-tetrahydroisoquinolin-1-yl)benzoic acid (22 mg, 82 μmol) in CH₂Cl₂ (0.5 mL) at RT was added 1-fluoro-4-isocyanatobenzene (28 mg, 206 μmol). The reaction was stirred 5 h and directly purified by HPLC to give 4-((1R,3S)-2-((4-fluorophenyl)carbamoyl)-3-methyl-1,2,3,4-tetrahydroisoquinolin-1-yl)benzoic acid as a white solid. MS (ESI pos. ion) m/z: 405 (M+1).

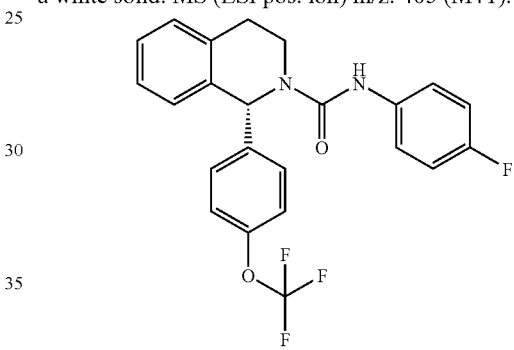

Example 85

N-(4-fluorophenyl)-1-(4-(trifluoromethoxy)phenyl)-3,4-dihydroisoquinoline-2(1H)-carboxamide A round-bottomed flask containing a solution of 1-bromo-4-(trifluoromethoxy)-benzene (0.093 mL, 626 μmol) and dry THF (2.5 mL) was cooled to −78° C. The solution was treated with 2.5M butyllithium in toluene (0.25 mL, 625 μmol) and after 2 min a solution of 3,4-dihydroisoquinoline (76 mg, 579 μmol) in THF (1 mL) was added. After 2 min LC-MS shows a predominant peak (MS (ESI pos. ion) m/z: 294 (M+1)). The reaction was quenched with sat'd NH₄Cl (2 mL). The organic layer was separated and the aqueous layer extracted with EtOAc (2 mL). The combined organic layers were dried over MgSO₄. The solution was then treated with 1-fluoro-4-isocyanatobenzene (0.06 mL, 528 μmol). After 16 h, a solid was filtered and the solids washed with EtOAc (2 mL) to give 1,3-bis(4-fluorophenyl)urea as a white solid. The filtrate was concentrated in vacuo and taken up in 1.5 mL of DMF and purified by reverse-phase preparative HPLC (Shimadzu) on a Phenomenex Gemini® column (5 micron, C18, 110 Å, Axia, 100×50 mm) eluting at 90 mL/min with an linear gradient of 10% to 100% MeCN (0.1% TFA) in water (0.1% TFA) over 30 min to give N-(4-fluorophenyl)-1-(4-(trifluoromethoxy)phenyl)-3,4-dihydroisoquinoline-2(1H)-carboxamide (40 mg, 16% yield), as colorless film. MS (ESI pos. ion) m/z: 431 (M+1).

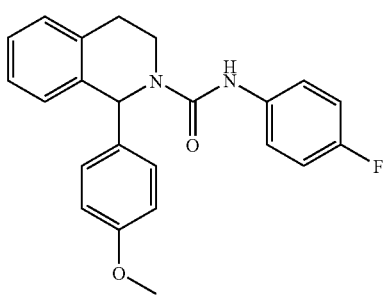 [SMILES: COc1ccc(C2c3ccccc3CCN2C(=O)Nc2ccc(F)cc2)cc1]

Example 86

N-(4-Fluorophenyl)-1-(4-methoxy)phenyl)-3,4-dihydroisoquinoline-2(1H)-carboxamide Step 1:
1-(4-Methoxyphenyl)-1,2,3,4-tetrahydroisoquinoline To a round-bottomed flask containing ethyl 1-(4-methoxyphenyl)-3,4-dihydroisoquinoline-2(1H)-carboxylate (199 mg, 639 μmol) and EtOH (10 mL) was added 1N NaOH (5 mL). The solution was stirred at 100° C. After 3 h, a pellet of KOH was added and heating continued. After a further 16 h the condenser was removed and 2 pellets of solid KOH were added. After a further 24 h, LC-MS shows ~50% conversion. 10 mL of water was added and the condenser was replaced. After a further 24 h, the reaction was allowed to cool and extracted with $CH_2Cl_2$ (3×15 mL) and the combined organics concentrated in vacuo to give a mixture of starting material and 1-(4-methoxyphenyl)-1,2,3,4-tetrahydroisoquinoline (170 mg) as a golden oil. The crude product was used in the next step. MS (ESI pos. ion) m/z: 240 (M+1).

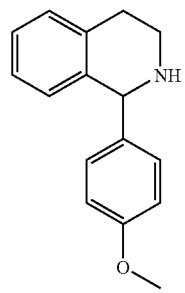 [SMILES: COc1ccc(C2NCCc3ccccc32)cc1]

Step 2: N-(4-fluorophenyl)-1-(4-methoxyphenyl)-3,4-dihydroisoquinoline-2(1H)-carboxamide To a round-bottomed flask containing crude 1-(4-methoxyphenyl)-1,2,3,4-tetrahydroisoquinoline (25 mg, 104 μmol)

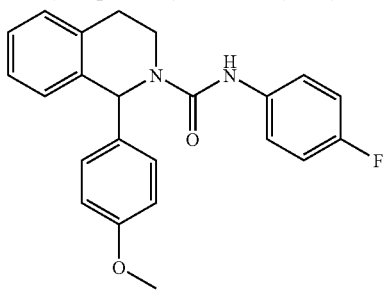 [SMILES: COc1ccc(C2c3ccccc3CCN2C(=O)Nc2ccc(F)cc2)cc1]

and $CH_2Cl_2$ (10 mL) was added 1-fluoro-4-isocyanatobenzene (0.03 mL, 264 μmol). The solution was stirred at RT. After 1 h, the reaction was concentrated in vacuo and taken up in DMF and purified by reverse-phase preparative HPLC (Shimadzu) on a Phenomenex Gemini™ column (5 micron, C18, 110 Å, Axia, 100×50 mm) eluting at 90 mL/min with an linear gradient of 10% to 100% MeCN (0.1% TFA) in water (0.1% TFA) over 10 min to give crude product, that was lypholized and resubjected to the same purification conditions to give N-(4-fluorophenyl)-1-(4-methoxyphenyl)-3,4-dihydroisoquinoline-2(1H)-carboxamide, as a white solid that contained 0.66 eq of TFA. MS (ESI pos. ion) m/z: 377 (M+1).

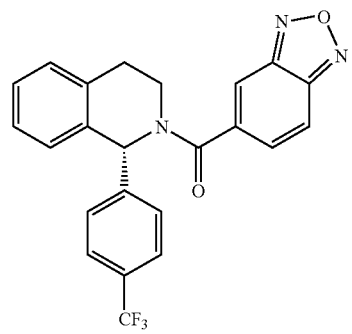 [SMILES: O=C(c1ccc2nonc2c1)N1CCc2ccccc2[C@H]1c1ccc(C(F)(F)F)cc1]

Example 87

(R)-Benzo[c][1,2,5]oxadiazol-5-yl(1-(4-(trifluoromethyl)phenyl)-3,4-dihydro-isoquinolin-2(1H)-yl)methanone

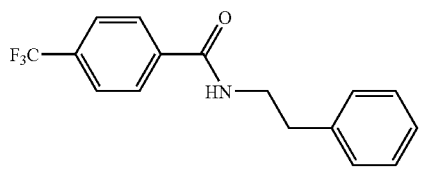 [SMILES: O=C(NCCc1ccccc1)c1ccc(C(F)(F)F)cc1]

Step 1: N-Phenethyl-4-(trifluoromethyl)benzamide

To a solution of phenylethylamine (14.0 g, 14.6 mL, 115.5 mmol) and diea (20.1 mL, 115.5 mmol) in DCM (500 mL) at 0° C. was added 4-(trifluoromethyl)benzoyl chloride (17.2 mL, 115.5 mmol) dropwise. After addition, the reaction mixture was then stirred at 0° C. and warmed up itself to RT overnight. An off-white solid precipitation was observed. The off-white solid was collected by filtration. The solid was then washed with DCM (2×50 mL), and dried under vacuum to give 31.8 g of the title compound as a white solid. MS (ESI, positive ion) m/z: 294 (M+H).

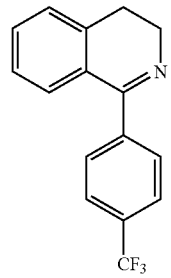 [SMILES: FC(F)(F)c1ccc(C2=NCCc3ccccc32)cc1]

Step 2: 1-(4-(Trifluoromethyl)phenyl)-3,4-dihydroisoquinoline

To a round-bottomed flask was added n-phenethyl-4-(trifluoromethyl)benzamide (5.0 g, 17 mmol), phosphoric pentoxide (0.526 mL, 8.52 mmol), and polyphosphoric acid (60.0 g). The reaction mixture was then heated to 165° C. for 2 h. A brown thick solution was observed. Then, the hot oil solution was carefully poured into ice in an erlenmeyer flask and a solution of KOH (20%, 40 mL) was added to break the oil. The mixture was stirred at RT for 5 min and an additional KOH solution was added until pH 7. Then, ethyl ether (250 mL) was added and the mixture was stirred at RT for 15 min. The organic layer was collected and the aqueous layer was extracted with EtOAc (2×200 mL). The combined organic extracts were dried over $MgSO_4$ and concentrated to give the title compound as an orange oil, which was used in the next step without purification requirement. MS (ESI, positive ion) m/z: 276 (M+H).

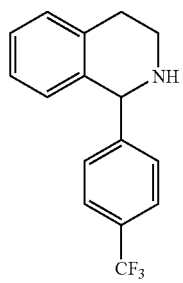 [SMILES: FC(F)(F)c1ccc(C2NCCc3ccccc32)cc1]

Step 3: 1-(4-(Trifluoromethyl)phenyl)-1,2,3,4-tetrahydroisoquinoline

To a solution of 1-(4-(trifluoromethyl)phenyl)-3,4-dihydroisoquinoline (4.693 g, 17 mmol) (example 1b) in MeOH (24 mL) was added sodium borohydride (1.94 g, 51.1 mmol) slowly at 0° C. After addition, the mixture was stirred at 0° C. for 15 min and at RT for 2 h. The solvent was then removed and $H_2O$ (20 mL) was added to the residue. Then, a saturated $NaHCO_3$ solution (150 mL) was added slowly and the mixture was extracted with EtOAc (2×200 mL). The combined organic extracts were dried over $MgSO_4$ and concentrated. The residue was mixed with silica gel (4:1; residue:silica gel). The solid mixture was purified by silica gel flash column chromatography using ISCO instrument (solid loading, 20%-100% EtOAc/hexane) to give the title compound as a white solid. MS (ESI, positive ion) m/z: 278 (M+H).

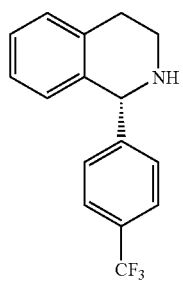 [SMILES: FC(F)(F)c1ccc([C@H]2NCCc3ccccc32)cc1]

Step 4: (R)-1-(4-(Trifluoromethyl)phenyl)-1,2,3,4-tetrahydroisoquinoline

Enantiomers of 1-(4-(trifluoromethyl)phenyl)-1,2,3,4-tetrahydroisoquinoline (2.120 g, 7.46 mmol, racemic mixture) were separated by using chiral SFC (Chiralcel AD-H (250×21 Mm), 45% methanol/$CO_2$ (100 bar), 65 mL/min, 220 nm) to give 877 mg of the title compound as a light yellow solid. MS (ESI, positive ion) m/z: 278 (M+H).

Step 5: (R)-Benzo[c][1,2,5]oxadiazol-5-yl(1-(4-(trifluoromethyl)phenyl)-3,4-dihydroisoquinolin-2(1H)-yl)methanone To a solution of (R)-1-(4-(trifluoromethyl)phenyl)-1,2,3,4-tetrahydroisoquinoline (50 mg, 180 μmol) and diea (31 μL, 180 μmol) in DCM (1 mL) was added benzo[c][1,2,5]oxadiazole-5-carbonyl chloride (43 mg, 234 μmol). The resulting mixture was then stirred at RT for overnight. Then, the mixture was concentrated and the residue was dissolved in MeOH (1 mL). The solution mixture was then purified by preparative HPLC (0%-100% MeCN 0.1% TFA/H2O 0.1% TFA) to give a desired product, which was then dissolved in MeOH (1 mL). The solution was then washed through PL-$HCO_3$ resin and the resin was then washed with MeOH (1 mL). The combined washings were concentrated and dried under vacuum to give the title compound as a white solid. MS (ESI, positive ion) m/z: 424 (M+H).

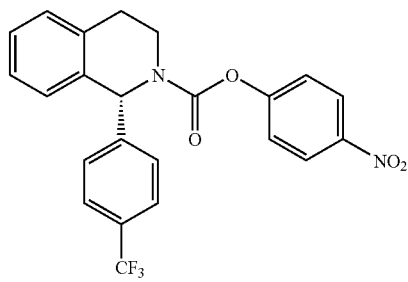 [SMILES: O=C(Oc1ccc([N+](=O)[O-])cc1)N1CCc2ccccc2[C@H]1c1ccc(C(F)(F)F)cc1]

Example 88

(R)-4-Nitrophenyl 1-(4-(trifluoromethyl)phenyl)-3,4-dihydroisoquinoline-2(1H)-carboxylate To a solution of (R)-1-(4-(trifluoromethyl)phenyl)-1,2,3,4-tetrahydroisoquinoline (1550 mg, 5590 μmol) and diea (1071 μL, 6149 μmol) in DCM (36 mL) at 0° C. was added 4-nitrophenyl chloroformate (1465 mg, 7267 μmol, Aldrich). After addition, the reaction mixture was stirred at RT for overnight. Then, $H_2O$ (60 mL) was added and the mixture was stirred at RT for 15 min. The organic layer was collected and the aqueous was extracted with DCM (1×50 mL). The combined organic extracts were dried over $MgSO_4$ and concentrated. The residue was then mixed with silica gel (4:1, residue: silica gel) and the solid mixture was purified by silica gel flash column chromatography using ISCO instrument (solid loading, 0%-100% EtOAc/hexane) to give the compound as an off-white solid. MS (ESI, positive ion) m/z: 443 (M+H).

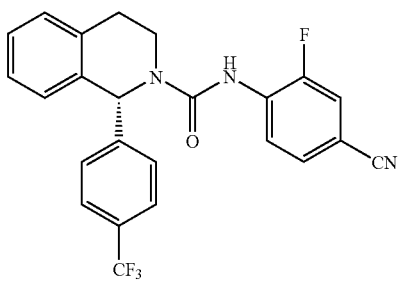

Example 89

(R)—N-(4-Cyano-2-fluorophenyl)-1-(4-(trifluoromethyl)phenyl)-3,4-dihydro-isoquinoline-2(1H)-carboxamide A solution of (R)-4-nitrophenyl 1-(4-(trifluoromethyl)phenyl)-3,4-dihydroisoquinoline-2(1H)-carboxylate (50 mg, 113 μmol, example 88) and 4-amino-3-fluorobenzonitrile (17 mg, 124 mop in MeCN (0.7 mL) was subjected to a microwave irradiation at 120° C. for 15 min and at 150° C. for 15 min. Then, NaH (60% dispersion in mineral oil, 20 mg) was added and the mixture was then stirred at RT for overnight. Then, H₂O (1.0 mL) was added and the mixture was extracted with EtOAc (2×1.5 mL). The combined organic extracts were dried over MgSO₄ and concentrated. The residue was then dissolved in a solution of DMSO and MeOH (1:1, 0.1 mL). The solution mixture was then purified by preparative HPLC (0%-100% MeCN 0.1% TFA/H2O 0.1% TFA) to give a desired product, which was then dissolved in MeOH (1.0 mL). The solution was then washed through PL-HCO₃ MP-resin and the resin was washed with MeOH (2×0.5 mL). The combined washings were concentrated and dried under vacuum to give the title compound as a colorless solid. MS (ESI, positive ion) m/z: 440 (M+H).

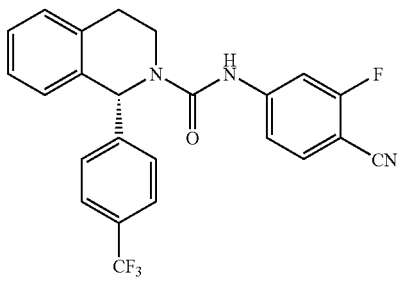 [SMILES: N#Cc1ccc(NC(=O)N2CCc3ccccc3[C@H]2c2ccc(C(F)(F)F)cc2)cc1F]

Example 90

(R)—N-(4-Cyano-3-fluorophenyl)-1-(4-(trifluoromethyl)phenyl)-3,4-dihydro-isoquinoline-2(1H)-carboxamide To a solution of (R)-4-nitrophenyl 1-(4-(trifluoromethyl)phenyl)-3,4-dihydroisoquinoline-2(1H)-carboxylate (70 mg, 158 μmol, example 88) in MeCN (0.5 mL) was added 4-amino-2-fluorobenzonitrile (65 mg, 475 μmol). The resulting mixture was then subjected to a microwave irradiation at 180° C. for 15 min. Then, sodium hydride, 60% dispersion in mineral oil (22 μL, 475 μmol) was added and the mixture was stirred at RT for overnight. Then, H₂O (0.5 mL) was added and the solvents were removed. The residue was then dissolved in a solution of MeOH and DMSO (1:1, 1.0 mL). The solution mixture was then purified by preparative HPLC (0%-100% MeCN 0.1% TFA/H2O 0.1% TFA) to give the desired product, which was then dissolved in MeOH (1.0 mL). The solution was then washed through PL-HCO₃ MP resin (polymerlabs, 200 mg/6 mL tube) and the resin was washed with MeOH (2×0.5 mL). The combined washings were then concentrated and dried under vacuum to give the title compound as a yellow solid. MS (ESI, positive ion) m/z: 440 (M+H).

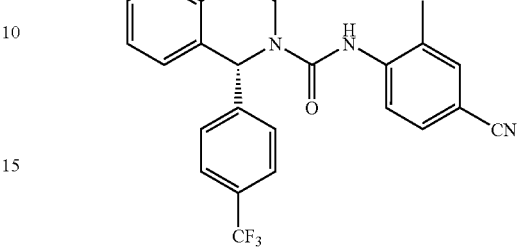

Example 91

(R)—N-(4-Cyano-2-methylphenyl)-1-(4-(trifluoromethyl)phenyl)-3,4-dihydro-isoquinoline-2(1H)-carboxamide To a solution of 4-amino-3-methylbenzonitrile (30 mg, 226 μmol) in THF (2 mL) was added sodium hydride, 60% dispersion in mineral oil (15 μL, 339 pimp. The resulting mixture was then stirred at RT for 2 min. Then, (R)-4-nitrophenyl 1-(4-(trifluoromethyl)phenyl)-3,4-dihydroisoquinoline-2(1H)-carboxylate (100 mg, 226 μmol, example 88) was added and the mixture was stirred at RT for overnight. Then, 26 mg of NaH (60% dispersion in mineral oil) was added and the mixture was stirred at RT for overnight. Then, H₂O (0.2 mL) was added and the solvents were removed. The residue was then dissolved in a solution of DMSO and MeOH (1:1, 1.0 mL). The solution was then purified by preparative HPLC (0%-100% MeCN 0.1% TFA/H₂O 0.1% TFA) to give the desired product, which was dissolved in MeOH (1.0 mL). The solution was then washed through PL-HCO₃ MP resin (polymerlabs, 200 mg/6 mL tube) and the resin was then washed with MeOH (2×0.5 mL). The combined washings were then concentrated and dried under vacuum to give the title compound as a yellow solid. MS (ESI, positive ion) m/z: 436 (M+H).

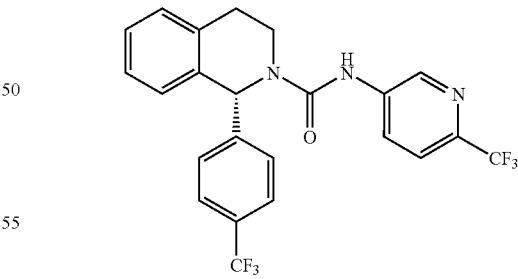

Example 92

(R)-1-(4-(Trifluoromethyl)phenyl)-N-(6-(trifluoromethyl)pyridin-3-yl)-3,4-dihydroisoquinoline-2(1H)-carboxamide To a solution of (R)-4-nitrophenyl 1-(4-(trifluoromethyl)phenyl)-3,4-dihydroisoquinoline-2(1H)-carboxylate (70 mg, 158 example 88) in MeCN (0.5 mL) was added 3-amino-6-(trifluoromethyl)pyridine (77 mg, 475 μmol). The resulting mixture was then subjected to a microwave irradiation at 150° C. for 15 min and at 180° C. for 15 min. Then, sodium hydride, 60% dispersion in mineral oil (18 mg, 475 μmol) was added and the mixture was stirred at RT for overnight. Then, H₂O (0.5 mL) was added and the solvents were removed. The residue was then dissolved in a solution of MeOH and DMSO (1:1. 1.0 mL). The solution mixture was purified by preparative HPLC (0%-100% MeCN 0.1% TFA/H₂O 0.1% TFA) to give the desired product, which was then dissolved in MeOH (1.0 mL). The solution was then washed through PL-HCO₃ MP resin (polymerlabs, 200 mg/6 mL tube) and the resin was washed with MeOH (2×0.5 mL). The combined washings were then concentrated and dried under vacuum to give the title compound as a yellow solid. MS (ESI, positive ion) m/z: 466 (M+H).

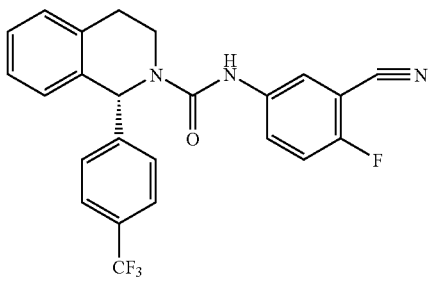 [SMILES: N#Cc1cc(NC(=O)N2CCc3ccccc3[C@H]2c2ccc(C(F)(F)F)cc2)ccc1F]

Example 93

(R)—N-(3-Cyano-4-fluorophenyl)-1-(4-(trifluoromethyl)phenyl)-3,4-dihydro-isoquinoline-2(1H)-carboxamide A solution of 5-amino-2-fluorobenzonitrile (62 mg, 452 μmol) and sodium hydride, 60% dispersion in mineral oil (26 mg, 678 μmol) in THF (1.0 mL) was stirred at RT for 15 min. Then, (R)-4-nitrophenyl 1-(4-(trifluoromethyl)phenyl)-3,4-dihydroisoquinoline-2(1H)-carboxylate (100 mg, 226 μmol, example 88) was added and the mixture was stirred at RT for overnight. Then, a solution of H₂O and MeOH (1:1, 0.2 mL) was added and the solvents were removed. The residue was then dissolved in a solution of DMSO and MeOH (1:1, 1 mL). The solution mixture was then purified by preparative HPLC (0%-100% MeCN 0.1% TFA/H₂O 0.1% TFA) to give the desired product, which was dissolved in MeOH (1 mL). The solution was then washed through PL-HCO3 MP resin (polymerlabs, 200 mg/6 mL tube) and the resin was washed with MeOH (2×0.5 mL). The combined washings were then concentrated and dried under vacuum to give the title compound as an orange solid. MS (ESI, positive ion) m/z: 440 (M+H).

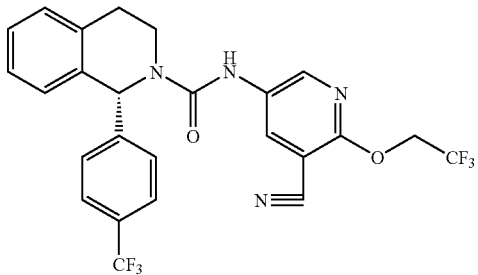 [SMILES: N#Cc1cc(NC(=O)N2CCc3ccccc3[C@H]2c2ccc(C(F)(F)F)cc2)cnc1OCC(F)(F)F]

Example 94

(R)—N-(5-cyano-6-(2,2,2-trifluoroethoxy)pyridin-3-yl)-1-(4-(trifluoro-methyl)phenyl)-3,4-dihydroisoquinoline-2(1H)-carboxamide To a solution of 5-amino-2-(2,2,2-trifluoroethoxy)nicotinonitrile (49 mg, 226 μmol) in THF (1.0 mL) was added sodium hydride, 60% dispersion in mineral oil (26 mg, 678 μmol). The resulting mixture was then stirred at RT for 15 min. Then, (R)-4-nitrophenyl 1-(4-(trifluoromethyl)phenyl)-3,4-dihydroisoquinoline-2(1H)-carboxylate (100 mg, 226 μmol, example 88) was added and the mixture was stirred at RT for overnight. Then, a solution of H₂O and MeOH (1:1, 0.2 mL) was added and the solvents were removed. The residue was then dissolved in a solution of DMSO and MeOH (1:1, 1 mL). The solution mixture was then purified by preparative HPLC (0%-100% MeCN 0.1% TFA/H₂O 0.1% TFA) to give the desired product, which was dissolved in MeOH (1.0 mL). The solution was then washed through PL-HCO3 MP resin (polymerlabs, 200 mg/6 mL tube) and the resin was washed with MeOH (2×0.5 mL). The combined washings were then concentrated and dried under vacuum to give the title compound as a light yellow solid. MS (ESI, positive ion) m/z: 521 (M+H).

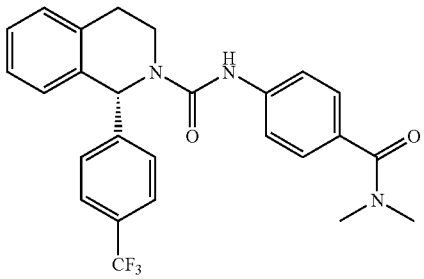 [SMILES: CN(C)C(=O)c1ccc(NC(=O)N2CCc3ccccc3[C@H]2c2ccc(C(F)(F)F)cc2)cc1]

Example 95

(R)—N-(4-(Dimethylcarbamoyl)phenyl)-1-(4-(trifluoromethyl)phenyl)-3,4-dihydroisoquinoline-2(1H)-carboxamide To a solution of 4-amino-N,N-dimethylbenzamide (74 mg, 452 μmol) in THF (0.5 mL) was added sodium hydride, 60% dispersion in mineral oil (19 μL, 452 μmol). The resulting mixture was then subjected to a microwave irradiation at 150° C. for 5 min. Then, (R)-4-nitrophenyl 1-(4-(trifluoromethyl)phenyl)-3,4-dihydroisoquinoline-2(1H)-carboxylate (100 mg, 226 μmol, example 88) was added and the mixture was stirred at RT for overnight. Then, H₂O (0.5 mL) was added slowly and the mixture was extracted with EtOAc (2×1 mL). The combined organic extracts were dried over MgSO₄ and concentrated. The residue was dissolved in DMSO (1.0 mL) and the solution mixture was then purified by preparative HPLC (0%-100% MeCN 0.1% TFA/H₂O 0.1% TFA) to give the desired compound, which was dissolved in MeOH (1.0 mL). Then, the solution was washed through PL-HCO3 MP-Resin (200 mg per 6 mL tube) and the resin was washed with MeOH (2×0.3 mL). The combined washings were concentrated and dried under vacuum to give the title compound as light brown solid. MS (ESI, positive ion) m/z: 468 (M+H).

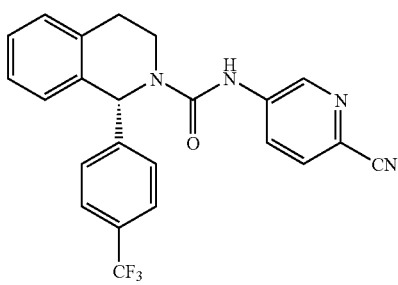 [SMILES: N#Cc1ccc(NC(=O)N2CCc3ccccc3[C@H]2c2ccc(C(F)(F)F)cc2)cn1]

Example 96

(R)—N-(6-Cyanopyridin-3-yl)-1-(4-(trifluoromethyl)phenyl)-3,4-dihydroisoquinoline-2(1H)-carboxamide To a solution of 5-amino-2-pyridinecarbonitrile (81 mg, 678 μmol) in THF (1.0 mL) was added sodium hydride, 60% dispersion in mineral oil (17 mg, 452 μmol). The resulting mixture was then subjected to a microwave irradiation at 160° C. for 15 min. Then, (R)-4-nitrophenyl 1-(4-(trifluoromethyl)phenyl)-3,4-dihydroisoquinoline-2(1H)-carboxylate (100 mg, 226 example 88) was added and the mixture was stirred at RT for overnight. Then, H₂O (0.5 mL) was added and the mixture was extracted with EtOAc (2×1 mL). The combined organic extracts were dried over MgSO₄ and concentrated. The residue was dissolved in DMSO (1.0 mL) and the solution was then purified by preparative HPLC (0%-100% MeCN 0.1% TFA/H₂O 0.1% TFA) to give the desired compound, which was dissolved in MeOH (1.0 mL). The solution was then washed through PL-HCO3 MP-Resin (200 mg per 6 mL tube) and the resin was washed with MeOH (2×0.3 mL). The combined washings were concentrated and dried under vacuum to give the title compound as a light yellow solid. MS (ESI, positive ion) m/z: 423 (M+H).

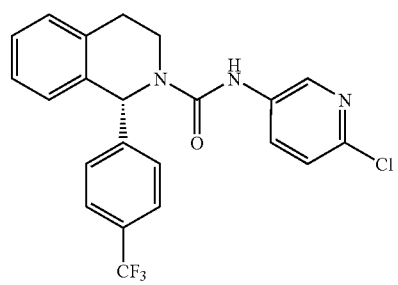 [SMILES: O=C(Nc1ccc(Cl)nc1)N1CCc2ccccc2[C@H]1c1ccc(C(F)(F)F)cc1]

Example 97

(R)—N-(6-chloropyridin-3-yl)-1-(4-(trifluoromethyl)phenyl)-3,4-dihydroisoquinoline-2(1H)-carboxamide

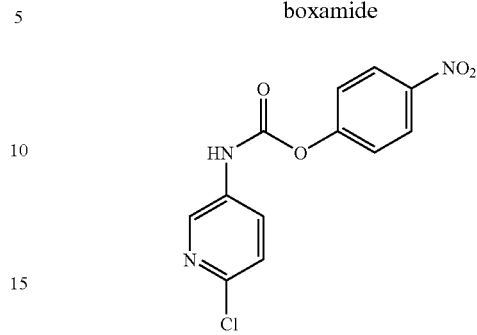

Step 1: 4-Nitrophenyl 6-chloropyridin-3-ylcarbamate

To a solution of 5-amino-2-chloropyridine (162 mg, 1262 μmol) and DIEA (275 μL, 1578 mmol) in DCM (6.0 mL) was added 4-nitrophenyl chloroformate (212 mg, 1052 μmol). The resulting mixture was then stirred at RT for overnight. A yellow precipitation was observed. The yellow solid was collected by filtration to give the title compound as a light yellow solid, which was used in the next step without purification requirement.

Step 2: (R)—N-(6-Chloropyridin-3-yl)-1-(4-(trifluoromethyl)phenyl)-3,4-dihydroisoquinoline-2(1H)-carboxamide A solution of (R)-1-(4-(trifluoromethyl)phenyl)-1,2,3,4-tetrahydroisoquinoline (50 mg, 180 μmol, example 87, Step 3) and 4-nitrophenyl 6-chloropyridin-3-yl-carbamate (119 mg, 406 μmol) in toluene (1.0 mL) was subjected to a microwave irradiation at 180° C. for 30 min. Then, DMSO (1.0 mL) was added and the solution mixture was filtered. The filtrate was then purified by preparative HPLC (0%-100% MeCN 0.1% TFA/H₂O 0.1% TFA) to give the title compound, which was dissolved in MeOH (1.0 mL). Then, the solution was washed through PL-HCO3 MP-Resin (200 mg per 6 mL tube) and the resin was washed with MeOH (2×0.3 mL). The combined washings were concentrated and dried under vacuum to give the title compound as a light yellow solid. MS (ESI, positive ion) m/z: 432 (M+H).

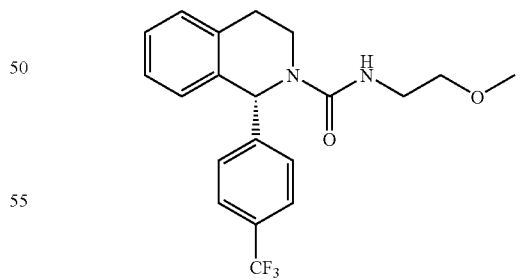

Example 98

(R)—N-(2-Methoxyethyl)-1-(4-(trifluoromethyl)phenyl)-3,4-dihydroisoquinoline-2(1H)-carboxamide To a solution of (R)-4-nitrophenyl 1-(4-(trifluoromethyl)phenyl)-3,4-dihydroisoquinoline-2(1H)-carboxylate (170 mg, 384 µmol, example 88) in MeCN (0.2 mL) was added 2-methoxyethylamine (36.7 µL, 423 µmol). The resulting mixture was then subjected to a microwave irradiation at 180° C. for 15 min. Then, 2-methoxy-ethylamine (0.02 mL) was added and the mixture was subjected to a microwave irradiation at 180° C. for an additional 15 min. Then, the solvent was removed and the residue was dissolved in a solution of DMSO and MeOH (1:1, 1.0 mL). The solution mixture was then purified by preparative HPLC (0%-100% MeCN 0.1% TFA/ $H_2O$ 0.1% TFA) to give the desired product, which was then dissolved in MeOH (2.0 mL). The solution was washed through PL-HCO3 MP resin (200 mg per 6 mL tube) and the resin was washed with MeOH (2×0.5 mL). The combined washings were then concentrated and dried under vacuum to give the title compound as a yellow solid. MS (ESI, positive ion) m/z: 379 (M+H).

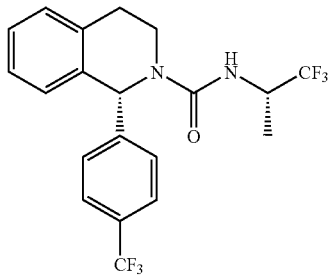

Example 99

(R)-1-(4-(trifluoromethyl)phenyl)-N—((S)-1,1,1-trifluoropropan-2-yl)-3,4-dihydroisoquinoline-2(1H)-carboxamide To a solution of (S)-1,1,1-trifluoropropan-2-amine (90.9 µl, 884 µmol) in 4:1 $CH_2Cl_2$:THF (5 mL) is added di(1H-imidazol-1-yl)methanone (215 mg, 1326 µmol) and the flask was sealed and stirred at room temperature for 1.5 h. (R)-1-(4-(trifluoromethyl)phenyl)-1,2,3,4-tetrahydroisoquinoline (307 mg, 1105 µmol) was added and the reaction stirred at 2 h. The reaction was directly purified by reverse phase HPLC to give (R)-1-(4-(trifluoromethyl)phenyl)-N—((S)-1,1,1-trifluoropropan-2-yl)-3,4-dihydroisoquinoline-2(1H)-carboxamide as a white powder. MS (ESI pos. ion) m/z: 417 (M+1).

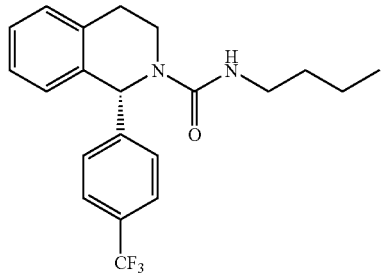 [SMILES: CCCCNC(=O)N1CCc2ccccc2[C@H]1c1ccc(C(F)(F)F)cc1]

Example 100

(R)—N-Butyl-1-(4-(trifluoromethyl)phenyl)-3,4-dihydroisoquinoline-2(1H)-carboxamide To a solution of (R)-1-(4-(trifluoromethyl)phenyl)-1,2,3,4-tetrahydroisoquinoline (198 mg, 714 µmol, Example 87, Step 3) in DCM (2.0 mL) was added n-butyl isocyanate (88 µL, 785 µmol). The resulting mixture was then stirred at RT for overnight. Then, the solvent was removed and the residue was mixed with silica gel. The solid mixture was the purified by silica gel flash column chromatography using ISCO instrument (solid loading, 0%-400% EtOAc/hexane) to give the title compound as a colorless solid. MS (ESI, positive ion) m/z: 377 (M+H).

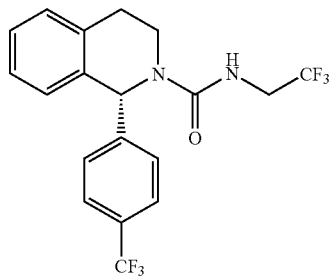 [SMILES: O=C(NCC(F)(F)F)N1CCc2ccccc2[C@H]1c1ccc(C(F)(F)F)cc1]

Example 101

(R)—N-(2,2,2-Trifluoroethyl)-1-(4-(trifluoromethyl)phenyl)-3,4-dihydroisoquinoline-2(1H)-carboxamide

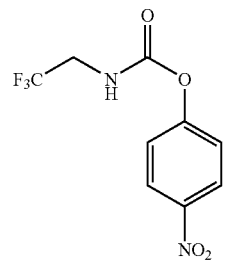 [SMILES: O=C(NCC(F)(F)F)Oc1ccc([N+](=O)[O-])cc1]

Step 1: 4-Nitrophenyl 2,2,2-trifluoroethylcarbamate

To a solution of 4-nitrophenyl chloroformate (4578 mg, 22715 µmol) and DIEA (2638 µL, 15143 µmol) in DCM (100 mL) at 0° C. was added 2,2,2-trifluoro-ethylamine (1500 µL, 15143 µmol). The resulting mixture was then stirred at 0° C. for 4 h and at RT for overnight. Then, the mixture was concentrated and a white precipitation was observed. The mixture was then filtered to give the title compound as a white solid, which was used in the next step without purification requirement.

Step 2: (R)—N-(2,2,2-Trifluoroethyl)-1-(4-(trifluoromethyl)phenyl)-3,4-dihydroisoquinoline-2(1H)-carboxamide To a solution of (R)-1-(4-(trifluoromethyl)phenyl)-1,2,3,4-tetrahydroisoquinoline (150 mg, 541 µmol, Example 87, Step 3) in MeCN (2 mL) was added 4-nitrophenyl 2,2,2-trifluoroethylcarbamate (286 mg, 1082 µmol). The resulting mixture was then subjected to a microwave irradiation at 100° C. for 15 min. Then, the solvent was removed and the residue was dissolved in a solution of DMSO and MeOH (1:1, 2 mL). The solution mixture was then purified by preparative HPLC (0%-100% MeCN 0.1% TFA/$H_2O$ 0.1% TFA) to give the desired product, which was then dissolved in MeOH (2.0 mL). The solution was then washed through PL-HCO3 MP-resin and the resin was then washed with MeOH (2×2 mL). The combined washings were concentrated and dried under vacuum to give the title compound as a light yellow solid. MS (ESI, positive ion) m/z: 403 (M+H).

General Procedure of Examples (102-103)

To a solution of (R)-1-(4-(trifluoromethyl)phenyl)-1,2,3,4-tetrahydroisoquinoline (180 μmol, example 87, Step 3) and DIEA (31 μL, 180 μmol) in DCM (1 mL) was added isocyanate (25 μL, 216 μmol). The resulting mixture was then stirred at RT for overnight. Then, the mixture was mixed with silica gel (1:1) and the solid mixture was purified by silica gel flash column chromatography using ISCO instrument (solid loading, 0%-100% EtOAc/hexane) to provide the title compound.

| Example | Structure | Name | MS (ESI, positive ion) M + H |
|---|---|---|---|
| 102 | 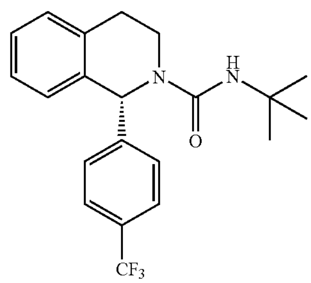 [SMILES: CC(C)(C)NC(=O)N1CCc2ccccc2[C@H]1c1ccc(C(F)(F)F)cc1] | (R)-N-tert-butyl-1-(4-(trifluoromethyl)phenyl)-3,4-dihydroisoquinoline-2(1H)-carboxamide | 377 |
| 103 | 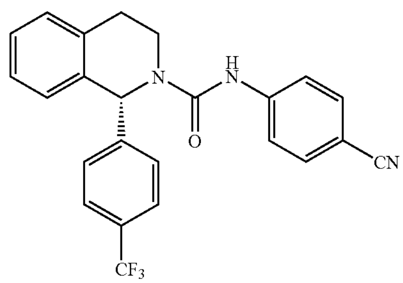 | (R)-N-(4-cyanophenyl)-1-(4-(trifluoromethyl)phenyl)-3,4-dihydroisoquinoline-2(1H)-carboxamide | 422 |

General Procedure of Examples (104-108)

To a solution of (R)-1-(4-(trifluoromethyl)phenyl)-1,2,3,4-tetrahydroisoquinoline (252 μmol, example 87, Step 3) in DCM (1.7 mL) was added isocynate (278 μmol). The resulting mixture was then stirred at RT for overnight. Then, the solvent (DCM) was removed and the residue was dissolved in a solution of MeOH and DMSO (1:1, 1.0 mL). The solution mixture was then purified by preparative HPLC (0%-100% MeCN 0.1% TFA/H$_2$O 0.1% TFA) to give a desired product, which was then dissolved in MeOH (1.0 mL). The solution was then washed through PL-HCO3 MP resin (polymerlabs, 200 mg/6 mL tube). The resin was then washed with MeOH (2×0.5 mL). The combined washings were then concentrated and dried under vacuum to give the title compound.

| | | | |
|---|---|---|---|
| 104 | | (R)-N-(2-(trifluoromethyl)phenyl)-1-(4-(trifluoromethyl)phenyl)-3,4-dihydroisoquinoline-2(1H)-carboxamide | 465 |

-continued

| | | | |
|---|---|---|---|
| 105 | | (R)-N-(3-cyanophenyl)-1-(4-(trifluoromethyl)phenyl)-3,4-dihydroisoquinoline-2(1H)-carboxamide | 422 |
| 106 | | (R)-N-(2-cyanophenyl)-1-(4-(trifluoromethyl)phenyl)-3,4-dihydroisoquinoline-2(1H)-carboxamide | 422 |
| 107 | | (R)-N-(3-(trifluoromethyl)phenyl)-1-(4-(trifluoromethyl)phenyl)-3,4-dihydroisoquinoline-2(1H)-carboxamide | 465 |
| 108 | | (R)-N-(4-fluoro-3-(trifluoromethyl)phenyl)-1-(4-(trifluoromethyl)phenyl)-3,4-dihydroisoquinoline-2(1H)-carboxamide | 483 |

Example 109

(R)—N-(Thiazol-2-yl)-1-(4-trifluoromethyl)phenyl)-3,4-dihydroisoquinoline-2(1H)-carboxamide

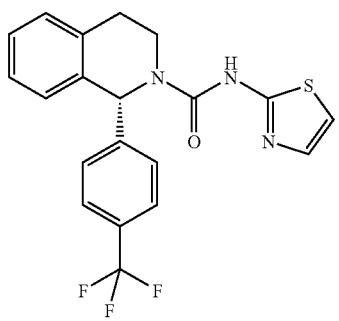 [SMILES: O=C(Nc1nccs1)N1CCc2ccccc2[C@H]1c1ccc(C(F)(F)F)cc1]

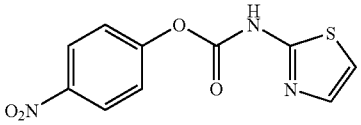

Step 1: 4-Nitrophenyl thiazol-2-yl-ylcarbamate

To a stirred mixture of thiazol-2-amine (1.00 g, 9.99 mmol) and pyridine (1.21 mL, 15.0 mmol) in DCM (30 mL) at 0° C. was added a solution of 4-nitrophenyl chloroformate (2.42 g, 12.0 mmol) in DCM (10 mL). The reaction mixture was continued to stir overnight, concentrated and taken up in H$_2$O. The tan solid was filtered, air dried, and used in the next step. MS (ESI, positive ion) m/z: 266 (M+1).

Step 2: (R)—N-(Thiazol-2-yl)-1-(4-trifluoromethyl) phenyl)-3,4-dihydroisoquinoline-2(1H)-carboxamide A mixture of 4-nitrophenyl thiazol-2-ylcarbamate (0.0957 g, 0.361 mmol) and (R)-1-(4-(trifluoromethyl)phenyl)-1,2,3,4-tetrahydroisoquinoline (0.100 g, 0.361 mmol) in p-dioxane (2 mL) was heated at 110° C. in 2 h. The reaction mixture was cooled, concentrated and purified by ISCO (30% EtOAc/hexanes) to give the title compound. MS (ESI, positive ion) m/z: 404 (M+1).

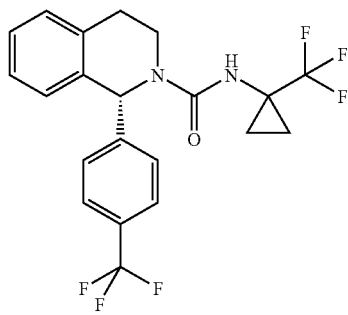

Example 110

(R)—N-(1-(Trifluoromethyl)cyclopropyl)-1-(4-(trifluoromethyl)phenyl)-3,4-dihydroisoquinoline-2(1H)-carboxamide A mixture of 1-(trifluoromethyl)cyclopropane carboxylic acid (0.36 g, 2.3 mmol), DIEA (0.41 mL, 2.3 mmol), and diphenylphosphoryl azide (0.51 mL, 2.3 mmol) in p-dioxane (8 mL) was stirred at RT for 1 h. (R)-1-(4-(trifluoromethyl) phenyl)-1,2,3,4-tetrahydroisoquinoline (0.500 g, 1.8 mmol) was added and the mixture was heated to reflux for 16 h. The mixture was cooled, concentrated and purified by ISCO (0-40% EtOAc/hexanes) to give the title compound. MS (ESI, positive ion) m/z: 429 (M+1).

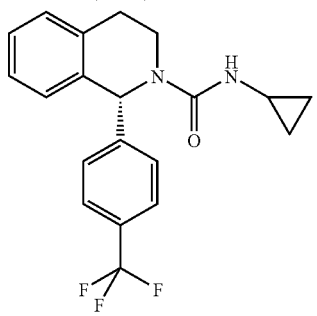 [SMILES: O=C(NC1CC1)N1CCc2ccccc2[C@H]1c1ccc(C(F)(F)F)cc1]

Example 111

(R)—N-Cyclopropyl-1-(4-(trifluoromethyl)phenyl)-3,4-dihydroisoquinoline-2(1H)-carboxamide To a stirred solution of triphosgene (0.05 mL, 0.4 mmol) in DCM (1 mL) at 0° C. was added a mixture of (R)-1-(4-(trifluoromethyl)phenyl)-1,2,3,4-tetrahydroisoquinoline (0.200 g, 0.7 mmol) and diisopropylethylamine (0.1 mL, 0.8 mmol) in DCM (1 mL). After stirring at 0° C. in 30 min, cyclopropylamine (0.04 mL, 0.7 mmol) was added and the mixture was continued to stir at RT for 24 h. H$_2$O was added and layers were separated. The organic extracts were dried over MgSO$_4$, concentrated and purified by ISCO (20% EtOAc/hexanes) to give the white solid title compound. MS (ESI, positive ion) m/z: 361 (M+1).

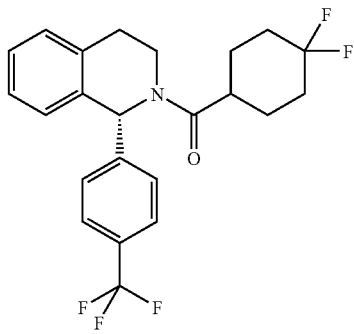 [SMILES: O=C(C1CCC(F)(F)CC1)N1CCc2ccccc2[C@H]1c1ccc(C(F)(F)F)cc1]

Example 112

(R)-(4,4-Difluorocyclohexyl)(1-(4-(trifluoromethyl) phenyl)-3,4-dihydroisoquinoline-2(1H)-yl)methanone To a stirred mixture of (R)-1-(4-(trifluoromethyl)phenyl)-1, 2,3,4-tetrahydroisoquinoline (0.205 g, 0.74 mmol), DIEA (0.14 mL, 0.81 mmol), and 4,4-difluoro-cyclohexanecarboxylic acid (0.13 g, 0.81 mmol) in DMF (4 mL) was added HATU (0.31 g, 0.81 mmol). The reaction mixture was continued to stir for 2 h, quenched with H$_2$O, and extracted with DCM (3×). The organic extracts were dried over Na$_2$SO$_4$, concentrated and purified by ISCO (20% EtOAc/hexanes) to give the white solid. MS (ESI, positive ion) m/z: 424 (M+1).

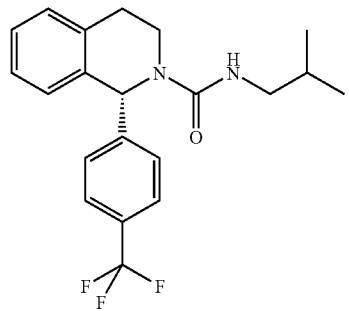 [SMILES: CC(C)CNC(=O)N1CCc2ccccc2[C@H]1c1ccc(C(F)(F)F)cc1]

Example 113

(R)—N-Isobutyl-1-(4-(trifluoromethyl)phenyl)-3,4-dihydroisoquinoline-2(1H)-carboxamide To a stirred mixture of (R)-1-(4-(trifluoromethyl)phenyl)-1, 2,3,4-tetrahydroisoquinoline (0.100 g, 0.36 mmol) and DIEA (0.082 mL, 0.47 mmol) in THF (2 mL) was added 4-nitrophenyl chloroformate (0.080 g, 0.40 mmol). The reaction mixture was stirred for 30 min, 2-methylpropan-1-amine (0.036 mL, 0.36 mmol) was added and stirring was continued for 14 h, then heated at reflux for 24 h, cooled, taken up in H$_2$O, extracted with EtOAc (3×), dried over MgSO$_4$, concentrated and purified by ISCO (20% EtOAc/hexanes) to give the title compound. MS (ESI, positive ion) m/z: 377 (M+1).

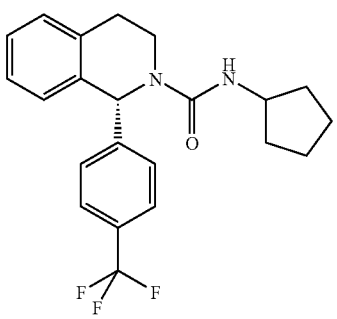 [SMILES: O=C(NC1CCCC1)N1CCc2ccccc2[C@H]1c1ccc(C(F)(F)F)cc1]

Example 114

(R)—N-Cyclopentyl-1-(4-(trifluoromethyl)phenyl)-3,4-dihydroisoquinoline-2(1H)-carboxamide A mixture of (R)-1-(4-(trifluoromethyl)phenyl)-1,2,3,4-tetrahydroisoquinoline (0.100 g, 0.361 mmol), N-ethyl-N-isopropylpropan-2-amine (0.0754 mL, 0.433 mmol), and isocyanatocyclopentane (0.0421 g, 0.379 mmol) in DCM (4 mL) was stirred at RT for 24 h. The mixture was concentrated and purified by ISCO (20% EtOAc/hexanes) to give the white solid. MS (ESI, positive ion) m/z: 389 (M+1).

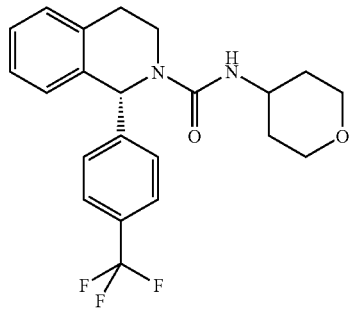 [SMILES: O=C(NC1CCOCC1)N1CCc2ccccc2[C@H]1c1ccc(C(F)(F)F)cc1]

Example 115

(R)—N-(Tetrahydro-2H-pyran-4-yl)-1-(4-(trifluoromethyl)phenyl)-3,4-dihydroisoquinoline-2(1H)-carboxamide This compound was prepared under similar conditions as described for example 111. MS (ESI, positive ion) m/z: (405 (M+1).

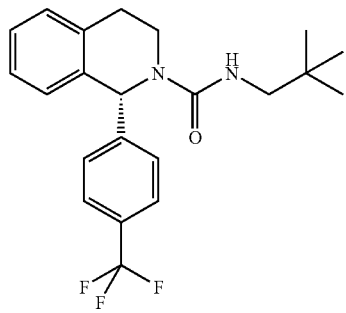 [SMILES: CC(C)(C)CNC(=O)N1CCc2ccccc2[C@H]1c1ccc(C(F)(F)F)cc1]

Example 116

(R)—N-Cyclopentyl-1-(4-(trifluoromethyl)phenyl)-3,4-dihydroisoquinoline-2(1H)-carboxamide This compound was prepared under similar conditions as described for example 111. MS (ESI, positive ion) m/z: 391 (M+1).

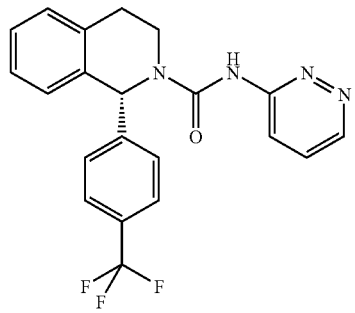 [SMILES: O=C(Nc1cccnn1)N1CCc2ccccc2[C@H]1c1ccc(C(F)(F)F)cc1]

Example 117

(R)—N-(Pyridazin-3-yl)-1-(4-(trifluoromethyl)phenyl)-3,4-dihydroisoquinoline-2(1H)-carboxamide This compound was prepared under similar conditions as described for example 111. MS (ESI, positive ion) m/z: 399 (M+1).

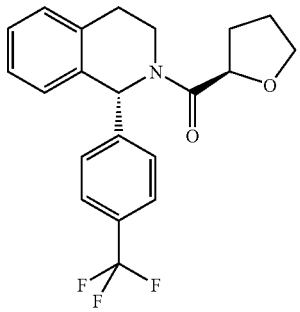 [SMILES: O=C([C@H]1CCCO1)N1CCc2ccccc2[C@H]1c1ccc(C(F)(F)F)cc1]

Example 118

((R)-Tetrahydrofuran-2-yl)((R)-1-(4-(trifluoromethyl)phenyl)-3,4-dihydro-isoquinoline-2(1H)-yl)methanone This compound was prepared under similar conditions as described for example 112. MS (ESI, positive ion) m/z: 376 (M+1).

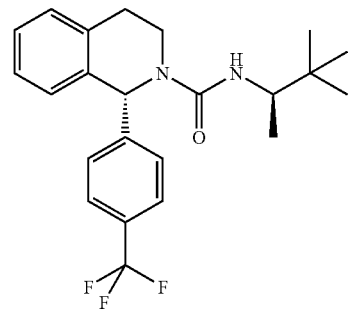 [SMILES: C[C@@H](NC(=O)N1CCc2ccccc2[C@H]1c1ccc(C(F)(F)F)cc1)C(C)(C)C]

Example 119

(R)—N—((R)-3,3-Dimethylbutan-2-yl)-1-(4-(trifluoromethyl)phenyl)-3,4-dihydroisoquinoline-2(1H)-carboxamide This compound was prepared under similar conditions as described for example 112. MS (ESI, positive ion) m/z: 405 (M+1).

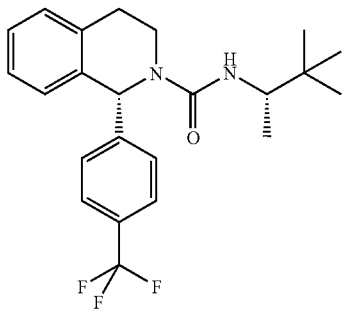 [SMILES: C[C@H](NC(=O)N1CCc2ccccc2[C@H]1c1ccc(C(F)(F)F)cc1)C(C)(C)C]

Example 120

(R)—N—((S)-3,3-Dimethylbutan-2-yl)-1-(4-(trifluoromethyl)phenyl)-3,4-dihydroisoquinoline-2(1H)-carboxamide This compound was prepared under similar conditions as described for example 112. MS (ESI, positive ion) m/z: 405 (M+1).

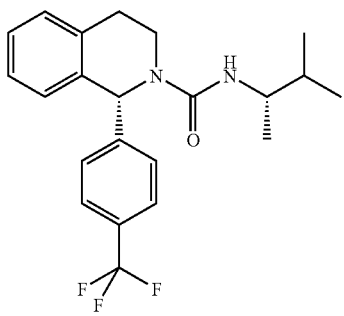 [SMILES: CC(C)[C@H](C)NC(=O)N1CCc2ccccc2[C@H]1c1ccc(C(F)(F)F)cc1]

Example 121

(R)—N—((S)-3,3-Methylbutan-2-yl)-1-(4-(trifluoromethyl)phenyl)-3,4-dihydro-isoquinoline-2(1H)-carboxamide This compound was prepared under similar conditions as described for example 112. MS (ESI, positive ion) m/z: 391 (M+1).

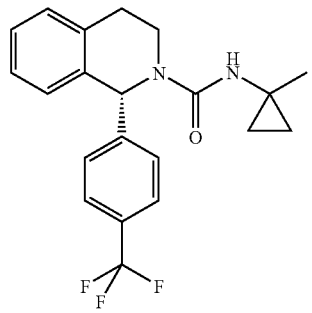 [SMILES: CC1(NC(=O)N2CCc3ccccc3[C@H]2c2ccc(C(F)(F)F)cc2)CC1]

Example 122

(R)—N-(1-(Methylcyclopropyl)-1-(4-(trifluoromethyl)phenyl)-3,4-dihydroisoquinoline-2(1H)-carboxamide This compound was prepared under similar conditions as described for example 110. MS (ESI, positive ion) m/z: 375 (M+1).

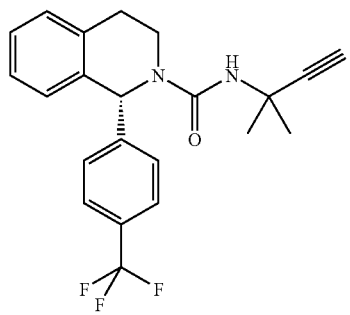 [SMILES: C#CC(C)(C)NC(=O)N1CCc2ccccc2[C@H]1c1ccc(C(F)(F)F)cc1]

Example 123

(R)—N-(2-Methylbut-3-yn-2-yl)-1-(4-(trifluoromethyl)phenyl)-3,4-dihydroisoquinoline-2(1H)-carboxamide This compound was prepared under similar conditions as described for example 111. MS (ESI, positive ion) m/z: 387 (M+1).

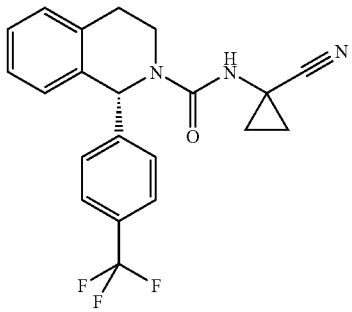 [SMILES: N#CC1(NC(=O)N2CCc3ccccc3[C@H]2c2ccc(C(F)(F)F)cc2)CC1]

Example 124

(R)—N-(1-(Cyanocyclopropyl)-1-(4-(trifluoromethyl)phenyl)-3,4-dihydroisoquinoline-2(1H)-carboxamide This compound was prepared under similar conditions as described for example 110. MS (ESI, positive ion) m/z: 386 (M+1).

Example 125

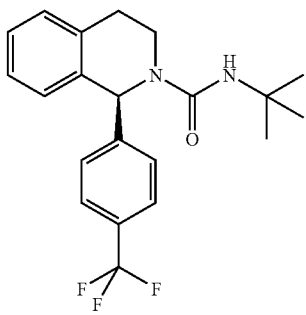 [SMILES: CC(C)(C)NC(=O)N1CCc2ccccc2[C@@H]1c1ccc(C(F)(F)F)cc1]

(S)—N-tert-Butyl-1-(4-(trifluoromethyl)phenyl)-3,4-dihydroisoquinoline-2(1H)-carboxamide This compound was prepared under similar conditions as described for example 114. MS (ESI, positive ion) m/z: 377 (M+1).

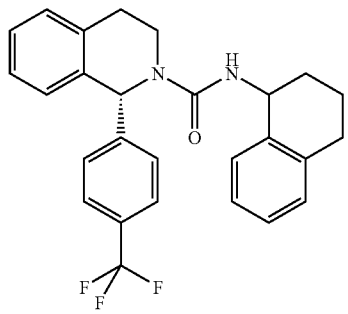 [SMILES: O=C(NC1CCCc2ccccc21)N1CCc2ccccc2[C@H]1c1ccc(C(F)(F)F)cc1]

Example 126

(R)—N-(1,2,3,4-Tetrahydronaphthalen-1-yl)-1-(4-(trifluoromethyl)phenyl)-3,4-dihydroisoquinoline-2(1H)-carboxamide This compound was prepared under similar conditions as described for example 114. MS (ESI, positive ion) m/z: 451 (M+1).

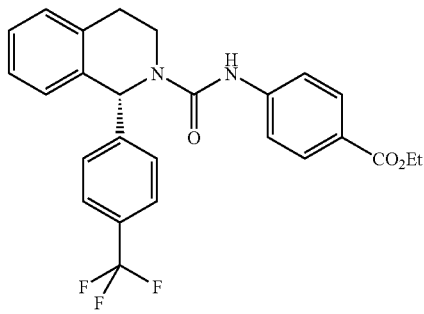 [SMILES: CCOC(=O)c1ccc(NC(=O)N2CCc3ccccc3[C@H]2c2ccc(C(F)(F)F)cc2)cc1]

Example 127

(R)-Ethyl 4-(1-(4-(trifluoromethyl)phenyl)-1,2,3,4-tetrahydroisoquinoline-2-carboxamido)benzoate This compound was prepared under similar conditions as described for example 114. MS (ESI, positive ion) m/z: 469 (M+1).

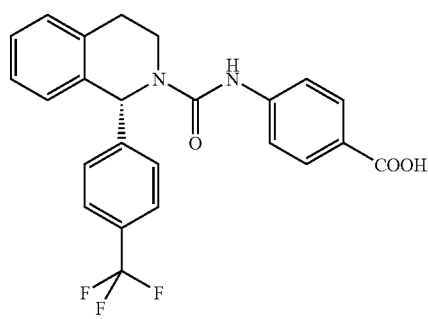 [SMILES: O=C(O)c1ccc(NC(=O)N2CCc3ccccc3[C@H]2c2ccc(C(F)(F)F)cc2)cc1]

Example 128

(R)-4-(1-(4-(Trifluoromethyl)phenyl)-1,2,3,4-tetrahydroisoquinoline-2-carboxamido)benzoic acid A mixture of (R)-ethyl 4-(1-(4-(trifluoromethyl)-phenyl)-1,2,3,4-tetrahydroisoquinoline-2-carboxamido)benzoate (0.210 g, 0.4 mmol) and NaOH (0.4 mL, 2 mmol) in EtOH (5 mL) was stirred at RT in 24 h. The mixture was concentrated, taken up in H$_2$O and neutralized with 10% HCl. The white solid was collected by filtration and dried. MS (ESI, positive ion) m/z: 441 (M+1).

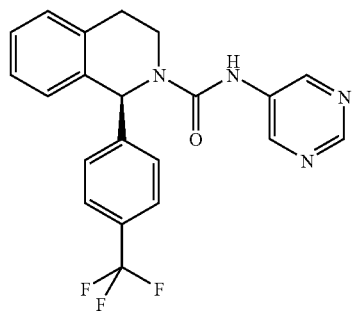 [SMILES: O=C(Nc1cncnc1)N1CCc2ccccc2[C@@H]1c1ccc(C(F)(F)F)cc1]

Example 129

(S)—N-(Pyrimidin-5-yl)-1-(4-(trifluoromethyl)phenyl)-3,4-dihydroisoquinoline-2(1H)-carboxamide This compound was prepared under similar conditions as described for example 110. MS (ESI, positive ion) m/z: 399 (M+1).

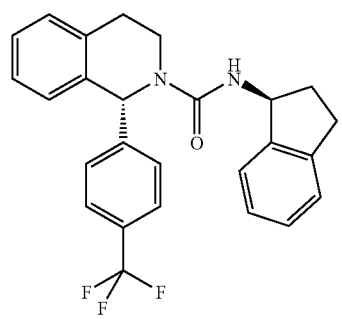 [SMILES: O=C(N[C@H]1CCc2ccccc21)N1CCc2ccccc2[C@H]1c1ccc(C(F)(F)F)cc1]

Example 130

(R)—N—((S)-2,3-Dihydro-1H-inden-1-yl)-1-(4-(trifluoromethyl)phenyl)-3,4-dihydroisoquinoline-2(1H)-carboxamide This compound was prepared under similar conditions as described for example 114. MS (ESI, positive ion) m/z: 437 (M+1).

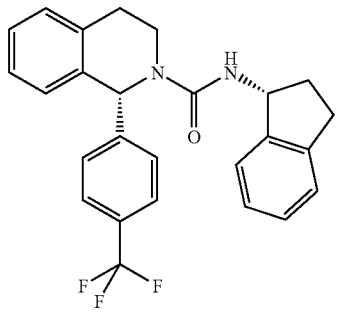 [SMILES: O=C(N[C@@H]1CCc2ccccc21)N1CCc2ccccc2[C@H]1c1ccc(C(F)(F)F)cc1]

Example 131

(R)—N—((R)-2,3-Dihydro-1H-inden-1-yl)-1-(4-(trifluoromethyl)phenyl)-3,4-dihydroisoquinoline-2(1H)-carboxamide This compound was prepared under similar conditions as described for example 114. MS (ESI, positive ion) m/z: 437 (M+1).

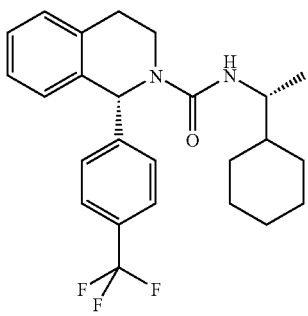 [SMILES: C[C@@H](NC(=O)N1CCc2ccccc2[C@H]1c1ccc(C(F)(F)F)cc1)C1CCCCC1]

Example 132

(R)—N—((R)-1-Cyclohexylethyl)-1-(4-(trifluoromethyl)phenyl)-3,4-dihydroisoquinoline-2(1H)-carboxamide This compound was prepared under similar conditions as described for example 114. MS (ESI, positive ion) m/z: 431 (M+1).

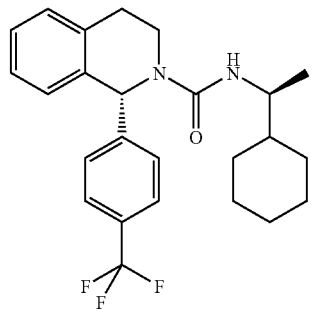 [SMILES: C[C@H](NC(=O)N1CCc2ccccc2[C@H]1c1ccc(C(F)(F)F)cc1)C1CCCCC1]

Example 133

(R)—N—((S)-1-cyclohexylethyl)-1-(4-(trifluoromethyl)phenyl)-3,4-dihydroisoquinoline-2(1H)-carboxamide This compound was prepared under similar conditions as described for example 114. MS (ESI, positive ion) m/z: 431 (M+1).

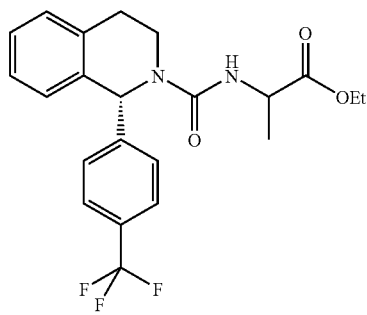 [SMILES: CCOC(=O)C(C)NC(=O)N1CCc2ccccc2[C@H]1c1ccc(C(F)(F)F)cc1]

Example 134

(R)-Ethyl 2-(1-(4-(trifluoromethyl)phenyl)-1,2,3,4-tetrahydroisoquinoline-2-carboxamido)propanoate This compound was prepared under similar conditions as described for example 114. MS (ESI, positive ion) m/z: 421 (M+1).

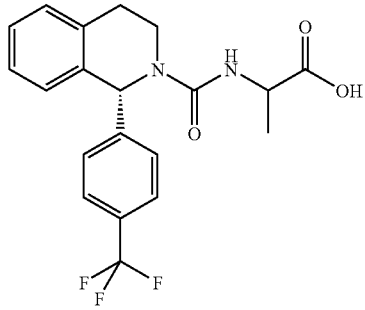 [SMILES: CC(NC(=O)N1CCc2ccccc2[C@H]1c1ccc(C(F)(F)F)cc1)C(=O)O]

Example 135

(R)-2-(1-(4-(trifluoromethyl)phenyl)-1,2,3,4-tetrahydroisoquinoline-2-carboxamido)propanoic acid This compound was prepared under similar conditions as described for example 128. MS (ESI, positive ion) m/z: 393 (M+1).

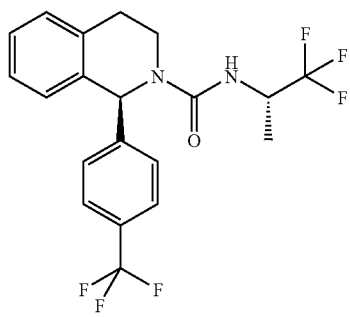 [SMILES: C[C@H](NC(=O)N1CCc2ccccc2[C@@H]1c1ccc(C(F)(F)F)cc1)C(F)(F)F]

Example 136

(S)-1-(4-(trifluoromethyl)phenyl)-N—((S)-1,1,1-trifluoropropan-2-yl)-3,4-dihydroisoquinoline-2(1H)-carboxamide This compound was prepared under similar conditions as described for example 109. MS (ESI, positive ion) m/z: 417 (M+1).

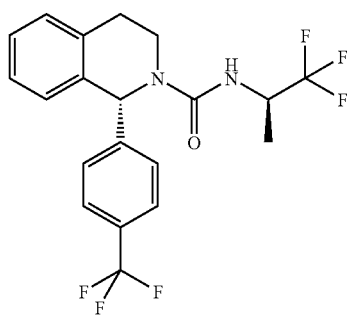 [SMILES: C[C@@H](NC(=O)N1CCc2ccccc2[C@H]1c1ccc(C(F)(F)F)cc1)C(F)(F)F]

Example 137

(R)-1-(4-(trifluoromethyl)phenyl)-N—((R)-1,1,1-trifluoropropan-2-yl)-3,4-dihydroisoquinoline-2(1H)-carboxamide This compound was prepared under similar conditions as described for example 109. MS (ESI, positive ion) m/z: 417 (M+1).

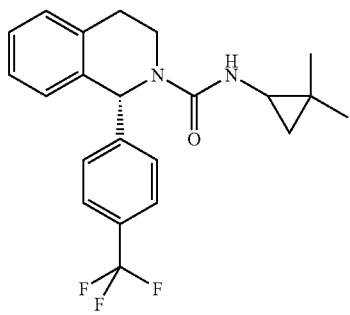 [SMILES: CC1(C)CC1NC(=O)N1CCc2ccccc2[C@H]1c1ccc(C(F)(F)F)cc1]

Example 138

(R)—N-(Dimethylcyclopropyl)-1-(4-(trifluoromethyl)phenyl)-3,4-dihydroisoquinoline-2(1H)-carboxamide This compound was prepared under similar conditions as described for example 110. MS (ESI, positive ion) m/z: 389 (M+1).

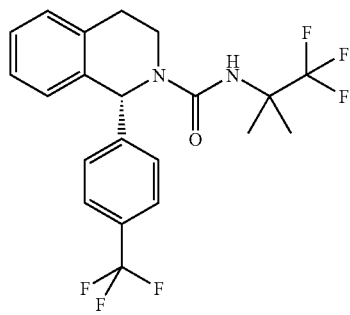 [SMILES: CC(C)(NC(=O)N1CCc2ccccc2[C@H]1c1ccc(C(F)(F)F)cc1)C(F)(F)F]

Example 139

(R)—N-(1,1,1-Trifluoro-2-methylpropan-2-yl)-1-(4-(trifluoromethyl)phenyl)-3,4-dihydroisoquinoline-2(1H)-carboxamide This compound was prepared under similar conditions as described for example 110. MS (ESI, positive ion) m/z: 431 (M+1).

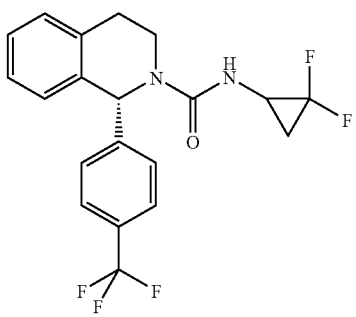 [SMILES: O=C(NC1CC1(F)F)N1CCc2ccccc2[C@H]1c1ccc(C(F)(F)F)cc1]

Example 140

(R)—N-(2,2-Difluorocyclopropyl)-1-(4-(trifluoromethyl)phenyl)-3,4-dihydro-isoquinoline-2(1H)-carboxamide This compound was prepared under similar conditions as described for example 110. MS (ESI, positive ion) m/z: 397 (M+1).

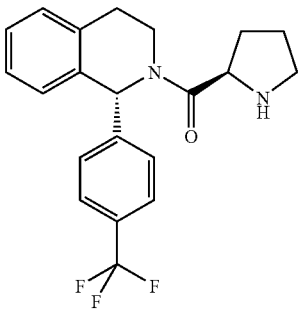 [SMILES: O=C([C@H]1CCCN1)N1CCc2ccccc2[C@H]1c1ccc(C(F)(F)F)cc1]

Example 141

(R)-Pyrrolidin-2-yl((R)-1-(4-(trifluoromethyl)phenyl)-3,4-dihydroisoquinoline-2(1H)-yl)methanone To a stirred mixture of (R)-1-(tert-butoxy-carbonyl)pyrrolidine-2-carboxylic acid (0.078 g, 0.36 mmol), (R)-1-(4-(trifluoro-methyl)phenyl)-1,2,3,4-tetrahydroisoquinoline (0.100 g, 0.36 mmol) and DIEA (0.047 g, 0.36 mmol) in DMF (2 mL) was added HATU (0.14 g, 0.36 mmol). The reaction mixture was continued to stir overnight at RT, hydrolyzed with H₂O, extracted with DCM (3×), dried over Na₂SO₄, concentrated and purified by ISCO (20% EtOAc/hexanes) to give the white solid which was dissolved in p-dioxane (2 mL) and added 1 mL of 4M HCl in p-dioxane. The mixture was continued to stir at RT overnight, concentrated, taken up in H₂O, and neutralized by saturated aqueous NaHCO₃, and filtered the light yellow solid which was dried by air. MS (ESI, positive ion) m/z: 375 (M+1).

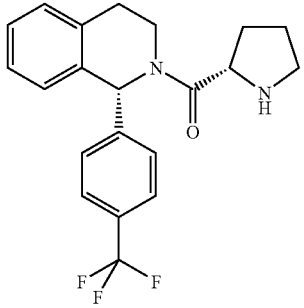 [SMILES: O=C([C@@H]1CCCN1)N1CCc2ccccc2[C@H]1c1ccc(C(F)(F)F)cc1]

Example 142

(S)-Pyrrolidin-2-yl((R)-1-(4-(trifluoromethyl)phenyl)-3,4-dihydroisoquinoline-2(1H)-yl)methanone This compound was prepared under similar conditions as described for example 141. MS (ESI, positive ion) m/z: 375 (M+1).

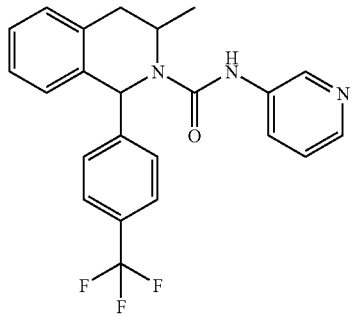 [SMILES: CC1Cc2ccccc2C(c2ccc(C(F)(F)F)cc2)N1C(=O)Nc1cccnc1]

Example 143

3-Methyl-N-(pyridin-3-yl)-1-(4-(trifluoromethyl)phenyl)-3,4-dihydroisoquinoline-2(1H)-carboxamide

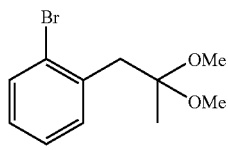

Step 1: 1-Bromo-2-(2,2-dimethoxypropyl)benzene

2-Bromophenylacetone (4.45000 g, 21 mmol) was dissolved in 10 mL MeOH and trimethyl orthoformate (11 mL, 104 mmol) and hydrogen chloride, 4.0M solution in 1,4-dioxane (5.2 mL, 21 mmol) were added. The mixture was stirred for 1 h and neutralized carefully with DIEA (pH 7). The mixture was evaporated and filtered through a plug of silica providing 1-bromo-2-(2,2-dimethoxypropyl)benzene as a colorless liquid.

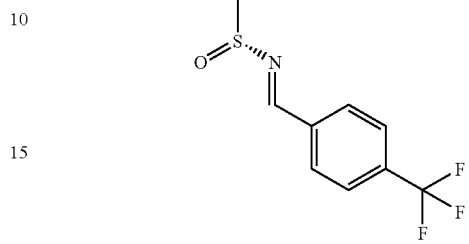

Step 2: (R)—N-(4-(Trifluoromethyl)benzylidene)-2-methylpropane-2-sulfinamide (R)-2-methylpropane-2-sulfinamide (31.6 g, 260 mmol), 4-(trifluoromethyl)-benzaldehyde (22.7 g, 130 mmol) and cupric sulfate (83.2 g, 521 mmol) were added to 300 mL DCM and the mixture was stirred for 36 h. The mixture was filtered through a pad of celite and the filtrate was evaporated and purified via silica plug filtration. (R)—N-(4-(trifluoromethyl)benzylidene)-2-methylpropane-2-sulfinamide was obtained as a white solid.

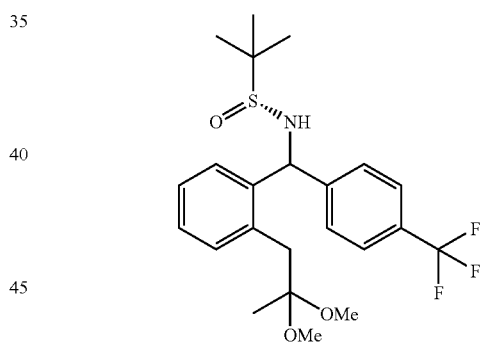

Step 3: (R)—N-((2-(2,2-Dimethoxypropyl)phenyl)(4-(trifluoromethyl)phenyl)-methyl)-2-methylpropane-2-sulfinamide 1-Bromo-2-(2,2-dimethoxypropyl)benzene (4.00 g, 15.43 mmol) was dissolved in 150 mL THF and tert-butyllithium (18.160 mL, 30.871 mmol) was added dropwise at −78° C. After addition a solution of (R)—N-(4-(trifluoromethyl)-benzylidene)-2-methylpropane-2-sulfinamide (8.5608 g, 30.871 mmol) in THF (10 mL) was added and stirring was continued for 10 min in the cold. The reaction was hydrolyzed with 50 mL water and the mixture was warmed to RT. TLC showed a 1:1 mixture of the 2 diastereomers. No attempt was undertaken to separate the isomers. Glass column chromatography provided the title compound as a mixture of diastereomers. MS (ESI, positive ion) m/z: 412.0 (M+1; hydrolysis of the dimethyl acetal to the corresponding ketone).

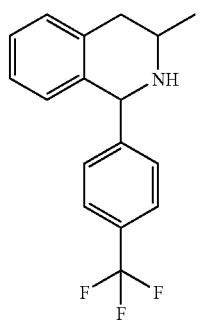 [SMILES: CC1Cc2ccccc2C(c2ccc(C(F)(F)F)cc2)N1]

Step 4: 3-Methyl-1-(4-(trifluoromethyl)phenyl)-1,2,3,4-tetrahydroisoquinoline (R)—N-((2-(2,2-Dimethoxypropyl)phenyl)(4-(trifluoromethyl)phenyl)methyl)-2-methylpropane-2-sulfinamide (6.650000 g, 15 mmol) was dissolved in 150 mL of DCE and hydrogen chloride, 4.0 m solution in 1,4-dioxane (11 mL, 44 mmol) was added. Stirring was continued for 20 min and trimethyl orthoformate (8.0 mL, 73 mmol) and sodium triacetoxyborohydride (11 g, 51 mmol) were added. TLC-analysis showed a complex product mixture but LCMS showed the formation of some desired product along with a lot of fully aromatized product. The crude was semi-purified via glass colm chrom and used w/o further clean up in the next steps. MS (ESI, positive ion) m/z: 292.0 (M+1)

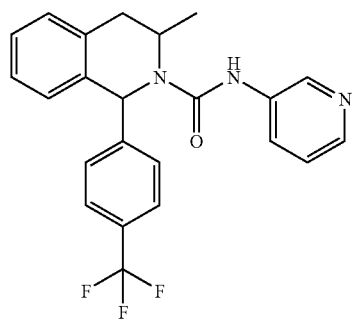 [SMILES: CC1Cc2ccccc2C(c2ccc(C(F)(F)F)cc2)N1C(=O)Nc1cccnc1]

Step 5: 3-Methyl-N-(pyridin-3-yl)-1-(4-(trifluoromethyl)phenyl)-3,4-dihydro-isoquinoline-2(1H)-carboxamide 3-Methyl-1-(4-(trifluoromethyl)phenyl)-1,2,3,4-tetrahydroisoquinoline (0.100 g, 0.343 mmol, semi-pure from the previous reaction) was dissolved in 3 mL DCM and DIEA (0.119 mL, 0.687 mmol) and 3-isocyanatopyridine (79 mg, 0.659 mmol) were added. Stirring was continued for 2 h and the mixture was hydrolyzed with 3 drops of water, diluted with 3 mL DMF and injected on the HPLC for purification. The title compound was obtained. No stereochemical assignment was performed.

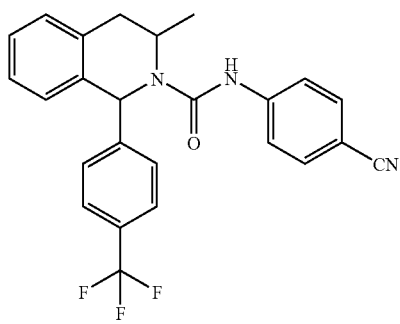 [SMILES: CC1Cc2ccccc2C(c2ccc(C(F)(F)F)cc2)N1C(=O)Nc1ccc(C#N)cc1]

Example 144

N-(4-Cyanophenyl)-3-methyl-1-(4-(trifluoromethyl)phenyl)-3,4-dihydroisoquinoline-2(1H)-carboxamide The reaction was performed under similar conditions as described for example 143. The title compound were obtained. No stereochemical assignment was performed.

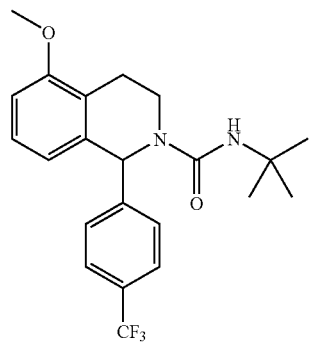 [SMILES: COc1cccc2c1CCN(C(=O)NC(C)(C)C)C2c1ccc(C(F)(F)F)cc1]

Example 145

N-tert-Butyl-5-methoxy-1-(4-(trifluoromethyl)phenyl)-3,4-dihydroisoquinoline-2(1H)-carboxamide Synthetic Scheme:

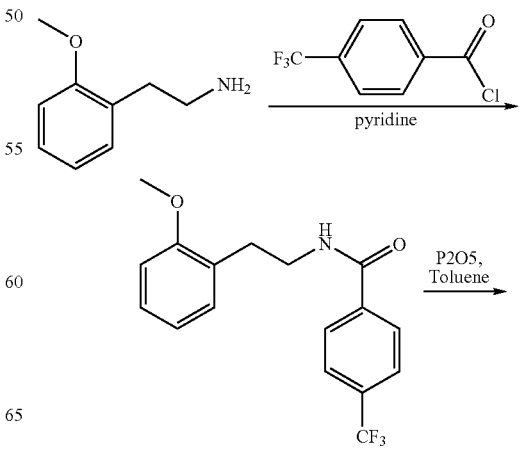

-continued

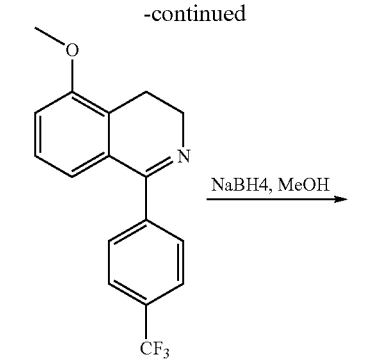

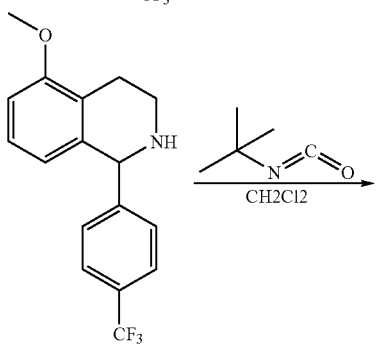

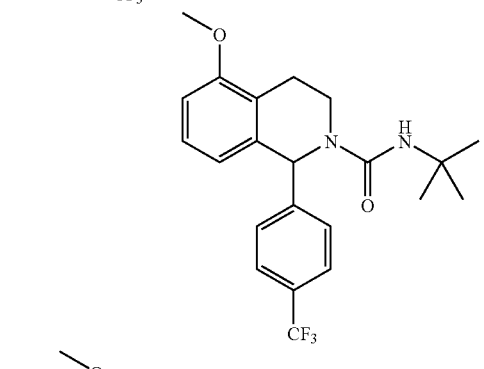

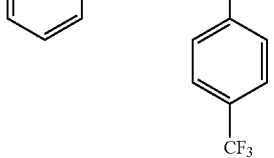

Step 1: N-(2-Methoxyphenethyl)-4-(trifluoromethyl) benzamide

To a 100 mL round-bottomed flask was added 2-(2-methoxyphenyl)ethylamine (1510 mg, 10 mmol, Aldrich), pyridine (10 mL), 4-(trifluoromethyl)benzoyl chloride (2 mL, 10 mmol, Fluka). The reaction mixture was stirred at RT for 1 h. The reaction mixture was diluted with water (20 mL) and extracted with EtOAc (2×50 mL). The organic extract was washed with saturated NaHCO$_3$ (20 mL), saturated NaCl (20 mL), dried over Na$_2$SO$_4$, filtered and concentrated in vacuo and the residue was purified by silica gel chromatography, eluting with 20% EtOAc/CH$_2$Cl$_2$ to give N-(2-methoxyphenethyl)-4-(trifluoromethyl)benzamide. MS (ESI pos. ion) m/z: 324 (M+1).

Step 2: 5-Methoxy-1-(4-(trifluoromethyl)phenyl)-3,4-dihydroisoquinoline

To a 100 mL round-bottomed flask was added N-(2-methoxyphenethyl)-4-(trifluoromethyl)benzamide (1.41 g, 4361 µmol, from step 1), toluene (30 mL), phosphorus pentoxide (1077 µL, 17445 µmol, Aldrich). The reaction mixture was stirred at reflux for overnight (ca 18 h). The mixture was cooled down to RT and poured it to ice (ca 100 g). The mixture was neutralized with KOH until pH 12. The mixture was extracted with EtOAc (2×100 mL). The organic extract was washed with saturated NaCl (50 mL), dried over Na$_2$SO$_4$, filtered and concentrated in vacuo and the residue was purified by silica gel chromatography, eluting with 20% EtOAc/hexanes to give 5-methoxy-1-(4-(trifluoromethyl)phenyl)-3,4-dihydroisoquinoline. MS (ESI pos. ion) m/z: 306 (M+1).

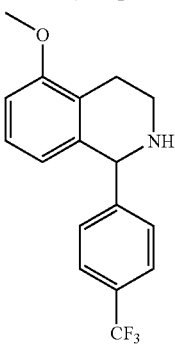 [SMILES: COc1cccc2c1CCNC2c1ccc(C(F)(F)F)cc1]

Step 3: 5-Methoxy-1-(4-(trifluoromethyl)phenyl)-1,2,3,4-tetrahydroisoquinoline

To a 50 mL round-bottomed flask was added 5-methoxy-1-(4-(trifluoromethyl)-phenyl)-3,4-dihydroisoquinoline (189 mg, 619 µmol, from step 2), MeOH (3 mL), sodium borohydride (21.8 µL, 619 µmol, Aldrich). The reaction mixture was stirred at RT for 1 h. The reaction mixture was diluted with water (5 mL) and extracted with EtOAc (2×20 mL). The organic extract was washed with saturated NaCl (5 mL), dried over Na$_2$SO$_4$, filtered and concentrated in vacuo and the residue was purified by silica gel chromatography, eluting with 80% EtOAc/hexanes to give 5-methoxy-1-(4-(trifluoromethyl)phenyl)-1,2,3,4-tetrahydroisoquinoline. MS (ESI pos. ion) m/z: 308 (M+1).

Step 4: N-tert-Butyl-5-methoxy-1-(4-(trifluoromethyl)phenyl)-3,4-dihydroisoquinoline-2(1H)-carboxamide To a 50 mL round-bottomed flask was added 5-methoxy-1-(4-(trifluoromethyl)-phenyl)-1,2,3,4-tetrahydroisoquinoline (44 mg, 143 μmol, from step 3), CH$_2$Cl$_2$ (2 mL), t-butylisocyanate (16 μL, 143 μmol, Aldrich). The solution was stirred at RT for 5 h. The solvent was removed in vacuo and the residue was purified by silica gel chromatography, eluting with 20% EtOAc/hexanes to give N-tert-butyl-5-methoxy-1-(4-(trifluoromethyl)phenyl)-3,4-dihydroisoquinoline-2(1H)-carboxamide. MS (ESI pos. ion) m/z: 407 (M+1).

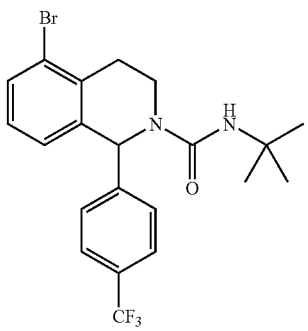 [SMILES: CC(C)(C)NC(=O)N1CCc2c(Br)cccc2C1c1ccc(C(F)(F)F)cc1]

Example 146

5-Bromo-N-tert-butyl-1-(4-(trifluoromethyl)phenyl)-3,4-dihydroisoquinoline-2(1H)-carboxamide

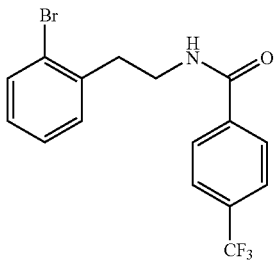 [SMILES: O=C(NCCc1ccccc1Br)c1ccc(C(F)(F)F)cc1]

Step 1:
N-(2-Bromophenethyl)-4-(trifluoromethyl)benzamide

To a 100 mL round-bottomed flask was added 2-bromophenethylamine (1800 mg, 9 mmol, Aldrich), pyridine (5 mL), 4-(trifluoromethyl)benzoyl chloride (2 mL, 9 mmol, Fluka). The reaction mixture was stirred at RT for 1 h. The reaction mixture was diluted with water (30 mL) and extracted with EtOAc (2×50 mL). The organic extract was washed with water (30 mL), saturated NaCl (30 mL), dried over Na$_2$SO$_4$, filtered and concentrated in vacuo and the residue was purified by silica gel chromatography, eluting with 30% EtOAc/hexanes to give N-(2-bromophenethyl)-4-(trifluoromethyl)benzamide. MS (ESI pos. ion) m/z: 372 (M+1).

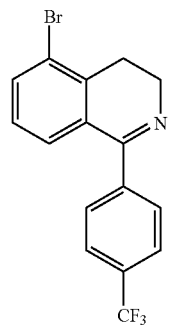

Step 2. 5-Bromo-1-(4-(trifluoromethyl)phenyl)-3,4-dihydroisoquinoline

To a 100 mL round-bottomed flask was added N-(2-bromophenethyl)-4-(tri-fluoromethyl)benzamide (1.6 g, 4299 μmol, from step 1), toluene (50 mL), phosphorus pentaoxide (1061 μL, 17196 μmol, Aldrich). The reaction mixture was stirred at reflux for 5 h. The mixture was cooled down and then poured into ice (ca 50 g), and extracted with EtOAc (2×50 mL). The organic extract was washed with water (30 mL), saturated NaCl (30 mL), dried over Na$_2$SO$_4$, filtered and concentrated in vacuo and the residue was purified by silica gel chromatography, eluting with 10% EtOAc/hexanes to give 5-bromo-1-(4-(trifluoromethyl)phenyl)-3,4-dihydroisoquinoline. MS (ESI pos. ion) m/z: 354 (M+1).

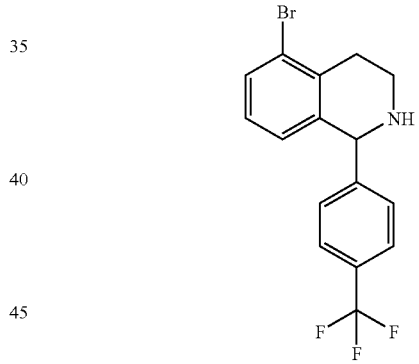

Step 3: 5-Bromo-1-(4-(trifluoromethyl)phenyl)-1,2,3,4-tetrahydroisoquinoline

To a 100 mL round-bottomed flask was added 5-bromo-1-(4-(trifluoromethyl)-phenyl)-3,4-dihydroisoquinoline (1.18 g, 3332 μmol, from step 2), MeOH (5 mL), sodium borohydride (117 μL, 3332 μmol, Aldrich). The reaction mixture was stirred at RT for 1 h. The reaction mixture was diluted with water (30 mL) and extracted with EtOAc (2×40 mL). The organic extract was washed with water (20 mL), saturated NaCl (20 mL), dried over Na$_2$SO$_4$, filtered and concentrated in vacuo and the residue was purified by silica gel chromatography, eluting with 40% EtOAc/hexanes to give 5-bromo-1-(4-(trifluoromethyl)phenyl)-1,2,3,4-tetrahydroisoquinoline. MS (ESI pos. ion) m/z: 356 (M+1).

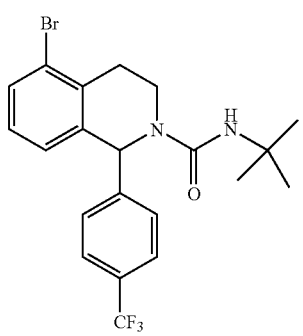 [SMILES: CC(C)(C)NC(=O)N1CCc2c(Br)cccc2C1c1ccc(C(F)(F)F)cc1]

Step 4. 5-Bromo-N-tert-butyl-1-(4-(trifluoromethyl)phenyl)-3,4-dihydroisoquinoline-2(1H)-carboxamide To a 50 mL round-bottomed flask was added 5-bromo-1-(4-(trifluoromethyl)-phenyl)-1,2,3,4-tetrahydroisoquinoline (44 mg, 124 μmol, from step 3), CH₂Cl₂ (2 mL), 2-isocyanato-2-methylpropane (12 mg, 124 μmol, Aldrich). The reaction mixture was stirred at RT for 2 h. The solvent was removed in vacuo and the residue was purified by silica gel chromatography, eluting with 50% EtOAc/hexanes to give 5-bromo-N-tert-butyl-1-(4-(trifluoromethyl)phenyl)-3,4-dihydroisoquinoline-2(1H)-carboxamide. MS (ESI pos. ion) m/z: 455 (M+1).

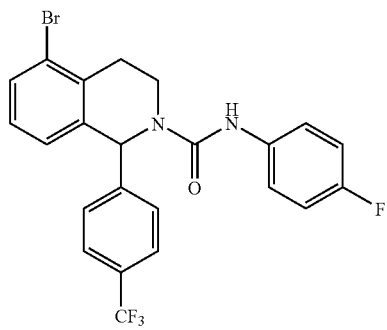 [SMILES: O=C(Nc1ccc(F)cc1)N1CCc2c(Br)cccc2C1c1ccc(C(F)(F)F)cc1]

Example 147

5-bromo-N-(4-fluorophenyl)-1-(4-(trifluoromethyl)phenyl)-3,4-dihydroisoquinoline-2(1H)-carboxamide To a 50 mL round-bottomed flask was added 5-bromo-1-(4-(trifluoromethyl)-phenyl)-1,2,3,4-tetrahydroisoquinoline (44 mg, 124 μmol, from step 3, example 146), CH₂Cl₂ (2 mL), 4-fluorophenyl isocyanate (17 mg, 124 μmol, Aldrich). The reaction mixture was stirred at RT for 1 h. The solvent was removed in vacuo and the residue was purified by silica gel chromatography, eluting with 50% EtOAc/hexanes to give 5-bromo-N-(4-fluorophenyl)-1-(4-(trifluoromethyl)-phenyl)-3,4-dihydroisoquinoline-2(1H)-carboxamide. MS (ESI pos. ion) m/z: 493 (M+1).

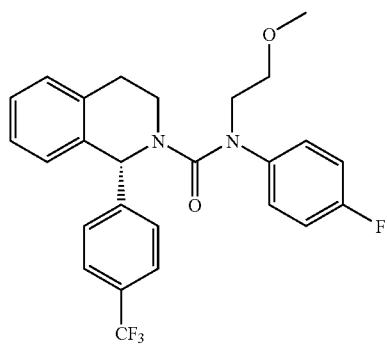 [SMILES: COCCN(C(=O)N1CCc2ccccc2[C@H]1c1ccc(C(F)(F)F)cc1)c1ccc(F)cc1]

Example 148

(R)—N-(4-Fluorophenyl)-N-(2-methoxyethyl)-1-(4-(trifluoromethyl)phenyl)-3,4-dihydroisoquinoline-2(1H)-carboxamide

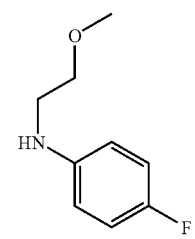

Step 1: 4-Fluoro-N-(2-methoxyethyl)aniline

To a 50 mL round-bottomed flask was added 4-fluoroaniline (383 μL, 3971 μmol, Aldrich), 2-bromoethyl methyl ether (552 μL, 3971 μmol, Aldrich), sodium carbonate (667 mg, 7943 μmol), DMF (2 mL). The reaction mixture was stirred at 80° C. for overnight (ca 17 h). The mixture was cooled down to RT. The reaction mixture was diluted with water (30 mL) and extracted with EtOAc (2×40 mL). The organic extract was washed with water (20 mL), saturated NaCl (20 mL), dried over Na₂SO₄, filtered and concentrated in vacuo and the residue was purified by silica gel chromatography, eluting with 30% EtOAc/hexanes to give 4-fluoro-N-(2-methoxyethyl)benzenamine. MS (ESI pos. ion) m/z: 170 (M+1).

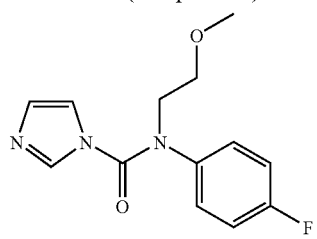

Step 2: N-(4-Fluorophenyl)-N-(2-methoxyethyl)-1H-imidazole-1-carboxamide

To a 50 mL round-bottomed flask was added 4-fluoro-N-(2-methoxyethyl)-benzenamine (512 mg, 3026 μmol, from step 1), 1,1'-carbonyldiimidazole (736 mg, 4539 μmol, Aldrich), THF (2 mL). The reaction mixture was stirred at 80° C. for 28 h. The solvent was removed in vacuo and the residue was purified by silica gel chromatography, eluting with 80%

EtOAc/hexanes to give N-(4-fluoro-phenyl)-N-(2-methoxyethyl)-1H-imidazole-1-carboxamide. MS (ESI pos. ion) m/z: 264 (M+1).

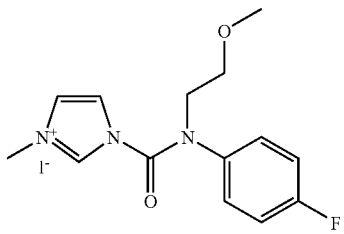 [SMILES: COCCN(C(=O)n1cc[n+](C)c1)c1ccc(F)cc1]

Step 3: 1-((4-Fluorophenyl)(2-methoxyethyl)carbamoyl)-3-methyl-1H-imidazol-3-ium iodide To a 50 mL round-bottomed flask was added N-(4-fluorophenyl)-N-(2-methoxy-ethyl)-1H-imidazole-1-carboxamide (91 mg, 346 μmol, from step 2), acetonitrile (2 mL), methyl iodide (86 μL, 1383 μmol, Aldrich). The solution was stirred at RT for 24 h. The solvent was removed in vacuo to give the product, which was used for the next step reaction without purification.

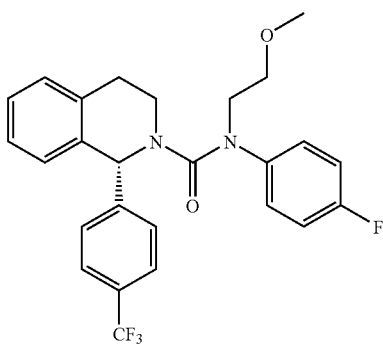 [SMILES: COCCN(C(=O)N1CCc2ccccc2[C@H]1c1ccc(C(F)(F)F)cc1)c1ccc(F)cc1]

Step 4: (R)—N-(4-Fluorophenyl)-N-(2-methoxyethyl)-1-(4-(trifluoromethyl)-phenyl)-3,4-dihydroisoquinoline-2(1H)-carboxamide To a 50 mL round-bottomed flask was added 1-((4-fluorophenyl)(2-methoxy-ethyl)carbamoyl)-3-methyl-1H-imidazol-3-ium iodide (70 mg, 173 μmol, from step 3), (R)-1-(4-(trifluoromethyl)phenyl)-1,2,3,4-tetrahydroisoquinoline (24 mg, 87 μmol), CH$_2$Cl$_2$ (1 mL), triethylamine (12 μL, 87 μmol). The reaction mixture was stirred at 40° C. for 28 h. The solvent was removed in vacuo and the residue was purified by silica gel chromatography, eluting with 30% EtOAc/hexanes to give (R)—N-(4-fluorophenyl)-N-(2-methoxyethyl)-1-(4-(trifluoromethyl)phenyl)-3,4-dihydroisoquinoline-2(1H)-carboxamide. MS (ESI pos. ion) m/z: 473 (M+1).

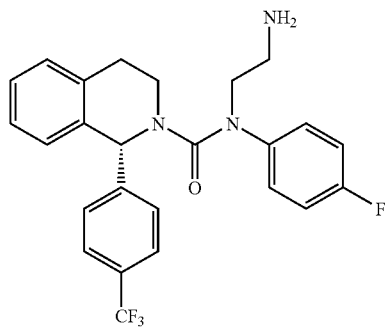 [SMILES: NCCN(C(=O)N1CCc2ccccc2[C@H]1c1ccc(C(F)(F)F)cc1)c1ccc(F)cc1]

Example 149

(R)—N-(2-Aminoethyl)-N-(4-fluorophenyl)-1-(4-(trifluoromethyl)phenyl)-3,4-dihydroisoquinoline-2(1H)-carboxamide

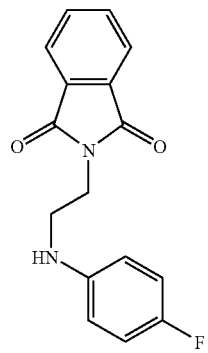 [SMILES: O=C1c2ccccc2C(=O)N1CCNc1ccc(F)cc1]

Step 1: 2-(2-(4-Fluorophenylamino)ethyl)isoindoline-1,3-dione

To a 50 mL round-bottomed flask was added n-(2-bromoethyl)phthalimide, 95% (508 mg, 1999 μmol, Aldrich), 4-fluoroaniline (193 μL, 1999 μmol, Aldrich), DMF (2 mL), sodium carbonate (336 mg, 3999 μmol). The reaction mixture was stirred at 80° C. for overnight. The reaction mixture was diluted with water (20 mL) and extracted with EtOAc (2×40 mL). The organic extract was washed with water (20 mL), saturated NaCl (20 mL), dried over Na$_2$SO$_4$, filtered and concentrated in vacuo and the residue was purified by silica gel chromatography, eluting with 30% EtOAc/hexanes to give 2-(2-(4-fluorophenylamino)ethyl)iso-indoline-1,3-dione. MS (ESI pos. ion) m/z: 285 (M+1).

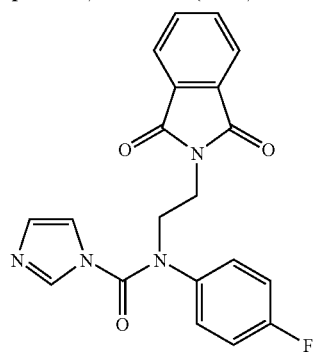

Step 2: N-(2-(1,3-Dioxoisoindolin-2-yl)ethyl)-N-(4-fluorophenyl)-1H-imidazole-1-carboxamide To a 50 mL round-bottomed flask was added 2-(2-(4-fluorophenylamino)ethyl)-isoindoline-1,3-dione (204 mg, 718 µmol, from step 1), 1,1'-carbonyldiimidazole (175 mg, 1076 µmol, Aldrich), THF (2 mL). The reaction mixture was stirred at 80° C. for 24 h. The solvent was removed in vacuo and the residue was purified by silica gel chromatography, eluting with 80% EtOAc/hexanes to give N-(2-(1,3-dioxoisoindolin-2-yl)ethyl)-N-(4-fluorophenyl)-1H-imidazole-1-carboxamide. MS (ESI pos. ion) m/z: 379 (M+1).

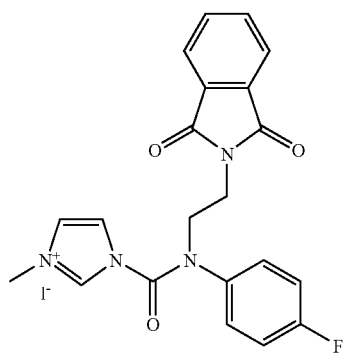 [SMILES: C[n+]1ccn(C(=O)N(CCN2C(=O)c3ccccc3C2=O)c2ccc(F)cc2)c1]

Step 3: 1-((2-(1,3-Dioxoisoindolin-2-yl)ethyl)(4-fluorophenyl)carbamoyl)-3-methyl-1H-imidazol-3-ium iodide To a 50 mL round-bottomed flask was added N-(2-(1,3-dioxoisoindolin-2-yl)ethyl)-N-(4-fluorophenyl)-1H-imidazole-1-carboxamide (110 mg, 291 µmol, from step 2), acetonitrile (2 mL), methyl iodide (72.4 µl, 1163 µmol, Aldrich). The reaction mixture was stirred at RT for 24 h. The solvent was removed in vacuo to give the product (151 mg, 99.8% yield), which was used for the next step reaction without purification.

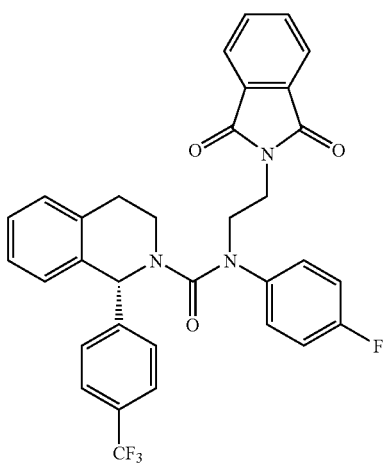 [SMILES: O=C1c2ccccc2C(=O)N1CCN(C(=O)N1CCc2ccccc2[C@H]1c1ccc(C(F)(F)F)cc1)c1ccc(F)cc1]

Step 4: (R)—N-(2-(1,3-Dioxoisoindolin-2-yl)ethyl)-N-(4-fluorophenyl)-1-(4-(trifluoromethyl)phenyl)-3,4-dihydroisoquinoline-2(1H)-carboxamide To a 50 mL round-bottomed flask was added (R)-1-(4-(trifluoromethyl)phenyl)-1,2,3,4-tetrahydroisoquinoline (80 mg, 290 µmol), 1-((2-(1,3-dioxoisoindolin-2-yl)ethyl)(4-fluorophenyl)carbamoyl)-3-methyl-1H-imidazol-3-ium iodide (151 mg, 290 µmol, from step 3), $CH_2Cl_2$ (2 mL). The reaction mixture was stirred at 40° C. for 48 h. The solvent was removed in vacuo and the residue was purified by silica gel chromatography, eluting with 30% EtOAc/hexanes to give (R)—N-(2-(1,3-dioxoisoindolin-2-yl)ethyl)-N-(4-fluorophenyl)-1-(4-(trifluoromethyl)-phenyl)-3,4-dihydroisoquinoline-2(1H)-carboxamide. MS (ESI pos. ion) m/z: 588 (M+1).

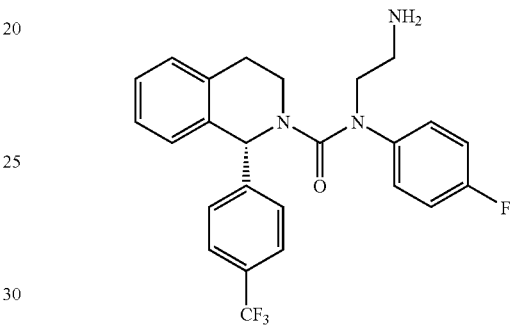

Step 5: (R)—N-(2-Aminoethyl)-N-(4-fluorophenyl)-1-(4-(trifluoromethyl)-phenyl)-3,4-dihydroisoquinoline-2(1H)-carboxamide To a 50 mL round-bottomed flask was added (R)—N-(2-(1,3-dioxoisoindolin-2-yl)ethyl)-N-(4-fluorophenyl)-1-(4-(trifluoromethyl)phenyl)-3,4-dihydroisoquinoline-2(1H)-carboxamide (16 mg, 27 µmol, from step 4), EtOH (1 mL), hydrazine, anhydrous (3.5 µL, 109 µmol, Aldrich). The solution was stirred at RT for 18 h. The solvent was removed in vacuo and the residue was purified by silica gel chromatography, eluting with 10% MeOH/$CH_2Cl_2$+1% ammonia (37% in water) to give (R)—N-(2-aminoethyl)-N-(4-fluorophenyl)-1-(4-(trifluoromethyl)-phenyl)-3,4-dihydroisoquinoline-2(1H)-carboxamide. MS (ESI pos. ion) m/z: 458 (M+1).

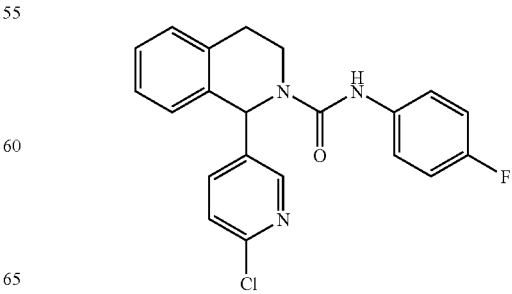

Example 150

1-(6-Chloropyridin-3-yl)-N-(4-fluorophenyl)-3,4-dihydroisoquinoline-2(1H)-carboxamide

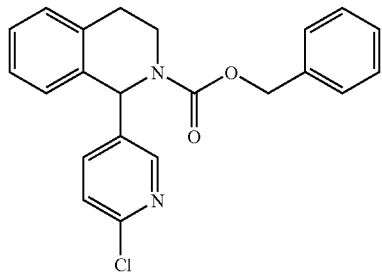 [SMILES: O=C(OCc1ccccc1)N1CCc2ccccc2C1c1ccc(Cl)nc1]

Step 1: Benzyl 1-(6-chloropyridin-3-yl)-3,4-dihydroisoquinoline-2(1H)-carboxylate To a pear-shaped flask was added 5-bromo-2-chloropyridine (440 mg, 2286 μmol), dry THF (10 mL), and an ice bath. After stirring for 5 min, a 2M solution of isopropylmagnesium chloride (1.15 mL, 2300 μmol) was added. The solution was allowed to stir in the ice bath for 2 h, then transferred to a solution of 3,4-dihydroisoquinoline (165 mg, 1258 μmol), dry THF (5 mL), and benzyl chloroformate (0.20 mL, 1350 μmol) that had been stirring in an ice bath for 15 min. The solution was allowed to warm to RT. After 1 h, LC-MS indicated only partial conversion. Another 2 eq of the Grignard were prepared as described above and added to the reaction. After a further 15 h, LC-MS shows no further progress. The reaction was poured into sat'd Rochelle's salt and extracted with EtOAc (3×20 mL). The combined organics were washed with brine and concentrated in vacuo and adsorbed onto a plug of silica gel and chromatographed through a Redi-Sep® pre-packed silica gel column (12 g), eluting with 0% to 20% EtOAc in hexanes, to provide crude benzyl 1-(6-chloropyridin-3-yl)-3,4-dihydro-isoquinoline-2(1H)-carboxylate as a yellow oil. The crude oil was carried into the next step.

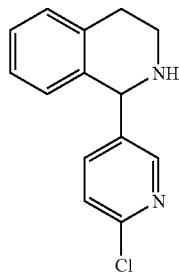 [SMILES: Clc1ccc(C2NCCc3ccccc32)cn1]

Step 2: 1-(6-Chloropyridin-3-yl)-1,2,3,4-tetrahydroisoquinoline

To a round-bottomed flask was added crude benzyl 1-(6-chloropyridin-3-yl)-3,4-dihydroisoquinoline-2(1H)-carboxylate (170 mg, 449 μmol), $CH_2Cl_2$ (10 mL) and TFA (10 mL). The reaction was allowed to stir at RT. After 3 days, LC-MS shows little progress. The reaction was concentrated in vacuo to remove $CH_2Cl_2$ and the resulting solution allowed to stir for another 3 days, then cautiously poured into 10% $Na_2CO_3$ and extracted with $CH_2Cl_2$ (3×20 mL). The combined organic layers were concentrated in vacuo and purified by reverse-phase preparative HPLC (Shimadzu) on a Phe-nomenex Gemini® column (5 micron, C18, 110 Å, Axia, 100×50 mm) eluting at 90 mL/min with an linear gradient of 10% to 100% MeCN (0.1% TFA) in water (0.1% TFA) over 20 min to give crude 1-(6-chloropyridin-3-yl)-1,2,3,4-tetrahydroisoquinoline as a white solid. The crude solid was carried into the next step. MS (ESI pos. ion) m/z: 245 (M+1).

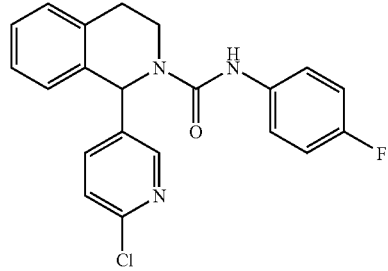

Step 3: 1-(6-chloropyridin-3-yl)-N-(4-fluorophenyl)-3,4-dihydroisoquinoline-2(1H)-carboxamide To a round-bottomed flask was added crude 1-(6-chloropyridin-3-yl)-1,2,3,4-tetrahydroisoquinoline (7 mg, 29 μmol), $CH_2Cl_2$ (3 mL), and 1 drop of 1-fluoro-4-isocyanatobenzene. The solution was stirred overnight, then concentrated in vacuo and purified by reverse-phase preparative HPLC (Shimadzu) on a Phenomenex Gemini® column (10 micron, C18, 110 Å, Axia, 100×30 mm) eluting at 45 mL/min with an linear gradient of 10% to 100% MeCN (0.1% TFA) in water (0.1% TFA) over 10 min to give 1-(6-chloropyridin-3-yl)-N-(4-fluorophenyl)-3,4-dihydroisoquinoline-2(1H)-carboxamide as a TFA salt. MS (ESI pos. ion) m/z: 382 (M+1).

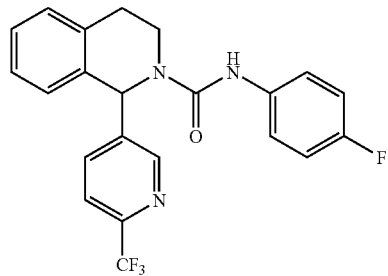

Example 151

N-(4-Fluorophenyl)-1-(6-(trifluoromethyl)pyridin-3-yl)-3,4-dihydroisoquinoline-2(1H)-carboxamide

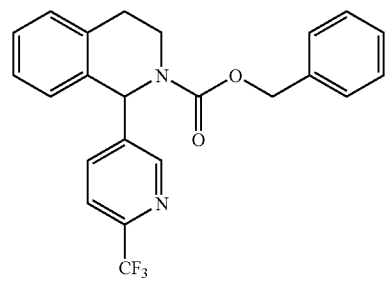 [SMILES: O=C(OCc1ccccc1)N1CCc2ccccc2C1c1ccc(C(F)(F)F)nc1]

Step 1: Benzyl 1-(6-(trifluoromethyl)pyridin-3-yl)-3,4-dihydroisoquinoline-2(1H)-carboxylate To a solution of 5-bromo-2-(trifluoromethyl)pyridine (258 mg, 1144 μmol) in THF (5 mL) at 0° C. was added isopropylmagnesium chloride (572 μL, 1144 μmmol) and the red/brown solution was stirred 2 h under N₂. To a solution of 3,4-dihydroisoquinoline (75 mg, 572 μmol) in THF (2 mL) at 0° C. was added benzyl chloroformate (90 μL, 629 μmol) and the reaction was warmed to RT and stirred 15 min. The solution of Grignard reagent was added to the iminium salt and the reaction warmed to RT and stirred 1 h. The reaction was quenched with saturated NH₄Cl (20 mL) and extracted with CH₂Cl₂ (3×20 mL). The combined organic layers were dried (MgSO₄) and concentrated to give a yellow oil. Purification by ISCO (12 g SiO₂, 0-50% EtOAc/hexane) gives benzyl 1-(6-(trifluoromethyl)-pyridin-3-yl)-3,4-dihydroisoquinoline-2(1H)-carboxylate as a yellow oil.

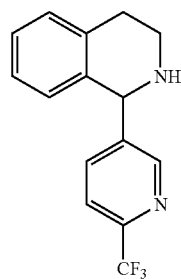

Step 2: 1-(6-(Trifluoromethyl)pyridin-3-yl)-1,2,3,4-tetrahydroisoquinoline

To a solution of benzyl 1-(6-(trifluoromethyl)pyridin-3-yl)-3,4-dihydroisoquinoline-2(1H)-carboxylate (90 mg, 218 μmol) in MeOH (3 mL) at RT under N₂ was added 10% palladium on carbon (46 mg, 44 μmol) and suspension was sparged with H₂ 15 min. The reaction was stirred under H₂ at RT 3.5 h. The reaction was filtered through a pad of Celite® (2×5 mL EtOAc wash) and concentrated to give 1-(6-(trifluoromethyl)pyridin-3-yl)-1,2,3,4-tetrahydroisoquinoline which was carried on to the next step without purification.

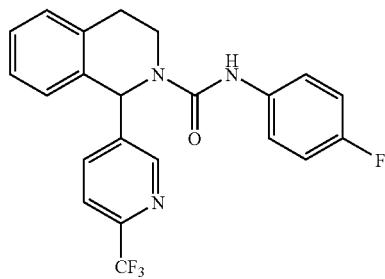

Step 3: N-(4-fluorophenyl)-1-(6-(trifluoromethyl)pyridin-3-yl)-3,4-dihydroisoquinoline-2(1H)-carboxamide The crude 1-(6-(trifluoromethyl)pyridin-3-yl)-1,2,3,4-tetrahydroisoquinoline was dissolved in CH₂Cl₂ (1.0 mL) and 1-fluoro-4-isocyanatobenzene (32 μL, 273 μmol) was added. The reaction was stirred 17 h under N₂ at RT. The reaction was directly purified by HPLC to give N-(4-fluorophenyl)-1-(6-(trifluoromethyl)-pyridin-3-yl)-3,4-dihydroisoquinoline-2(1H)-carboxamide as a white solid. MS (ESI pos. ion) m/z: 416 (M+1).

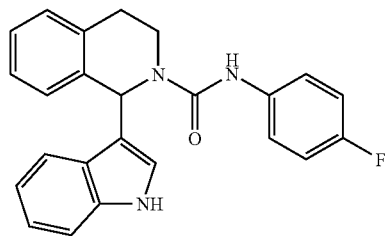 [SMILES: O=C(Nc1ccc(F)cc1)N1CCc2ccccc2C1c1c[nH]c2ccccc12]

Example 152

N-(4-Fluorophenyl)-1-(1H-indol-3-yl)-3,4-dihydroisoquinoline-2(1H)-carboxamide

Step 1: 1-(1-(1H-Indol-3-yl)-3,4-dihydroisoquinolin-2(1H)-yl)ethanone

To a solution of 3,4-dihydroisoquinoline (4.00 g, 30.5 mmol) and CH₃CN (50 mL) at 0° C. was added acetyl chloride (2.13 mL, 30.5 mmol) over 2 min. The reaction was stirred 30 min and 1H-indole (3.57 g, 30.5 mmol) and triethylamine (4.25 mL, 30.5 mmol) in CH₃CN (5 mL) were added and the reaction warmed to RT. The reaction was stirred under N₂ 3 h, then quenched with 10% HCl (100 mL), and extracted with CH₂Cl₂ (3×100 mL). The combined organic layers were washed with NaHCO₃ (100 mL), dried (Na₂SO₄), and concentrated to give the crude product as a white solid (9.2 g). The solid was dissolved in CH₂Cl₂ (50 mL) to give a suspension which was filtered and the solid collected. The white solid (3.55 g) was recrystallized from hot acetone (230 mL) and cooled at −20° C. overnight to give 1-(1-(1H-indol-3-yl)-3,4-dihydroisoquinolin-2(1H)-yl)ethanone as a white crystalline solid.

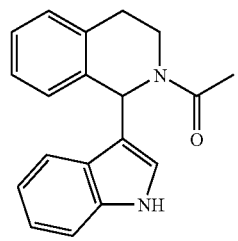 [SMILES: CC(=O)N1CCc2ccccc2C1c1c[nH]c2ccccc12]

Step 2: 1-(1H-Indol-3-yl)-1,2,3,4-tetrahydroisoquinoline

To a solution 1-(1-(1H-indol-3-yl)-3,4-dihydroisoquinolin-2(1H)-yl)ethanone (50 mg, 172 μmol in MeOH (1.0 mL) was added 5 M HCl (1.0 mL, 5000 μmol). The reaction was heated to 100° C. under microwave 30 min. The reaction was concentrated to give 1-(1H-indol-3-yl)-1,2,3,4-tetrahydroisoquinoline, which was used in the next step without purification.

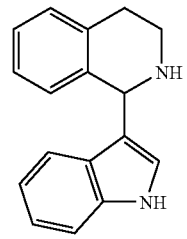 [SMILES: c1ccc2c(c1)CCNC2c1c[nH]c2ccccc12]

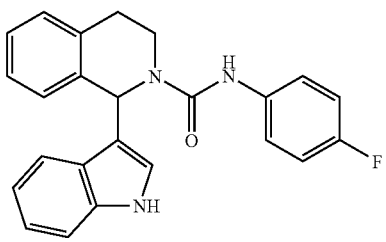 [SMILES: O=C(Nc1ccc(F)cc1)N1CCc2ccccc2C1c1c[nH]c2ccccc12]

Step 3: N-(4-Fluorophenyl)-1-(1H-indol-3-yl)-3,4-dihydroisoquinoline-2(1H)-carboxamide To a solution of 1-(1H-indol-3-yl)-1,2,3,4-tetrahydroisoquinoline (16.3 mg, 66 µmol) in $CH_2Cl_2$ (0.5 mL) at RT was added 1-fluoro-4-isocyanatobenzene (10 µL, 66 µmol). The reaction was stirred 48 h, the suspension dissolved in DMF and purified by HPLC to give N-(4-fluorophenyl)-1-(1H-indol-3-yl)-3,4-dihydroisoquinoline-2(1H)-carboxamide as a white solid. MS (ESI pos. ion) m/z: 386 (M+1).

Absolute stereochemistries of the examples were determined using Vibrational Circular Dichroism (VCD, Biotools, Inc.). Comparison of experimental VCD data with ab initio DFT calculations provide for the assigned absolute stereochemistry.

Assays

Luminescence Readout Assay for Measuring Intracellular Calcium.

Stable CHO cell lines expressing human TRPM8 were generated using tetracycline inducible T-REx™ expression system from Invitrogen, Inc (Carlsbad, Calif.). In order to enable a luminescence readout based on intracellular increase in calcium (Le Poul et al., 2002), each cell line was also co-transfected with pcDNA3.1 plasmid containing jelly fish aequorin cDNA. Twenty four h before the assay, cells were seeded in 96-well plates and TRP channel expression was induced with 0.5 µg/ml tetracycline. On the day of the assay, culture media was removed and cells were incubated with assay buffer (F12 containing 30 mM HEPES for TRPM8 containing 15 µM coelenterazine (P.J.K, Germany) for 2 h. Potential antagonists were added and cells were incubated for 2.5 min prior to adding agonist, 1 µM Icilin, or 1 min prior to addition of cold buffer (<10° C.). The luminescence was measured by a CCD camera based FLASH-luminometer built by Amgen, Inc. Compound activity was calculated using GraphPad Prism 4.01 (GraphPad Software Inc, San Diego, Calif.).

The following compounds exhibit $IC_{50}$ values of less than 5 µM in the above assay using the cold buffer and human TRPM8: Examples 1-22, 24-65, 70-72, 78, 87-107, 109, 111-124, 145-149.

Icilin Biochemical Challenge Model:

Male Sprague Dawley rats (275-500 g, Harlan, n=4-6/treatment) were administered icilin in 2% HPMC/1% HPbCD at the following doses: 0.1, 0.3, 1.0, 3.0, 10.0 mg/kg, i.p.; 0:32, 1.0, 3.2, 10, 32 mg/kg, p.o. Spontaneous wet dog shakes were counted over 30 min post-icilin. Example compounds were tested (i.v., p.o.) to assess the ability to block the spontaneous wet dog shake phenomena induced by Icilin.

CCI Model

Surgery—A chronic constriction injury (CCI) was produced as previously described (Bennett & Xie, 1988). Under gaseous anesthesia with a mixture of iso-flurane (3% for induction and 2% for maintenance) in $O_2$, the sciatic nerve was exposed at the mid-thigh level proximal to the sciatic trifurcation. Four chromic gut ligatures (4-0) were tied loosely around nerve, 1-2 mm apart such that the vascular supply was not compromised.

Behavioral testing—A behavioral test was performed to estimate cold-induced ongoing pain as previously described (Choi et al., 1994). The rat was placed under a transparent plastic cover on an aluminum plate (IITC PE34, Woodland, Calif.) which was kept at a cold temperature (5±0.5° C.). After 2 min of adaptation, the cumulative duration of time that the rat lifted the foot off the plate for the next 5 min was measured. Foot lifts associated with locomotion or grooming were not counted. Seven to 9 days after the CCI surgery, baseline of the cold-induced ongoing pain was measured. Any rat showing a cold-induced ongoing pain less than 100 sec out of 300 sec observation period was eliminated from the study. Twenty four h after the baseline measurement, test compound, positive control, morphine (2 mg/kg, Sigma, St. Louis) or a vehicle (saline or 2% HPMC/1% Tween 80) was administered orally (test compound) or subcutaneously (morphine). Two hrs (test compound) or 30 mins (morphine) after the drug administration, the cold-induced ongoing pain was measured again.

Chung Model

Surgery—Spinal nerve ligation surgery was performed as previously described (Kim & Chung, 1992). Briefly, under gaseous anesthesia with a mixture of iso-flurane (3% for induction and 2% for maintenance) in $O_2$, the spinal nerve injury was produced by ligating the left L5 and L6 spinal nerves taking special care to avoid any possible damage to the L4 spinal nerve or surrounding area. Additional treatments were performed to increase the development of mechanical allodynia. First, L5 spinal nerve was cut approximately 1 mm distal to the suture as described by Li et al. (2000). Second, immediately after ligation and cut, the L4 spinal nerve was lightly manipulated by slightly stretching it with a fine hooked glass rod and gently sliding the hook back and forth 20 times along the nerve as described by Lee et al. (2003). The whole surgery procedure from anesthesia to the clipping of the incised skin took at most 15 min.

Behavioral testing—Two weeks later, mechanical sensitivity was measured by determining the median 50% foot withdrawal threshold for von Frey filaments using the up-down method (Chaplan et al., 1994). The rats were placed under a plastic cover (9×9×20 cm) on a metal mesh floor. The area tested was the middle glabrous area between the footpads of the plantar surface of the hind paw. The plantar area was touched with a series of 9 von Frey hairs with approximately exponentially incremental bending forces (von Frey values: 3.61, 3.8, 4.0, 4.2, 4.41, 4.6, 4.8, 5.0 and 5.2; equivalent to: 0.41, 0.63, 1.0, 1.58, 2.51, 4.07, 6.31, 10 and 15.8 g). The von Frey hair was presented perpendicular to the plantar surface with sufficient force to cause slight bending, and held for approximately 3-4 seconds. Abrupt withdrawal of the foot (paw flinching, shaking or licking for more than 1 sec.) was recorded as a response. Any rat showing a mechanical threshold of more than 3.16 g or less than 0.7 g after surgery was eliminated from the study. After measuring basal threshold, test compound, positive control gabapentin (Sigma, St. Louis) or a vehicle (saline or 2% HPMC/1% Tween 80) was administered orally (test compound) or intraperitoneally (gabapentin). The measurement of the tactile threshold was reassessed at 1.5 and 2 hrs after drug administration.

Data—Since the von Frey filament set was calibrated on a logarithmic scale by the vendor (Stoelting) and our selection of 9 filaments for the up-down method was also based on near equal logarithmic intervals (Dixon et al., 1980), data were treated using logarithmic values in every aspect (statistical treatment as well as plotting). However, an equivalent gram value scale is labeled on the Y-axis of the figures for convenience. Data are expressed as mean±standard error of the mean (S.E.M.).

For the treatment of TRP-M8-receptor-diseases, such as acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders, the compounds of the present invention may be administered orally, parentally, by inhalation spray, rectally, or topically in dosage unit formulations containing conventional pharmaceutically acceptable carriers, adjuvants, and vehicles. The term parenteral as used herein includes, subcutaneous, intravenous, intramuscular, intrasternal, infusion techniques or intraperitoneally.

Treatment of diseases and disorders herein is intended to also include the prophylactic administration of a compound of the invention, a pharmaceutical salt thereof, or a pharmaceutical composition of either to a subject (i.e., an animal, preferably a mammal, most preferably a human) believed to be in need of preventative treatment, such as, for example, pain, inflammation and the like.

The dosage regimen for treating TRP-M8-receptor-mediated diseases, cancer, and/or hyperglycemia with the compounds of this invention and/or compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods. Dosage levels of the order from about 0.01 mg to 30 mg per kilogram of body weight per day, preferably from about 0.1 mg to 10 mg/kg, more preferably from about 0.25 mg to 1 mg/kg are useful for all methods of use disclosed herein.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a capsule, a tablet, a suspension, or liquid. The pharmaceutical composition is preferably made in the form of a dosage unit containing a given amount of the active ingredient. For example, these may contain an amount of active ingredient from about 1 to 2000 mg, preferably from about 1 to 500 mg, more preferably from about 5 to 150 mg. A suitable daily dose for a human or other mammal may vary widely depending on the condition of the patient and other factors, but, once again, can be determined using routine methods.

The active ingredient may also be administered by injection as a composition with suitable carriers including saline, dextrose, or water. The daily parenteral dosage regimen will be from about 0.1 to about 30 mg/kg of total body weight, preferably from about 0.1 to about 10 mg/kg, and more preferably from about 0.25 mg to 1 mg/kg.

Injectable preparations, such as sterile injectable aqueous or oleaginous suspensions, may be formulated according to the known are using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

Formulations suitable for topical administration include liquid or semi-liquid preparations suitable for penetration through the skin (e.g., liniments, lotions, ointments, creams, or pastes) and drops suitable for administration to the eye, ear, or nose.

For administration, the compounds of this invention are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulfuric acids, acacia, gelatin, sodium alginate, polyvinyl-pyrrolidine, and/or polyvinyl alcohol, and tableted or encapsulated for conventional administration. Alternatively, the compounds of this invention may be dissolved in saline, water, polyethylene glycol, propylene glycol, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be made up in a solid form (including granules, powders or suppositories) or in a liquid form (e.g., solutions, suspensions, or emulsions). The pharmaceutical compositions may be subjected to conventional pharmaceutical operations such as sterilization and/or may contain conventional adjuvants, such as preservatives, stabilizers, wetting agents, emulsifiers, buffers etc.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting, sweetening, flavoring, and perfuming agents.

Compounds of the present invention can possess one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using active starting materials. These isomers may be in the form of a free acid, a free base, an ester or a salt.

Likewise, the compounds of this invention may exist as isomers, that is compounds of the same molecular formula but in which the atoms, relative to one another, are arranged differently. In particular, the alkylene substituents of the compounds of this invention, are normally and preferably arranged and inserted into the molecules as indicated in the definitions for each of these groups, being read from left to right. However, in certain cases, one skilled in the art will appreciate that it is possible to prepare compounds of this invention in which these substituents are reversed in orientation relative to the other atoms in the molecule. That is, the substituent to be inserted may be the same as that noted above except that it is inserted into the molecule in the reverse orientation. One skilled in the art will appreciate that these isomeric forms of the compounds of this invention are to be construed as encompassed within the scope of the present invention.

The compounds of the present invention can be used in the form of salts derived from inorganic or organic acids. The salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methansulfonate, nicotinate, 2-naphthalenesulfonate, oxalate, palmoate, pectinate, persulfate, 2-phenylpropionate, picrate, pivalate, propionate, succinate, tartrate, thiocyanate, tosylate, mesylate, and undecanoate. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to from pharmaceutically acceptable acid addition salts include such inorganic acids as hydrochloric acid, sulfuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases.

Also encompassed in the scope of the present invention are pharmaceutically acceptable esters of a carboxylic acid or hydroxyl containing group, including a metabolically labile ester or a prodrug form of a compound of this invention. A metabolically labile ester is one which may produce, for example, an increase in blood levels and prolong the efficacy of the corresponding non-esterified form of the compound. A prodrug form is one which is not in an active form of the molecule as administered but which becomes therapeutically active after some in vivo activity or biotransformation, such as metabolism, for example, enzymatic or hydrolytic cleavage. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use. Esters of a compound of this invention, may include, for example, the methyl, ethyl, propyl, and butyl esters, as well as other suitable esters formed between an acidic moiety and a hydroxyl containing moiety. Metabolically labile esters, may include, for example, methoxymethyl, ethoxymethyl, iso-propoxymethyl, α-methoxyethyl, groups such as α-(($C_1$-$C_4$) alkyloxy)ethyl, for example, methoxyethyl, ethoxyethyl, propoxyethyl, iso-propoxyethyl, etc.; 2-oxo-1,3-dioxolen-4-ylmethyl groups, such as 5-methyl-2-oxo-1,3,dioxolen-4-ylmethyl, etc.; $C_1$-$C_3$ alkylthiomethyl groups, for example, methylthiomethyl, ethylthiomethyl, isopropylthiomethyl, etc.; acyloxymethyl groups, for example, pivaloyloxymethyl, α-acetoxymethyl, etc.; ethoxycarbonyl-1-methyl; or α-acyloxy-α-substituted methyl groups, for example α-acetoxyethyl.

Further, the compounds of the invention may exist as crystalline solids which can be crystallized from common solvents such as ethanol, N,N-dimethyl-formamide, water, or the like. Thus, crystalline forms of the compounds of the invention may exist as polymorphs, solvates and/or hydrates of the parent compounds or their pharmaceutically acceptable salts. All of such forms likewise are to be construed as falling within the scope of the invention.

While the compounds of the invention can be administered as the sole active pharmaceutical agent, they can also be used in combination with one or more compounds of the invention or other agents. When administered as a combination, the therapeutic agents can be formulated as separate compositions that are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

We claim:

1. A compound having the structure:

or any pharmaceutically-acceptable salt thereof, wherein:
J is —N($R^a$)—;
m is 0 or 1;
n is independently in each instance 0, 1, 2 or 3;
o is 1;
X is O;
$R^1$ is selected from H or F;
$R^2$ is selected from H or F;
$R^3$ is $R^4$ is selected from $CH_3$, $CF_3$, F, or Cl;
$R^5$ is $C_{1-11}$alkyl, $C_{6-11}$cycloalkyl or a saturated, partially saturated or unsaturated 5-, 6- or 7-membered monocyclic or 8-, 9-, 10- or 11-membered bicyclic ring containing 0, 1, 2, 3 or 4 atoms selected from N, O and S, wherein the $C_{1-11}$alkyl, $C_{6-11}$cycloalkyl and ring are substituted by 0, 1, 2 or 3 substituents selected from $C_{1-8}$alk, $C_{1-4}$-haloalk, halo, cyano, nitro, —C(═O)$R^b$, —C(═O)O$R^b$, —C(═O)N$R^aR^a$, —C(═N$R^a$)N$R^aR^a$, —O$R^a$, —OC(═O)$R^b$, —OC(═O)N$R^aR^a$, —O$C_{2-6}$alkN$R^aR^a$, —O$C_{2-6}$alkO$R^a$, —S$R^a$, —S(═O)$R^b$, —S(═O)$_2R^b$, —S(═O)$_2$N$R^aR^a$, —N$R^aR^a$, —N($R^a$)C(═O)$R^b$, —N($R^a$)C(═O)O$R^b$, —N($R^a$)C(═O)N$R^aR^a$, —N($R^a$)C(═N$R^a$)N$R^aR^a$, —N($R^a$)S(═O)$_2R^b$, —N($R^a$)S(═O)$_2$N$R^aR^a$, —N$R^aC_{2-6}$alkN$R^aR^a$ and —N$R^aC_{2-6}$alkO$R^a$; or $R^5$ may also be $C_{3-5}$cycloalkyl substituted by 0, 1, 2 or 3 substituents selected from $C_{1-8}$alk, $C_{1-4}$-haloalk, halo, cyano, nitro, —C(═O)$R^b$, —C(═O)O$R^b$, —C(═O)N$R^aR^a$, —C(═N$R^a$)N$R^aR^a$, —O$R^a$, —OC(═O)$R^b$, —OC(═O)N$R^aR^a$, —O$C_{2-6}$alkN$R^aR^a$, —O$C_{2-6}$alkO$R^a$, —S$R^a$, —S(═O)$R^b$, —S(═O)$_2R^b$, —S(═O)$_2$N$R^aR^a$, —N$R^aR^a$, —N($R^a$)C(═O)$R^b$, —N($R^a$)C(═O)O$R^b$, —N($R^a$)C(═O)N$R^aR^a$, —N($R^a$)C(═N$R^a$)N$R^aR^a$, —N($R^a$)S(═O)$_2R^b$, —N($R^a$)S(═O)$_2$N$R^aR^a$, —N$R^aC_{2-6}$alkN$R^aR^a$ and —N$R^aC_{2-6}$alkO$R^a$;

$R^6$ is independently in each instance, selected from F, Cl, Br, I, $C_{2-6}$alk, cyano, —O$R^a$, —C(═O)$R^b$, —C(═O)O$R^b$, —C(═O)N$R^aR^a$, —C(═N$R^a$)N$R^aR^a$, —S(═O)$R^b$, —S(═O)$_2R^b$, —S(═O)$_2$N$R^aR^a$, —N$R^aR^a$, —N($R^a$)C(═O)$R^b$, —N($R^a$)C(═O)O$R^b$, —N($R^a$)C(═O)N$R^aR^a$, —N($R^a$)C(═N$R^a$)N$R^aR^a$, —N($R^a$)S(═O)$_2R^b$, —N($R^a$)S(═O)$_2$N$R^aR^a$, —N$R^aC_{2-6}$alkN$R^aR^a$ and —N$R^aC_{2-6}$alkO$R^a$; or $R^6$ is $C_{1-6}$alk substituted by 1, 2 or 3 substituents selected from $C_{1-4}$haloalk, halo, cyano, nitro, —C(═O)$R^b$, —C(═O)O$R^b$, —C(═O)N$R^aR^a$, —C(═N$R^a$)N$R^aR^a$, —O$R^a$, —OC(═O)$R^b$, —OC(═O)N$R^aR^a$, —O$C_{2-6}$alkN$R^aR^a$, —O$C_{2-6}$alkO$R^a$, —S$R^a$, —S(═O)$R^b$, —S(═O)$_2R^b$, —S(═O)$_2$N$R^aR^a$, —N$R^aR^a$, —N($R^a$)C(═O)$R^b$, —N($R^a$)C(═O)O$R^b$, —N($R^a$)C(═O)N$R^aR^a$, —N($R^a$)C(═N$R^a$)N$R^aR^a$, —N($R^a$)S(═O)$_2R^b$, —N($R^a$)S(═O)$_2$ N$R^aR^a$, —N$R^aC_{2-6}$alkN$R^aR^a$ and —N$R^aC_{2-6}$alkO$R^a$;

$R^7$ is selected from $C_{1-6}$alk, cyano, —C(═O)$R^b$, —C(═O)O$R^b$, —C(═O)N$R^aR^a$, —C(═N$R^a$)N$R^aR^a$, —S(═O)$R^b$, —S(═O)$_2R^b$, —S(═O)$_2$N$R^aR^a$, —N$R^aR^a$, —N($R^a$)C(═O)$R^b$, —N($R^a$)C(═O)O$R^b$, —N($R^a$)C(═O)N$R^aR^a$, —N($R^a$)C(═N$R^a$)N$R^aR^a$, —N($R^a$)S(═O)$_2R^b$, —N($R^a$)S(═O)$_2$N$R^aR^a$, —N$R^aC_{2-6}$alkN$R^aR^a$ and —N$R^aC_{2-6}$alkO$R^a$; or $R^7$ is $C_{1-6}$alk substituted by 1, 2 or 3 substituents selected from $C_{1-4}$haloalk, halo, cyano, nitro, —C(═O)$R^b$, —C(═O)O$R^b$, —C(═O)N$R^aR^a$, —C(═N$R^a$)N$R^aR^a$, —O$R^a$, —OC(═O)$R^b$, —OC(═O)N$R^aR^a$, —O$C_{2-6}$alkN$R^aR^a$, —O$C_{2-6}$alkO$R^a$, —S$R^a$, —S(═O)$R^b$, —S(═O)$_2R^b$, —S(═O)$_2$N$R^aR^a$, —N$R^aR^a$, —N($R^a$)C(═O)$R^b$, —N($R^a$)C(═O)O$R^b$, —N($R^a$)C(═O)N$R^aR^a$, —N($R^a$)C(═N$R^a$)N$R^aR^a$, —N($R^a$)S(═O)$_2R^b$, —N($R^a$)S(═O)$_2$N$R^aR^a$, —N$R^aC_{2-6}$alkN$R^aR^a$ and —N$R^aC_{2-6}$alkO$R^a$;

$R^a$ is H;
$R^b$ is independently, at each instance, phenyl, benzyl or $C_{1-6}$alk;
and
$R^f$ is independently in each instance H or F.

2. A compound according to claim 1, wherein $R^3$ is and
$R^6$ is $C_{1-6}$alk substituted by 1, 2 or 3 substituents selected from $C_{1-4}$haloalk, halo, cyano, nitro, —C(═O)$R^b$, —C(═O)O$R^b$, —C(═O)N$R^aR^a$, —C(═N$R^a$)N$R^aR^a$, —O$R^a$, —OC(═O)$R^b$, —OC(═O)N$R^aR^a$, —O$C_{2-6}$alkN$R^aR^a$, —O$C_{2-6}$alkO$R^a$, —S$R^a$, —S(═O)$R^b$, —S(═O)$_2R^b$, —S(═O)$_2$N$R^aR^a$, —N$R^aR^a$, —N($R^a$)C(═O)$R^b$, —N($R^a$)C(═O)O$R^b$, —N($R^a$)C(═O)N$R^aR^a$, —N($R^a$)C(═N$R^a$)N$R^aR^a$, —N($R^a$)S(═O)$_2R^b$, —N($R^a$)S(═O)$_2$N$R^aR^a$, —N$R^aC_{2-6}$alkN$R^aR^a$ and —N$R^aC_{2-6}$alkO$R^a$.

3. A compound according to claim 1, wherein $R^5$ is $C_{1-11}$alkyl or $C_{6-11}$cycloalkyl both of which are substituted by 0, 1, 2 or 3 substituents selected from $C_{1-8}$alk, $C_{1-4}$haloalk, halo, cyano, nitro, —C(=O)$R^b$, —C(=O)O$R^b$, —C(=O)NR$^a$R$^a$, —C(=NR$^a$)NR$^a$R$^a$, —OR$^a$, —OC(=O)$R^b$, —OC(=O)NR$^a$R$^a$, —OC$_{2-6}$alkNR$^a$R$^a$, —OC$_{2-6}$alkOR$^a$, —SR$^a$, —S(=O)$R^b$, —S(=O)$_2$$R^b$, —S(=O)$_2$NR$^a$R$^a$, —NR$^a$R$^a$, —N(R$^a$)C(=O)$R^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$$R^b$, —N(R$^a$)S(=O)$_2$NR$^a$R$^a$, —NR$^a$C$_{2-6}$alkNR$^a$R$^a$ and —NR$^a$C$_{2-6}$alkOR$^a$.

4. A compound according to claim 1, wherein $R^5$ is a saturated, partially saturated or unsaturated 5-, 6- or 7-membered monocyclic or 8-, 9-, 10- or 11-membered bicyclic ring containing 0, 1, 2, 3 or 4 atoms selected from N, O and S, wherein the ring is substituted by 0, 1, 2 or 3 substituents selected from $C_{1-8}$alk, $C_{1-4}$haloalk, halo, cyano, nitro, —C(=O)$R^b$, —C(=O)OR$^b$, —C(=O)NR$^a$R$^a$, —C(=NR$^a$)NR$^a$R$^a$, —OR$^a$, —OC(=O)$R^b$, —OC(=O)NR$^a$R$^a$, —OC$_{2-6}$alkNR$^a$R$^a$, —OC$_{2-6}$alkOR$^1$, —SR$^a$, —S(=O)$R^b$, —S(=O)$_2$$R^b$, —S(=O)$_2$NR$^a$R$^a$, —NR$^a$R$^a$, —N(R$^a$)C(=O)$R^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$$R^b$, —N(R$^a$)S(=O)$_2$NR$^a$R$^a$, —NR$^a$C$_{2-6}$alkNR$^a$R$^a$, and —NR$^a$C$_{2-6}$alkOR$^a$.

5. The compound of claim 1, wherein the compound is

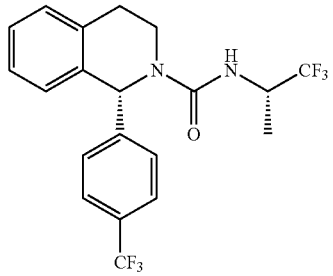 [SMILES: C[C@H](NC(=O)N1CCc2ccccc2[C@H]1c1ccc(C(F)(F)F)cc1)C(F)(F)F]

or the pharmaceutically-acceptable salt thereof.

6. The compound of claim 1, wherein the compound is

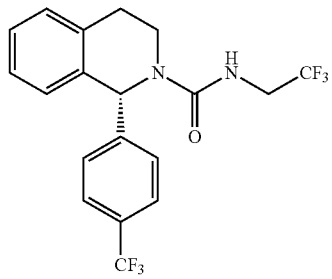

or the pharmaceutically-acceptable salt thereof.

7. The compound of claim 1, wherein the compound is

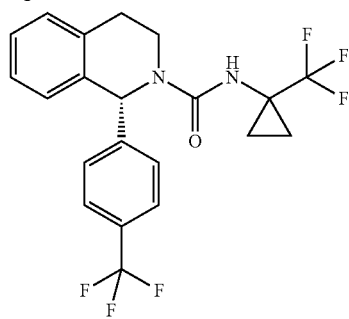

or the pharmaceutically-acceptable salt thereof.

8. The compound of claim 1, wherein the compound is

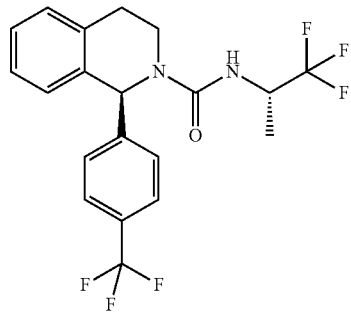 [SMILES: C[C@H](NC(=O)N1CCc2ccccc2[C@@H]1c1ccc(C(F)(F)F)cc1)C(F)(F)F]

or the pharmaceutically-acceptable salt thereof.

9. The compound of claim 1, wherein the compound is

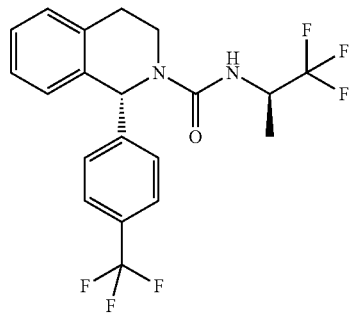 [SMILES: C[C@@H](NC(=O)N1CCc2ccccc2[C@H]1c1ccc(C(F)(F)F)cc1)C(F)(F)F]

or the pharmaceutically-acceptable salt thereof.

10. The compound of claim 1, wherein the compound is

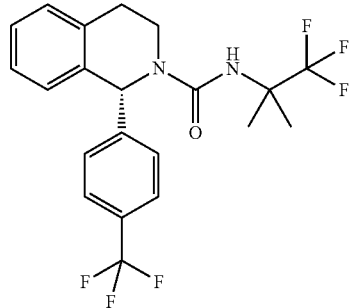 [SMILES: CC(C)(NC(=O)N1CCc2ccccc2[C@H]1c1ccc(C(F)(F)F)cc1)C(F)(F)F]

or the pharmaceutically-acceptable salt thereof.

11. A pharmaceutical composition comprising a compound according to claim 1 and a pharmaceutically-acceptable diluent or carrier.

* * * * *